United States Patent
Bock et al.

(10) Patent No.: US 8,946,260 B2
(45) Date of Patent: Feb. 3, 2015

(54) 17α-HYDROXYLASE/C$_{17,20}$-LYASE INHIBITORS

(75) Inventors: Mark Gary Bock, Boston, MA (US); Christoph Gaul, Aesch (CH); Venkateshwar Rao Gummadi, Bangalore (IN); Henrik Moebitz, Freiburg (DE); Saumitra Sengupta, Kolkata (IN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/823,792

(22) PCT Filed: Sep. 14, 2011

(86) PCT No.: PCT/EP2011/065965
§ 371 (c)(1),
(2), (4) Date: Jun. 20, 2013

(87) PCT Pub. No.: WO2012/035078
PCT Pub. Date: Mar. 22, 2012

(65) Prior Publication Data
US 2014/0045872 A1   Feb. 13, 2014

(30) Foreign Application Priority Data
Sep. 16, 2010  (IN) .......................... 2719/CHE/2010

(51) Int. Cl.
| | | |
|---|---|---|
| A01N 43/42 | (2006.01) | |
| A61K 31/47 | (2006.01) | |
| A61K 31/44 | (2006.01) | |
| C07D 513/02 | (2006.01) | |
| C07D 515/02 | (2006.01) | |
| C07D 221/06 | (2006.01) | |
| C07D 207/22 | (2006.01) | |
| C07D 455/04 | (2006.01) | |
| C07D 471/00 | (2006.01) | |
| C07D 491/00 | (2006.01) | |
| C07D 498/00 | (2006.01) | |
| C07D 513/00 | (2006.01) | |
| C07D 515/00 | (2006.01) | |
| C07D 401/04 | (2006.01) | |
| C07D 471/04 | (2006.01) | |
| C07D 471/14 | (2006.01) | |
| C07D 495/04 | (2006.01) | |
| A61K 31/4365 | (2006.01) | |
| A61K 31/437 | (2006.01) | |
| A61K 31/4725 | (2006.01) | |
| A61K 31/506 | (2006.01) | |
| A61K 45/06 | (2006.01) | |
| C07D 401/14 | (2006.01) | |

(52) U.S. Cl.
CPC ............ *A60K 31/473* (2013.01); *C07D 401/04* (2013.01); *C07D 471/04* (2013.01); *C07D 471/14* (2013.01); *C07D 495/04* (2013.01); *A61K 31/4365* (2013.01); *A61K 31/437* (2013.01); *A61K 31/4725* (2013.01); *A61K 31/506* (2013.01); *A61K 45/06* (2013.01); *C07D 401/14* (2013.01)
USPC ........... 514/309; 514/290; 514/291; 546/114; 546/110; 546/141; 546/80; 546/86

(58) Field of Classification Search
USPC .............. 514/290, 291, 309; 546/80, 86, 110, 546/114, 141
See application file for complete search history.

(56) References Cited

U.S. PATENT DOCUMENTS

| 5,304,556 | A | * | 4/1994 | Yamamoto et al. ........... 514/243 |
| 8,263,635 | B2 | | 9/2012 | Bock et al. |
| 2004/0198773 | A1 | | 10/2004 | Hart et al. |

FOREIGN PATENT DOCUMENTS

| EP | 2223919 A1 | 9/2010 |
| WO | 2010090347 A1 | 8/2010 |

OTHER PUBLICATIONS

De Oliveira et al. BMC Cancer, May 2010, vol. 10, pp. 1-12.*
Akhtar, M. K. et al., "Cytochrome b5 modulation of 17a hydroxylase and 17-20 lyase (CYP17) activities in steroidogenesis", Journal of Endocrinology, vol. 187, pp. 267-274, 2005.
Barnes, Henry J. et al., "Expression and enzymatic activity of recombinant cytochrome P450 17a-hydroxylase in *Escherichia coli*", Proc. Natl. Acad. Sci. USA, vol. 88, pp. 5597-5601, 1991.
Grigoryev, Dmitry N. et al., "Cytochrome P450c17-Expressing *Escherichia coli* as a First-Step Screening System for 17a-Hydroxylase-C17,20-lyase Inhibitors", Analytical Biochemistry, vol. 267, pp. 319-330, 1999.
Handratta, Venkatesh D. et al., "Novel C-17-Heteroaryl Steroidal CYP17 Inhibitors/Antiandrogens: Synthesis, in Vitro Biological Activity, Pharmacokinetics, and Antitumor Activity in the LAPC4 Human Prostate Cancer Xenograft Model", J. Med. Chem., vol. 48, pp. 2972-2984, 2005.
Imai, Tsuneo et al., "Expression and Purification of Functional Human 17a-Hydroxylase/17,20-Lyase (P450c17) in *Escherichia coli*", The Journal of Biological Chemistry, vol. 268, No. 26, Issue of Sep. 15, pp. 19681-19689, 1993.

(Continued)

*Primary Examiner* — Samira Jean-Louis
(74) *Attorney, Agent, or Firm* — Stephen Johnson

(57) ABSTRACT

The present invention provides compounds of Formula (I), or a pharmaceutically acceptable salt thereof, where $R_1$, $R_2$, $R_3$, $R_4$, $R_5$, $R_6$, A and n are as defined herein. A deuterated derivative of the compound of Formula (I) is also provided.

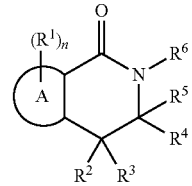

(I)

9 Claims, No Drawings

(56) References Cited

OTHER PUBLICATIONS

Katagiri, Masayuki et al., "Role of Cytochrome b5 in the Cytochrome P-450-Mediated C21-Steroid 17,20-Lyase Reaction", Biochemical and Biophysical Research Communications, vol. 108, No. 1, pp. 379-384, 1982.

Lee-Robichaud, Peter et al., "Interaction of human CYP17 (P-450 17a' 17a-hydroxylase-17,20-lyase) with cytochrome b5: importance of the orientation of hydrophobic domain of cytochrome b5", Biochem J., vol. 321, pp. 857-863, 1997.

Madan, Ravi A. et al., "Abiraterone Cougar Biotechnology", IDrugs, vol. 9, No. 1, pp. 49-55, 2006.

Njar, Vincent C. O. et al., "Novel 17-Azolyl Steroids, Potent Inhibitors of Human Cytochrome 17a-Hydroxylase-C17,20-lyase (P450 17a): Potential Agents for the Treatment of Prostate Cancer", J. Med. Chem., vol. 41, pp. 902-912, 1998.

Njar, V.C.O. et al., "Inhibitors of 17a-Hydroxylase/17,20-Lyase (CYP17): Potential Agents for the Treatment of Prostate Cancer", Current Pharmaceutical Design, vol. 5, No. 3, 1999.

Sakaki, Toshiyuki et al., "Expression of Bovine Cytochrome P450c17 cDNA in *Saccharomyces cerevisiae*", DNA, vol. 8, No. 6, pp. 409-418, 1989.

Zuber, Mauricio X. et al., "Expression of Bovine 17a-Hydroxylase Cytochrome P-450 cDNA in Nonsteroidogenic (COS 1) Cells", Science, vol. 234, pp. 1258-1261.

\* cited by examiner

17α-HYDROXYLASE/C$_{17,20}$-LYASE INHIBITORS

FIELD OF THE INVENTION

The present invention relates to aryl and heteroaryl fused pyridinone, pyridine, pyrrolidinone, and pyrrolidine derivatives and their use for the treatment of various disease conditions mediated by the regulation of 17α-hydroxylase/C$_{17,20}$-lyase.

BACKGROUND

The number of people diagnosed with cancer world wide has significantly increased and continues to rise at an alarming rate. Cancer is characterized by an increase in the number of abnormal cells derived from a given normal tissue, invasion of adjacent tissues by these abnormal cells, or lymphatic or blood-borne spread of malignant cells to regional lymph nodes and to distant sites (i.e., metastasis).

Of special interest are individuals diagnosed with androgen-dependent disorders, such as prostate cancer, and estrogen-dependent disorders, such as breast, uterine, and ovarian cancer.

Prostate cancer is currently the most common non-skin cancer and the second leading cause of cancer-related death in men after lung cancer. The primary course of treatment for patients diagnosed with organ-confined prostate cancer is usually prostatectomy or radiotherapy. These treatments for prostate and breast cancer are highly invasive and characterized by undesirable and serious side effects. Furthermore, a large percent of individuals who receive localized treatments such as surgery or radiotherapy may suffer from recurring cancer and widespread metastases. As with surgery and radiation therapies, there are several drawbacks to chemotherapy, including the fact that almost all chemotherapeutic agents are toxic, and chemotherapy causes significant, and often dangerous, side effects, such as severe nausea, bone marrow depression, and immunosuppression. Additionally, many tumor cells are resistant or become resistant to chemotherapeutic agents through multi-drug resistance.

Treatments such as hormone therapy are another option for individuals diagnosed with hormone-dependent, hormone-responsive, or hormone-sensitive cancers, such as prostate or breast cancer. However, some individuals who have been administered current hormone therapy treatments may not show a significant response to such treatments and some may suffer from relapsing of cancer.

Currently chemo-refractory and hormone-refractory cancer patients are left with very few treatment options and there remains an unmet need for more effective ways to treat cancer such as, but not limited to, prostate cancer and breast cancer.

The demonstration by Huggins and Hodges C. V., (*Cancer Res.*, 1941, 1, 293) and Huggins et al in *Arch. Surg.*, 1941, 43, 209 lead to androgen ablation being considered as a possible approach to treatment. It has been demonstrated that testosterone levels are reduced by orchidectomy or by administration of GnRH analogs (gonadotropic releasing hormones). GnRH analogs can have side effects such as cardiovascular degeneration and osteoporosis, which are the two most potentially serious conditions induced by the continuous presence of GnRH. Moreover these treatment options only eliminate testosterone production from the testes and not that produced by the adrenal.

In the adrenal glands, the biosynthetic cascade also leads to the formation of gluco- and mineralcorticoids.

Since androgen and estrogen are hormones having various physiological activities such as differentiation and proliferation of cells and the like, it was thought that potent and specific compounds that inhibit androgen synthesis in the testes, adrenals, and other tissue may be more effective for the treatment of PCa (Njar, V. C. O.; Brodie, A. M. H., "Inhibitors of 17α-hydroxylase-C$_{17-20}$-lyase (CYP17): Potential agents for the treatment of prostate cancer", *Current Pharm. Design*, 1999, 5: 163-180).

In order to avoid unwanted side effects, androgen biosynthesis inhibitors have to be specific enough not to influence corticosteroid biosynthesis. A promising novel strategy for the treatment of prostate cancer is the development of strong and selective inhibitors of CYP 17 as this would result in complete and exclusive elimination of androgen biosynthesis as suggested in Current Medicinal Chemistry, 2005, 12, 1623-1629.

Steroid-type compounds and non-steroid-type compounds are already known as steroid C$_{17-20}$-lyase inhibitors. The steroid-type compounds are disclosed in, for example, WO 92/15404, WO 93/20097, EP-A 288053, EP-A 413270 and the like. As non-steroid-type compounds, for example, in WO94/27989, WO96/14090 and WO97/00257 azole derivatives are described in WO95/09157 1H-benzimidazole derivatives are described in U.S. Pat. No. 5,491,161, dihydronaphthalene derivatives are described in WO99/18075, and naphthalene derivatives are shown in WO99/54309.

A variety of potent steroidal and non-steroidal inhibitors of CYP 17 have been reported and some have been shown to be potent inhibitors of testosterone production in rodent models (Njar and Brodie, above). Jarman and colleagues have described the hormonal impact of their most potent CYP 17 inhibitor, abiraterone in patients with prostate cancer (O'Donnell et al., "Hormonal impact of the 17α-hydroxylase/C17,20-lyase inhibitors abiraterone acetate (CB7630) in patients with prostate cancer", *Br. J. Cancer*, 2004, 90: 2317-2325). Abiraterone has been discussed in patents such as WO 200900132, WO 2008024485, WO 2006021776, WO 09509178, WO 09320097

Non-steroidal small molecule inhibitors have been described for example in *BMC* 2004, 12, (4313), YM 116, 2-(1H-imidazol-4-ylmethyl)-9H-carbazole, and their effects in decreasing adrenal androgen synthesis by inhibiting C17-20 lyase activity in NCI-H295 human adrenocortical carcinoma cells has been described by Ideyama Y, Kudoh M, Tanimoto K, Susaki Y, Nanya T, Nakahara T, Ishikawa H, Fujikura T, Akaza H, Shikama H in "*Jpn. J. Pharmacol.*, 1999, 79: No. 2(213-20)". Novel non-steroidal inhibitor of cytochrome P450 (17 alpha-hydroxylase/C17-20 lyase), YM 116, and its role in decreased prostatic weights by reducing the serum concentrations of testosterone and adrenal androgens in rats has been reported by Ideyama Y, Kudoh M, Tanimoto K, Susaki Y, Nanya T, Nakahara T, Ishikawa H, Yoden T, Okada M, Fujikura T, Shikama H *Proc. Am. Assoc. Cancer Res.*, 1998, 39:89 Meet. (384)

Synthesis and biological evaluation of novel non-steroidal inhibitors of steroid 17,20 lyase has been described by -Yoden T, Okada M, Kawaminami E, Kinoyama I, Ideyama Y, Isomura Y in *Abstr. Pap. Am. Chem. Soc.*, 1997, 213 Meet.: Pt. 2(MEDI206)

Further illustrative of the background of the invention are patent applications such as US20080280864A1 or WO28154382A1.

SUMMARY

The present invention provides compounds of formula (I) which have been shown to be inhibitors of 17α-hydroxylase/C$_{17-20}$-lyase.

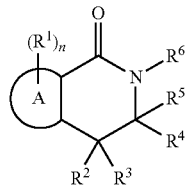

wherein:

ring A is phenyl, naphthyl, or a 5- to 6-membered heteroaryl containing 1 to 3 heteroatoms each independently selected from N, O or S and optionally fused to a phenyl or a 5- to 6-membered heteroaryl containing 1 to 3 heteroaroms each independently selected from N, O or S;

n is 0, 1, 2, or 3;

R$^1$ is halo, (C$_1$-C$_4$)alkyl, halo-substituted (C$_1$-C$_4$)alkyl, —OH, CN, —NR$^{1a}$R$^{1b}$, —O—R$^{1c}$, or phenyl optionally substituted with 1 to 3 substituents selected from halo, (C$_1$-C$_4$) alkyl, or halo-substituted (C$_1$-C$_4$)alkyl, where R$^{1a}$ is H or (C$_1$-C$_4$)alkyl, R$^{1b}$ is (C$_1$-C$_4$)alkyl, —C(O)—(C$_1$-C$_4$)alkyl, —C(O)—(C$_3$-C$_6$)cycloalkyl, phenyl, or —CH$_2$—(C$_3$-C$_6$)cycloalkyl, and R$^{1c}$ is (C$_1$-C$_4$)alkyl, halo-substituted (C$_1$-C$_4$) alkyl, —CH$_2$—(C$_3$-C$_6$)cycloalkyl, or 5- to 6-membered heteroaryl containing 1 to 3 heteroatoms selected from O, N or S and optionally substituted with 1 to 3 substituents selected from halo, (C$_1$-C$_4$)alkyl, or halo-substituted (C$_1$-C$_4$)alkyl;

R$^2$, R$^3$, R$^4$, and R$^5$ are each independently H or (C$_1$-C$_4$) alkyl, or R$^2$ or R$^3$ taken together with R$^4$ or R$^5$ forms a double bond or a cyclopropyl;

R$^6$ is quinolin-3-yl, pyridin-3-yl or 1H-imidazol-5-yl optionally substituted with 1 to 3 substituents each independently selected from halo, —OH, —CN, (C$_1$-C$_4$)alkyl, halo-substituted(C$_1$-C$_4$)alkyl, hydroxy-substituted (C$_1$-C$_4$)alkyl, (C$_3$-C$_5$)cycloalkyl, where said cycloalkyl is optionally substituted with hydroxy, —NH$_2$, —NH(C$_1$-C$_4$)alkyl, —N((C$_1$-C$_4$)alkyl)$_2$, —NHC(O)—(C$_1$-C$_4$)alkyl, —C(O)NH$_2$, —C(O)—NH(C$_1$-C$_4$)alkyl, —C(O)—N((C$_1$-C$_4$)alkyl)$_2$, —C(O)—O(C$_1$-C$_4$)alkyl, —(CH$_2$)$_r$—O(C$_1$-C$_4$)alkyl, —(CH$_2$)$_r$—CH(O(C$_1$-C$_4$)alkyl)$_2$, —(CH$_2$)$_r$—NH—(C$_3$-C$_6$) cycloalkyl, or pyrrolidin-1-yl-(CH$_2$)$_r$—, where r is 0, 1 or 2; or a pharmaceutically acceptable salt thereof.

Another embodiment of a compound of Formula (I) is provided wherein ring A is phenyl, naphthyl, or a 5- to 6-membered heteroaryl containing 1 to 3 heteroatoms each independently selected from N, O or S and optionally fused to a phenyl or a 5- to 6-membered heteroaryl containing 1 to 3 heteroaroms each independently selected from N, O or S;

n is 1, 2, or 3;

R$^1$ is halo, (C$_1$-C$_4$)alkyl, halo-substituted (C$_1$-C$_4$)alkyl, —OH, CN, —NR$^{1a}$R$^{1b}$, —O—R$^{1c}$, or phenyl optionally substituted with 1 to 3 substituents selected from halo, (C$_1$-C$_4$) alkyl, or halo-substituted (C$_1$-C$_4$)alkyl, where R$^{1a}$ is H or (C$_1$-C$_4$)alkyl, R$^{1b}$ is (C$_1$-C$_4$)alkyl, —C(O)—(C$_1$-C$_4$)alkyl, —C(O)—(C$_3$-C$_6$)cycloalkyl, phenyl, or —CH$_2$—(C$_3$-C$_6$)cycloalkyl, and R$^{1c}$ is (C$_1$-C$_4$)alkyl, —CH$_2$—(C$_3$-C$_6$)cycloalkyl, or 5- to 6-membered heteroaryl containing 1 to 3 heteroatoms selected from O, N or S and optionally substituted with 1 to 3 substituents selected from halo, (C$_1$-C$_4$) alkyl, or halo-substituted (C$_1$-C$_4$)alkyl;

R$^2$, R$^3$, R$^4$, and R$^5$ are each independently H or (C$_1$-C$_4$) alkyl, or R$^2$ or R$^3$ taken together with R$^4$ or R$^5$ forms a double bond;

R$^6$ is quinolin-3-yl or pyridin-3-yl optionally substituted with 1 to 3 substituents each independently selected from halo, —OH, —CN, (C$_1$-C$_4$)alkyl, halo-substituted(C$_1$-C$_4$) alkyl, hydroxy-substituted (C$_1$-C$_4$)alkyl, —NH$_2$, —NH(C$_1$-C$_4$)alkyl, —N((C$_1$-C$_4$)alkyl)$_2$, —NHC(O)—(C$_1$-C$_4$)alkyl, —C(O)NH$_2$, —C(O)—NH(C$_1$-C$_4$)alkyl, —C(O)—N((C$_1$-C$_4$)alkyl)$_2$, —C(O)—O(C$_1$-C$_4$)alkyl, —(CH$_2$)$_r$—O(C$_1$-C$_4$) alkyl, —(CH$_2$)$_r$—, —CH(O(C$_1$-C$_4$)alkyl)$_2$, where r is 0, 1 or 2; or a pharmaceutically acceptable salt thereof.

In one particular embodiment of Formula (I), R$^6$ is pyridin-3-yl optionally substituted with 1 to 3 substituents each independently selected from halo, —OH, —CN, (C$_1$-C$_4$)alkyl, halo-substituted(C$_1$-C$_4$)alkyl, hydroxy-substituted (C$_1$-C$_4$) alkyl, (C$_3$-C$_5$)cycloalkyl, where said cycloalkyl is optionally substituted with hydroxy, —(CH$_2$)$_r$—O(C$_1$-C$_4$)alkyl, —(CH$_2$)$_r$—CH(O(C$_1$-C$_4$)alkyl)$_2$, —NH$_2$, —NH(C$_1$-C$_4$) alkyl, —N((C$_1$-C$_4$)alkyl)$_2$, —NHC(O)—(C$_1$-C$_4$)alkyl, —C(O)NH$_2$, —C(O)—NH(C$_1$-C$_4$)alkyl, —C(O)—N((C$_1$-C$_4$)alkyl)$_2$, or —C(O)—O(C$_1$-C$_4$)alkyl; or a pharmaceutically acceptable salt thereof.

In another particular embodiment of Formula (I), R$^6$ is pyridin-3-yl optionally substituted with 1 to 3 substituents each independently selected from halo, —OH, —CN, (C$_1$-C$_4$)alkyl, halo-substituted(C$_1$-C$_4$)alkyl, hydroxy-substituted (C$_1$-C$_4$)alkyl, —(CH$_2$)$_r$—O(C$_1$-C$_4$)alkyl, —(CH$_2$)$_r$—CH(O(C$_1$-C$_4$)alkyl)$_2$, —NH$_2$, —NH(C$_1$-C$_4$)alkyl, —N((C$_1$-C$_4$) alkyl)$_2$, —NHC(O)—(C$_1$-C$_4$)alkyl, —C(O)NH$_2$, —C(O)—NH(C$_1$-C$_4$)alkyl, —C(O)—N((C$_1$-C$_4$)alkyl)$_2$, or —C(O)—O(C$_1$-C$_4$)alkyl; or a pharmaceutically acceptable salt thereof.

More preferably, R$^6$ is group of Formula (6)

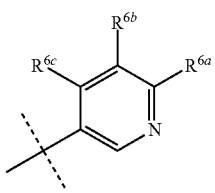

where R$^{6a}$ is H; R$^{6b}$ is H, halo, methyl, trifluoromethyl, methoxy, or —C(O)OCH$_3$; and R$^{6c}$ is halo, —CN, methyl, ethyl, methoxy, hydroxymethyl, 1-hydroxyethyl, 2-hydroxypropan-2-yl, cyclopropyl, where said cyclopropyl is optionally substituted with hydroxy, difluoromethyl, trifluoromethyl, dimethoxymethyl, —NH$_2$, or NHC(O)CH$_3$. Preferably, R$^{6a}$ is H; R$^{6b}$ is H; and R$^{6c}$ is methyl or cyclopropyl.

In one particular embodiment, R$^6$ is a group of Formula (6) where R$^{6a}$ is H; R$^{6b}$ is H, halo, methyl, trifluoromethyl, methoxy, or —C(O)OCH$_3$; and R$^{6c}$ is halo, —CN, methyl, ethyl, methoxy, hydroxymethyl, 1-hydroxyethyl, 2-hydroxypropan-2-yl, difluoromethyl, trifluoromethyl, dimethoxymethyl, cyclopropyl, where said cyclopropyl is optionally substituted with hydroxy, —NH$_2$, or NHC(O)CH$_3$; or a pharmaceutically acceptable salt thereof.

Alternatively, R$^6$ is a group of Formula (6) where R$^{6a}$ is H; R$^{6b}$ is H, halo, methyl, trifluoromethyl, methoxy, or —C(O) OCH$_3$; and R$^{6c}$ is halo, —CN, methyl, ethyl, methoxy, hydroxymethyl, 1-hydroxyethyl, 2-hydroxypropan-2-yl, difluoromethyl, trifluoromethyl, dimethoxymethyl, —NH$_2$, or NHC(O)CH$_3$; or a pharmaceutically acceptable salt thereof.

Preferably, R$^{6a}$ is H; R$^{6b}$ is H; and R$^{6c}$ is methyl or cyclopropyl. In one particular embodiment, R$^{6c}$ is methyl. In another particular embodiment, R$^{6c}$ is cyclopropyl.

In one particular embodiment of any one of the embodiments described above, ring A is a phenyl or naphthyl; or a pharmaceutically acceptable salt thereof.

Preferred compounds of Formula (I) where ring A is a phenyl or naphthyl, include 7-Chloro-2-pyridin-3-yl-3,4-dihydro-2H-isoquinolin-1-one; 7-Chloro-2-(4-methyl-pyridin-3-yl)-3,4-dihydro-2H-isoquinolin-1-one; 2-(4-Methyl-pyridin-3-yl)-7-trifluoromethyl-3,4-dihydro-2H-isoquinolin-1-one; 2-(4-Methyl-pyridin-3-yl)-3,4-dihydro-2H-benzo[h]isoquinolin-1-one; 6-Methoxy-2-(4-methyl-pyridin-3-yl)-3,4-dihydro-2H-isoquinolin-1-one; 6-Hydroxy-2-(4-methyl-pyridin-3-yl)-3,4-dihydro-2H-isoquinolin-1-one; 2-Pyridin-3-yl-7-trifluoromethyl-3,4-dihydro-2H-isoquinolin-1-one; 2-(4-Methyl-pyridin-3-yl)-6-trifluoromethyl-3,4-dihydro-2H-isoquinolin-1-one; 7-Trifluoromethyl-3,4-dihydro-[2,4']biisoquinolinyl-1-one; 7-Trifluoromethyl-2-(4-trifluoromethyl-pyridin-3-yl)-3,4-dihydro-2H-isoquinolin-1-one; 7-Methoxy-2-(4-methyl-pyridin-3-yl)-3,4-dihydro-2H-isoquinolin-1-one; 7-Hydroxy-2-(4-methyl-pyridin-3-yl)-3,4-dihydro-2H-isoquinolin-1-one; 7-Chloro-8-fluoro-2-(4-methylpyridin-3-yl)-3,4-dihydroisoquinolin-1(2H)-one; 8-Chloro-7-fluoro-2-(4-methylpyridin-3-yl)-3,4-dihydroisoquinolin-1(2H)-one; 2-(Pyridin-3-yl)-7-(trifluoromethyl)isoquinolin-1(2H)-one; 3-Methyl-2-(pyridin-3-yl)-7-(trifluoromethyl)-3,4-dihydroisoquinolin-1(2H)-one; 8-Fluoro-2-(4-methyl-pyridin-3-yl)-7-trifluoromethyl-3,4-dihydro-2H-isoquinolin-1-one; 3-Methyl-2-(4-methyl-pyridin-3-yl)-7-trifluoromethyl-3,4-dihydro-2H-isoquinolin-1-one; 6,7-Difluoro-2-(4-methylpyridin-3-yl)-3,4-dihydroisoquinolin-1(2H)-one; 2-(4-Methylpyridin-3-yl)-7-(trifluoromethoxy)-3,4-dihydroisoquinolin-1(2H)-one; 2-(4-((Cyclopropylamino)methyl)pyridin-3-yl)-7-(trifluoromethyl)-3,4-dihydroisoquinolin-1(2H)-one; 2-(1-Methyl-1H-imidazol-5-yl)-7-(trifluoromethyl)-3,4-dihydroisoquinolin-1(2H)-one; 6,7-Dichloro-2-(4-(trifluoromethyl)pyridin-3-yl)-3,4-dihydroisoquinolin-1(2H)-one; 2-(4-Cyclopropylpyridin-3-yl)-7-(trifluoromethyl)-3,4-dihydroisoquinolin-1(2H)-one; 7-Chloro-2-(4-cyclopropylpyridin-3-yl)-3,4-dihydroisoquinolin-1(2H)-one; 7-Chloro-2-(4-ethylpyridin-3-yl)-3,4-dihydroisoquinolin-1(2H)-one; 6-Fluoro-7-iodo-2-(4-(trifluoromethyl)pyridin-3-yl)-3,4-dihydroisoquinolin-1(2H)-one; 7-Chloro-2-(4-cyclopropylpyridin-3-yl)-6-fluoro-3,4-dihydroisoquinolin-1(2H)-one; 7-Chloro-6-fluoro-2-(4-methylpyridin-3-yl)-3,4-dihydroisoquinolin-1(2H)-one; 6-Chloro-7-(trifluoromethyl)-2-(4-(trifluoromethyl)pyridin-3-yl)-3,4-dihydroisoquinolin-1(2H)-one; 7-Chloro-6-methoxy-2-(4-methylpyridin-3-yl)-3,4-dihydroisoquinolin-1(2H)-one; 7-Chloro-2-(4-methylpyridin-3-yl)-1-oxo-1,2,3,4-tetrahydroisoquinoline-6-carbonitrile; 7-Chloro-2-(4-cyclopropylpyridin-3-yl)-6-methoxy-3,4-dihydroisoquinolin-1(2H)-one; and 7-Chloro-2-(4-cyclopropylpyridin-3-yl)-1-oxo-1,2,3,4-tetrahydroisoquinoline-6-carbonitrile; or a pharmaceutically acceptable salt thereof.

In another particular embodiment of any one of the embodiments described above, a compound of Formula (I) is provided where ring A is 5- to 6-membered heteroaryl containing 1 to 3 heteroatoms each independently selected from N, O or S and optionally fused to a phenyl or a 5- to 6-membered heteroaryl containing 1 to 3 heteroaroms each independently selected from N, O or S; or a pharmaceutically acceptable salt thereof.

Preferred compounds of Formula (I) where ring A is a heteoaryl include 2-(4-Methyl-pyridin-3-yl)-3,4-dihydro-2H-benzo[4,5]thieno[3,2-c]pyridin-1-one; 1-Ethyl-6-(4-methyl-pyridin-3-yl)-1,4,5,6-tetrahydro-pyrrolo[2,3-c]pyridin-7-one; 9-Ethyl-2-(4-methylpyridin-3-yl)-2,3,4,9-tetrahydro-1H-pyrido[3,4-b]indol-1-one; 9-Ethyl-3-methyl-2-(pyridin-3-yl)-2,3,4,9-tetrahydro-1H-pyrido[3,4-b]indol-1-one; 9-Ethyl-3-methyl-2-(4-methyl-pyridin-3-yl)-2,3,4,9-tetrahydro-b-carbolin-1-one; 2-(4-Methylpyridin-3-yl)-3,4-dihydro-2H-benzo[4,5]thieno[3,2-c]pyridine-1-one; 8-Fluoro-2-(4-methylpyridine-3-yl)3,4-dihydro-2H-benzo[4,5]thieno[3,2-c]pyridin-1-one; 5-Ethyl-8-fluoro-2-(4-methylpyridin-3-yl)-2,3,4,5-tetrahydro-1H-pyrido[4,3-b]indol-1-one; 8-Fluoro-2-(4-methylpyridin-3-yl)-2,3,4,5-tetrahydro-1H-pyrido[4,3-b]indol-1-one; 2-(4-Methyl pyridin-3-yl)-2,5-dihydro-1H-pyrido[4,3-b]indol-1-one; 8-(4-Methylpyridin-3-yl)-7,8-dihydrothiazolo[4,5-h]isoquinolin-9(6H)-one; 7-(4-Methyl pyridin-3-yl)-6,7-dihydro-1H-pyrazolo[4,3-g]isoquinolin-8(5H)-one; and 2-(4-Cyclopropylpyridin-3-yl)-3,4-dihydrobenzo[4,5]thieno[3,2-c]pyridin-1(2H)-one; or a pharmaceutically acceptable salt thereof.

In another aspect of the present invention, a compound of Formula (II) is provided.

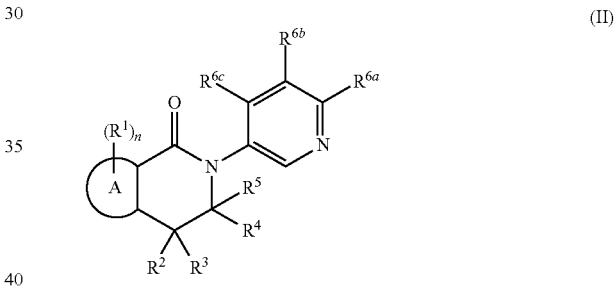

(II)

wherein:
ring A is phenyl, naphthyl, or a 5- to 6-membered heteroaryl containing 1 to 3 heteroatoms each independently selected from N, O or S and optionally fused to a phenyl or a 5- to 6-membered heteroaryl containing 1 to 3 heteroaroms each independently selected from N, O or S;
n is 0, 1, 2, or 3;
R$^1$ is halo, (C$_1$-C$_4$)alkyl, halo-substituted (C$_1$-C$_4$)alkyl, —OH, CN, —NR$^{1a}$R$^{1b}$, —O—R$^{1c}$, or phenyl optionally substituted with 1 to 3 substituents selected from halo, (C$_1$-C$_4$)alkyl, or halo-substituted (C$_1$-C$_4$)alkyl, where R$^{1a}$ is H or (C$_1$-C$_4$)alkyl, R$^{1b}$ is (C$_1$-C$_4$)alkyl, —C(O)—(C$_1$-C$_4$)alkyl, —C(O)—(C$_3$-C$_6$)cycloalkyl, phenyl, or —CH$_2$—(C$_3$-C$_6$)cycloalkyl, and R$^{1c}$ is (C$_1$-C$_4$)alkyl, halo-substituted (C$_1$-C$_4$)alkyl, —CH$_2$—(C$_3$-C$_6$)cycloalkyl, or 5- to 6-membered heteroaryl containing 1 to 3 heteroatoms selected from O, N or S and optionally substituted with 1 to 3 substituents selected from halo, (C$_1$-C$_4$)alkyl, or halo-substituted (C$_1$-C$_4$)alkyl;
R$^2$, R$^3$, R$^4$, and R$^5$ are each independently H or (C$_1$-C$_4$)alkyl, or R$^2$ or R$^3$ taken together with R$^4$ or R$^5$ forms a double bond or a cyclopropyl;
R$^{6a}$ is H;
R$^{6b}$ is H; and
R$^{6c}$ is a deuterium-substituted (C$_1$-C$_4$)alkyl or deuterium-substituted cyclopropyl; or a pharmaceutically acceptable salt thereof.

In a preferred embodiment, a compound of Formula (II) is provided where $R^{6c}$ is $d_3$-methyl; or a pharmaceutically acceptable salt thereof.

Preferably, $R^2$, $R^3$, $R^4$, and $R^5$ are each independently H or methyl. More preferably, $R^2$, $R^3$, $R^4$, and $R^5$ are each H.

In yet another aspect of the present invention a pharmaceutical composition is provided which comprises a compound of Formula (I) (including compounds of Formulae (I-A), (I-B), (I-C), (I-D) and (I-E) described herein below) or Formula (II), or a pharmaceutically acceptable salt thereof, and a pharmaceutically acceptable carrier or excipient. The pharmaceutical composition optionally comprises at least one additional pharmaceutical agent (suitable pharmaceutical agents are described herein below).

In yet another aspect of the present invention, a method of treating a disease, disorder, or syndrome mediated by Cyp17 inhibition is provided, where the method comprises administering to a subject in need of such treatment a Compound of Formula (I) (including compounds of Formulae (I-A), (I-B), (I-C), (I-D) and (I-E)) or Formula (II), or a pharmaceutically acceptable salt thereof, or a pharmaceutical composition comprising the Compound of Formula (I) (including compounds of Formulae (I-A), (I-B), (I-C), (I-D) and (I-E)) or Formula (II), or pharmaceutically acceptable salt thereof, and a pharmaceutically acceptable carrier or excipient.

Alternatively, the method for treating a disease, disorder or syndrome mediated by Cyp17 inhibition may include a combination therapy which comprises the step(s) of administering (i) a first composition comprising a compound of Claim 1 through 12, or a pharmaceutically acceptable salt thereof, and a pharmaceutically acceptable carrier or excipient; and (ii) a second composition comprising at least one additional pharmaceutical agent and a pharmaceutically acceptable carrier or excipient;

wherein said at least one additional pharmaceutical agent is an anticancer agent, chemotherapy agent, or antiproliferative compound.

The first composition and the second composition may be administered simultaneously or sequentially in any order.

Preferably, the disease, disorder, or syndrome is hyperproliferative in a subject, wherein said subject is an animal including humans, and is selected from the group consisting of cancer and inflammation.

Another aspect of the present invention includes a Compound of Formula (I) (including compounds of Formulae (I-A), (I-B), (I-C), (I-D) and (I-E)) or Formula (II) for use in therapy (e.g., the use of a Compound of Formula (I) for the treatment of a disease, disorder, or syndrome mediated by Cyp17 inhibition).

DEFINITIONS

As used herein, the terms "alkyl" refers to a hydrocarbon radical of the general formula $C_nH_{2n+1}$. The alkane radical may be straight or branched. For example, the term "($C_1$-$C_6$) alkyl" refers to a monovalent, straight, or branched aliphatic group containing 1 to 6 carbon atoms (e.g., methyl, ethyl, n-propyl, i-propyl, n-butyl, butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above.

"Halo-substituted alkyl" refers to an alkyl group, as defined above, substituted with at least one halogen atom. For example, when the halogen atom is fluoro, common haloalkyl groups include fluoromethyl, difluoromethyl, trifluoromethyl, 2,2,2-trifluoroethyl, 2,2,2,1,1-pentafluoroethyl, and the like. Mixed halogen substitution are also included (e.g., chlorofluoromethyl).

"Deuterium-substituted alkyl" refers to an alkyl group, as defined above, substituted with at least one deuterium atom ("D"). For example, a deuterium-substituted methyl would be represented by $CH_2D$ (also referred to as "$d_1$-methyl"), —$CHD_2$ (also referred to as "$d_2$-methyl") or —$CD_3$ (also referred to as "$d_3$-methyl")

The term "alkenyl" refers to a monovalent group derived from a hydrocarbon having at least one carbon-carbon double bond. The term "$C_2$-$C_6$-alkenyl" refers to a monovalent group derived from a hydrocarbon having two to six carbon atoms and comprising at least one carbon-carbon double bond. The alkenyl group can be unbranched or branched. Representative examples of alkenyl include vinyl, 1-propenyl, 2-propenyl, 1-methyl-1-propenyl, 1-methyl-2-propenyl, 2-methyl-1-propenyl, 2-methyl-2-propenyl, 1-butenyl, 2-butenyl, 3-butenyl, and so on.

The term "alkynyl" refers to a monovalent group derived from a hydrocarbon having at least one carbon-carbon triple bond. The term "$C_2$-$C_6$-alkynyl" refers to a monovalent group derived from a hydrocarbon having two to six carbon atoms and comprising at least one carbon-carbon triple bond. The alkynyl group can be unbranched or branched. Representative examples include ethynyl, propynyl, butyn-1-yl, butyn-2-yl, and so on.

The term "hydroxy-substituted alkyl" refers to an alkyl group, as defined above, substituted with one or more hydroxyl (—OH) groups (e.g., —$CH_2OH$, —$CH(OH)_2$, —CH(OH)—CH(OH, —CH(OH)—$CH_3$, and so on). Preferably, the alkyl group is substituted with 1 to 2 hydroxyl groups, more preferably one hydroxyl group.

"Halogen" or "halo" may be fluorine, chlorine, bromine or iodine (preferred halogens as substituents are fluorine and chlorine).

The term "oxo" or —C(O)— refers to a carbonyl group. For example, a ketone, aldehyde, or part of an acid, ester, amide, lactone, or lactam group.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring. For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like.

The term "fused phenyl" refers to a phenyl group fused to another ring, such as an another phenyl (i.e., naphthalenyl), or a heteroaryl (e.g., indolyl, benzothiazolyl, benzo[b]thiophenyl, quinolinyl, isoquinolinyl, indazolyl, benzofuranyl, benzimidazolyl, quinoxalinyl, benzooxazolyl, benzo[d]isoxazolyl, 1H-benzoimidazolyl, 1H-benzotriazolyl, etc.). When substituted, the fused phenyl can be substituted on any of the atoms within the fused system. For example, a benzofuranyl group may be substituted on the phenyl or furanyl portion of the benzofuranyl group. The term "heteroaryl" or "heteroaromatic ring" refers to aromatic moieties containing at least one heteratom (e.g., oxygen, sulfur, nitrogen or combinations thereof) within a 5- to 6-membered aromatic ring system (e.g., pyrrolyl, pyridyl, pyrazolyl, thienyl, furanyl, oxazolyl, imidazolyl, tetrazolyl, triazinyl, pyrimidyl, pyrazinyl, thiazolyl, isothiazolyl, etc.). A typical single heteroaryl ring is generally a 5- to 6-membered ring containing one to three heteroatoms each independently selected from oxygen, sulfur and nitrogen.

The term "fused heteroaryl" refers to a heteroaryl group fused to another ring, such as another heteroaryl (e.g. purinyl, thieno[3,2-c]pyridinyl, imidazo[1,2-a]pyridinyl, benzo[b]thiophenyl, quinolinyl, benzooxazolyl, benzothiazolyl, indolyl, isoquinolinyl, benzofuranyl, indazolyl, benzimidazolyl, etc.). When substituted, the fused heteroaryl can be substituted on any of the atoms within the fused system. For example, an imidazo[1,2-a]pyridinyl group may be substituted on the imidazole or pyridine portion of the fused system.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The term "animal" refers to humans (male or female), companion animals (e.g., dogs, cats and horses), zoo animals, marine animals, birds and other similar animal species. A preferred animal is human.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The term "compounds of the present invention" (unless specifically identified otherwise) refer to compounds of Formula (I), (I-A), (I-B), (I-C), (I-D) (I-E) and (II), and pharmaceutically acceptable salts of the compounds, as well as, all stereoisomers (including diastereoisomers and enantiomers), tautomers and isotopically labeled compounds.

DETAILED DESCRIPTION

The present invention provides compounds and pharmaceutical formulations thereof that are useful in the treatment of diseases, conditions and/or disorders modulated by the inhibition of 17α-hydroxylase/$C_{17-20}$-lyase.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

The schemes detailed below show general schemes for synthesizing compounds of the present invention (e.g., compounds of Formula (I-A), (I-B), (I-C), (I-D) and (I-E) or (II)).

General Schemes

Scheme I below provides a synthetic route for making compounds of the present invention, especially where $R^2$ and $R^4$ are other than hydrogen.

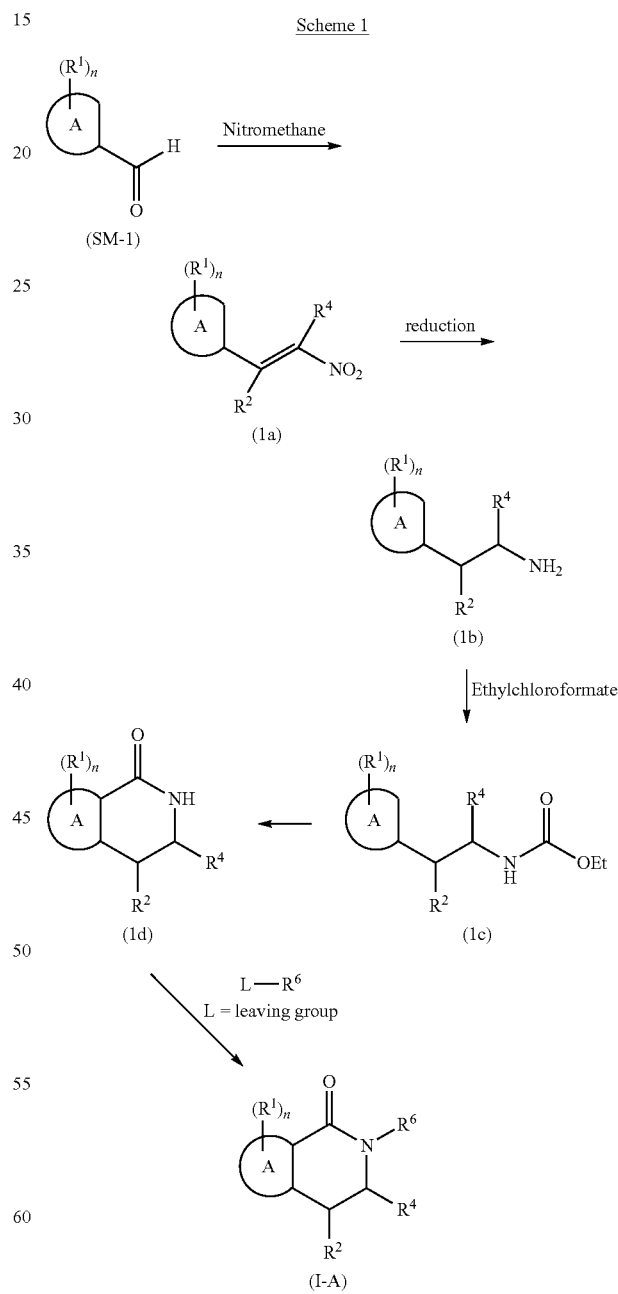

The nitro-vinyl intermediate (1a) can be made by condensing the desired aldehyde (SM-1) with nitromethane in a polar solvent (e.g., ethanol) at about 0° C. followed by the addition of a strong base (e.g., NaOH). After warming to about room temperature and quenching with acid (e.g., aqueous HCl), intermediate (1a) can be isolated. Intermediate (1a) can then be reduced to the corresponding alkylamine derivative (1b) by treatment with a reducing agent, such as lithium aluminum hydride (LAH) or lithium borohydride (LiBH$_4$) under an inert and dry atmosphere. Ethyl chloroformate is then added to the alkylamine intermediate (1b) in the presence of a base (e.g., sodium carbonate) to produce the carbamate acid ethyl ester intermediate (1c). Intermediate (1c) can then be cyclized to the lactam intermediate (1d) by treatment with phosphorus pentoxide and phosphorus oxychloride at refluxing temperatures. When $R^1$ is a halo group in the lactam intermediate (1d), further derivatives can be made via a Suzuki coupling of a desired borane ($R^1$—B(OH)$_2$) with the lactam intermediate (1d) prior to the addition of the $R^6$ group. See, e.g., Examples 3 and 14 in the Example section below. The desired $R^6$ group may then be added to the lactam intermediate (1d) by coupling intermediate (1d) with the desired ($R^6$-L), where L is a leaving group, such as bromo or iodo, to produce a compound of the present invention (I-A), where $R^3$ and $R^5$ are both hydrogen. For example, lactam intermediate (1d) is reacted with the desired $R^6$-L in the presence of copper iodide, 1,4-dixoane, trans-N,N'-dimethylcyclohexyl-1,2-diamine, and potassium phosphate.

Scheme II below provides an alternative synthetic route for making compounds of the present invention, especially where $R^2$ and $R^3$ are other than hydrogen.

Scheme II

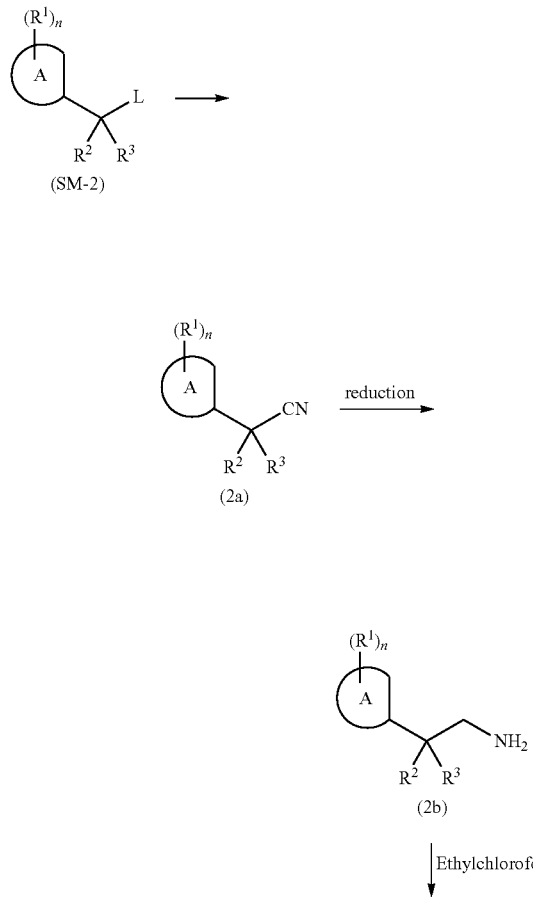

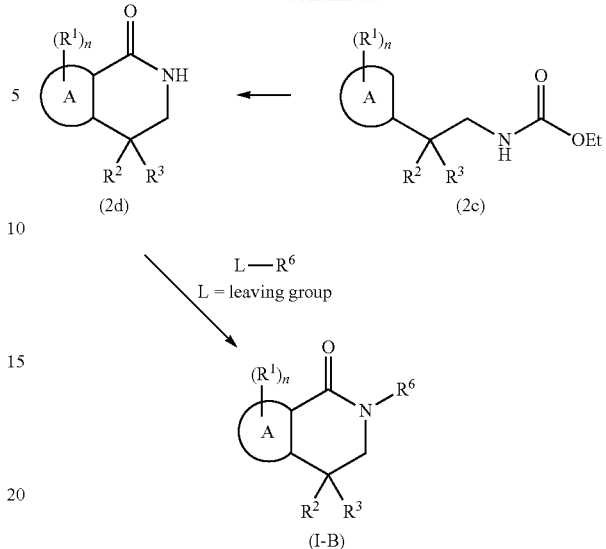

Cyano intermediate (2a) can be prepared by reacting starting material (SM-2), where L is a leaving group, with sodium cyanide. The cyano group can then be reduced to the amine using methods well-known to those of skill in the art, e.g., reacting cyano intermediate (2a) under pressure in a parr hydrogenator in the presence of Raney nickel and methanolic ammonia. The compound of the present invention (1-B) can then be prepared from intermediate (2b) using procedures analogous to those described in Scheme I above for Intermediates (1c) and (1d) and Compound (I-A).

Scheme III below provides yet an alternative synthetic route for making compounds of the present invention.

Scheme III

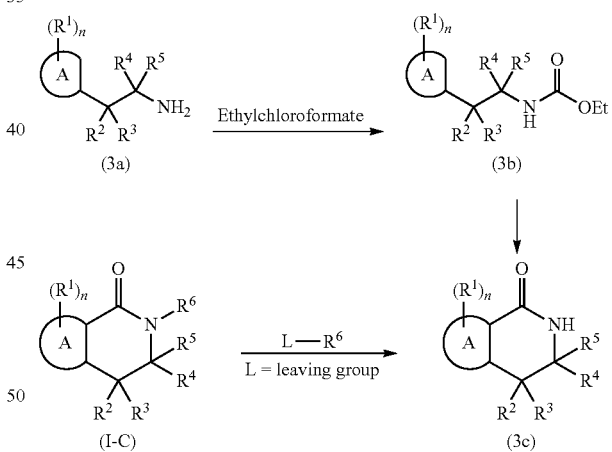

Carbamate acid ethyl ester intermediate (3b) can be synthesized by condensing ethylchloroformate with the desired alkyl amino intermediate (3a) in the presence of a base (e.g., sodium carbonate). Cyclization to form lactam intermediate (3c) can be accomplished in the presence of polyphorphoric acid at elevated temperatures (e.g., about 120° C.). Alternatively, the cyclization may be accomplished using the procedures described in Scheme I above (e.g., treatment with phosphorus pentoxide and phosphorus oxychloride at refluxing temperatures). The desired $R^6$ may then be attached using procedures analogous to those described in above in Schemes I and II (e.g., Suzuki coupling) to produce a compound of the present invention (I-C).

Scheme IV below illustrates how to prepare compounds of the present invention where $R^2$ or $R^3$ is taken together with $R^4$ or $R^5$ to form a double bond.

Scheme IV

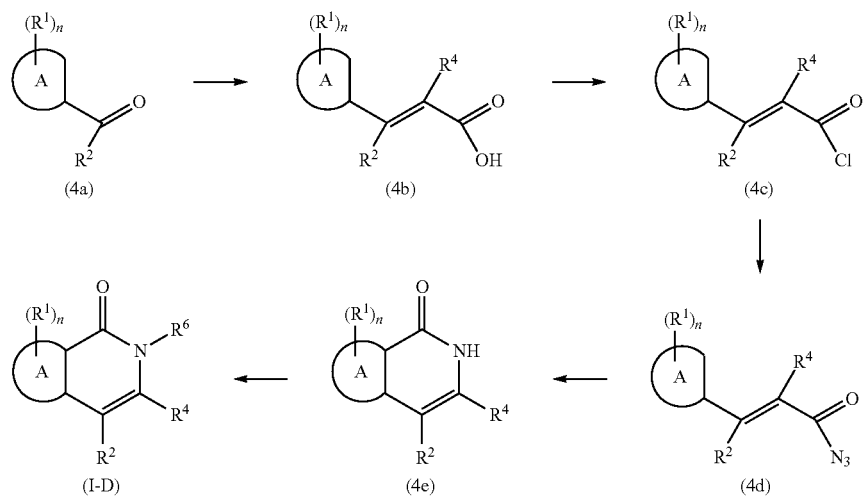

The acrylic acid intermediate (4b) is accessible by condensing a carboxaldehyde with malonic acid in the presence of a base (e.g. piperidine) in a suitable solvent (e.g. pyridine) at room temperature. The temperature of the reaction can be raised to complete the reaction. The resulting acid is then converted to its acid chloride (4c) with thionyl chloride in an organic solvent (e.g. toluene or dichloromethane) at room temperature up to the refluxing temperature of the reaction solvent. The unsaturated acid chloride (4c) is then stirred in dioxane under an inert atmosphere at 0° C. and treated with an aqueous solution of sodium azide to give (4d). The acylazide (4d) is dissolved in dichloromethane and this solution is added to diphenyl ether. This mixture is then heated to the reflux temperature of the solvent to effect Curtius rearrangement and yielding the cyclization product (4e). The amide nitrogen may then be substituted with the requisite $R^6$ using procedures analogous to those described above for Schemes I and II to produce a compound of the present invention (I-D).

Scheme V below illustrates an alternative procedure for the preparation of compounds of the present invention where A is a phenyl. Although the scheme illustrates the preparation of compounds where A is a phenyl, one of skill in the art would know how to modify the procedure to include compounds where A is a fused phenyl.

Scheme V

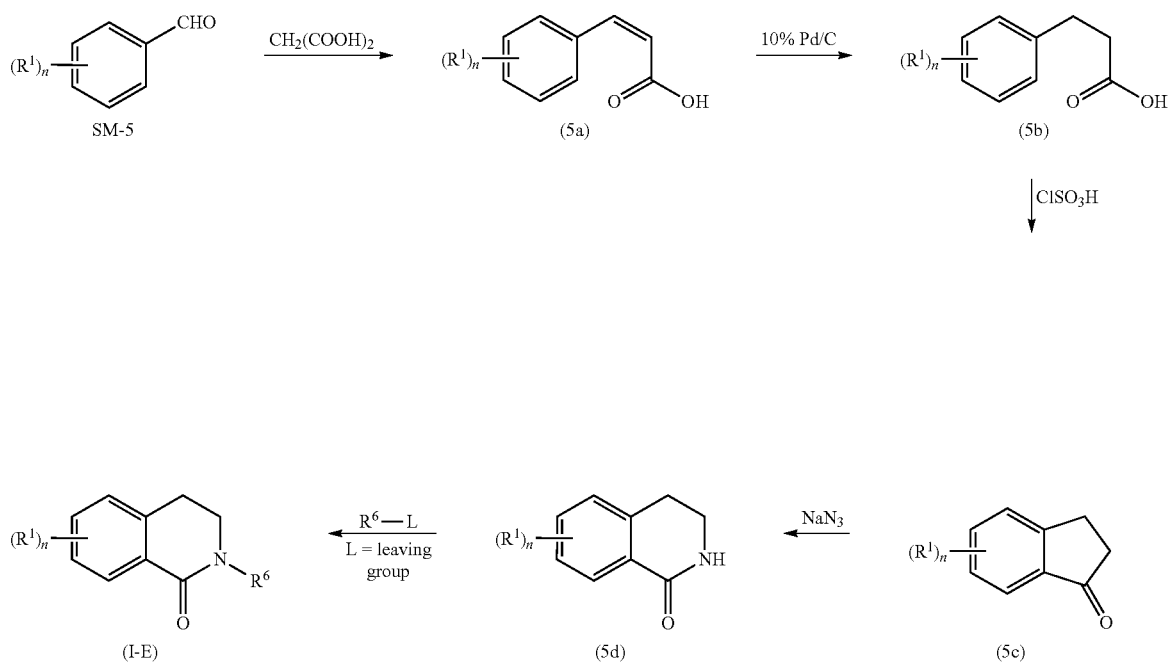

The acrylic acid intermediate (5a) can be prepared from a desired aldehyde (SM-5) and malonic acid using a standard aldo condensation reaction in pyridine (optionally, in the presence of piperidine) at elevated temperatures. Although intermediate 5a is depicted above in the cis configuration, it is mostly likely trans or a cis/trans mixture. The acrylic acid unsaturation can then be reduced to the hydrocarbon chain using standard hydrogenation processes well-know to those of skill in the art (e.g., $H_2$ atmosphere in the presence of Pd/C). Cyclization to the cycloketo intermediate (5c) can be accomplished by treating intermediate (5b) with chlorosulfonic acid. The 2,3-dihydro-1H-inden-1-one intermediate (5c) can then be treated with sodium azide in the presence of an acid (e.g., trifluoroacetic acid (TFA)) to produce 3,4-dihydroisoquinolin-1(2H)-one intermediate (5d). The amide nitrogen may then be substituted with the desired $R^6$ using procedures analogous to those described above for Schemes I and II to produce a compound of the present invention (I-E). For a more detailed description of the conditions and alternative starting materials, see Examples 85-90 below.

For compounds where A is an indole, procedures such as those described below for the preparation of Examples 59 and 60 below may also be used with the appropriate starting materials to produce the desired 2,3,4,5-tetrahydro-1H-pyrido[4,3-b]indol-1-one derivatives or Examples 62, 63 and 64 to produce the desired 2,5-dihydro-1H-pyrido[4,3-b]indol-1-one derivatives. Those skilled in the art will know how to make the appropriate modifications to acquire the desired derivative.

For compounds where A is a pyridine, procedures such as those described below for the preparation of Example 65 may also be used with the appropriate starting materials to produce a desired 3,4-dihydro-2,7-naphthyridin-1(2H)-one derivative or Example 67 may be used with the appropriate starting materials to produce a desired 3,4-dihydro-2,6-naphthyridin-1(2H)-one derivative. Those skilled in the art will know how to make the appropriate modifications to produce the desired derivative.

Alternative methods for making a variety of derivatives are exemplified in the Examples below. Those skilled in the art will know how to make the appropriate modifications to produce the desired compound.

The deuterium-substituted compounds (compounds of Formula II) may be prepared using the Schemes described above using a deuterium-substituted starting material. For example, 4-trideuteromethyl-3-bromopyridine can be prepared from 3-bromopyridine and iodomethane-$d_3$ according to the procedure described in *Tetrahedron* (1982), 38(20, 3035-3042 (see compound II therein below). Alternatively, 4-trideuteromethyl-3-bromopyridine can be prepared from 3-bromo-4-ethynylpyridine using procedures well-known to those skilled in the art.

The compounds and intermediates described herein may be isolated and used as the compound per se or its corresponding salt. Many of the compounds of the present invention are capable of forming acid addition salts, particularly pharmaceutically acceptable acid addition salts. Pharmaceutically acceptable acid addition salts of the compound of Formula (I) or (II) include those of inorganic acids, for example, hydrohalic acids such as hydrochloric acid, hydrobromic acid or hydroiodic acid, nitric acid, sulfuric acid, phosphoric acid; and organic acids, for example aliphatic monocarboxylic acids such as formic acid, acetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of Formula (I) or (II) by known salt-forming procedures.

Compounds of the present invention which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of Formula (I) or (II) by known salt-forming procedures.

In those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof.

The present invention includes all pharmaceutically acceptable isotopically-labeled compounds of the present invention wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

When a particular position is designated as having deuterium, it is understood that the abundance of deuterium at that position is greater than the natural abundance of deuterium (typically 0.015%). Unless otherwise stated, when a position is designated specifically as "D" or "deuterium", the position is understood to have deuterium at an abundance that is greater than the natural abundance of deuterium.

The term "isotopic enrichment factor" as used herein means the ratio between the isotopic abundance and the natural abundance of that isotope (or percentage of deuterium incorporation).

For a compound of the present invention having a deuterated substitution, the isotopic enrichment factor for each deuterium present at a site designated as a potential site of deuteration on the compound is generally about 98% deuterium incorporation, preferably, >98.5% deuterium incorporation.

Isotopically-labeled compounds of the present invention can generally be prepared by conventional techniques known to those skilled in the art or by processes analogous to those described in the accompanying Examples and Preparations Sections using an appropriate isotopically-labeled reagent in place of the non-labeled reagent previously employed.

The compounds of the present invention may exist in unsolvated as well as solvated forms with pharmaceutically acceptable solvents such as water, ethanol, and the like, and it is intended that the invention embrace both solvated and unsolvated forms. For purposes of the present invention, solvates (including hydrates) are considered pharmaceutical compositions, e.g., a Compound of the present invention in combination with an excipient, wherein the excipient is a solvent.

Compounds of the present invention are useful for treating diseases, conditions and disorders mediated by the regulation of 17α-hydroxylase/$C_{17,20}$-lyase; consequently, the compounds of the present invention (including the compositions and processes used therein) may be used in the manufacture of a medicament for the therapeutic applications described herein. Hence, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

A Cyp17 inhibitor of the present invention may be usefully combined with at least one additional pharmacologically active compound, particularly in the treatment of cancer. For example, a compound of the present invention, as defined above, may be administered simultaneously, sequentially or separately in combination with one or more agents selected from chemotherapy agents, e.g. mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine. Such combinations may offer significant advantages, including synergistic activity, in therapy.

A compound of the present invention may also be used in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylamino-gelda-namycin, NSC330507), 17-DMAG (17-dimethylaminoethylamino-17-demethoxy-geldana-mycin, NSC707545), IPI-504, CNF1010, CNF2024, CNF1010 from Conforma Therapeutics; temozolomide (TEMODAL); kinesin spindle protein inhibitors, such as SB715992 or SB743921 from GlaxoSmithKline, or pentamidine/chlorpromazine from CombinatoRx; PI3K inhibitors; RAF inhibitors; EDG binders, antileukemia compounds, ribonucleotide reductase inhibitors, S-adenosylmethionine decarboxylase inhibitors, antiproliferative anti-bodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atame-stane, exemestane and formestane and, in part-icular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. un-der the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Amino glutethimide can be administered, e.g., in the form as it is marketed, e.g. under the trademark, ORIMETEN. A combination of the invention comprising a chemo-therapeutic agent which is an aromatase inhibitor is particularly useful for the treatment of hormone receptor positive tumors, e.g., breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of in-hibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g., under the trademark HOLOXAN.

The term "antineoplastic antimetabolite" includes, but is not limited to, 5-Fluorouracil or 5-FU, capecitabine, gemcitabine, DNA demethylating compounds, such as 5-azacy-tidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR. The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib; h) compounds targeting, decreasing or inhibiting the activity of members of the c-Abl family, their gene-fusion products (e.g. BCR-Abl kinase) and mutants, such as corn-pounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD 173955 from ParkeDavis; or dasatinib (BMS-354825); i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor); j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (mw<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin), cetuximab (Erbitux), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and 1) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g., inhibitors of phosphatase 1, phosphatase 2A, or CDC25, e.g. okadaic acid or a derivative thereof.

Compounds which induce cell differentiation processes are e.g. retinoic acid, or tocopherol or tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune), everolimus (CerticanO), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. An example HSP90 inhibitor is AUY922.

The term "antiproliferative antibodies" as used herein includes, but is not limited to, trastuzumab (Herceptin), Trastuzumab-DM1, erbitux, bevacizumab (Avastin), rituximab (Rituxan), PRO64553 (anti-CD40) and 2C4 Antibody. By antibodies is meant e.g. intact monoclonal antibodies, polyclonal antibodies, multispe-cific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2-alpha-hydroxy ribose (arabinoside) derivative of deoxycytidine. Also included is the purine analog of hypoxanthine, 6-mercaptopurine (6-MP) and fludarabine phosphate.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res, Vol.* 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-epihydrocotisol, cortexolone, 17-hydroxyprogesterone, corticosterone, desoxycorticosterone, testosterone, estrone and dexamethasone. Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

EXAMPLES

The following abbreviations used in the examples below have the corresponding meanings:
DABCO 1,4-Diazabicyclo[2.2.2]octane
DCM Dichloromethane
DEAD Diethyl azodicarboxylate
DIBAL-H Diisobutyl aluminium hydride
BINAP 2,2'-bis(diphenylphosphino)-1,1'-binaphthyl
DIPEA Diisopropyl ethyl amine
DMAP 4-Dimethylaminopyridine
DMF Dimethylformamide
DMSO Dimethylsulfoxide
Dppf 1,1'-Bis(diphenylphosphino)ferrocene
EDCI 1-(3-Dimethylaminopropyl)-3-ethylcarbodiimide
KHMDS Potassium hexamethyldisilazane LAH Lithium Aluminum Hydride
Pd$_2$(dba)$_3$ Tris(dibenzylideneacetone)dipalladium (0)
PTSA p-Toluene sulfonic acid
TBAF Tetrabutyl ammonium fluoride
TEA Triethylamine
THF Tetrahydrofuran
TLC Thin Layer Chromatography
X-Phos 2-Dicyclohexylphosphino-2',4',6'-triisopropylbiphenyl Example 1

Preparation of 7-Chloro-2-pyridin-3-yl-3,4-dihydro-2H-isoquinolin-1-one (IA)

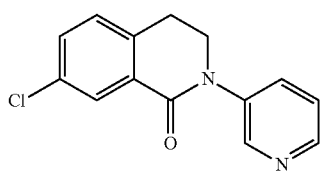

(IA)

Step 1: Preparation of Intermediate 1-Chloro-4-(2-nitro-vinyl)-benzene (I-1a)

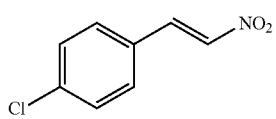

(I-1a)

Nitro methane (1.156 mL, 0.02135 mmol) was added to a stirred solution of 4-chloro-benzaldehyde (3 g, 0.02135 mmol) in ethanol (100 mL) at 0° C., followed by dropwise addition of 10N NaOH solution (896 mg, 0.0224 mmol) over a period of 10 minutes. The resulting mixture was stirred at room temperature for 1 hour. The reaction was monitored by TLC (20% ethylacetate in hexane). The reaction mixture was quenched with HCl (50 mL) and water (50 mL) followed by stirring for an additional 1 hour at room temperature. The solid formed was collected and dried under reduced pressure to afford 3.4 g of the product (87% yield).
$^1$H NMR (CDCl$_3$, 300 MHz): δ 8.16-7.84 (m, 1H), 7.71-7.34 (m, 5H)

Step 2: Preparation of Intermediate 2-(4-Chloro-phenyl)-ethylamine (I-1b)

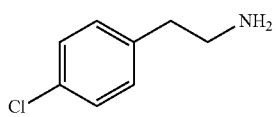

(I-1b)

1-Chloro-4-(2-nitro-vinyl)-benzene (I-1a: 3.4 g, 0.0185 mmol) dissolved in dry THF (50 mL) was added dropwise to a stirred suspension of LAH (1.3 g, 0.03707 mmol) in dry THF (50 mL) over a period of 20 minutes at 0° C. under nitrogen atmosphere. The resulting mixture was stirred at 45° C. for 3 hours. The reaction was monitored by TLC (10% ethylacetate in hexane). The reaction mixture was cooled to room temperature, quenched with 10% NaOH solution (3 mL), and filtered through Celite® bed. The filtrate was washed with ethylacetate and concentrated under reduced pressure to afford 2.6 g of the crude product which was used in the next step without further purification.
$^1$H NMR (CDCl$_3$, 300 MHz): δ 7.49-7.00 (m, 6H), 2.9 (t, 2H), 2.6 (t, 2H)

Step 3: Preparation of Intermediate [2-(4-Chloro-phenyl)-ethyl]-carbamic acid ethyl ester (I-1c)

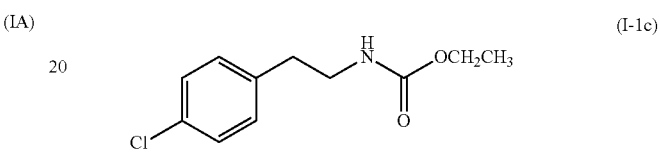

(I-1c)

Chloro ethyl formate (1.92 mL) and 2N Na$_2$CO$_3$ solution (20 mL) were added to a stirred solution of 2-(4-chloro-phenyl)-ethylamine (I-1b: 2.6 g, 0.01667 mmol) in chloroform (20 mL). The resulting mixture was stirred at room temperature for 3 hours. The reaction was monitored by TLC (20% ethylacetate in hexane). The reaction mixture was partitioned between water and chloroform. The organic layer was washed with water, brine solution, dried over Na$_2$SO$_4$ and concentrated under reduced pressure. Purification by column chromatography on silica gel (10% ethylacetate in hexane) afforded 2 g of the product (52.6% yield).
$^1$H NMR (CDCl$_3$, 300 MHz): δ 7.6-6.8 (m, 4H), 4.9-4.4 (br s, 1H), 4.35-3.76 (m, 2H), 3.64-3.15 (m, 2H), 3.1-2.6 (m, 2H), 1.5-0.9 (m, 3H)

Step 4: Preparation of Intermediate 7-Chloro-3,4-dihydro-2H-isoquinolin-1-one (I-1d)

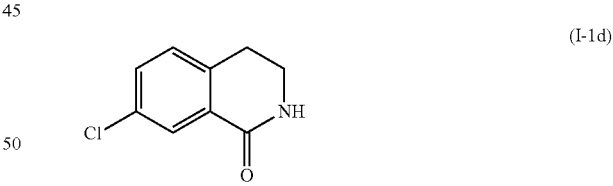

(I-1d)

P$_2$O$_5$ (3.1 g, 0.0495 mmol) was added to a stirred solution of [2-(4-chloro-phenyl)-ethyl]-carbamic acid ethyl ester (2.5 g, 0.01097 mmol) in POCl$_3$ (10 mL) The resulting mixture was heated to reflux for 3 hours. The reaction was monitored by TLC (10% methanol in DCM). The reaction mixture was cooled to room temperature and concentrated under reduced pressure. The concentrate was quenched with chilled water, basified with NaHCO$_3$ solution and extracted with ethylacetate. The organic layer was washed with water, brine solution, dried over Na$_2$SO$_4$ and concentrated under reduced pressure. Purification by column chromatography on silica gel (10% methanol in CHCl$_3$) afforded 500 mg of the product (26.3% yield).
LCMS: m/z=181.9 (M+1)

Preparation of 7-Chloro-2-pyridin-3-yl-3,4-dihydro-2H-isoquinolin-1-one (1A)

Copper iodide (15.6 mg, 0.0824 mmol), trans-N,N'-dimethyl-cyclohexyl-1,2-diamine (28.3 mg, 0.2472 mmol) and potassium phosphate (437.3 mg, 2.0604 mmol) were added to 1,4-dioxane (20 mL) degassed with argon for 30 minutes. The reaction mixture was purged with argon for a further 20 minutes followed by the addition of 7-chloro-3,4-dihydro-2H-isoquinolin-1-one (I-1d: 150 mg, 0.82417 mmol) and 3-bromo-pyridine (88.9 mL, 0.9065 mmol). The reaction mixture was heated to reflux at 110° C. for 12 hours. The reaction was monitored by TLC (10% methanol in $CHCl_3$). The reaction mixture was filtered and the filtrate was concentrated. Purification by column chromatography on silica gel (10% methanol in $CHCl_3$) afforded 90 mg of the product (42.2% yield).

$^1$H NMR (DMSO-$D_6$, 300 MHz): δ 8.90-8.24 (d, 2H), 8.1-7.0 (m, 5H), 4.20-3.84 (m, 2H), 3.3-3.2 (m, 2H)

LCMS purity: 90.81%, m/z=259.0 (M+1)

HPLC: 94.25%

Example 2

Preparation of 7-Chloro-2-(4-methyl-pyridin-3-yl)-3,4-dihydro-2H-isoquinolin-1-one (2A)

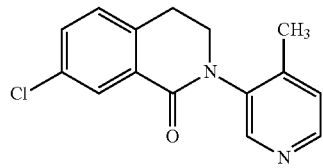

(2A)

Using analogous reaction conditions as described in Example 1, 7-chloro-3,4-dihydro-2H-isoquinolin-1-one (I-1d: 150 mg, 0.824 mmol) was reacted with 3-iodo-4-methyl-pyridine (216 mg, 0.989 mmol), 1,4-dioxane (10 mL), copper iodide (15.69 mg, 0.0824 mmol), trans-N,N'-dimethyl-cyclohexyl-1,2-diamine (35.10 mg, 0.2472 mmol) and potassium phosphate (524 mg, 2.472 mmol) to afford the crude product. Purification by column chromatography on silica gel (1% methanol in $CHCl_3$) afforded 70 mg of the product (31.25% yield).

$^1$H NMR (DMSO-$D_6$, 300 MHz): δ 8.54-8.24 (m, 2H), 8.06-7.76 (br s, 1H), 7.74-7.20 (m, 3H), 4.15-3.65 (m, 2H), 3.30-3.02 (m, 2H), 2.2 (s, 3H)

LCMS purity: 99.36%, m/z=273.0 (M+1)

HPLC: 95.59%

Example 3

Preparation of 7-(4-Fluoro-phenyl)-2-(4-methyl-pyridin-3-yl)-3,4-dihydro-2H-isoquinolin-1-one (3A)

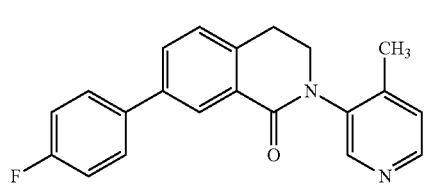

(3A)

Step 1: Preparation of Intermediate 1-Bromo-4-(2-nitro-vinyl)-benzene (I-3a)

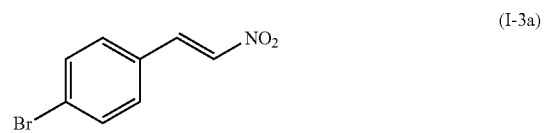 [SMILES: O=[N+]([O-])/C=C/c1ccc(Cl)cc1]

(I-3a)

Using analogous reaction conditions and workup as described in Example 1, step 1,4-bromo-benzaldehyde (10 g, 0.05404 mmol) in ethanol (250 mL) was reacted with nitro methane (2.92 mL, 0.5404 mmol) and 10N NaOH (2.26 g, 0.05674 mmol) to afford 10.7 g of the product (84.2% yield).

$^1$H NMR ($CDCl_3$, 300 MHz): δ 8.06-7.88 (m, 1H), 7.70-7.52 (m, 3H), 7.51-7.32 (m, 2H)

Step 2: Preparation of Intermediate 2-(4-Bromo-phenyl)-ethylamine (I-3b)

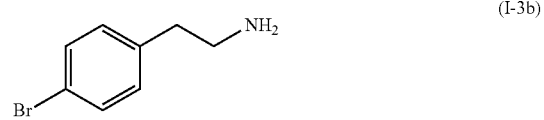

(I-3b)

Using analogous reaction conditions and workup as described in Example 1, step 2,1-bromo-4-(2-nitro-vinyl)-benzene (I-3a: 10.5 g, 0.046055 mmol) in dry THF (100 mL) was reacted with LAH (3.4 g, 0.09210 mmol) in dry THF (100 mL) to afford 7.5 g of the crude product which was used in the next step without further purification.

$^1$H NMR ($CDCl_3$, 300 MHz): δ 7.79-6.90 (m, 4H), 3.15-2.58 (m, 4H).

LCMS purity: 82.92%, m/z=199.9 (M+1)

Step 3: Preparation of Intermediate [2-(4-Bromo-phenyl)-ethyl]-carbamic acid ethyl ester (I-3c)

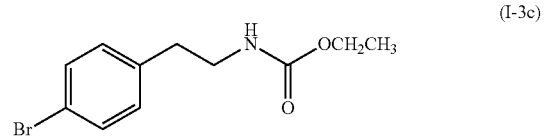 [SMILES: CCOC(=O)NCCc1ccc(Br)cc1]

(I-3c)

Using analogous reaction conditions and workup as described in Example 1, step 3,2-(4-bromo-phenyl)-ethylamine (I-3b: 7.5 g, 0.0372 mmol) in chloroform (60 mL) was reacted with chloro ethyl formate (4.3 mL, 0.0451 mmol) and 2N $Na_2CO_3$ solution (60 mL) to afford the crude product. Purification by column chromatography on silica gel (10% ethylacetate in hexane) afforded 5.1 g of the product (50% yield).

$^1$H NMR ($CDCl_3$, 300 MHz): δ 7.62-6.84 (m, 4H), 4.80-4.43 (br s, 1H), 4.40-3.78 (m, 2H), 3.55-3.18 (m, 2H), 2.7 (t, 2H), 1.2 (t, 3H)

Step 4: Preparation of Intermediate 7-Bromo-3,4-dihydro-2H-isoquinolin-1-one (I-3d)

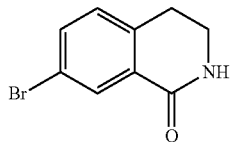

(I-3d)

Using analogous reaction conditions and workup as described in Example 1, step 4, [2-(4-bromo-phenyl)-ethyl]-carbamic acid ethyl ester (I-3c: 5 g, 0.01838 mmol) in POCl$_3$ (20 mL) was reacted with P$_2$O$_5$ (5.2 g, 0.03676 mmol) to afford the crude product. Purification by column chromatography on silica gel (50% ethylacetate in hexane) afforded 500 mg of the product (12% yield).

LCMS: m/z=228.1 (M+2)

Step 5: Preparation of Intermediate 7-(4-Fluoro-phenyl)-3,4-dihydro-2H-isoquinolin-1-one (I-3e)

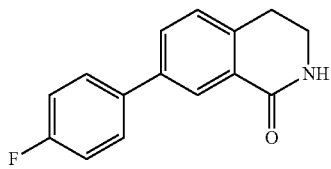

(I-3e)

1M Na$_2$CO$_3$ (211.8 mg, 2.0175 mmol) was added to a mixture of ethanol (10 mL) and toluene (10 mL) previously degassed with argon for 30 minutes. The reaction mixture was degassed with argon for a further 20 minutes. This was followed by the addition of 7-bromo-3,4-dihydro-2H-isoquinolin-1-one (I-3e: 200 mg, 0.877191=4 (4-fluoro-phenyl)-dihydroxy-borane (245 mg, 1.7543 mmol) and Pd(PPh$_3$)$_4$ (20.2 mg, 0.01754 mmol). The resulting mixture was stirred at 110° C. for 5 hours. The reaction was monitored by TLC (50% ethylacetate in hexane). The reaction mixture was cooled to room temperature, filtered and the filtrate was concentrated under reduced pressure. Purification by column chromatography on silica gel (40% ethylacetate in hexane) afforded 200 mg of the product (94.7% yield).

LCMS: m/z=242.0 (M+1)

Preparation of 7-(4-Fluoro-phenyl)-2-(4-methyl-pyridin-3-yl)-3,4-dihydro-2H-isoquinolin-1-one (3A)

Using analogous reaction conditions as described in example 1, 7-(4-fluoro-phenyl)-3,4-dihydro-2H-isoquinolin-1-one (100 mg, 0.4132 mmol) was reacted with 3-iodo-4-methyl-pyridine (108.5 mg, 0.4958 mmol), 1,4-dioxane (25 mL), copper iodide (2.8 mg, 0.01432 mmol), trans-N,N'-dimethyl-cyclohexyl-1,2-diamine (14.2 mg, 0.1239 mmol) and potassium phosphate (219.2 mg, 1.0330 mmol) to afford the crude product. Purification by column chromatography on silica gel (2% methanol in CHCl$_3$), followed by preparative HPLC afforded 15 mg of the product (11.1% yield).

$^1$H NMR (CDCl$_3$, 300 MHz): δ 8.72-8.17 (m, 3H), 7.86-6.96 (m, 7H), 4.25-3.98 (m, 1H), 3.95-3.60 (m, 1H), 3.45-3.02 (m, 2H), 2.32 (s, 3H)

LCMS purity: 98.34%, m/z=333.1 (M+1)
HPLC: 98.89%

Example 4

Preparation of 2-(4-Methyl-pyridin-3-yl)-7-trifluoromethyl-3,4-dihydro-2H-isoquinolin-1-one (4A)

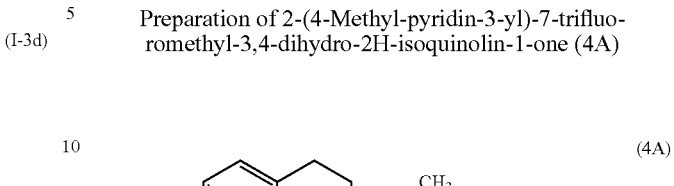

(4A)

Step 1: Preparation of Intermediate 1-(2-Nitro-vinyl)-4-trifluoromethyl-benzene (I-4a)

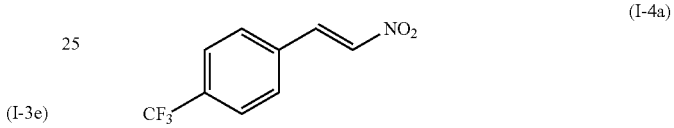

(I-4a)

Using analogous reaction conditions and workup as described in Example 1, step 1,4-trifluoromethyl-benzaldehyde (3 g, 17.24 mmol) in ethanol (50 mL) was reacted with nitro methane (1.052 g, 17.24 mmol) and 10N NaOH (724 mg, 18.10 mmol) to afford 2.5 g of the product (67.56% yield).

$^1$H NMR (DMSO-D$_6$, 300 MHz): δ 8.45-8.30 (m, 1H), 8.28-8.15 (m, 1H), 8.08 (d, 2H), 7.85 (d, 2H)

Step 2: Preparation of Intermediate 2-(4-Trifluoromethyl-phenyl)-ethylamine (I-4-b)

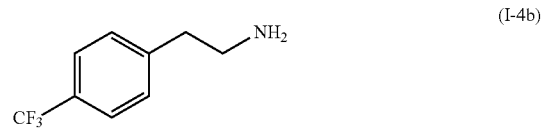 [SMILES: NCCc1ccc(C(F)(F)F)cc1]

(I-4b)

Using analogous reaction conditions and workup as described in Example 1, step 2, 1-(2-nitro-vinyl)-4-trifluoromethyl-benzene (I-4a: 2.5 g, 11.52 mmol) was reacted with LAH (856 mg, 23.04 mmol) in dry THF (50 mL) to afford 2.1 g of the product (96.77%).

LCMS: m/z=189.9 (M+1)

Step 3: Preparation of Intermediate [2-(4-Trifluoromethyl-phenyl)-ethyl]-carbamic acid ethyl ester (I-4-c)

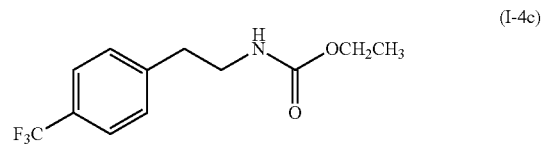 [SMILES: CCOC(=O)NCCc1ccc(C(F)(F)F)cc1]

(I-4c)

Using an analogous procedure and workup as described in Example 1, step 3, 2-(4-trifluoromethyl-phenyl)-ethylamine (I-4-b: 1.5 g, 7.94 mmol) in chloroform (10 mL) was reacted with chloro ethyl formate (1.097 g, 9.5 mmol) and 2N Na$_2$CO$_3$ solution (5 mL) at 0° C. The resulting mixture was stirred at room temperature for 1 hour to afford the crude product. Purification by column chromatography on silica gel (10% ethylacetate in hexane) afforded 700 mg of the product (33.78% yield).

$^1$H NMR (DMSO-D$_6$, 300 MHz): δ 7.78-7.56 (m, 2H), 7.56-7.34 (m, 2H), 7.2-7.0 (m, 1H), 4.10-3.72 (m, 2H), 3.3-3.1 (m, 2H), 2.78 (t, 2H), 1.1 (t, 3H)

Step 4: Preparation of Intermediate 7-Trifluoromethyl-3,4-dihydro-2H-isoquinolin-1-one (I-4-d)

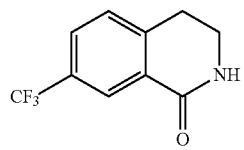

(I-4d)

Using an analogous procedure and workup as described in Example 1, step 4, [2-(4-trifluoromethyl-phenyl)-ethyl]-carbamic acid ethyl ester (I-4-c: 700 mg, 2.68 mmol) in POCl$_3$ (5 mL) was reacted with P$_2$O$_5$ (756 mg, 5.36 mmol). The resulting mixture was stirred at 105° C. for 2 hours to afford the crude product. Purification by column chromatography on silica gel (10% ethylacetate in hexane) afforded 120 mg of the product (20.83% yield).

LCMS: m/z=216.2 (M+1)

Preparation of 2-(4-Methyl-pyridin-3-yl)-7-trifluoromethyl-3,4-dihydro-2H-isoquinolin-1-one (4A)

Using analogous reaction conditions as described in Example 1, 7-trifluoromethyl-3,4-dihydro-2H-isoquinolin-1-one (I-4-d: 120 mg, 0.558 mmol) was reacted with 3-iodo-4-methyl-pyridine (134 mg, 0.613 mmol), 1,4-dioxane (5 mL), copper iodide (10.6 mg, 0.0558 mmol), trans-N,N'-dimethyl-cyclohexyl-1,2-diamine (23.7 mg, 0.167 mmol) and potassium phosphate (354 mg, 1.674 mmol) to afford the crude product. Purification by column chromatography on silica gel (2% methanol in CHCl$_3$), followed by preparative HPLC afforded 20 mg of the product (11.71% yield).

$^1$H NMR (CDCl$_3$, 300 MHz): δ 8.64-8.26 (m, 3H), 7.74 (d, 1H), 7.54-7.36 (m, 2H), 4.19-3.93 (m, 1H), 3.92-3.70 (m, 1H), 3.4-3.1 (m, 2H), 2.3 (s, 3H)

LCMS purity: 98.68%, m/z=307.0 (M+1)
HPLC: 98.02%

Example 5

Preparation of 6-(4-Methyl-pyridin-3-yl)-5,6-dihydro-4H-thieno[2,3-c]pyridin-7-one (5A)

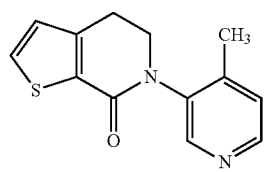

(5A)

Step 1: Preparation of Intermediate 3-(2-Nitro-vinyl)-thiophene (I-5a)

(I-5a)

Using an analogous reaction procedure and workup as described in Example 1, step 1, thiophene-3-carbaldehyde (3 g, 26.78 mmol) in ethanol (50 mL) was reacted with nitro methane (1.45 mL, 26.78 mmol) and 10N NaOH (3.5 mL, 28.11 mmol). The resulting mixture was stirred at 0° C. for 1.30 hours to afford 3 g of the product (72.28% yield).

$^1$H NMR (CDCl$_3$, 300 MHz): δ 8.10-7.93 (m, 1H), 7.80-7.65 (m, 1H), 7.59-7.36 (m, 2H), 7.36-7.15 (m, 1H)

Step 2: Preparation of Intermediate 2-Thiophen-3-yl-ethylamine (I-5b)

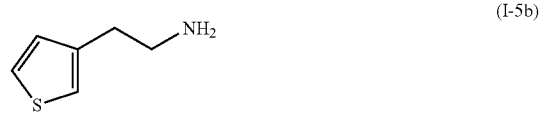

(I-5b)

Using analogous reaction conditions and workup as described in Example 1, step 2,3-(2-nitro-vinyl)-thiophene (I-5a: 3 g, 19.35 mmol) in dry THF (25 mL) was reacted with LAH (2.14 g, 58.05 mmol) in dry THF (25 mL) to afford 1.7 g of the product (69.19%).

$^1$H NMR (CDCl$_3$, 300 MHz): δ 7.36-7.21 (m, 1H), 7.04-6.88 (m, 2H), 3.05-2.90 (m, 2H), 2.90-2.65 (m, 2H)

Step 3: Preparation of Intermediate (2-Thiophen-3-yl-ethyl)-carbamic acid ethyl ester (I-5c)

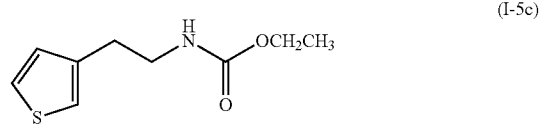 [SMILES: CCOC(=O)NCCc1ccsc1]

(I-5c)

Using an analogous procedure and workup as described in Example 1, 2-thiophen-3-yl-ethylamine (I-5b: 1.7 g, 13.38 mmol) in chloroform (10 mL) was reacted with chloro ethyl formate (1.6 mL, 16.73 mmol) and 2N Na$_2$CO$_3$ solution (10 mL) at 0° C. The resulting mixture was stirred at room temperature for 2 hours to afford the crude product. Purification by column chromatography on silica gel (6% ethylacetate in hexane) afforded 1.1 g of the product (41.35% yield).

$^1$H NMR (CDCl$_3$, 300 MHz): δ 7.40-7.15 (m, 1H), 7.08-6.84 (m, 2H), 4.80-4.56 (br s, 1H), 4.1 (q, 2H), 3.42 (q, 2H), 2.82 (t, 2H), 1.23 (t, 3H)

Step 4: Preparation of Intermediate 5,6-Dihydro-4H-thieno[2,3-c]pyridin-7-one (I-5d)

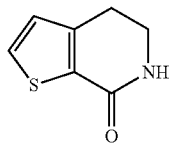

(I-5d)

Using an analogous procedure and workup as described in Example 1, (2-thiophen-3-yl-ethyl)-carbamic acid ethyl ester (I-5c: 1.1 g, 5.527 mmol) in POCl$_3$ (10 mL) was reacted with P$_2$O$_5$ (1.6 g, 11.05 mmol). The resulting mixture was stirred at 110° C. for 3 hours to afford the crude product. Purification by column chromatography on silica gel (1.5% methanol in DCM) afforded 280 mg of the product (33.13% yield).

$^1$H NMR (CDCl$_3$, 300 MHz): δ 7.5 (d, 1H), 6.96 (d, 1H), 6.09-5.80 (br s, 1H), 3.72-3.49 (m, 2H), 2.92 (t, 2H)

LCMS purity: 83.21%, m/z=154.0 (M+1)

Preparation of 6-(4-Methyl-pyridin-3-yl)-5,6-dihydro-4H-thieno[2,3-c]pyridin-7-one (5A)

Using analogous reaction conditions as described in example 1, 5,6-dihydro-4H-thieno[2,3-c]pyridin-7-one (I-5d: 130 mg, 0.849 mmol) was reacted with 3-iodo-4-methyl-pyridine (185 mg, 0.849 mmol), 1,4-dioxane (5 mL), copper iodide (16 mg, 0.0849 mmol), trans-N,N'-dimethyl-cyclohexyl-1,2-diamine (0.04 mL, 0.254 mmol) and potassium phosphate (538 mg, 2.54 mmol) to afford the crude product. Purification by column chromatography on silica gel (1% methanol in CHCl$_3$) afforded 105 mg of the product (51.4% yield).

$^1$H NMR (CDCl$_3$, 300 MHz): δ 8.62-8.21 (m, 2H), 7.56 (d, 1H), 7.40-7.13 (m, 1H), 7.0 (d, 1H), 4.2-4.0 (m, 1H), 3.95-3.71 (m, 1H), 3.26-3.00 (m, 2H), 2.3 (s, 3H)

LCMS purity: 99.2%, m/z=245.1 (M+1)
HPLC: 96.28%

Example 6

Preparation of 6-Pyridin-3-yl-5,6-dihydro-4H-thieno[2,3-c]pyridin-7-one (6A)

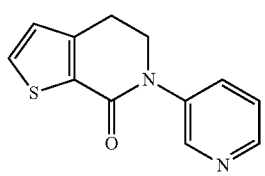

(6A)

Using analogous reaction conditions as described in example 1, 5,6-dihydro-4H-thieno[2,3-c]pyridin-7-one (I-5d: 110 mg, 0.718 mmol) was reacted with 3-bromo-pyridine (136 mg, 0.861 mmol), 1,4-dioxane (5 mL), copper iodide (13.5 mg, 0.071 mmol), trans-N,N'-dimethyl-cyclohexyl-1,2-diamine (0.033 mL, 0.215 mmol) and potassium phosphate (456 mg, 2.15 mmol) to afford the crude product. Purification by column chromatography on silica gel (1% methanol in DCM) afforded 65 mg of the product (39.3% yield).

$^1$H NMR (CDCl$_3$, 300 MHz): δ 8.74-8.59 (m, 1H), 8.58-8.38 (m, 1H), 7.88-7.70 (m, 1H), 7.7-7.5 (d, 1H), 7.49-7.30 (m, 1H), 7.0 (d, 1H), 4.1 (t, 2H), 3.1 (t, 2H)

LCMS purity: 98.04%, m/z=230.9 (M+1)
HPLC: 95.87%

Example 7

Preparation of 5-(4-Methyl-pyridin-3-yl)-6,7-dihydro-5H-thieno[3,2-a]pyridin-4-one (7A)

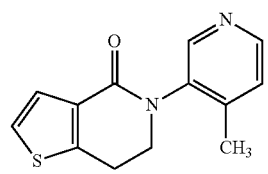

(7A)

Step 1: Preparation of Intermediate 2-(2-Nitro-vinyl)-thiophene (I-7a)

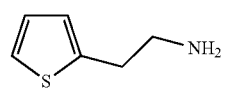

(I-7a)

Sodium acetate (3.6 g, 43.90 mmol) and methylamine hydrochloride (3.01 g, 44.57 mmol) were added to a stirred solution of thiophene-2-carbaldehyde (5 g, 44.64 mmol) in methanol (95.64 mL). This was followed by dropwise addition of nitro methane (108.08 g, 1770.14 mmol) over a period of 5 minutes. The resulting mixture was stirred at room temperature for 2 hours. The reaction was monitored by TLC (10% ethylacetate in hexane). The reaction mixture was partitioned between water and DCM. The organic layer was washed with water, brine solution, dried over Na$_2$SO$_4$ and concentrated. Purification by column chromatography on silica gel (5% ethylacetate in hexane) afforded 1 g of the product (15% yield).

$^1$H NMR (CDCl$_3$, 300 MHz): δ 8.16 (d, 1H), 7.56 (d, 1H), 7.54-7.40 (m, 2H), 7.22-7.30 (m, 1H)

Step 2: Preparation of Intermediate 2-Thiophen-2-yl-ethylamine (I-7b)

(I-7b)

Using analogous reaction conditions and workup as described in Example 1, step 2,2-(2-nitro-vinyl)-thiophene (I-7a: 1.5 g, 9.677 mmol) in dry THF (15 mL) was reacted with LAH (730 mg, 19.210 mmol) in dry THF (15 mL) to afford 1.2 g of the crude product which was used in the next step without further purification.

Step 3: Preparation of Intermediate (2-Thiophen-2-yl-ethyl)-carbamic acid ethyl ester (I-7c)

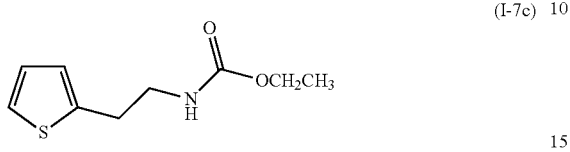

(I-7c)

Using an analogous procedure and workup as described in Example 1, step 3, 2-thiophen-2-yl-ethylamine (I-7b: 1.2 g, 9.448 mmol) in chloroform (15 mL) was reacted with chloro ethyl formate (1.22 g, 11.296 mmol) and 2N $Na_2CO_3$ solution (1.12 g, 10.66 mmol) at 0° C. The resulting mixture was stirred at room temperature for 2 hours to afford the crude product. Purification by column chromatography on silica gel (10% ethylacetate in hexane) afforded 100 mg of the product (10% yield).

$^1$H NMR ($CDCl_3$, 300 MHz): δ 7.2-7.1 (m, 1H), 7.0-6.9 (m, 1H), 6.9-6.79 (m, 1H), 4.9-4.7 (br s, 1H), 4.1 (q, 2H), 3.44 (q, 2H), 3.02 (t, 2H), 1.22 (t, 3H)

Step 4: Preparation of Intermediate 6,7-Dihydro-5H-thieno[3,2-c]pyridin-4-one (I-7d)

(I-7d)

Using an analogous procedure and workup as described in Example 1, step 4, (2-thiophen-2-yl-ethyl)-carbamic acid ethyl ester (I-7c: 800 mg, 3.50887 mmol) in $POCl_3$ (10 mL) was reacted with $P_2O_5$ (996 mg, 7.0175 mmol). The resulting mixture was stirred at 110° C. for 4 hours to afford the crude product. Purification by column chromatography on silica gel (2% methanol in $CHCl_3$) afforded 180 mg of the product (33.5% yield).

$^1$H NMR ($CDCl_3$, 300 MHz): δ 7.45 (d, 1H), 7.13 (d, 1H), 5.9-5.7 (br s, 1H), 3.7-3.6 (m, 2H), 3.1 (t, 2H)
LCMS purity: 98.63%, m/z=154.1 (M+1)

Preparation of 5-(4-Methyl-pyridin-3-yl)-6,7-dihydro-5H-thieno[3,2-c]pyridin-4-one (7A)

Using analogous reaction conditions as described in example 1, 6,7-dihydro-5H-thieno[3,2-c]pyridin-4-one (I-7d: 100 mg, 0.6527 mmol) was reacted with 3-iodo-4-methyl-pyridine (171.5 mg, 0.7832 mmol), 1,4-dioxane (20 mL), copper iodide (9.7 mg, 0.0652 mmol), trans-N,N'-dimethyl-cyclohexyl-1,2-diamine (27.8 mg, 0.1958 mmol) and potassium phosphate (346.3 mg, 1.6318 mmol) to afford the crude product. Purification by column chromatography on silica gel (2% methanol in $CHCl_3$) afforded 90 mg of the product (56.2% yield).

$^1$H NMR (DMSO-$D_6$, 300 MHz): δ 8.61-8.30 (m, 2H), 7.45 (d, 1H), 7.44-7.28 (m, 2H), 4.18-4.00 (m, 1H), 3.90-3.72 (m, 1H), 3.25 (t, 2H), 2.2 (s, 3H)
LCMS purity: 94.19%, m/z=244.9 (M+1)
HPLC: 94.16%

Example 8

Preparation of 5-Pyridin-3-yl-6,7-dihydro-5H-thieno[3,2-c]pyridin-4-one (8A)

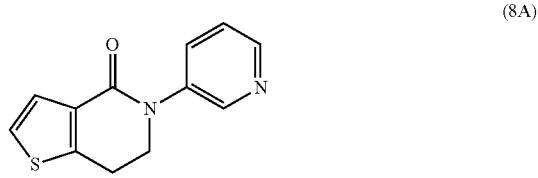 [SMILES: O=C1c2ccsc2CCN1c1cccnc1]

(8A)

Using analogous reaction conditions as described in Example 1, 6,7-dihydro-5H-thieno[3,2-c]pyridin-4-one (I-7d: 80 mg, 0.5221 mmol) was reacted with 3-bromo-pyridine (99 mg, 0.6266 mmol), 1,4-dioxane (15 mL), copper iodide (9.9 mg, 0.05221 mmol), trans-N,N'-dimethyl-cyclohexyl-1,2-diamine (22.2 mg, 0.15667 mmol) and potassium phosphate (277.1 mg, 1.3054 mmol) to afford the crude product. Purification by column chromatography on silica gel (1% methanol in DCM) afforded 60 mg of the product (50% yield).

$^1$H NMR (DMSO-$D_6$, 300 MHz): δ 9.03-8.21 (m, 2H), 7.82 (d, 1H), 7.64-7.16 (m, 3H), 425-3.96 (t, 2H), 3.40-3.15 (t, 2H)
LCMS purity: 97.99%, m/z=231.0 (M+1)
HPLC: 98.24%

Example 9

Preparation of 2-(4-Methyl-pyridin-3-yl)-3,4-dihydro-2H-benzo[4,5]thieno[3,2-c]pyridin-1-one (9A)

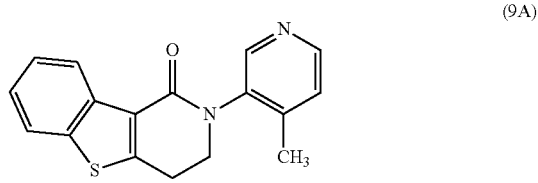 [SMILES: Cc1ccncc1N1CCc2sc3ccccc3c2C1=O]

(9A)

Step 1: Preparation of Intermediate 2-(2-Nitro-vinyl)-benzo[b]thiophene (I-9a)

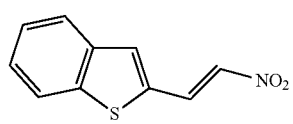

(I-9a)

Using an analogous reaction procedure and workup as described in Example 1, step 1, benzo[b]thiophene-2-carbaldehyde (2.1 g, 0.012 mol) in ethanol (100 mL) was reacted with nitro methane (0.7 mL, 0.012 mol) and 10N NaOH (0.51 g, 0.012 mol). The resulting mixture was stirred at 0° C. for 1 hr to afford 2.1 g of the product (84% yield).

$^1$H NMR (CDCl$_3$, 300 MHz): δ 8.30-8.19 (m, 1H), 7.90-7.78 (m, 2H), 7.7 (s, 1H), 7.56-7.34 (m, 3H)

Step 2: Preparation of Intermediate
2-Benzo[b]thiophen-2-yl-ethylamine (I-9b)

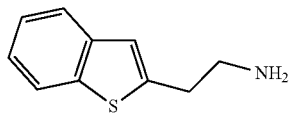

Using analogous reaction conditions and workup as described in Example 1, step 2, 2-(2-nitro-vinyl)-benzo[b]thiophene (I-9a: 2.1 g, 0.010 mol) in dry THF (30 mL) was reacted with LAH (0.81 g, 0.021 mol) in dry THF (20 mL) to afford 1.6 g of the product (87.91% yield).

LCMS: m/z=178.0 (M+1)

Step 3: Preparation of Intermediate
(2-Benzo[b]thiophen-2-yl-ethyl)-carbamic acid ethyl ester (I-9c)

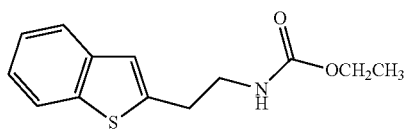

Using an analogous procedure and workup as described in Example 1, step 3, 2-benzo[b]thiophen-2-yl-ethylamine (I-9b: 1.6 g, 0.0090 mol) in chloroform (30 mL) was reacted with chloro ethyl formate (1.17 g, 0.010 mol) and 2N Na$_2$CO$_3$ solution (1.13 g, 0.010 mol) at 0° C. The resulting mixture was stirred at 0° C. for 1 hr to afford the crude product. Purification by column chromatography on silica gel (8% ethylacetate in hexane) afforded 1.2 g of the product (54.5% yield).

$^1$H NMR (CDCl$_3$, 300 MHz): δ 7.86-7.62 (m, 2H), 7.40-7.22 (m, 2H), 7.06 (s, 1H), 5.0-4.7 (br s, 1H), 4.30-3.98 (q, 2H), 3.7-3.4 (q, 2H), 3.1 (t, 2H), 1.2 (t, 3H)

Step 4: Preparation of Intermediate 3,4-Dihydro-2H-benzo[4,5]thieno[3,2-d]pyridin-1-one (I-9d)

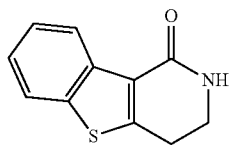

Using an analogous procedure and workup as described in Example 1, step 4, (2-benzo[b]thiophen-2-yl-ethyl)-carbamic acid ethyl ester (I-9c: 1.1 g, 0.028 mol) in POCl$_3$ (15 mL) was reacted with P$_2$O$_5$ (1.37 g, 0.0097 mol). The resulting mixture was stirred at 105° C. for 3 hours to afford the crude product. Purification by column chromatography on silica gel (40% ethylacetate in hexane) afforded 0.15 g of the product (16.88% yield).

$^1$H NMR (CDCl$_3$, 300 MHz): δ 8.62 (d, 1H), 7.8 (d, 1H), 7.59-7.30 (m, 2H), 5.90-5.65 (br s, 1H), 3.79-3.65 (m, 2H), 3.18 (t, 2H)

LCMS purity: 95.05%, m/z=204.0 (M+1)

Preparation of 2-(4-Methyl-pyridin-3-yl)-3,4-dihydro-2H-benzo[4,5]thieno[3,2-c]pyridin-1-one (9A)

Using analogous reaction conditions as described in Example 1, 3,4-dihydro-2H-benzo[4,5]thieno[3,2-c]pyridin-1-one (I-9d: 0.15 g, 0.0007 mol) was reacted with 3-iodo-4-methyl-pyridine (0.178 g, 0.0008 mol), 1,4-dioxane (50 mL), copper iodide (0.014 g, 0.00007 mol), trans-1,2-diamino cyclohexane (0.03 g, 0.0002 mol) and potassium phosphate (0.39 g, 0.0018 mol) to afford the crude product. Purification by column chromatography on silica gel (1.5% methanol in CHCl$_3$) afforded 90 mg of the product (39.13% yield).

$^1$H NMR (CDCl$_3$, 300 MHz): δ 8.62 (d, 1H), 8.52 (s, 1H), 8.46 (d, 1H), 7.83 (d, 1H), 7.52-7.34 (m, 2H), 7.25 (s, 1H), 4.3-4.1 (m, 1H), 4.0-3.84 (m, 1H), 3.50-3.28 (m, 2H), 2.35 (s, 3H)

LCMS purity: 99.56%, m/z=295.0 (M+1)

HPLC: 98.59%

Example 10

Preparation of 2-(4-Methyl-pyridin-3-yl)-3,4-dihydro-2H-benzo[h]isoquinolin-1-one (10A)

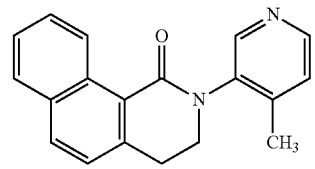

Step 1: Preparation of Intermediate
2-(2-Nitro-vinyl)-naphthalene (I-10a)

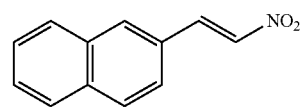

Using an analogous reaction procedure and workup as described in Example 1, step 1, naphthalene-2-carbaldehyde (3 g, 19.20 mmol) in ethanol (35 mL) was reacted with nitro methane (1.17 g, 19.49 mmol) and 10N NaOH (0.807 g, 20.17 mmol). The resulting mixture was stirred at 0° C. for 1 hour to afford 3.2 g of the product (84.21% yield).

¹H NMR (CDCl₃, 300 MHz): δ 8.28-8.10 (m, 1H), 8.10-7.99 (br s, 1H), 7.98-7.79 (m, 3H), 7.98-7.45 (m, 4H)

Step 2: Preparation of Intermediate
2-Naphthalen-2-yl-ethylamine (I-10b)

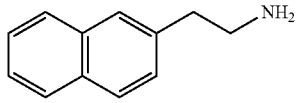

Using analogous reaction conditions and workup as described in Example 1, step 2,2-(2-nitro-vinyl)-naphthalene (I-10a: 3 g, 15.00 mmol) in dry THF (15 mL) was reacted with LAH (1.14 g, 30.00 mmol) in dry THF (15 mL) to afford 3.2 g of the crude product which was used in the next step without further purification.

¹H NMR (CDCl₃, 300 MHz): δ 7.94-7.70 (m, 3H), 7.70-7.58 (s, 1H), 7.58-7.30 (m, 3H), 3.04 (t, 2H), 2.9 (t, 2H)

Step 3: Preparation of Intermediate
(2-Naphthalen-2-yl-ethyl)-carbamic acid ethyl ester (I-10c)

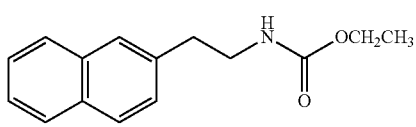

Using an analogous procedure and workup as described in Example 1, step 3, 2-naphthalen-2-yl-ethylamine (I-10b: 2.4 g, 14.03 mmol) in chloroform (25 mL) was reacted with chloro ethyl formate (1.8 g, 16.75 mmol) and 2N Na₂CO₃ solution (1.76 g, 16.75 mmol) at 0° C. The resulting mixture was stirred at room temperature for 2 hours to afford the crude product. Purification by column chromatography on silica gel (20% ethylacetate in hexane) afforded 1.4 g of the product (41.17% yield).

¹H NMR (CDCl₃, 300 MHz): δ 7.99-7.71 (m, 3H), 7.65 (s, 1H), 7.56-7.28 (m, 3H), 4.85-4.49 (br s, 1H), 4.1 (q, 2H), 3.5 (q, 2H), 3.0 (t, 2H), 1.21 (t, 3H)

Step 4: Preparation of Intermediate
3,4-Dihydro-2H-benzo[h]isoquinolin-1-one (I-10d)

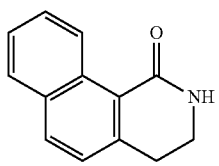

Using an analogous procedure and workup as described in Example 1, step 4, (2-naphthalen-2-yl-ethyl)-carbamic acid ethyl ester (I-10c: 1.3 g, 5.349 mmol) in POCl₃ (16 mL) was reacted with P₂O₅ (1.58 g, 11.205 mmol). The resulting mixture was stirred at 110° C. for 3 hours to afford the crude product. Purification by column chromatography on silica gel (20% ethylacetate in hexane) afforded 415 mg of the product (40% yield).

¹H NMR (CDCl₃, 300 MHz): δ 9.4 (d, 1H), 8.06-7.75 (m, 2H), 7.69-7.40 (m, 2H), 7.33 (d, 1H), 6.5-6.26 (br s, 1H), 3.68-3.48 (m, 2H), 3.12 (t, 2H)

Preparation of 2-(4-Methyl-pyridin-3-yl)-3,4-dihydro-2H-benzo[h]isoquinolin-1-one (10A)

Using analogous reaction conditions as described in Example 1, 3,4-dihydro-2H-benzo[h]isoquinolin-1-one (I-10d: 200 mg, 1.015 mmol) was reacted with 3-iodo-4-methyl-pyridine (266 mg, 1.214 mmol), 1,4-dioxane (15 mL), copper iodide (19 mg, 0.10 mmol), trans-N,N'-dimethyl-cyclohexyl-1,2-diamine (43 mg, 0.302 mmol) and potassium phosphate (538 mg, 2.53 mmol) to afford the crude product. Purification by column chromatography on silica gel (1% methanol in CHCl₃) afforded 162 mg of the product (55.47% yield).

¹H NMR (CDCl₃, 300 MHz): δ 9.34 (d, 1H), 8.69-8.34 (m, 2H), 8.10-7.74 (m, 2H), 7.71-7.46 (m, 2H), 7.45-7.16 (m, 2H), 4.20-3.93 (m, 1H), 3.92-3.67 (m, 1H), 3.50-3.12 (m, 2H), 2.36 (s, 3H)

LCMS purity: 99.93%, m/z=288.7 (M+1)
HPLC: 97.65%

Example 11

Preparation of 6-Methoxy-2-(4-methyl-pyridin-3-yl)-3,4-dihydro-2H-isoquinolin-1-one (11A) and 6-Hydroxy-2-(4-methyl-pyridin-3-yl)-3,4-dihydro-2H-isoquinolin-1-one (11B)

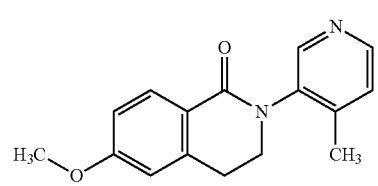

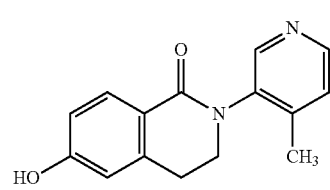

Step 1: Preparation of Intermediate 1-Methoxy-3-(2-nitro-vinyl)-benzene (I-11a)

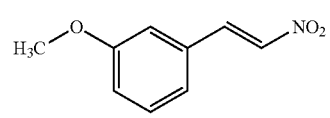

Using an analogous reaction procedure and workup as described in Example 1, step 1, 3-methoxy-benzaldehyde (16.0 g, 118.518 mmol) in ethanol (160 mL) was reacted with nitro methane (7.0 mL, 118.518 mmol) and 10N NaOH (4.7 g, 118.518 mmol). The resulting mixture was stirred at 0° C. for 4 hours to afford 10.5 g of the product (49% yield).

$^1$H NMR (CDCl$_3$, 300 MHz): δ 8.1-7.9 (d, 1H), 7.7-7.5 (d, 1H), 7.49-7.30 (m, 1H), 7.15 (d, 1H), 7.10-6.99 (m, 2H), 3.82 (s, 3H)

Step 2: Preparation of Intermediate
2-(3-Methoxy-phenyl)-ethylamine (I-11b)

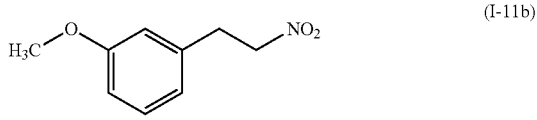

Using analogous reaction conditions and workup as described in Example 1, step 2, 1-methoxy-3-(2-nitro-vinyl)-benzene (I-11a: 10.5 g, 58.659 mmol) in dry THF (110 mL) was reacted with LAH (6.68 g, 175.97 mmol) to afford 6.5 g of the product (73% yield).

$^1$H NMR (CDCl$_3$, 300 MHz): δ 7.32-7.00 (m, 2H), 6.86-6.54 (m, 4H), 3.90-3.55 (s, 3H), 2.9 (t, 2H), 2.65 (t, 2H)

Step 3: Preparation of Intermediate
[2-(3-Methoxy-phenyl)-ethyl]-carbamic acid ethyl ester (I-11c)

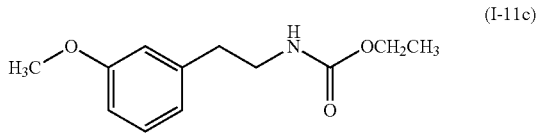 [SMILES: CCOC(=O)NCCc1cccc(OC)c1]

Using an analogous procedure and workup as described in Example 1, step 3, 2-(3-methoxy-phenyl)-ethylamine (I-11b: 6.5 g, 43.046 mmol) in chloroform (65 mL) was reacted with chloro ethyl formate (4.91 mL, 51.655 mmol) and 2N Na$_2$CO$_3$ solution (65 mL) at 0° C. The resulting mixture was stirred at room temperature for 3 hours to afford the crude product. Purification by column chromatography on silica gel (10% ethylacetate in hexane) afforded 6.2 g of the product (68% yield).

$^1$H NMR (CDCl$_3$, 300 MHz): δ 7.43-710 (m, 1H), 6.92-6.52 (m, 3H), 4.89-4.55 (m, 1H), 4.3-4.0 (m, 2H), 3.8 (s, 3H), 3.56-3.29 (m, 2H), 2.8 (t, 2H), 1.4-1.1 (m, 3H)

Step 4: Preparation of Intermediate
6-Methoxy-3,4-dihydro-2H-isoquinolin-1-one (I-11d)

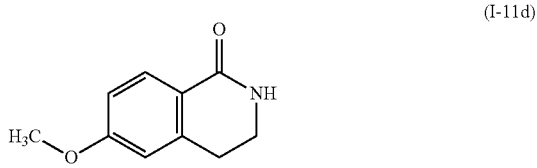

Using an analogous procedure and workup as described in Example 1, step 4, [2-(3-methoxy-phenyl)-ethyl]-carbamic acid ethyl ester (I-11c: 6.2 g, 29.5238 mmol) in POCl$_3$ (62 mL) was reacted with P$_2$O$_5$ (8.38 g, 59.047 mmol). The resulting mixture was stirred at 120° C. for 1 hour to afford the crude product. Purification by column chromatography on silica gel (2% methanol in DCM) afforded 0.400 g of the product (7.6% yield).

LCMS purity: 100%, m/z=178.0 (M+1)

Preparation of 6-Methoxy-2-(4-methyl-pyridin-3-yl)-3,4-dihydro-2H-isoquinolin-1-one (11A)

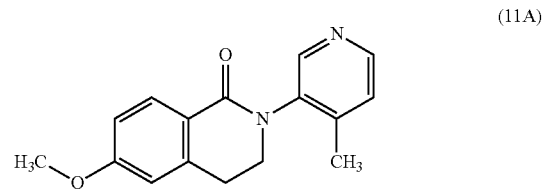 [SMILES: COc1ccc2c(c1)CCN(c1cnccc1C)C2=O]

Using analogous reaction conditions as described in Example 1, 6-methoxy-3,4-dihydro-2H-isoquinolin-1-one (I-11d: 0.400 g, 2.2471 mmol) was reacted with 3-iodo-4-methyl-pyridine (0.492 g, 2.2471 mmol), 1,4-dioxane (40 mL), copper iodide (0.042 g, 0.2247 mmol), trans-N,N'-dimethyl-cyclohexyl-1,2-diamine (0.095 g, 0.6741 mmol) and potassium phosphate (1.190 g, 5.6177 mmol) to afford the crude product. Purification by column chromatography on silica gel (80% ethylacetate in hexane) afforded 0.320 g of the product (53% yield).

$^1$H NMR (CDCl$_3$, 300 MHz): δ 8.51-8.36 (m, 1H), 8.09 (d, 1H), 7.26-7.20 (m, 2H), 6.9 (dd, 1H), 6.80-6.72 (m, 1H), 4.15-3.95 (m, 1H), 3.89 (s, 3H), 3.82-3.64 (m, 1H), 3.3-3.0 (m, 2H), 2.3 (s, 3H)

Preparation of 6-Hydroxy-2-(4-methyl-pyridin-3-yl)-3,4-dihydro-2H-isoquinolin-1-one (11B)

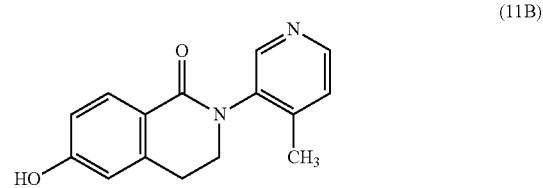 [SMILES: Cc1ccncc1N1CCc2cc(O)ccc2C1=O]

Boran tri-bromide (0.68 mL, 0.6715 mmol) was added dropwise to a solution of 6-methoxy-2-(4-methyl-pyridin-3-yl)-3,4-dihydro-2H-isoquinolin-1-one (11A: 0.120 g, 0.4477 mmol) in DCM (2 mL) at −78° C. over a period of 5 minutes under nitrogen atmosphere. The resulting mixture was stirred at room temperature for 16 hours. The reaction was monitored by TLC (80% ethylacetate in hexane). Since unreacted starting material was observed, a further 1.5 equivalents of boran tri-bromide (0.68 mL, 0.6715 mmol) was added and stirring was continued for a further 3 hours at room temperature. Methanol and saturated NaHCO$_3$ were added to the reaction mixture and diluted with DCM. The organic layer was dried over Na$_2$SO$_4$ and concentrated. Purification by column chromatography on silica gel (80% ethylacetate in hexane), followed by preparative TLC afforded 0.011 g of the product (9.7% yield).

$^1$H NMR (CDCl$_3$, 300 MHz): δ 8.60-8.31 (m, 2H), 7.95 (d, 1H), 7.4-7.1 (m, 1H), 6.91-6.58 (m, 2H), 4.11-3.86 (m, 1H), 3.86-3.62 (m, 1H), 3.5 (s, 1H), 3.30-2.92 (m, 2H), 2.3 (s, 3H)

LCMS purity: 100%, m/z=255.0 (M+1)

HPLC: 94.53%

Example 12

Preparation of 5-Chloro-2-(4-methyl-pyridin-3-yl)-3,4-dihydro-2H-isoquinolin-1-one (12A)

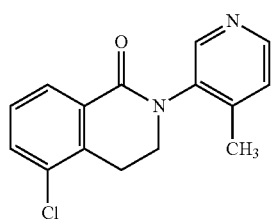
(12A)

Step 1: Preparation of Intermediate 1-Chloro-2-(2-nitro-vinyl)-benzene (I-12a)

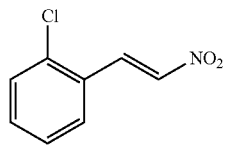
(I-12a)

Using an analogous reaction procedure and workup as described in Example 1, step 1, 2-chloro-benzaldehyde (5 g, 35.7142 mmol) in ethanol (161 mL) was reacted with nitro methane (1.93 mL, 35.7142 mmol) and 10N NaOH (1.35 g, 33.9607 mmol). The resulting mixture was stirred at 0° C. for 1 hr to afford 4.5 g of the product (75.73% yield).

$^1$H NMR (CDCl$_3$, 300 MHz): δ 8.4 (d, 1H), 7.72-7.27 (m, 5H)

Step 2: Preparation of intermediate 2-(2-Chloro-phenyl)-ethylamine (I-12b)

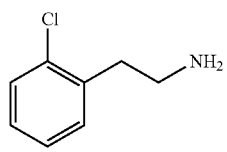
(I-12b)

Using analogous reaction conditions and workup as described in Example 1, step 2, 1-chloro-2-(2-nitro-vinyl)-benzene (I-12a: 4.5 g, 24.5901 mmol) in dry THF (50 mL) was reacted with LAH (1.86 g, 49.1803 mmol) in dry THF (50 mL) to afford 2.6 g of the crude product which was used in the next step without further purification.

Step 3: Preparation of intermediate [2-(2-Chloro-phenyl)-ethyl]-carbamic acid ethyl ester (I-12c)

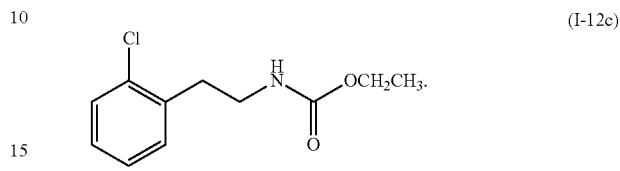
(I-12c)

Using an analogous procedure and workup as described in Example 1, step 3, 2-(2-chloro-phenyl)-ethylamine (I-12b: 3 g, 0.0193 mmol) in chloroform (30 mL) was reacted with chloro ethyl formate (2.50 g, 0.023 mmol) and 2N Na$_2$CO$_3$ solution (30 mL) at 0° C. The resulting mixture was stirred at 5° C. for 2 hours to afford the crude product. Purification by column chromatography on silica gel (15% ethylacetate in hexane) afforded 1.62 g of the product (37.2% yield).

$^1$H NMR (CDCl$_3$, 300 MHz): δ 7.44-7.08 (m, 4H), 4.85-4.57 (br s, 1H), 4.1 (q, 2H), 3.42 (q, 2H), 2.92 (t, 2H), 1.22 (t, 3H)

Step 4: Preparation of Intermediate 5-Chloro-3,4-dihydro-2H-isoquinolin-1-one (I-12d)

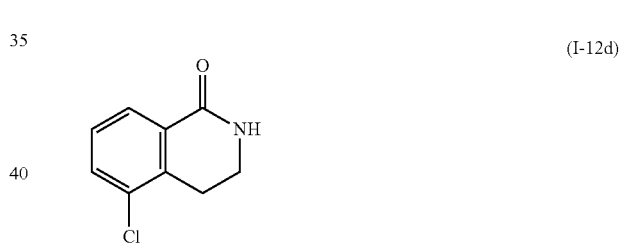
(I-12d)

Using an analogous procedure and workup as described in Example 1, step 4, [2-(2-chloro-phenyl)-ethyl]-carbamic acid ethyl ester (I-12c: 1.4 g, 6.167 mmol) in POCl$_3$ (14 mL) was reacted with P$_2$O$_5$ (1.75 g, 12.334 mmol). The resulting mixture was heated to reflux for 1 hour to afford the crude product. Purification by column chromatography on silica gel (2% methanol in DCM) afforded 100 mg of the product (9% yield).

LCMS: m/z=182.1 (M+1)

Preparation of 5-Chloro-2-(4-methyl-pyridin-3-yl)-3,4-dihydro-2H-isoquinolin-1-one (12A)

Using analogous reaction conditions as described in example 1, 5-chloro-3,4-dihydro-2H-isoquinolin-1-one (I-12d: 100 mg, 0.552 mmol) was reacted with 3-iodo-4-methyl-pyridine (121 mg, 0.552 mmol), 1,4-dioxane (6 mL), copper iodide (10.5 mg, 0.0552 mmol), trans-N,N'-dimethyl-cyclohexyl-1,2-diamine (23.51 mg, 0.165 mmol) and potassium phosphate (190.44 mg, 1.38 mmol) to afford the crude product. Purification by column chromatography on silica gel (35% ethylacetate in hexane) afforded 28 mg of the product (18% yield).

¹H NMR (CDCl₃, 300 MHz): δ 8.66-8.34 (m, 2H), 8.1 (d, 1H), 7.58 (d, 1H), 7.36 (t, 1H), 7.25 (s, 1H), 4.15-3.98 (m, 1H), 3.93-3.72 (m, 1H), 3.45-3.20 (m, 2H), 2.3 (s, 3H)

LCMS purity: 84.87%, m/z=273.0 (M+1)
HPLC: 88.42%

Example 13

Preparation of 5-Methoxy-2-(4-methyl-pyridin-3-yl)-3,4-dihydro-2H-isoquinolin-1-one (13A)

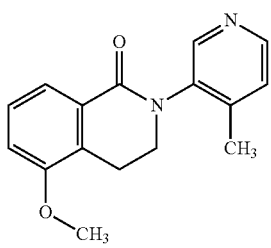

(13A)

Step 1: Preparation of Intermediate 1-Methoxy-2-(2-nitro-vinyl)-benzene (I-13a)

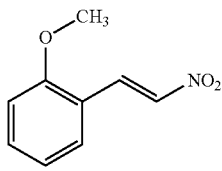

(I-13a)

Using the same reaction procedure and workup as described in Example 1, step 1, 2-methoxy-benzaldehyde (5 g, 36.7242 mmol) in ethanol (166 mL) was reacted with nitro methane (1.98 mL, 36.7242 mmol) and 10N NaOH (1.39 g, 34.9602 mmol). The resulting mixture was stirred at 0° C. for 1 hr to afford 4.5 g of the product (83.89% yield).

¹H NMR (CDCl₃, 300 MHz): δ 8.14 (d, 1H), 7.88 (d, 1H), 7.60-7.34 (m, 2H), 7.18-6.84 (m, 2H), 4.0 (s, 3H)

Step 2: Preparation of Intermediate 2-(2-Methoxy-phenyl)-ethylamine (I-13b)

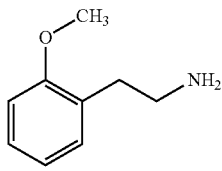

(I-13b)

Using analogous reaction conditions and workup as described in Example 1, step 2, 1-methoxy-2-(2-nitro-vinyl)-benzene (I-13a: 4.5 g, 25.1396 mmol) in dry THF (50 mL) was reacted with LAH (1.91 g, 50.2793 mmol) in dry THF (50 mL) to afford 2.7 g of the crude product which was used in the next step without further purification.

Step 3: Preparation of Intermediate [2-(2-Methoxy-phenyl)-ethyl]-carbamic acid ethyl ester (I-13c)

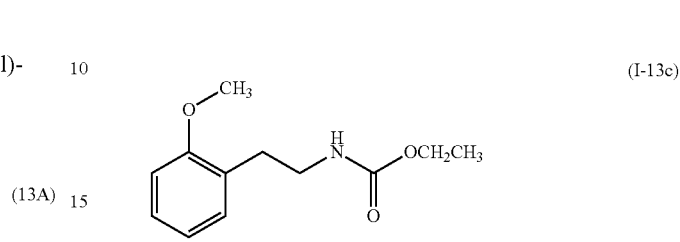

(I-13c)

Using the same procedure and workup as described in Example 1, step 3, 2-(2-methoxy-phenyl)-ethylamine (I-13b: 3 g, 0.019 mmol) in chloroform (30 mL) was reacted with chloro ethyl formate (2.57 g, 0.023 mmol) and 2N Na₂CO₃ solution (30 mL) at 0° C. The resulting mixture was stirred at 5° C. for 1.30 hours to afford the crude product. Purification by column chromatography on silica gel (8% ethylacetate in hexane) afforded 1.02 g of the product (25.2% yield).

¹H NMR (CDCl₃, 300 MHz): δ 7.34-7.10 (m, 2H), 7.00-6.78 (m, 2H), 4.90-4.68 (br s, 1H), 4.1 (q, 2H), 3.81 (s, 3H), 3.4 (q, 2H), 2.8 (t, 2H), 1.2 (t, 3H)

Step 4: Preparation of Intermediate 5-Methoxy-3,4-dihydro-2H-isoquinolin-1-one (I-13d)

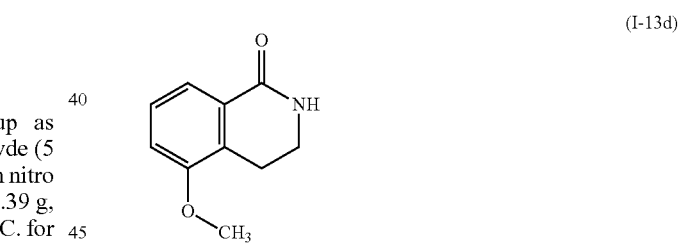

(I-13d)

Using the same procedure and workup as described in example 1, step 4, [2-(2-methoxy-phenyl)-ethyl]-carbamic acid ethyl ester (I-13c: 0.9 g, 0.0040 mmol) in POCl₃ (5 mL) was reacted with P₂O₅ (1.19 g, 0.0084 mmol). The resulting mixture was stirred at 110° C. for 3 hours to afford the crude product. Purification by column chromatography on silica gel (1% methanol in CHCl₃) afforded 90 mg of the product (12.8% yield).

LCMS purity: 100%, m/z=178.1 (M+1)

Preparation of 5-Methoxy-2-(4-methyl-pyridin-3-yl)-3,4-dihydro-2H-isoquinolin-1-one (13A)

Using analogous reaction conditions as described in Example 1, 5-methoxy-3,4-dihydro-2H-isoquinolin-1-one (I-13d: 0.09 g, 0.5 mmol) was reacted with 3-iodo-4-methyl-pyridine (0.133 g, 0.0006 mol), 1,4-dioxane (30 mL), copper iodide (0.0096 g, 0.05 mmol), trans-N,N'-dimethyl-cyclohexyl-1,2-diamine (0.021 g, 0.13 mmol) and potassium phosphate (0.269 g, 0.0012 mmol) to afford the crude product.

Purification by column chromatography on silica gel (1% methanol in DCM), followed by preparative TLC afforded 5 mg of the product (38.46% yield).

$^1$H NMR (CDCl$_3$, 300 MHz): δ 8.70-8.25 (m, 2H), 7.78 (d, 1H), 7.37 (t, 1H), 7.25 (s, 1H), 7.06 (d, 1H), 4.10-3.96 (m, 1H), 3.9 (s, 3H), 3.83-3.65 (m, 1H), 3.32-3.02 (m, 2H), 2.3 (s, 3H)

LCMS purity: 87.32%, m/z=269.1 (M+1)
HPLC: 87.69%

Example 14

Preparation of 2-(4-Fluoro-phenyl)-5-(4-methyl-pyridin-3-yl)-6,7-dihydro-5H-thieno[3,2-c]pyridin-4-one (14A)

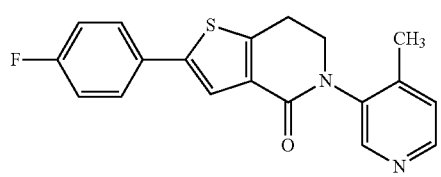

Step 1: Preparation of Intermediate 2-Bromo-5-(2-nitro-vinyl)-thiophene (I-14a)

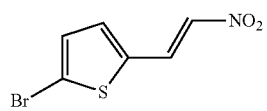

Using analogous reaction conditions and workup as described in Example 1, step 1, 5-bromo-thiophene-2-carbaldehyde (5 g, 26.17 mmol) in ethanol (100 mL) was reacted with nitro methane (1.4 mL, 26.17 mmol) and 10N NaOH (1.4 mL, 27.47 mmol) to afford 3 g of the product (48.99% yield).

$^1$H NMR (CDCl$_3$, 300 MHz): δ 8.04 (d, 1H), 7.38 (d, 1H), 7.31-7.06 (m, 2H)

Step 2: Preparation of Intermediate 2-(5-Bromo-thiophen-2-yl)-ethylamine (I-14b)

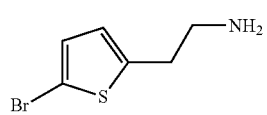

Dry THF (30 mL) and chloro trimethyl silane (12.42 mL, 98.24 mmol) were added dropwise to LiBH$_4$ (1.128 g, 51.28 mmol) over a period of 10 minutes under nitrogen atmosphere. This was followed by dropwise addition of 2-bromo-5-(2-nitro-vinyl)-thiophene (I-14a: 3 g, 12.82 mmol) in dry THF (30 mL) over a period of 20 minutes and the resulting mixture was stirred at room temperature for 48 hours. The reaction was monitored by TLC (10% methanol in CHCl$_3$). The reaction mixture was quenched with methanol and concentrated to afford 6.2 g of the crude product which was used in the next step without further purification.

$^1$H NMR (DMSO-D$_6$, 300 MHz): δ 9.0-8.5 (br s, 2H), 7.0 (d, 1H), 6.8 (d, 1H), 3.28-3.06 (m, 2H), 3.02-2.82 (m, 2H)

Step 3: Preparation of Intermediate [2-(5-Bromo-thiophen-2-yl)-ethyl]-carbamic acid ethyl ester (I-14c)

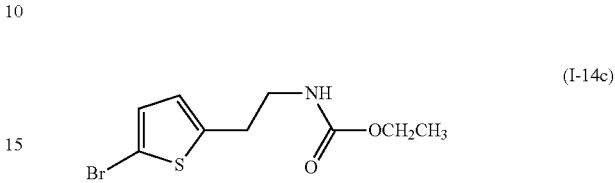

Using the same procedure and workup as described in Example 1, step 3, 2-(5-bromo-thiophen-2-yl)-ethylamine (I-14b: 2.64 g, 12.81 mmol) in DCM (30 mL) was reacted with chloro ethyl formate (1.53 mL, 16.01 mmol) and 2N Na$_2$CO$_3$ solution (30 mL) at 0° C. The resulting mixture was stirred at room temperature for 1 hour to afford the crude product. Purification by column chromatography on silica gel (10% ethylacetate in hexane) afforded 2.7 g of the product (66.17% yield).

$^1$H NMR (CDCl$_3$, 300 MHz): δ 6.88 (d, 1H), 6.58 (d, 1H), 4.95-4.61 (br s, 1H), 4.1 (q, 2H), 3.4 (q, 2H), 2.94 (t, 2H), 1.22 (t, 3H)

Step 4: Preparation of Intermediate 2-Bromo-6,7-dihydro-5H-thieno[3,2-c]pyridin-4-one (I-14d)

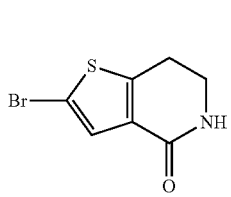

Using analogous reaction conditions and workup as described in example 1, step 4, [2-(5-bromo-thiophen-2-yl)-ethyl]-carbamic acid ethyl ester (I-14c: 2.7 g, 9.8 mmol) in POCl$_3$ (20 mL) was reacted with P$_2$O$_5$ (2.7 g, 19.64 mmol) to afford the crude product. Purification by column chromatography on silica gel (0.5% methanol in DCM) afforded 850 mg of the product (37.56% yield).

$^1$H NMR (CDCl$_3$, 300 MHz): δ 7.39 (s, 1H), 6.10-5.95 (br s, 1H), 3.76-3.52 (m, 2H), 3.0 (t, 2H)
LCMS purity: 99.14%, m/z=233.9 (M4-2)

Step 5: Preparation of Intermediate 2-(4-Fluoro-phenyl)-6,7-dihydro-5H-thieno[3,2-c]pyridin-4-one (I-14e)

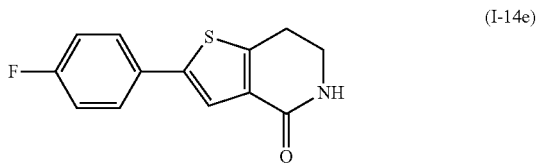 [SMILES: O=C1NCCc2sc(-c3ccc(F)cc3)cc21]

(4-Fluoro-phenyl)-dihydroxy-borane (232 mg, 1.66 mmol) was added to a stirred suspension of 2-bromo-6,7-dihydro-5H-thieno[3,2-c]pyridin-4-one (I-14d: 300 mg, 1.38 mmol) and Na$_2$CO$_3$ (211.8 mg, 2.0175 mmol) in toluene (20 mL) and water (3 mL) with continuous argon purging. This was followed by the addition of Pd(PPh$_3$)$_4$ (159 mg, 0.138 mmol) and the resulting mixture was stirred at 100° C. overnight. The reaction was monitored by TLC (50% ethylacetate in hexane). The reaction mixture was filtered; the filtrate was washed with water, dried over Na$_2$SO$_4$ and concentrated. Purification by column chromatography on silica gel (30% ethylacetate in hexane) afforded 300 mg of the product (88% yield).

LCMS purity: 94.98%, m/z=248.0 (M+1)

Preparation of 2-(4-Fluoro-phenyl)-5-(4-methyl-pyridin-3-yl)-6,7-dihydro-5H-thieno[3,2-c]pyridin-4-one (14A)

Using analogous reaction conditions as described in Example 1, 2-(4-fluoro-phenyl)-6,7-dihydro-5H-thieno[3,2-c]pyridin-4-one (I-14e: 150 mg, 0.61 mmol) was reacted with 3-iodo-4-methyl-pyridine (133 mg, 0.61 mmol), 1,4-dioxane (10 mL), copper iodide (11.6 mg, 0.061 mmol), trans-N,N'-dimethyl-cyclohexyl-1,2-diamine (25.98 mg, 0.183 mmol) and potassium phosphate (323.3 mg, 1.525 mmol) to afford the crude product which was treated with 6N HCl and filtered. The residue was washed with ethylacetate, neutralized with NaHCO$_3$ solution and extracted with ethylacetate. The organic layer was dried over Na$_2$SO$_4$ and concentrated under reduced pressure to afford 30 mg of the product (14.56% yield).

$^1$H NMR (CDCl$_3$, 300 MHz): δ 8.56-8.34 (m, 2H), 7.68-7.46 (m, 3H), 7.25 (s, 1H), 7.18-7.02 (t, 2H), 4.30-4.02 (m, 1H), 4.00-3.74 (m, 1H), 3.42-3.04 (m, 2H), 2.32 (s, 3H)

LCMS purity: 100%, m/z=339.1 (144-1)

HPLC: 86.14%

Example 15

Preparation of 3-(4-Fluoro-phenyl)-5-(4-methyl-pyridin-3-yl)-6,7-dihydro-5H-thieno[3,2-c]pyridin-4-one (15A)

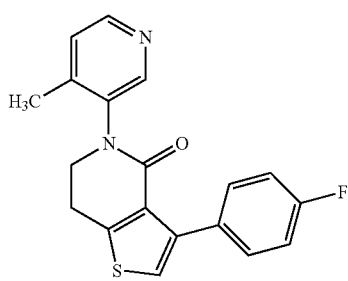

(15A)

Step 1: Preparation of Intermediate 4-Bromo-2-(2-nitro-vinyl)-thiophene (I-15a)

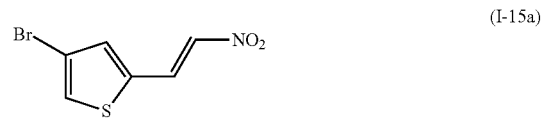 [SMILES: O=[N+]([O-])/C=C/c1cc(Br)cs1]

Using analogous reaction conditions and workup as described in Example 1, step 1,4-bromo-thiophene-2-carbaldehyde (5 g, 0.02617 mmol) in ethanol (100 mL) was reacted with nitro methane (1.7 mL, 0.0327 mmol) and 10N NaOH (1.09 g, 0.274 mmol) to afford 5 g of the product (81.9% yield).

$^1$H NMR (CDCl$_3$, 300 MHz): δ 8.04 (d, 1H), 7.52-7.40 (m, 2H), 7.34 (s, 1H)

Step 2: Preparation of Intermediate 2-(4-Bromo-thiophen-2-yl)-ethylamine (I-15b)

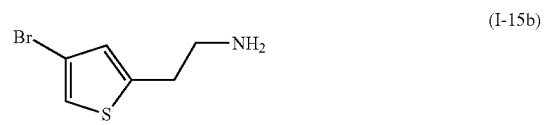

Using analogous reaction conditions and workup as described in Example 14, step 2, 4-bromo-2-(2-nitro-vinyl)-thiophene (5 g, 21.367 mmol) in dry THF (150 mL) was reacted with LiBH$_4$ (1.86 g, 85.470 mmol), chloro trimethyl silane (21.6 mL, 170.576 mmol) to afford 4.4 g of the crude product which was used in the next step without further purification.

Step 3: Preparation of Intermediate [2-(4-Bromo-thiophen-2-yl)-ethyl]-carbamic acid ethyl ester (I-15c)

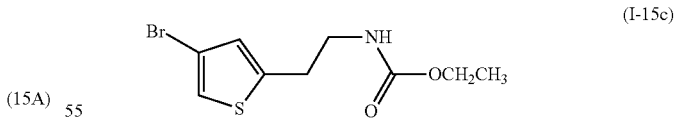

Using the same procedure and workup as described in Example 1, step 3, 2-(4-bromo-thiophen-2-yl)-ethylamine (I-15b: 4.4 g, 0.02125 mmol) in chloroform (50 mL) was reacted with chloro ethyl formate (2.1 mL, 0.0265 mmol) and 2N Na$_2$CO$_3$ solution (50 mL). The resulting mixture was stirred at room temperature for 4 hours to afford the crude product. Purification by column chromatography on silica gel (10% ethylacetate in hexane) afforded 5.5 g of the product (93% yield).

LCMS purity: 96.99%, m/z=277.8 (M+1)

Step 4: Preparation of Intermediate 3-Bromo-6,7-dihydro-5H-thieno[3,2-c]pyridin-4-one (I-15d)

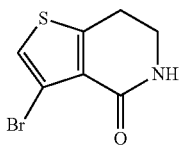
(I-15b)

Using analogous reaction conditions and workup as described in Example 1, step 4, [2-(4-bromo-thiophen-2-yl)-ethyl]-carbamic acid ethyl ester (I-15c: 6 g, 21.73 mmol) in POCl$_3$ (60 mL) was reacted with P$_2$O$_5$ (6.217 g, 43.782 mmol) to afford the crude product. Purification by column chromatography on silica gel (2% methanol in CHCl$_3$) afforded 2.6 g of the product (52% yield).

$^1$H NMR (CDCl$_3$, 300 MHz): δ 7.1 (s, 1H), 6.3-5.8 (br s, 1H), 3.72-3.52 (m, 2H), 3.06 (t, 2H)

Step 5: Preparation of Intermediate 3-(4-Fluoro-phenyl)-6,7-dihydro-5H-thieno[3,2-c]pyridin-4-one (I-15c)

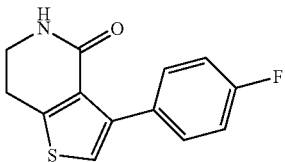
(I-15c)

Using analogous reaction conditions and workup as described in Example 3, step 5, 3-bromo-6,7-dihydro-5H-thieno[3,2-c]pyridin-4-one (I-15b: 300 mg, 1.293 mmol) was reacted with (4-fluoro-phenyl)-dihydroxy-borane (217.11 mg, 1.55 mmol), Pd(PPh$_3$)$_4$ (149.4 mg, 0.1293 mmol), toluene (20 mL) and water (3 mL) to afford the crude product. Purification by column chromatography on silica gel (2% methanol in CHCl$_3$) afforded 300 mg of the product (47.02% yield).

LCMS purity: 100%, m/z=247.8 (M+1)

Preparation of 3-(4-Fluoro-phenyl)-5-(4-methyl-pyridin-3-yl)-6,7-dihydro-5H-thieno[3,2-c]pyridin-4-one (15A)

Using analogous reaction conditions as described in Example 1, 3-(4-fluoro-phenyl)-6,7-dihydro-5H-thieno[3,2-c]pyridin-4-one (I-15c: 150 mg, 0.61 mmol) was reacted with 3-iodo-4-methyl-pyridine (133 mg, 0.61 mmol), 1,4-dioxane (10 mL), copper iodide (11.6 mg, 0.061 mmol), trans-N,N'-dimethyl-cyclohexyl-1,2-diamine (25.98 mg, 0.183 mmol) and potassium phosphate (323.3 mg, 1.525 mmol) to afford the crude product. Purification by column chromatography on silica gel (1% methanol in CHCl$_3$) afforded 35 mg of the product (17.5% yield).

$^1$H NMR (CDCl$_3$, 300 MHz): δ 8.60-8.08 (m, 2H), 7.68-7.36 (m, 2H), 7.34-6.80 (m, 4H), 4.35-4.05 (m, 1H), 4.03-3.70 (m, 1H), 3.50-3.09 (m, 2H), 2.3 (s, 3H)
LCMS purity: 98.57%, m/z=339.0 (M+1)
HPLC: 90.12%

Example 16

Preparation of 2-Pyridin-3-yl-7-trifluoromethyl-3,4-dihydro-2H-isoquinolin-1-one (16A)

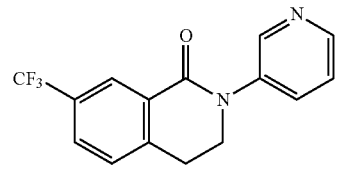
(16A)

Step 1: Preparation of Intermediate 2-(4-Trifluoromethyl-phenyl)-ethylamine (I-16a)

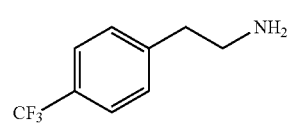
(I-16a)

(4-Trifluoromethyl-phenyl)-acetonitrile (2 g, 10.81 mmol) in methanolic ammonia (50 mL) was added to Raney nickel (400 mg) in methanol taken in a parr hydrogenator. The flask was stirred at 50 PSI overnight. The reaction was monitored by TLC (10% methanol in CHCl$_3$). The reaction mixture was filtered through celite bed and the filtrate was dried under reduced pressure to afford 2 g of the product (97.89% yield).

LCMS purity: 98.73%, m/z=190.0 (M+1)

Step 2: Preparation of Intermediate [2-(4-Trifluoromethyl-phenyl)-ethyl]-carbamic acid ethyl ester (I-16b)

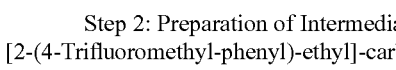
(I-16b)

Using the same procedure and workup as described in Example 1, step 3, 2-(4-trifluoromethyl-phenyl)-ethylamine (I-16a: 2 g, 10.58 mmol) in chloroform (20 mL) was reacted with chloro ethyl formate (1.37 g, 12.698 mmol) and 2N Na$_2$CO$_3$ solution (20 mL) at 0° C. The resulting mixture was stirred at room temperature for 30 minutes to afford 2.7 g of the product (97.79% yield).

$^1$H NMR (DMSO-D$_6$, 300 MHz): δ 7.78-7.56 (m, 2H), 7.56-7.34 (m, 2H), 7.2 (t, 1H), 3.95 (q, 2H), 3.23 (q, 2H), 2.8 (t, 2H), 1.1 (t, 3H)

Step 3: Preparation of Intermediate 7-Trifluoromethyl-3,4-dihydro-2H-isoquinolin-1-one (I-16c)

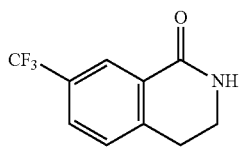
(I-16c)

Using the same procedure and workup as described in Example 1, step 4, [2-(4-trifluoromethyl-phenyl)-ethyl]-carbamic acid ethyl ester (I-16b: 2.7 g, 10.340 mmol) in POCl$_3$ (15 mL) was reacted with P$_2$O$_5$ (2.92 g, 20.69 mmol). The resulting mixture was stirred at 105° C. for 2 hours to afford the crude product. Purification by column chromatography on silica gel (2% methanol in DCM) afforded 450 mg of the product (20.24% yield).

Preparation of 2-Pyridin-3-yl-7-trifluoromethyl-3,4-dihydro-2H-isoquinolin-1-one (16A)

Using analogous reaction conditions as described in Example 1, 7-trifluoromethyl-3,4-dihydro-2H-isoquinolin-1-one (I-16c: 150 mg, 0.698 mmol) was reacted with 3-bromo-pyridine (220 mg, 1.395 mmol), 1,4-dioxane (10 mL), copper iodide (13.29 mg, 0.0698 mmol), trans-N,N'-dimethyl-cyclohexyl-1,2-diamine (29.33 mg, 0.209 mmol) and potassium phosphate (369.9 mg, 1.745 mmol) to afford the crude product. Purification by column chromatography on silica gel (1.5% methanol in DCM) afforded 45 mg of the product (22.05% yield).

$^1$H NMR (CDCl$_3$, 300 MHz): δ 8.82-8.60 (br s, 1H), 8.6-8.3 (m, 2H), 7.90-7.61 (m, 2H), 7.5-7.3 (m, 2H), 4.08 (t, 2H), 3.25 (t, 2H),
LCMS purity: 97.93%, m/z=292.8 (M+1)
HPLC: 95.2%

Example 17

Preparation of 2-(4-Methyl-pyridin-3-yl)-6-trifluoromethyl-3,4-dihydro-2H-Isoquinolin-1-one (17A)

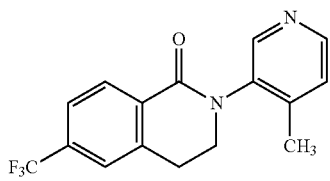
(17A)

Step 1: Preparation of Intermediate 2-(3-Trifluoromethyl-phenyl)-ethylamine (I-17a)

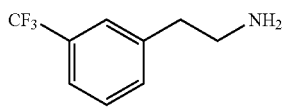
(I-17a)

Using analogous reaction conditions as described in Example 16, step 1, (3-trifluoromethyl-phenyl)-acetonitrile (2 g, 10.81 mmol) in methanolic ammonia (50 mL) was reacted with Raney nickel (400 mg) to afford 2 g of the product (97.89% yield).
LCMS: m/z=189.9 (M+2)

Step 2: Preparation of Intermediate [2-(3-Trifluoromethyl-phenyl)-ethyl]-carbamic acid ethyl ester (I-17b)

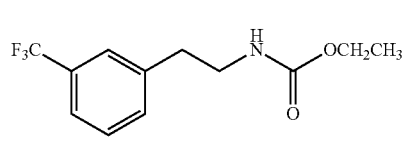
(I-17b)

Using the same procedure and workup as described in Example 1, step 3, 2-(3-trifluoromethyl-phenyl)-ethylamine (I-17a: 2 g, 10.58 mmol) in chloroform (25 mL) was reacted with chloro ethyl formate (1.37 g, 12.698 mmol) and 2N Na$_2$CO$_3$ solution (20 mL) at 0° C. The resulting mixture was stirred at room temperature for 30 minutes to afford 2.7 g of the product (97.79% yield).

$^1$H NMR (DMSO-D$_6$, 300 MHz): δ 7.70-7.42 (m, 4H), 7.2 (t, 1H), 3.92 (q, 2H), 3.22 (q, 2H), 2.8 (t, 2H), 1.1 (t, 3H)

Step 3: Preparation of Intermediate 6-Trifluoromethyl-3,4-dihydro-2H-isoquinolin-1-one (I-17c)

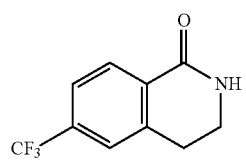
(I-17c)

Using the same procedure and workup as described in Example 1, step 4, [2-(3-trifluoromethyl-phenyl)-ethyl]-carbamic acid ethyl ester (I-17b: 2.7 g, 10.34 mmol) in POCl$_3$ (15 mL) was reacted with P$_2$O$_5$ (2.9 g, 20.68 mmol). The resulting mixture was stirred at 105° C. for 2 hours to afford the crude product. Purification by column chromatography on silica gel (1.5% methanol in DCM) afforded 350 mg of the product (15.74% yield).

$^1$H NMR (DMSO-D$_6$, 300 MHz): δ 7.63-7.40 (m, 3H), 5.9 (t, 1H), 3.22 (q, 2H), 2.65 (t, 2H)

Preparation of 2-(4-Methyl-pyridin-3-yl)-6-trifluoromethyl-3,4-dihydro-2H-isoquinolin-1-one (17A)

Using analogous reaction conditions as described in Example 1, 6-trifluoromethyl-3,4-dihydro-2H-isoquinolin-1-one (I-17c: 150 mg, 0.698 mmol) was reacted with 3-iodo-4-methyl-pyridine (152.8 mg, 0.698 mmol), 1,4-dioxane (10 mL), copper iodide (13.3 mg, 0.0698 mmol), trans-N,N'-dimethyl-cyclohexyl-1,2-diamine (29.73 mg, 0.209 mmol) and potassium phosphate (369.94 mg, 1.745 mmol) to afford the crude product. Purification by column chromatography on silica gel (1.5% methanol in DCM) afforded 20 mg of the product (9.38% yield).

$^1$H NMR (CDCl$_3$, 300 MHz): δ 8.58-8.40 (br s, 2H), 8.26 (d, 1H), 7.66 (d, 1H), 7.56 (s, 1H), 7.3 (m, 1H), 4.20-3.96 (m, 1H), 3.93-3.71 (m, 1H), 3.40-3.13 (m, 2H), 2.3 (s, 3H)
LCMS purity: 73.88%, m/z=307.0 (M+1)
HPLC: 87.41%

Example 18

Preparation of 2-(5-Fluoro-pyridin-3-yl)-7-trifluoromethyl-3,4-dihydro-2H-isoquinolin-1-one (18A)

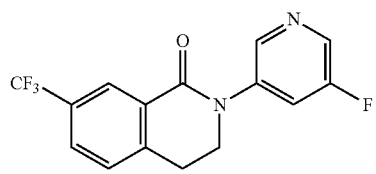

(18A)

Using analogous reaction conditions as described in Example 1, 7-trifluoromethyl-3,4-dihydro-2H-isoquinolin-1-one (I-16c: 90 mg, 0.419 mmol) was reacted with 3-bromo-5-fluoro-pyridine (73.67 mg, 0.419 mmol), 1,4-dioxane (10 mL), copper iodide (7.98 mg, 0.0419 mmol), trans-N,N'-dimethyl-cyclohexyl-1,2-diamine (17.85 mg, 0.126 mmol) and potassium phosphate (222 mg, 1.048 mmol) to afford the crude product. Purification by column chromatography on silica gel (0.5% methanol in DCM) afforded 35 mg of the product (27.19% yield).

$^1$H NMR (CDCl$_3$, 300 MHz): δ 8.7-8.2 (m, 3H), 7.85-7.39 (m, 3H), 4.1 (t, 2H), 3.23 (t, 2H),

LCMS purity: 84.45%, m/z=311.0 (M+1)

HPLC: 91.17%

Example 19

Preparation of 7-Trifluoromethyl-3,4-dihydro-[2,4']biisoquinolinyl-1-one (19A)

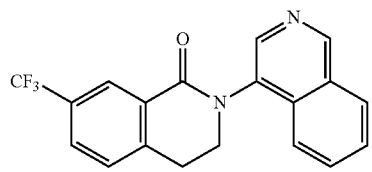

(19A)

Using analogous reaction conditions as described in Example 1, 7-trifluoromethyl-3,4-dihydro-2H-isoquinolin-1-one (I-16c: 150 mg, 0.698 mmol) was reacted with 4-bromo-isoquinoline (145 mg, 0.698 mmol), 1,4-dioxane (10 mL), copper iodide (13.29 mg, 0.0698 mmol), trans-N,N'-dimethyl-cyclohexyl-1,2-diamine (29.74 mg, 0.209 mmol) and potassium phosphate (369.94 mg, 1.745 mmol) to afford the crude product. Purification by column chromatography on silica gel (1.5% methanol in DCM) afforded 25 mg of the product (10.50% yield).

$^1$H NMR (CDCl$_3$, 300 MHz): δ 9.45-9.13 (br s, 1H), 8.71-8.31 (m, 2H), 8.1 (d, 1H), 7.95-7.40 (m, 5H), 4.30-4.09 (m, 1H), 4.08-3.90 (m, 1H), 3.55-3.21 (m, 2H)

LCMS purity: 100%, m/z=343.1 (M+1)

HPLC: 89.17%

Example 20

Preparation of 4,4-Dimethyl-2-(4-methyl-pyridin-3-yl)-7-trifluoromethyl-3,4-dihydro-2H-isoquinolin-1-one (20A)

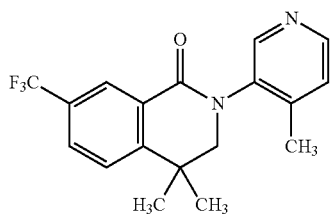

(20A)

Step 1: Preparation of Intermediate 2-Methyl-2-(4-trifluoromethyl-phenyl)-propionitrile (I-20a)

(I-20a)

(4-Trifluoromethyl-phenyl)-acetonitrile (1 g, 5.4010 mmol) in DMF (8.1 mL) was added to a stirred mixture of NaH (518.49 mg, 21.604 mmol) in DMF (8.1 mL) at 0° C. This was followed by the addition of methyl iodide (3.3 mL, 54.0102 mmol) and the resulting mixture was heated to 80° C. for 3 hours. The reaction was monitored by TLC (10% ethylacetate in hexane). The reaction mixture was diluted with cold water and extracted with diethyl ether. The organic layer was washed with brine solution, dried over Na$_2$SO$_4$ and concentrated to afford 1.2 g of the crude product which was used in the next step without further purification.

$^1$H NMR (CDCl$_3$, 300 MHz): δ 7.80-7.49 (m, 4H), 1.8 (s, 6H)

Step 2: Preparation of Intermediate 2-Methyl-2-(4-trifluoromethyl-phenyl)-propylamine (I-20b)

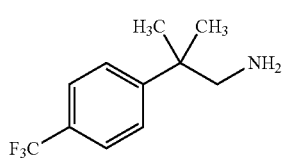

(I-20b)

Using analogous reaction conditions as described in Example 16, step 1, 2-methyl-2-(4-trifluoromethyl-phenyl)-propionitrile (I-20a: 1.2 g, 5.6338 mmol) in methanolic ammonia (10 mL) was reacted with to Raney nickel (200 mg) to afford 1.3 g of the crude product which was used in the next step without further purification.

¹H NMR (DMSO-D₆, 300 MHz): δ 7.90-7.35 (m, 4H), 2.65 (s, 2H), 1.22 (s, 6H).
LCMS purity: 99.43%, m/z=218.1 (M+1)

Step 3: Preparation of Intermediate [2-Methyl-2-(4-trifluoromethyl-phenyl)-propyl]-carbamic acid ethyl ester (I-20c)

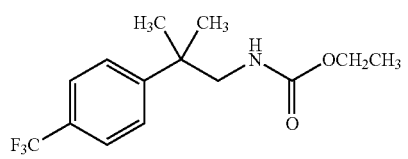

(I-20c)

Using the same procedure and workup as described in Example 1, step 3, 2-methyl-2-(4-trifluoromethyl-phenyl)-propylamine (I-20b: 1.3 g, 5.9907 mmol) in chloroform (10 mL) was reacted with chloro ethyl formate (690.3 mL, 7.1884 mmol) and 2N Na₂CO₃ solution (5 mL) at 0° C. The resulting mixture was stirred at 0° C. for 1 hour to afford the crude product. Purification by column chromatography on silica gel (10% ethylacetate in hexane) afforded 1.1 g of the product (64.7% yield).
¹H NMR (CDCl₃, 300 MHz): δ 7.76-7.36 (m, 4H), 4.55-4.26 (br s, 1H), 4.05 (q, 2H), 3.4 (d, 2H), 1.35 (s, 6H), 1.2 (t, 3H)
LCMS purity: 99.38%, m/z=290.0 (M+1)

Step 4: Preparation of Intermediate 4,4-Dimethyl-7-trifluoromethyl-3,4-dihydro-2H-isoquinolin-1-one (I-20d)

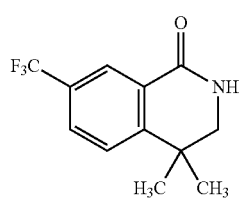

(I-20d)

Using the same procedure and workup as described in Example 1, step 4, [2-methyl-2-(4-trifluoromethyl-phenyl)-propyl]-carbamic acid ethyl ester (I-20c: 1.1 g, 3.8062 mmol) in POCl₃ (8 mL) was reacted with P₂O₅ (1.08 g, 7.6162 mmol) to afford the crude product. Purification by column chromatography on silica gel (1.5% methanol in DCM) afforded 360 mg of the product (33.3% yield).
¹H NMR (CDCl₃, 300 MHz): δ 7.68-7.30 (m, 3H), 3.9 (t, 1H), 3.33 (d, 2H), 1.3 (s, 6H)
LCMS purity: 82.39%, m/z=244.1 (M+1)

Preparation of 4,4-Dimethyl-2-(4-methyl-pyridin-3-yl)-7-trifluoromethyl-3,4-dihydro-2H-isoquinolin-1-one (20A)

Using analogous reaction conditions as described in Example 1, 4,4-dimethyl-7-trifluoromethyl-3,4-dihydro-2H-isoquinolin-1-one (I-20d: 200 mg, 0.8230 mmol) was reacted with 3-bromo-4-methyl-pyridine (91.9 mL, 0.8230 mmol), 1,4-dioxane (3 mL), copper iodide (15.6 mg, 0.0823 mmol), trans-N,N'-dimethyl-cyclohexyl-1,2-diamine (38.8 mL, 0.2469 mmol) and potassium phosphate (436.1 mg, 2.0575 mmol) to afford the crude product. Purification by column chromatography on silica gel (50% ethylacetate in hexane) afforded 15 mg of the product (5.44% yield).
¹H NMR (CDCl₃, 300 MHz): δ 8.6-8.34 (m, 3H), 7.9-7.7 (m, 1H), 7.53 (d, 1H), 7.38-7.14 (m, 1H), 3.7 (q, 2H), 2.31 (s, 3H), 1.53 (s, 3H), 1.48 (s, 3H)
LCMS purity: 98.09%, m/z=335.1 (M+1)
HPLC: 97.31%

Example 21

Preparation of 7-Trifluoromethyl-2-(4-trifluoromethyl-pyridin-3-yl)-3,4-dihydro-2H-isoquinolin-1-one (21A)

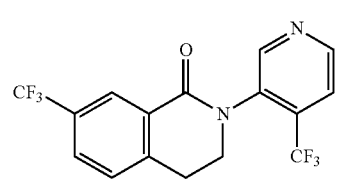

(21A)

Using analogous reaction conditions as described in Example 1, 7-trifluoromethyl-3,4-dihydro-2H-isoquinolin-1-one (I-16c: 150 mg, 0.684 mmol) was reacted with 3-bromo-4-trifluoromethyl-pyridine (154.7 mg, 0.684 mmol), 1,4-dioxane (5 mL), copper iodide (12.96 mg, 0.0684 mmol), trans-1,2-diamino cyclohexane (23.39 mg, 0.2084 mmol) and potassium phosphate (434.6 mg, 2.05 mmol) to afford the crude product. Purification by preparative HPLC afforded 16 mg of the product (6.5% yield).
¹H NMR (CDCl₃, 300 MHz): δ 8.99-8.60 (m, 2H), 8.41 (s, 1H), 7.89-7.65 (m, 2H), 7.42 (d, 1H), 4.19-3.70 (m, 2H), 3.55-3.04 (m, 2H)
LCMS purity: 99.14%, m/z=360.9 (M+1)
HPLC: 97.47%

Example 22

Preparation of 2-(4-Methyl-pyridin-3-yl)-5-trifluoromethyl-3,4-dihydro-2H-isoquinolin-1-one (22A)

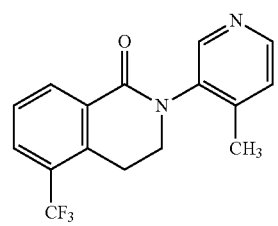

(23A)

Step 1: Preparation of Intermediate (2-Trifluoromethyl-phenyl)-acetonitrile (I-22a)

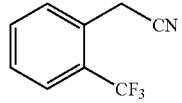
(I-22a)

A solution of 1-bromomethyl-2-trifluoromethyl-benzene (3.5 g, 14.641 mmol) in DMSO (18 mL) and sodium cyanide (1.076 g, 21.962 mmol) were taken in a flask and the flask was heated to 90° C. for 3 hours. The reaction was monitored by TLC (2% ethylacetate in hexane). The reaction mixture was partitioned between water and ethylacetate. The organic layer was washed with brine solution, dried over $Na_2SO_4$ and concentrated to afford 2.4 g of the crude product which was used in the next step without further purification.

FTIR showed the presence of CN group at 2254.10 $cm^{-1}$
$^1$H NMR (CDCl$_3$, 300 MHz): δ 7.82-7.34 (m, 4H), 4.0 (s, 2H)

Step 2: Preparation of Intermediate 2-(2-Trifluoromethyl-phenyl)-ethylamine (I-22b)

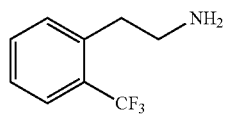
(I-22b)

Using analogous reaction conditions as described in Example 16, step 1, (2-trifluoromethyl-phenyl)-acetonitrile (I-22a: 2.4 g) in methanolic ammonia (10 mL) was reacted with Raney nickel (5 g) and methanol (30 mL) to afford 1.1 g of the product (44% yield).

$^1$H NMR (DMSO-D$_6$, 300 MHz): δ 7.76-7.28 (m, 4H), 2.98-2.62 (m, 4H), 1.6-1.3 (m, 2H)

LCMS purity: 99.66%, m/z=189.9 (M+1)

Step 3: Preparation of Intermediate [2-(2-Trifluoromethyl-phenyl)-ethyl]-carbamic acid ethyl ester (I-22c)

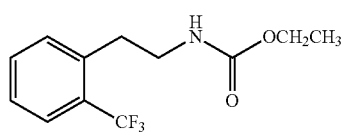
(I-22c)

Using the same procedure and workup as described in example 1, step 3, 2-(2-trifluoromethyl-phenyl)-ethylamine (1.1 g, 5.820 mmol) in chloroform (11 mL) was reacted with chloro ethyl formate (0.66 mL, 6.984 mmol) and 2N $Na_2CO_3$ solution (11 mL) at 0° C. The resulting mixture was stirred at room temperature for 2 hours to afford 1.2 g of the product (79% yield).

LCMS purity: 80.69%, m/z=261.8 (M+1)

Step 4: Preparation of Intermediate 5-Trifluoromethyl-3,4-dihydro-2H-isoquinolin-1-one (I-22d)

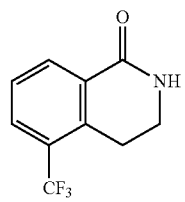
(I-22d)

Using the same procedure and workup as described in Example 1, step 4, [2-(2-trifluoromethyl-phenyl)-ethyl]-carbamic acid ethyl ester (I-22c: 1.2 g, 4.5977 mmol) in POCl$_3$ (13 mL) was reacted with P$_2$O$_5$ (1.3 g, 9.195 mmol). The resulting mixture was stirred at 115° C. for 2 hours to afford the crude product. Purification by column chromatography on silica gel (60% ethylacetate in hexane) afforded 0.090 g of the product (9.1% yield).

$^1$H NMR (CDCl$_3$, 300 MHz): δ 8.32 (d, 1H), 7.8 (d, 1H), 7.49 (t, 1H), 6.4-6.2 (br s, 1H), 3.73-3.54 (m, 2H), 3.2 (t, 2H)

LCMS purity: 100%, m/z=216.1 (M+1)

Preparation of 2-(4-Methyl-pyridin-3-yl)-5-trifluoromethyl-3,4-dihydro-2H-isoquinolin-1-one (22A)

Using analogous reaction conditions as described in Example 1, 5-trifluoromethyl-3,4-dihydro-2H-isoquinolin-1-one (I-22d: 0.090 g, 0.4186 mmol) was reacted with 3-iodo-4-methyl-pyridine (0.091 g, 0.4186 mmol), 1,4-dioxane (10 mL), copper iodide (0.007 g, 0.04186 mmol), trans-N,N'-dimethyl-cyclohexyl-1,2-diamine (0.017 g, 0.1255 mmol) and potassium phosphate (0.221 g, 1.0465 mmol) to afford the crude product. Purification by column chromatography on silica gel (60% ethylacetate in hexane) afforded 0.031 g of the product (24% yield).

$^1$H NMR (CDCl$_3$, 300 MHz): δ 8.56-8.46 (m, 2H), 8.38 (d, 1H), 7.86 (d, 1H), 7.52 (t, 1H), 7.25 (s, 1H), 4.20-3.95 (m, 1H), 3.94-3.62 (m, 1H), 3.50-3.29 (m, 2H), 2.32 (s, 3H)

LCMS purity: 81.17%, m/z=307.0 (M+1)
HPLC: 95.25%

Example 23

Preparation of 2-(4-Methyl-pyridin-3-yl)-3,4-dihydro-2H-isoquinolin-1-one (23A)

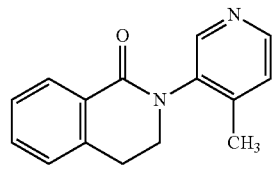
(23A)

Step 1: Preparation of Intermediate Phenethyl-carbamic acid ethyl ester (I-23a)

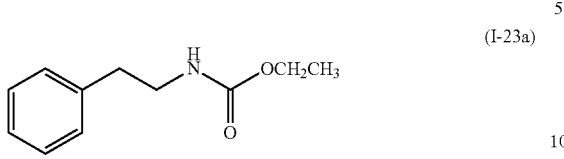

(I-23a)

Using the same procedure and workup as described in example 1, step 3, phenethylamine (7 g, 57.7653 mmol) in chloroform (60 mL) was reacted with chloro ethyl formate (6.6 mL, 69.3183 mmol) and 2N Na$_2$CO$_3$ solution (30 mL) at 0° C. The resulting mixture was stirred at room temperature for 1 hour to afford the crude product. Purification by column chromatography on silica gel (5% ethylacetate in hexane) afforded 9 g of the product (81% yield).

$^1$H NMR (CDCl$_3$, 300 MHz): δ 7.5-6.95 (m, 5H), 4.85-4.48 (br s, 1H), 4.1 (q, 2H), 3.42 (q, 2H), 2.8 (t, 2H), 1.22 (t, 3H)

Step 2: Preparation of Intermediate 3,4-Dihydro-2H-isoquinolin-1-one (I-23b)

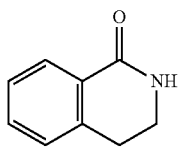

(I-23b)

Phenethyl-carbamic acid ethyl ester (I-23a: 9 g, 46.875 mmol) and poly phosphoric acid (187.5 g) were taken in a flask and the flask was heated to 120° C. for 4 hours. The reaction was monitored by TLC (30% ethylacetate in hexane). The reaction mixture was partitioned between chilled water and ethylacetate. The resulting mixture was stirred at 115° C. for 2 hours to afford the crude product. Purification by column chromatography on silica gel (60% ethylacetate in hexane) afforded 0.090 g of the product (9.1% yield).

$^1$H NMR (CDCl$_3$, 300 MHz): δ 8.16-7.92 (m, 1H), 7.56-6.80 (m, 4H), 3.70-3.46 (m, 2H), 2.96 (t, 2H)

LCMS purity: 100%, m/z=148.0 (M+1)

Preparation of 2-(4-Methyl-pyridin-3-yl)-3,4-dihydro-2H-isoquinolin-1-one (23A)

Using analogous reaction conditions as described in Example 1, 3,4-dihydro-2H-isoquinolin-1-one (I-23b: 150 mg, 1.0204 mmol) was reacted with 3-iodo-4-methyl-pyridine (223.4 mg, 1.0204 mmol), 1,4-dioxane (3 mL), copper iodide (19.4 mg, 0.1020 mmol), trans-N,N'-dimethyl-cyclohexyl-1,2-diamine (48.1 mL, 0.3061 mmol) and potassium phosphate (540.8 mg, 2.551 mmol) to afford the crude product. Purification by column chromatography on silica gel (50% ethylacetate in hexane) afforded 85 mg of the product (35% yield).

$^1$H NMR (CDCl$_3$, 300 MHz): δ 8.54-8.38 (m, 2H), 8.22-8.08 (m, 1H), 7.60-7.34 (m, 2H), 7.34-7.19 (m, 2H), 4.15-3.95 (m, 1H), 3.9-3.7 (m, 1H), 3.40-3.05 (m, 2H), 2.3 (s, 3H)

LCMS purity: 90.25%, m/z=239.1 (M+1)
HPLC: 91.99%

Example 24

Preparation of Cyclopropanecarboxylic acid [2-(4-methyl-pyridin-3-yl)-1-oxo-1,2-dihydro-isoquinolin-7-yl]-amide (24A)

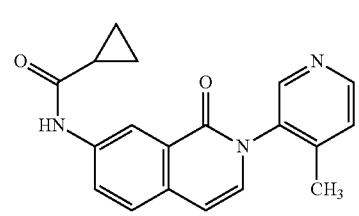

(24A)

Step 1: Preparation of Intermediate 7-Nitro-3,4-dihydro-2H-isoquinolin-1-one (I-24a)

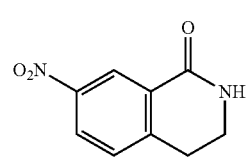

(I-24a)

KNO$_3$ (348 mg, 3.7414 mmol) was added to a solution of 3,4-dihydro-2H-isoquinolin-1-one (I-23b: 500 mg, 3.4013 mmol) in concentrated H$_2$SO$_4$ (10.2 mL) at 0° C. and the resulting mixture was stirred at room temperature for 3 hours. The reaction was monitored by TLC (80% ethylacetate in hexane). The reaction mixture was quenched in chilled water and extracted with ethylacetate. The organic layer was washed with brine solution, dried over Na$_2$SO$_4$ and concentrated. The concentrate was crystallized from diethyl ether to afford 400 mg of the product (61.2% yield).

$^1$H NMR (DMSO-D$_6$, 300 MHz): δ 8.60-8.48 (m, 1H), 8.40-8.24 (m, 2H), 7.63 (d, 1H), 3.52-3.40 (m, 2H), 3.05 (t, 2H)

Preparation of Intermediate 2-(4-Methyl-pyridin-3-yl)-7-nitro-2H-isoquinolin-1-one (I-24b)

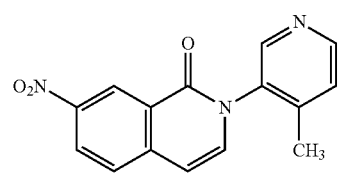

(I-24b)

Using analogous reaction conditions as described in Example 1, 7-nitro-3,4-dihydro-2H-isoquinolin-1-one (I-24a: 400 mg, 2.0833 mmol) was reacted with 3-iodo-4-methyl-pyridine (456.2 mg, 2.08331 mmol), 1,4-dioxane (4.1 mL), copper iodide (39.6 mg, 0.2083 mmol), trans-N,N'-dimethyl-cyclohexyl-1,2-diamine (88.7 mg, 0.6249 mmol) and potassium phosphate (1.1 g, 5.2082 mmol) to afford the crude product. Purification by column chromatography on silica gel (50% ethylacetate in hexane) afforded 140 mg of the product (23.9% yield).

$^1$H NMR (CDCl$_3$, 300 MHz): δ 9.40-9.22 (m, 1H), 8.76-8.42 (m, 3H), 7.74 (d, 1H), 7.5-7.1 (m, 2H), 6.71 (d, 1H), 2.22 (s, 3H)

LCMS purity: 97.75%, m/z=281.9 (M+1)

Preparation of Intermediate 7-Amino-2-(4-methyl-pyridin-3-yl)-2H-isoquinolin-1-one (I-24c)

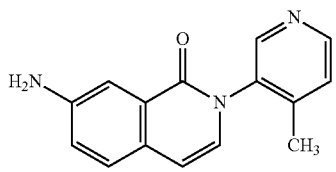

(I-24c)

10% Pd—C (20 mg) was added to a solution of 2-(4-methyl-pyridin-3-yl)-7-nitro-2H-isoquinolin-1-one (I-24b: 140 mg, 0.4982 mmol) in methanol (8 mL) under nitrogen atmosphere. The resulting mixture was hydrogenated in a Parr hydrogenator at room temperature for 3.30 hours. The reaction was monitored by TLC (5% methanol in CHCl$_3$). The reaction mixture was filtered; the filtrate was concentrated and dried to afford 100 mg of the product (79.9% yield).

$^1$H NMR (DMSO-D$_6$, 300 MHz): δ 8.62-8.37 (m, 2H), 7.57-7.30 (m, 3H), 7.19-6.92 (m, 2H), 6.55 (d, 1H), 5.64 (s, 2H), 2.1 (s, 3H)

LCMS purity: 98.54%, m/z=251.8 (M+1)

Preparation of Cyclopropanecarboxylic acid [2-(4-methyl-pyridin-3-yl)-1-oxo-1,2-dihydro-isoquinolin-7-yl]-amide (24A)

TEA (25.1 mL, 0.1792 mmol) and cyclopropanecarbonyl chloride (12 mL, 0.1314 mmol) were added to a solution of 7-amino-2-(4-methyl-pyridin-3-yl)-2H-isoquinolin-1-one (I-24c: 30 mg, 0.1195 mmol) at 0° C. The resulting reaction mixture was stirred at 0° C. for 30 minutes. The reaction was monitored by TLC (100% ethylacetate). The reaction mixture was diluted with water and extracted with ethylacetate. The organic layer was washed with brine solution, dried over Na$_2$SO$_4$ and concentrated. Purification by column chromatography on silica gel (70% ethylacetate in hexane) afforded 10 mg of the product (26.2% yield).

$^1$H NMR (CDCl$_3$, 300 MHz): δ 8.66-8.40 (m, 3H), 8.36-8.12 (m, 2H), 7.6 (d, 1H), 7.40-7.29 (m, 1H), 6.93 (d, 1H), 6.63 (d, 1H), 2.22 (s, 3H), 1.14-1.00 (m, 2H), 0.94-0.70 (m, 3H)

LCMS purity: 100%, m/z=320.0 (M+1)

HPLC: 77.8%

Example 25

Preparation of Cyclopropanecarboxylic acid [2-(4-methyl-pyridin-3-yl)-1-oxo-1,2,3,4-tetrahydro-iso-quinolin-7-yl]-amide (25A)

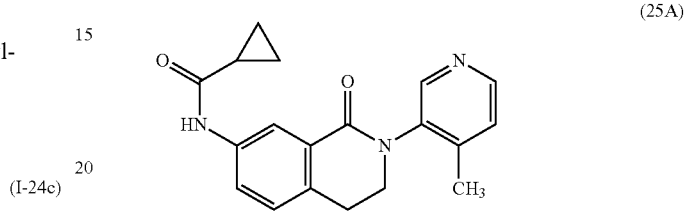

(25A)

Preparation of Intermediate 7-Amino-2-(4-methyl-pyridin-3-yl)-3,4-dihydro-2H-isoquinolin-1-one (I-25a)

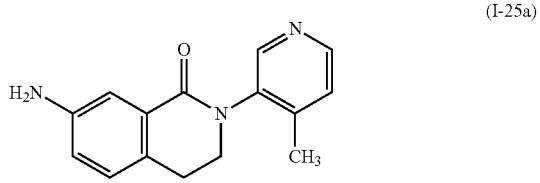

(I-25a)

Using analogous reaction conditions as described in Example 24, 2-(4-methyl-pyridin-3-yl)-7-nitro-2H-isoquinolin-1-one (I-24b: 120 mg, 0.4240 mmol) in methanol (10 mL) and acetic acid (0.1 mL) was reduced using Pd/C (40 mg) at 50 PSI in a Parr hydrogenator at room temperature for 3.30 hours.

LCMS purity: 93.95%, m/z=254.1 (M+1)

Preparation of Cyclopropanecarboxylic acid [2-(4-methyl-pyridin-3-yl)-1-oxo-1,2,3,4-tetrahydro-iso-quinolin-7-yl]-amide (25A)

Using analogous reaction conditions as described in Example 24, 7-amino-2-(4-methyl-pyridin-3-yl)-3,4-dihydro-2H-isoquinolin-1-one (I-25a: 100 mg, 0.3533 mmol) in THF (5 mL) was reacted with cyclopropanecarbonyl chloride (35.5 mL, 0.3886 mmol) and TEA (74.4 mL, 0.5299 mmol) to afford the crude product. Purification by column chromatography on silica gel (80% ethylacetate in hexane), followed by preparative HPLC afforded 16 mg of the product (14% yield).

¹H NMR (CDCl₃, 300 MHz): δ 8.75 (s, 1H), 8.56-8.36 (m, 2H), 8.3 (d, 1H), 8.06-7.85 (d, 1H), 7.35-7.25 (m, 2H), 4.05-3.69 (m, 2H), 3.15 (t, 2H), 2.3 (s, 3H), 1.08-0.76 (m, 3H), 0.72-0.50 (m, 2H)

LCMS purity: 97.38%, m/z=322.1 (M+1)

HPLC: 98.54%

Example 26

Preparation of 7-Methoxy-2-(4-methyl-pyridin-3-yl)-3,4-dihydro-2H-isoquinolin-1-one (26A)

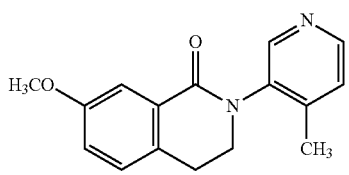

(26A)

Step 1: Preparation of Intermediate [2-(4-Methoxy-phenyl)-ethyl]-carbamic acid ethyl ester (I-26a)

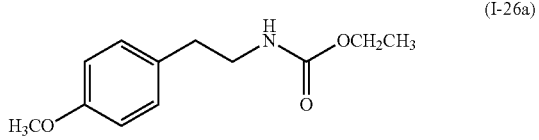 [SMILES: CCOC(=O)NCCc1ccc(OC)cc1]

(I-26a)

Using the same procedure and workup as described in Example 1, step 3, 2-(4-methoxy-phenyl)-ethylamine (5 g, 33.11 mmol) in chloroform (64 mL) was reacted with chloro ethyl formate (4.31 g, 39.73 mmol) and 2N Na₂CO₃ solution (64 mL) at 0° C. The resulting mixture was stirred at room temperature for 30 minutes to afford 6.5 g of the product (94% yield).

¹H NMR (CDCl₃, 300 MHz): δ 7.26-7.00 (m, 2H), 6.96-6.74 (m, 2H), 4.8-4.5 (br s, 1H), 4.1 (q, 2H), 3.8 (s, 3H), 3.4 (q, 2H), 2.75 (t, 2H), 1.21 (t, 3H)

Step 2: Preparation of Intermediate 7-Methoxy-3,4-dihydro-2H-isoquinolin-1-one (I-26b)

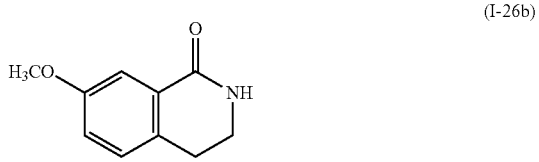 [SMILES: COc1ccc2c(c1)C(=O)NCC2]

(I-26b)

Using the same procedure and workup as described in Example 1, step 4, [2-(4-methoxy-phenyl)-ethyl]-carbamic acid ethyl ester (I-26a: 3 g, 13.452 mmol) in POCl₃ (30 mL) was reacted with P₂O₅ (3.793 g, 26.905 mmol). The resulting mixture was stirred at 110° C. for 1 hour to afford the crude product. Purification by column chromatography on silica gel (40% ethylacetate in hexane) afforded 400 mg of the product (16.8% yield).

¹H NMR (CDCl₃, 300 MHz): δ 7.69-7.54 (d, 1H), 7.2-7.1 (m, 1H), 7.09-6.98 (m, 1H), 6.15-5.95 (br s, 1H), 3.86 (s, 3H), 3.62-3.50 (m, 2H), 2.94 (t, 2H)

Preparation of 7-Methoxy-2-(4-methyl-pyridin-3-yl)-3,4-dihydro-2H-isoquinolin-1-one (26A)

Using analogous reaction conditions as described in Example 1, 7-methoxy-3,4-dihydro-2H-isoquinolin-1-one (I-26b: 400 mg, 2.259 mmol) was reacted with 3-iodo-4-methyl-pyridine (495 mg, 2.259 mmol), 1,4-dioxane (25 mL), copper iodide (43 mg, 0.225 mmol), trans-N,N'-dimethyl-cyclohexyl-1,2-diamine (96.23 mg, 0.677 mmol) and potassium phosphate (1.197 g, 5.647 mmol) to afford the crude product. Purification by column chromatography on silica gel (40% ethylacetate in hexane) afforded 170 mg of the product (23% yield).

¹H NMR (CDCl₃, 300 MHz): δ 8.54-8.40 (m, 2H), 7.66 (d, 1H), 7.24-7.14 (m, 2H), 7.1-7.0 (m, 1H), 4.12-3.92 (m, 1H), 3.87 (s, 3H), 3.81-3.65 (m, 1H), 3.30-2.95 (m, 2H), 2.32 (s, 3H)

LCMS purity: 97.33%, m/z=269.1 (M+1)

HPLC: 98.14%

Example 27

Preparation of 7-Hydroxy-2-(4-methyl-pyridin-3-yl)-3,4-dihydro-2H-isoquinolin-1-one (27A)

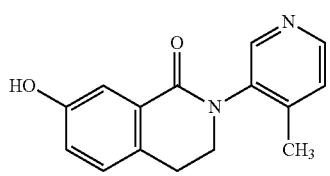

(27A)

1M solution of boran tri-bromide in DCM (0.839 mL, 0.839 mmol) was added to a stirred solution of 7-methoxy-2-(4-methyl-pyridin-3-yl)-3,4-dihydro-2H-isoquinolin-1-one (26A: 90 mg, 0.335 mmol) in DCM (3 mL) at 0° C. The resulting mixture was stirred at room temperature for 3 hours. The reaction was monitored by TLC (5% methanol in DCM). The reaction mixture was quenched with chilled water and extracted with DCM. The organic layer was washed with NaHCO₃ solution, brine solution, dried over Na₂SO₄ and concentrated. Purification by column chromatography on silica gel (3% methanol in DCM) afforded 40 mg of the product (47% yield).

¹H NMR (CDCl₃, 300 MHz): δ 8.56-8.34 (m, 2H), 7.56 (d, 1H), 7.25 (s, 1H), 7.2-7.1 (m, 1H), 7.04-6.94 (m, 1H), 4.10-3.94 (m, 1H), 3.82-3.65 (m, 1H), 3.26-2.98 (m, 2H), 2.3 (s, 3H)

LCMS purity: 97.06%, m/z=255.1 (M+1)

HPLC: 93.79%

Example 28

Preparation of 1-Ethyl-6-(4-methyl-pyridin-3-yl)-1,4,5,6-tetrahydro-pyrrolo[2,3-c]pyridin-7-one (28A)

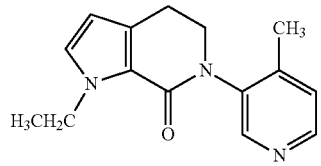

(28A)

Using similar reaction conditions as described in Example 5, 1-ethyl-1H-3-pyrrole-3-carbaldehyde was converted to 1-ethyl-1,4,5,6-tetrahydro-pyrrolo[2,3-c]pyridin-7-one. By employing analogous reaction conditions as described in Example 1, 1-ethyl-1,4,5,6-tetrahydro-pyrrolo[2,3-c]pyridin-7-one (75 mg, 0.4571 mmol) was reacted with 3-iodo-4-methyl-pyridine (100 mg, 0.457 mmol), 1,4-dioxane (5 mL), copper iodide (8.5 mg, 0.0457 mmol), trans-N,N'-dimethyl-cyclohexyl-1,2-diamine (0.021 mL, 0.137 mmol) and potassium phosphate (290 mg, 1.371 mmol) to afford the crude product. Purification by column chromatography on silica gel (1% methanol in CHCl₃) afforded 55 mg of the product (47.4% yield).

¹H NMR (CDCl₃, 300 MHz): δ 8.53-8.30 (m, 2H), 7.25-7.13 (d, 1H), 6.82 (d, 1H), 6.02 (d, 1H), 4.47-4.28 (m, 2H), 4.10-3.91 (m, 1H), 3.81-3.69 (m, 1H), 3.10-2.82 (m, 2H), 2.3 (s, 3H), 1.4 (t, 3H)

LCMS purity: 98.5%, m/z=255.9 (M+1)

HPLC: 91.47%

Example 29

Preparation of 2-(4-Methyl-pyridin-3-yl)-7-trifluoromethyl-2H-isoquinolin-1-one (29A)

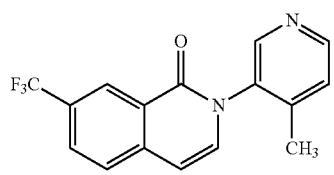

(29A)

Step 1: Preparation of Intermediate 3-(4-Trifluoromethyl-phenyl)-acrylic acid (I-29a)

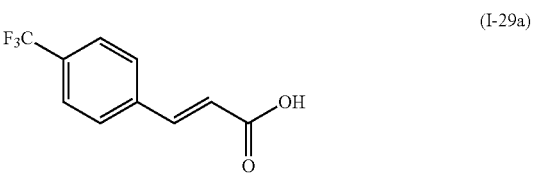 [SMILES: O=C(O)/C=C/c1ccc(C(F)(F)F)cc1]

(I-29a)

Malonic acid (3.58 g, 0.03 mol) and piperidine (0.28 mL, 0.0028 mol) were added to a solution of 4-trifluoromethyl-benzaldehyde (5 g, 0.028 mol) in pyridine (50 mL) at room temperature under nitrogen atmosphere. The resulting mixture was refluxed at 105° C. for 20 minutes under nitrogen atmosphere. The reaction was monitored by TLC (50% ethylacetate in hexane). The reaction mixture was cooled to room temperature, followed by the addition of 6N HCl and filtered. The residue was washed with n-hexane (20 mL) and dried under reduced pressure to afford 7.2 g of the crude product which was used in the next step without further purification.

¹H NMR (DMSO-D₆, 300 MHz): δ 13.00-12.21 (br s, 1H), 8.10-7.86 (m, 2H), 7.85-7.53 (m, 3H), 6.7 (d, 1H)

Step 2: Preparation of Intermediate 3-(4-Trifluoromethyl-phenyl)-acryloyl chloride (I-29b)

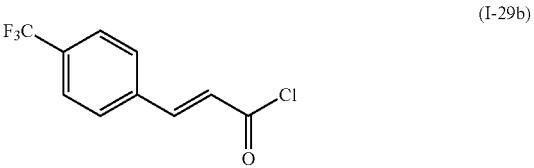 [SMILES: O=C(Cl)/C=C/c1ccc(C(F)(F)F)cc1]

(I-29b)

DMF (0.3 mL) was added to a solution of 3-(4-trifluoromethyl-phenyl)-acrylic acid (I-29a: 4 g, 0.018 mol) in DCM (30 mL). The reaction mixture was stirred at 0° C. under nitrogen atmosphere. This was followed by the addition of SOCl₂ (2.62 g, 0.022 mol) and the resulting mixture was refluxed at 75° C. for 3 hours. The reaction was monitored by TLC (30% ethylacetate in hexane). The reaction mixture was cooled to room temperature and concentrated to afford the crude product which was dissolved in 1,4-dioxane and used in the next step without further purification.

Step 3: Preparation of Intermediate 3-(4-Trifluoromethyl-phenyl)-acryloyl azide (I-29c)

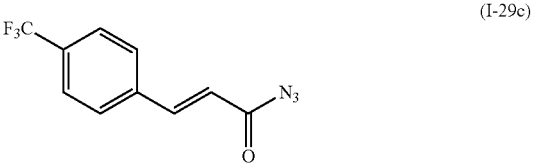 [SMILES: [N-]=[N+]=NC(=O)/C=C/c1ccc(C(F)(F)F)cc1]

(I-29c)

3-(4-Trifluoromethyl-phenyl)-acryloyl chloride (I-29b: 4.5 g, 0.019 mol) in 1,4-dioxane (20 mL) was added to a stirred mixture of sodium azide (2.7 g, 0.042 mol) in water (10 mL) at 0° C. under nitrogen atmosphere and the reaction mixture was stirred at 0° C. for 20 minutes under nitrogen atmosphere. The reaction was monitored by TLC (10% ethylacetate in hexane). The reaction mixture was partitioned between water and diethyl ether. The organic layer was washed with brine solution, dried over Na₂SO₄ and concentrated to afford 5.5 g of the crude product which was used in the next step without further purification.

Step 4: Preparation of Intermediate 7-Trifluoromethyl-2H-isoquinolin-1-one (I-29d)

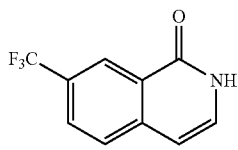

(I-29d)

3-(4-Trifluoromethyl-phenyl)-acryloyl azide (I-29c: 5.5 g, 22.82 mmol) in DCM (20 mL) was added to diphenyl ether (100 mL) refluxed at 260° C. The reaction was monitored by TLC (40% ethylacetate in hexane). The reaction mixture was cooled to room temperature and concentrated. The concentrate was partitioned between water and DCM. The organic layer was washed with brine solution, dried over Na₂SO₄ and concentrated. Purification by column chromatography on silica gel (18% ethylacetate in hexane) afforded 480 mg of the product (9.6% yield).

LCMS purity: 95.49%, m/z=214.0 (M+1)

Preparation of 2-(4-Methyl-pyridin-3-yl)-7-trifluoromethyl-2H-Isoquinolin-1-one (29A)

Using analogous reaction conditions as described in Example 1, 7-trifluoromethyl-2H-isoquinolin-1-one (I-29d: 0.15 g, 0.0007 mol) was reacted with 3-iodo-4-methyl-pyridine (0.185 g, 0.8 mmol), DMSO (30 mL), copper iodide (0.026 g, 0.00014 mol), quinolin-8-ol (0.02 g, 0.14 mmol) and potassium carbonate (0.126 g, 0.9 mmol) to afford the crude product. Purification by column chromatography on silica gel (8% ethylacetate in hexane) afforded 0.055 g of the product (23.8% yield).

¹H NMR (CDCl₃, 300 MHz): δ 8.78 (s, 1H), 8.55-8.35 (m, 2H), 8.12-7.85 (m, 3H), 7.4 (d, 1H), 7.35-7.20 (m, 1H), 2.2 (s, 3H)

LCMS purity: 93.84%, m/z=305.0 (M+1)
HPLC: 94.39%

Example 30

Preparation of 2-(4-methylpyridin-3-yl)-7-(phenylamino)-3,4-dihydroisoquinolin-1(2H)-one (30A)

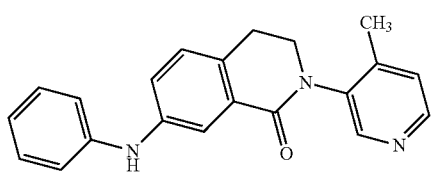

(30A)

Preparation of Intermediate 2-(4-Methyl-pyridin-3-yl)-7-nitro-3,4-dihydro-2H-isoquinolin-1-one (I-30a)

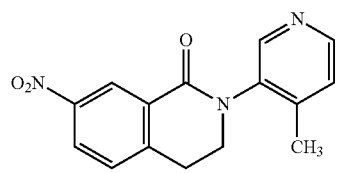

(I-30a)

Using analogous reaction conditions as described in Example 1, 7-nitro-3,4-dihydro-2H-isoquinolin-1-one (I-24a: 600 mg, 3.125 mmol) was reacted with 3-iodo-4-methyl-pyridine (684.3 mg, 3.125 mmol), 1,4-dioxane (10 mL), copper iodide (59.5 mg, 0.3125 mmol), trans-N,N'-dimethyl-cyclohexyl-1,2-diamine (147.5 mL, 0.9375 mmol) and potassium phosphate (1.65 g, 7.8125 mmol) to afford the crude product. Purification by column chromatography on silica gel (50% ethylacetate in hexane) afforded 150 mg of the product (17% yield).

¹H NMR (300 MHz, CDCl₃): δ 9.04-8.94 (d, 1H), 8.55-8.44 (m, 2H), 8.36 (dd, 1H), 7.50 (d, 1H), 7.34-7.22 (m, 1H), 4.15-4.05 (m, 1H), 3.9-3.8 (m, 1H), 3.4-3.3 (m, 2H), 2.30 (s, 3H)

LCMS: 100%, m/z=284.0 (M+1)

Preparation of Intermediate 7-Amino-2-(4-methyl-pyridin-3-yl)-3,4-dihydro-2H-isoquinolin-1-one (I-30b)

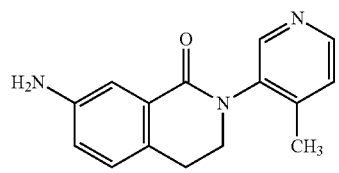

(I-30b)

Using analogous reaction conditions as described in Example 25, 2-(4-methyl-pyridin-3-yl)-7-nitro-3,4-dihydro-2H-isoquinolin-1-one (I-30a: 150 mg, 0.53 mmol) in methanol (100 mL) was reacted with 10% Pd/C (30 mg) to afford 110 mg of the product (82.02% yield).

¹H NMR (300 MHz, DMSO): δ 8.50-8.35 (m, 2H), 7.35 (d, 1H), 7.18 (d, 1H), 7.0 (d, 1H), 6.75-6.70 (dd, 1H), 5.20 (s, 2H), 3.95-3.80 (m, 1H), 3.7-3.6 (m, 1H), 3.10-2.85 (m, 2H), 2.2 (s, 3H)

LCMS: 96.15%, m/z=254.1 (M+1)

Preparation of 2-(4-Methyl-pyridin-3-yl)-7-phenylamino-3,4-dihydro-2H-isoquinolin-1-one (30A)

Palladium acetate (14.6 mg, 0.0652 mmol), BINAP (40.6 mg, 0.0652 mmol), cesium carbonate (212.4 mg, 0.06520 mmol) were dissolved in toluene (3 mL) and the resulting mixture was degassed for 10 mins at room temperature. This was followed by the addition of 7-amino-2-(4-methyl-pyridin-3-yl)-3,4-dihydro-2H-isoquinolin-1-one (110 mg, 0.4347 mol) and 3-iodo-4-methyl-pyridine (53.6 mL, 0.4782 mol) at room temperature under argon atmosphere. The resulting mixture was heated to 110° C. for 24 hours. The reaction was monitored by TLC (100% ethylacetate). The reaction mixture was filtered and the filtrate was partitioned between water and ethylacetate. The organic layer was washed with brine solution, dried over $Na_2SO_4$ and concentrated. Purification by column chromatography on silica gel (70% ethylacetate in hexane), followed by preparative HPLC afforded 22 mg of the product (15.37% yield).

$^1$H NMR (300 MHz, CDCl$_3$): δ 8.5-8.4 (m, 2H), 7.8 (d, 1H), 7.43-7.12 (m, 5H), 7.12-6.90 (m, 3H), 5.95 (s, 1H), 4.1-3.9 (m, 1H), 3.8-3.7 (m, 1H), 3.25-3.0 (m, 2H), 2.3 (s, 3H)

LCMS: 100%, m/z=329.9 (M+1)
HPLC: 98.34%

Example 31

Preparation of 7-(cyclopropylmethoxy)-2-(4-methylpyridin-3-yl)-3,4-dihydroisoquinolin-1 (2H)-one (31A)

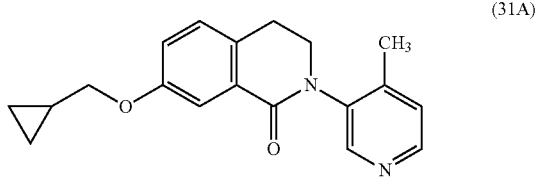 [SMILES: Cc1ccncc1N1CCc2ccc(OCC3CC3)cc2C1=O]

(31A)

7-hydroxy-2-(4-methyl-pyridin-3-yl)-3,4-dihydro-2H-isoquinolin-1-one (27A: 50 mg, 0.196 mmol) was reacted with bromomethyl-cyclopropane (32 mg, 0.236 mmol) and 60% NaH (10 mg, 0.236 mmol) in DMF (2 mL) to afford the crude product. Purification by column chromatography on silica gel (15% ethylacetate in hexane) afforded 250 mg of the product (50% yield).

$^1$H NMR (300 MHz, CDCl$_3$): δ 8.5-8.4 (m, 2H), 7.60 (d, 1H), 7.30-7.15 (m, 2H), 7.16-7.02 (m, 1H), 4.10-3.93 (m, 1H), 3.93-3.80 (d, 2H), 3.80-3.70 (m, 1H), 3.2-3.0 (m, 2H), 2.3 (s, 3H), 0.9-0.8 (m, 1H), 0.7-0.6 (m, 2H), 0.4-0.3 (m, 2H)

LCMS: 100%, m/z=309.2 (M+1)
HPLC: 90.10%

Example 32

Preparation of 2-(4-methylpyridin-3-yl)-1-oxo-1,2,3,4-tetrahydroisoquinoline-7-carbonitrile (32A)

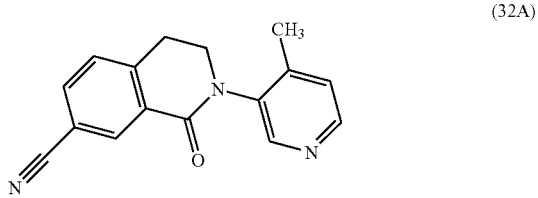 [SMILES: Cc1ccncc1N1CCc2ccc(C#N)cc2C1=O]

(32A)

Preparation of Intermediate 7-Amino-3,4-dihydro-2H-isoquinolin-1-one (I-32a)

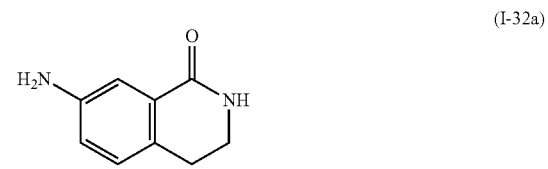 [SMILES: Nc1ccc2c(c1)C(=O)NCC2]

(I-32a)

10% Pd/C (100 mg) was added to a solution of 7-nitro-3,4-dihydro-2H-isoquinolin-1-one (I-24a: 900 mg, 4.6875 mmol) in methanol (20 mL) at room temperature under nitrogen atmosphere. The resulting mixture was hydrogenated at room temperature for 3.5 hours. The reaction was monitored by TLC (100% ethylacetate). The reaction mixture was filtered; the filtrate was concentrated and dried to afford 800 mg of the crude product which was used in the next step without further purification.

$^1$H NMR (300 MHz, DMSO): 17.85-7.63 (bs, 1H), 7.10 (d, 1H), 6.93 (d, 1H), 6.7-6.6 (dd, 1H), 5.15 (s, 2H), 3.35-3.21 (m, 2H), 2.68 (t, 2H)

LCMS: 99.94%, m/z=163.0 (M+1)

Preparation of Intermediate 7-Iodo-3,4-dihydro-2H-isoquinolin-1-one (I-32b)

(I-32b)

NaNO$_2$ (340 mg, 4.9382 mmol) was added to a solution of 7-amino-3,4-dihydro-2H-isoquinolin-1-one (I-32a: 800 mg, 4.9382 mmol) in concentrated HCl (2 mL) and water (2 mL) at 0° C. The reaction mixture was stirred at 0° C. for 15 minutes. The resulting diazonium salt solution was added portion wise to a vigorously stirred biphasic mixture of DCM (25 mL), potassium iodide (4.9 g, 29.6242 mmol), copper iodide (47 mg, 0.25 mmol) and water (8 mL). The resulting mixture was stirred at room temperature overnight. The reaction was monitored by TLC (80% ethylacetate in hexane). The reaction mixture was diluted with DCM. The organic layer was washed with 10% Na$_2$S$_2$SO$_3$ solution, dried over Na$_2$SO$_4$ and concentrated. Purification by column chromatography on silica gel (50% ethylacetate in hexane) afforded 640 mg of the product (44.50% yield).

$^1$H NMR (300 MHz, CDCl$_3$): δ 8.53-8.31 (m, 1H), 7.80-7.70 (m, 1H), 7.0 (d, 1H), 6.40-6.25 (bs, 1H), 3.70-3.51 (m, 2H), 3.0 (t, 2H)

LCMS: 100%, m/z=274.0 (M+1)

Preparation of Intermediate 1-Oxo-1,2,3,4-tetrahydro-isoquinoline-7-carbonitrile (I-32c)

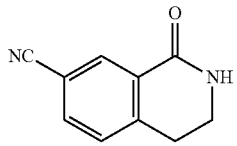
(I-32c)

7-Iodo-3,4-dihydro-2H-isoquinolin-1-one (I-32b: 200 mg, 0.7326 mmol) in DMA (1 mL) was added to a stirred solution of Pd(dba)₃ (4.02 mg, 0.0043 mmol), Zn dust (1.9 mg, 0.0293 mmol), Dppf (7.77 mg, 0.0095 mmol) in DMA (1 mL) previously degassed with argon for 15 mins. The reaction mixture was stirred for 5 mins. This was followed by the addition of Zn(CN)₂ (51.6 mg, 0.4395 mmol) and the resulting mixture was heated to 120° C. for 4 hrs. The reaction was monitored by TLC (80% ethylacetate). The reaction mixture was diluted with ethylacetate and washed with 2N NH₄OH solution. The organic layer was dried over Na₂SO₄ and concentrated. Purification by column chromatography on silica gel (70% ethylacetate in hexane) afforded 80 mg of the product (63.48% yield).

¹H NMR (300 MHz, CDCl₃): δ 8.40 (s, 1H), 7.70 (d, 1H), 7.40-7.35 (d, 1H), 6.5-6.4 (bs, 1H), 3.7-3.6 (m, 2H), 3.10 (t, 2H)

Preparation of 2-(4-Methyl-pyridin-3-yl)-1-oxo-1,2,3,4-tetrahydro-isoquinoline-7-carbonitrile (32A)

Using analogous reaction conditions as described in Example 1, 1-oxo-1,2,3,4-tetrahydro-isoquinoline-7-carbonitrile (I-32c: 120 mg, 0.6976 mmol) was reacted with 3-iodo-4-methyl-pyridine (152.7 mg, 0.6976 mmol), 1,4-dioxane (5 mL), copper iodide (13.2 mg, 0.06976 mmol), trans-N,N'-dimethyl-cyclohexyl-1,2-diamine (40 mL, 0.2092 mmol) and potassium phosphate (369.7 mg, 1.744 mmol) to afford the crude product. Purification by column chromatography on silica gel (80% ethylacetate in hexane) afforded 70 mg of the product (38.14% yield).

¹H NMR (300 MHz, CDCl₃): δ 8.55-8.40 (m, 3H), 7.86-7.70 (m, 1H), 7.43 (d, 1H), 7.25 (s, 1H), 4.1-4.0 (m, 1H), 3.90-3.76 (m, 1H), 3.38-3.20 (m, 2H), 2.3 (s, 3H)

LCMS: 98.61%, m/z=264.0 (M+1)
HPLC: 98.08%

Example 33

Preparation of 7-chloro-8-fluoro-2-(4-methylpyridin-3-yl)-3,4-dihydroisoquinolin-1(2H)-one (33A)

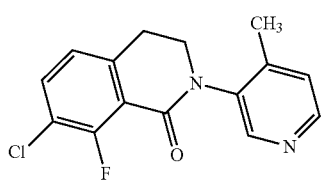
(33A)

Preparation of Intermediate 1-Chloro-2-fluoro-4-(2-nitro-vinyl)-benzene (I-33a)

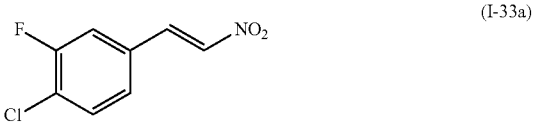 [SMILES: O=[N+]([O-])/C=C/c1ccc(Cl)c(F)c1]
(I-33a)

Using the same reaction procedure and workup as described in Example 1, 4-chloro-3-fluoro-benzaldehyde (2 g, 12.61 mmol) in ethanol (20 mL) was reacted with nitro methane (0.7 mL, 12.61 mmol), 10N NaOH solution (529 mg, 12.61 mmol) at 0° C. for 2 hours to afford 1.1 g of the product (44% yield).

¹H NMR (300 MHz, CDCl₃): δ 8.0-7.9 (d, 1H), 7.60-7.45 (m, 2H), 7.40-7.25 (m, 2H)

Preparation of Intermediate 2-(4-Chloro-3-fluoro-phenyl)-ethylamine (I-33b)

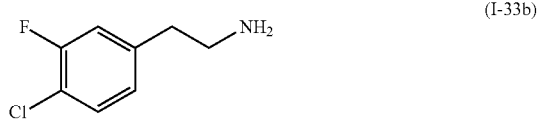 [SMILES: NCCc1ccc(Cl)c(F)c1]
(I-33b)

1-Chloro-2-fluoro-4-(2-nitro-vinyl)-benzene (I-33a: 1.1 g, 4.97 mmol) in dry THF (8 mL) was added to a stirred solution of lithium borohydride (433 mg, 19.90 mmol) and trimethylsilyl chloride (5 mL, 39.66 mmol) in dry THF (8 mL) at 0° C. The resulting mixture was stirred at room temperature for 78 hours. The reaction was monitored by TLC (10% methanol in DCM). The reaction mixture was cooled to 0° C., quenched with methanol and concentrated under reduced pressure to afford 1 g of the product (100% yield).

¹H NMR (300 MHz, DMSO): δ 7.55-7.50 (t, 1H), 7.40-7.30 (d, 1H), 7.2-7.1 (d, 1H), 3.0-2.85 (m, 4H)

LCMS: 87.44%, m/z=174.0 (M+1)

Preparation of Intermediate [2-(4-Chloro-3-fluoro-phenyl)-ethyl]-carbamic acid ethyl ester (I-33c)

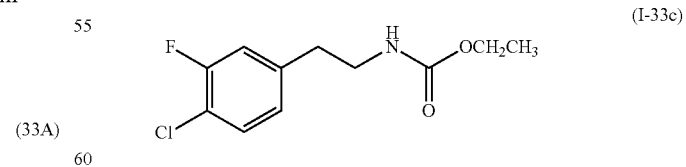
(I-33c)

Using the same reaction procedure and workup as described in Example 1, 2-(4-chloro-3-fluoro-phenyl)-ethylamine (1 g, 5.78 mmol) in chloroform (12 mL) was reacted with chloro ethyl formate (0.75 g, 6.95 mmol) and 2N Na₂CO₃ solution (12 mL) at 0° C. to afford 1.3 g of the product (92% yield).

$^1$H NMR (300 MHz, CDCl$_3$): δ 7.36-7.28 (m, 1H), 7.02-6.90 (m, 2H), 4.72-4.60 (bs, 1H), 4.12 (q, 2H), 3.50-3.35 (m, 2H), 2.8 (t, 2H), 1.23 (t, 3H)

Preparation of Intermediate 7-Chloro-8-fluoro-3,4-dihydro-2H-isoquinolin-1-one (I-33d)

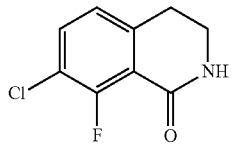

(I-33d)

Using the same reaction procedure and workup as described in example 1, [2-(4-chloro-3-fluoro-phenyl)-ethyl]-carbamic acid ethyl ester (I-33c: 1.3 g, 5.30 mmol) in POCl$_3$ (10 mL) was reacted with P$_2$O$_5$ (1.5 g, 10.60 mmol) at 110° C. for 1 hour to afford the crude product. Purification by column chromatography on silica gel (30% ethylacetate in hexane) afforded 150 mg of the product (14% yield).

LCMS: 65.71%, m/z=200.1 (M+1)

HPLC: 82.76%

Preparation of 7-Chloro-8-fluoro-2-(4-methyl-pyridin-3-yl)-3,4-dihydro-2H-isoquinolin-1-one (33A)

Using analogous reaction conditions as described in Example 1, 7-chloro-8-fluoro-3,4-dihydro-2H-isoquinolin-1-one (I-33d: 150 mg, 0.753 mmol) was reacted with 3-iodo-4-methyl-pyridine (165 mg, 0.73 mmol), 1,4-dioxane (10 mL), copper iodide (143 mg, 0.075 mmol), trans-N,N'-dimethyl-cyclohexyl-1,2-diamine (32 mg, 0.225 mmol) and potassium phosphate (399 mg, 1.88 mmol) to afford the crude product. Purification by column chromatography on silica gel (1% methanol in CHCl$_3$) afforded 60 mg of the product (27.6% yield).

$^1$H NMR (300 MHz, DMSO): δ 8.50 (s, 1H), 8.41 (d, 1H), 8.01 (d, 1H), 7.56 (d, 1H), 7.38 (d, 1H), 4.10-3.93 (m, 1H), 3.83-3.66 (m, 1H), 3.27-3.10 (m, 2H), 2.22 (s, 3H)

LCMS: 100%, m/z=291.3 (M+1)

HPLC: 98.09%

Example 34

Preparation of 8-chloro-7-fluoro-2-(4-methylpyridin-3-yl)-3,4-dihydroisoquinolin-1(2H)-one (34A)

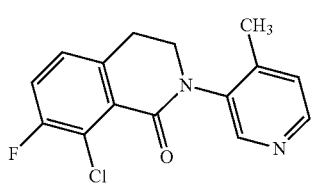

(34A)

Preparation of Intermediate 2-Chloro-1-fluoro-4-(2-nitro-vinyl)-benzene (I-34a)

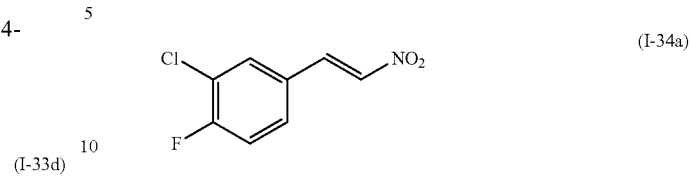

(I-34a)

Using the same reaction procedure and workup as described in Example 1, 3-chloro-4-fluoro-benzaldehyde (2 g, 12.6135 mmol) in ethanol (63 mL) was reacted with nitro methane (0.68 mL, 12.6135 mmol), 10N NaOH solution (529.7 mL, 13.2441 mmol) at 0° C. for 1 hr to afford 1.7 g of the product (67.05% yield).

$^1$H NMR (300 MHz, CDCl$_3$): δ 7.95-7.90 (d, 1H), 7.65-7.40 (m, 3H), 7.3-7.2 (m, 1H)

Preparation of Intermediate 2-(3-Chloro-4-fluoro-phenyl)-ethylamine (I-34b)

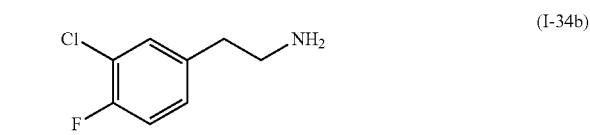 [SMILES: NCCc1ccc(F)c(Cl)c1]

(I-34b)

Using the same reaction procedure and workup as described in Example 33, 2-Chloro-1-fluoro-4-(2-nitro-vinyl)-benzene (I-34a: 1.7 g, 8.4577 mmol) in dry THF (17 mL) was reacted with lithium borohydride (736.8 mg, 33.8308 mmol) and trimethylsilyl chloride (8.6 mL, 67.6616 mmol) in dry THF (9 mL) to afford 1.3 g of the product (100% yield).

LCMS: 98.27%, m/z=174.0 (M+1)

Preparation of Intermediate [2-(3-Chloro-4-fluoro-phenyl)-ethyl]-carbamic acid ethyl ester (I-34c)

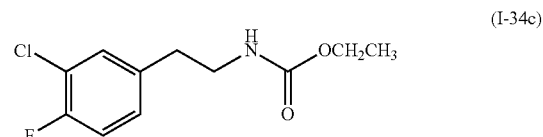

(I-34c)

Using the same reaction procedure and workup as described in Example 1, 2-(3-chloro-4-fluoro-phenyl)-ethylamine (I-34b: 1.3 g, 7.5144 mmol) in chloroform (12 mL) was reacted with chloro ethyl formate (0.918 mL, 9.0173 mmol) and 2N Na$_2$CO$_3$ solution (6 mL) at 0° C. to afford 1.3 g of the product (92% yield).

$^1$H NMR (300 MHz, CDCl$_3$): δ 7.25-7.20 (d, 1H), 7.18-7.02 (m, 2H), 4.75-4.62 (bs, 1H), 4.12 (q, 2H), 3.40 (q, 2H), 2.75 (t, 2H), 1.20 (t, 3H)

LCMS: 100%, m/z=246.0 (M+1)

Preparation of Intermediate 8-Chloro-7-fluoro-3,4-dihydro-2H-isoquinolin-1-one (I-34d)

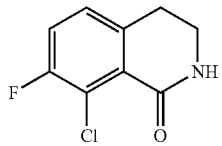
(I-34d)

Using the same reaction procedure and workup as described in Example 1, [2-(3-chloro-4-fluoro-phenyl)-ethyl]-carbamic acid ethyl ester (I-34c: 1.4 g, 5.7142 mmol) in POCl$_3$ (11.4 mL) was reacted with P$_2$O$_5$ (1.62 g, 11.4285 mmol) at 110° C. for 2 hours to afford the crude product. Purification by column chromatography on silica gel (35% ethylacetate in hexane) afforded 250 mg of the product (21.98% yield).

LCMS: 95.45%, m/z=200.1 (M+1)

Preparation of 8-Chloro-7-fluoro-2-(4-methyl-pyridin-3-yl)-3,4-dihydro-2H-isoquinolin-1-one (34A)

Using analogous reaction conditions as described in Example 1, 8-chloro-7-fluoro-3,4-dihydro-2H-isoquinolin-1-one (250 mg, 1.2562 mmol) was reacted with 3-iodo-4-methyl-pyridine (275.12 mg, 1.2562 mmol), 1,4-dioxane (10 mL), copper iodide (23.9 mg, 0.12562 mmol), trans-N,N'-dimethyl-cyclohexyl-1,2-diamine (60 mL, 0.3768 mmol) and potassium phosphate (665.7 mg, 3.1405 mmol) to afford the crude product. Purification by column chromatography on silica gel (40% ethylacetate in hexane) afforded 100 mg of the product (27.44% yield).

$^1$H NMR (300 MHz, CDCl$_3$): δ 8.50-8.40 (bs, 2H), 7.91 (d, 1H), 7.36 (d, 1H), 7.31-7.22 (m, 1H), 4.10-3.96 (m, 1H), 3.85-3.72 (m, 1H), 3.28-3.04 (m, 2H), 2.3 (s, 3H)

LCMS: 99.79%, m/z=291.0 (M+1)

HPLC: 94.67%

Example 35

Preparation of 2-(4-methylpyridin-3-yl)-7-(4-(trifluoromethyl)pyridin-2-yloxy)-3,4-dihydroisoquinolin-1(2H)-one (35C)

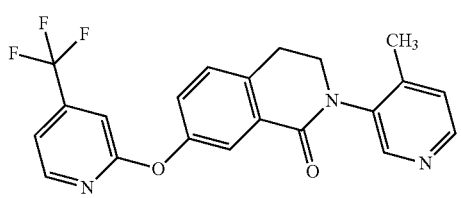
(35C)

Preparation of Intermediate [2-(4-Methoxy-phenyl)-ethyl]-carbamic acid ethyl ester (I-35a)

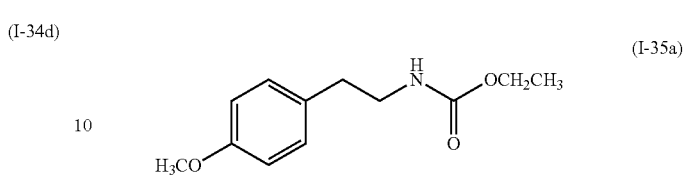
(I-35a)

Using the same reaction procedure and workup as described in Example 1, 2-(4-methoxy-phenyl)-ethylamine (10 g, 66.22 mmol) in chloroform (128 mL) was reacted with chloro ethyl formate (8.623 g, 79.47 mmol) and 2N Na$_2$CO$_3$ solution (128 mL) at 0° C. to afford 14 g of the product (95% yield).

$^1$H NMR (300 MHz, CDCl$_3$): δ 7.10 (d, 2H), 6.85 (d, 2H), 4.78-4.56 (bs, 1H), 4.10 (q, 2H), 3.80 (s, 3H), 3.51-3.21 (m, 2H), 2.74 (t, 2H), 1.2 (t, 3H)

Preparation of Intermediate 7-Methoxy-3,4-dihydro-2H-isoquinolin-1-one (I-35b)

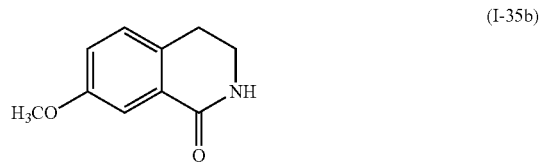 [SMILES: COc1ccc2c(c1)C(=O)NCC2]
(I-35b)

[2-(4-methoxy-phenyl)-ethyl]-carbamic acid ethyl ester (I-35a: 10 g, 44.84 mmol) was added to PPA (100 mg) at 145° C. The resulting mixture was stirred at 145° C. for 45 minutes. The reaction was monitored by TLC (50% ethylacetate in hexane). The reaction mixture was quenched with chilled water and extracted with ethylacetate. The organic layer was washed with brine solution, dried over Na$_2$SO$_4$ and concentrated. Purification by column chromatography on silica gel (40% ethylacetate in hexane) afforded 1.8 g of the product (22.69% yield).

$^1$H NMR (300 MHz, CDCl$_3$): δ 7.62-7.54 (d, 1H), 7.15-7.10 (d, 1H), 7.05-6.95 (m, 1H), 6.20-6.04 (bs, 1H), 3.85 (s, 3H), 3.6-3.5 (m, 2H), 2.94 (t, 2H)

LCMS: 100%, m/z=178.1 (M+1)

Preparation of 7-Methoxy-2-(4-methyl-pyridin-3-yl)-3,4-dihydro-2H-isoquinolin-1-one (35A)

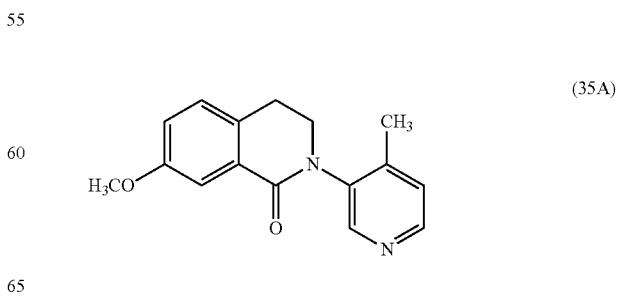
(35A)

Using analogous reaction conditions as described in Example 1, 7-methoxy-3,4-dihydro-2H-isoquinolin-1-one (I-35b: 1 g, 5.64 mmol) was reacted with 3-iodo-4-methyl-pyridine (1.237 g, 5.64 mmol), 1,4-dioxane (300 mL), copper iodide (107.4 mg, 0.564 mmol), trans-N,N'-dimethyl-cyclohexyl-1,2-diamine (240.2 mg, 1.69 mmol) and potassium phosphate (2.98 g, 141 mmol) to afford the crude product. Purification by column chromatography on silica gel (40% ethylacetate in hexane) afforded 850 mg of the product (56% yield).

$^1$H NMR (300 MHz, CDCl$_3$): δ 8.52-8.40 (bs, 2H), 7.72-7.64 (bs, 1H), 7.3-7.0 (m, 3H), 4.10-3.95 (m, 1H), 3.95-3.70 (m, 4H), 3.3-3.0 (m, 2H), 2.30 (s, 3H)

LCMS: 73.83%, m/z=269.1 (M+1)

Preparation of 7-Hydroxy-2-(4-methyl-pyridin-3-yl)-3,4-dihydro-2H-isoquinolin-1-one (35B)

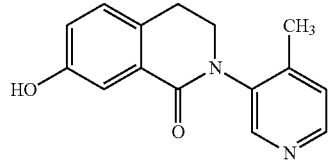

(35B)

Boran tri-bromide in DCM (10 mL) was added to a stirred solution of 7-methoxy-2-(4-methyl-pyridin-3-yl)-3,4-dihydro-2H-isoquinolin-1-one (35A: 1.1 g, 4.104 mmol) in DCM (20 mL) at 0° C. The resulting mixture was stirred at room temperature for 3 hours. The reaction was monitored by TLC (10% methanol in DCM). The reaction mixture was quenched with methanol and concentrated. The concentrate was partitioned between water and DCM. The organic layer was washed with brine solution, dried over Na$_2$SO$_4$ and concentrated. Purification by column chromatography on silica gel (3% methanol in DCM) afforded 850 mg of the product (77% yield).

$^1$H NMR (300 MHz, DMSO): δ 9.81-9.52 (bs, 1H), 8.92 (s, 1H), 8.72 (d, 1H), 7.93 (d, 1H), 7.35 (d, 1H), 7.23 (d, 1H), 7.0 (dd, 1H), 4.1-4.0 (m, 1H), 3.82-3.70 (m, 1H), 3.19 (s, 2H), 2.40 (s, 3H)

LCMS: 98.6%, m/z=255.2 (M+1)

Preparation of 2-(4-Methyl-pyridin-3-yl)-7-(4-trifluoromethyl-pyridin-2-yloxy)-3,4-dihydro-2H-isoquinolin-1-one (35C)

2-Chloro-4-trifluoromethyl-pyridine (97 mg, 0.59 mmol), KOH (26.4 mg, 0.471 mmol) and 18-crown-6-ether (156 mg, 0.59 mmol) were added to a solution of 7-hydroxy-2-(4-methyl-pyridin-3-yl)-3,4-dihydro-2H-isoquinolin-1-one (35B: 100 mg, 0.393 mmol) in toluene (3 mL). The resulting mixture was heated to 110° C. for 3 hours. The reaction was monitored by TLC (50% ethylacetate in hexane). The reaction mixture was filtered and the filtrate was concentrated to afford the crude product. Purification by column chromatography on silica gel (30% ethylacetate in hexane) afforded 20 mg of the product (12.8% yield).

$^1$H NMR (300 MHz, CDCl$_3$): δ 8.5-8.4 (bs, 2H), 8.35 (d, 1H), 7.95 (d, 1H), 7.48-7.20 (m, 5H), 42-4.0 (m, 1H), 190-3.73 (m, 1H), 3.39-3.10 (m, 2H), 2.3 (s, 3H)

LCMS: 100%, m/z=399.7 (M+1)
HPLC: 95.8%

Example 36

Preparation of 2-(pyridin-3-yl)-7-(trifluoromethyl)isoquinolin-1(2H)-one (36A)

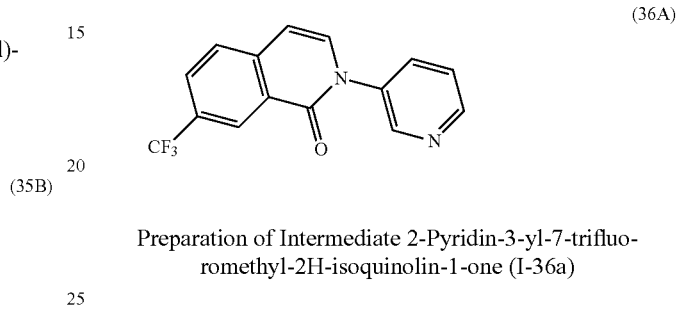

Preparation of Intermediate 2-Pyridin-3-yl-7-trifluoromethyl-2H-isoquinolin-1-one (I-36a)

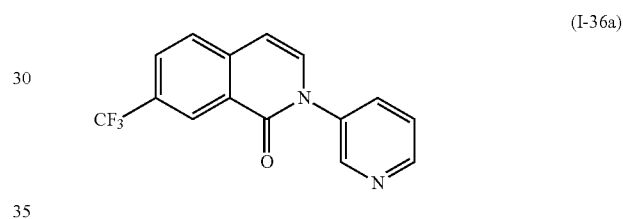

Using analogous reaction conditions as described in Example 1, 7-trifluoromethyl-2H-isoquinolin-1-one (I-29d: 0.12 g, 0.56 mmol) was reacted with 3-bromo-pyridine (0.106 g, 0.6 mmol), DMSO (2 mL), copper iodide (0.021 g, 0.12 mmol), 8-hydroxy-quinoline (0.018 g, 0.12 mmol) and potassium carbonate (0.15 g, 1.1 mmol) to afford the crude product. Purification by column chromatography on silica gel (0.5% methanol in DCM) afforded 96 mg of the product (70.58% yield).

$^1$H NMR (300 MHz, DMSO): 9.0-8.6 (m, 2H), 8.5 (s, 1H), 8.2-7.9 (m, 3H), 7.75-7.60 (m, 2H), 6.91 (d, 1H)

LCMS: 92.35%, m/z=291.0 (M+1)
HPLC: 9328%

Example 37

Preparation of 7-(5-fluoropyrimidin-2-yloxy)-2-(4-methylpyridin-3-yl)-3,4-dihydroisoquinolin-1(2H)-one (37A)

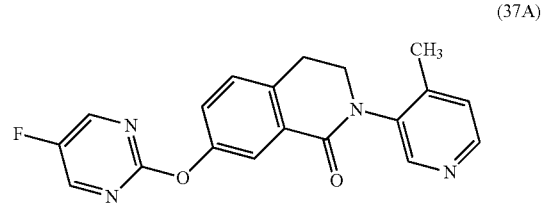 [SMILES: Cc1ccncc1N1CCc2ccc(Oc3ncc(F)cn3)cc2C1=O]

60% NaH (13 mg, 0.33 mmol) was added to a stirred solution of 7-hydroxy-2-(4-methyl-pyridin-3-yl)-3,4-dihydro-2H-isoquinolin-1-one (27A: 70 mg, 0.275 mmol) in DMF (2 mL) at 0° C. The reaction mixture was stirred at room temperature for 1 hour. This was followed by the addition of 2-chloro-5-fluoro-pyrimidine (44 mg, 0.33 mmol) at 0° C. and stirring was continued for a further 1 hour at room temperature. The reaction was monitored by TLC (5% methanol in DCM). The reaction mixture was quenched with chilled water and extracted with ethylacetate. The organic layer was washed with brine solution, dried over $Na_2SO_4$ and concentrated. Purification by column chromatography on silica gel (2% methanol in DCM) afforded 10 mg of the product (10.4% yield).

$^1$H NMR (300 MHz, $CDCl_3$): δ 8.50-8.40 (m, 3H), 7.95 (d, 1H), 7.4-7.3 (m, 2H), 7.25 (m, 2H), 4.16-4.0 (m, 1H), 3.88-3.74 (m, 1H), 3.36-3.12 (m, 2H), 2.3 (s, 3H)

LCMS: 100%, m/z=351.0 (M+1)

HPLC: 98.73%

Example 38

Preparation of 9-ethyl-2-(4-methylpyridin-3-yl)-2,3,4,9-tetrahydro-1H-pyrido[3,4-b]indol-1-one (38A)

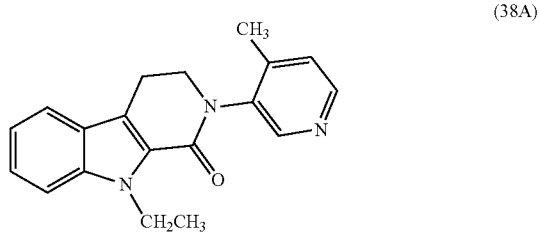 [SMILES: CCn1c2c(c3ccccc31)CCN(c1cnccc1C)C2=O]

(38A)

Preparation of Intermediate
1H-Indole-3-carbaldehyde (I-38a)

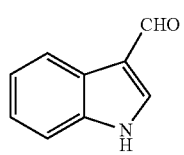

(I-38a)

1H-Indole (10 g, 85.360 mmol) in DMF (10 mL) was added dropwise to a stirred solution of $POCl_3$ (8.67 mL, 93.896 mmol) in DMF over a period of 10 minutes at 0° C. The resulting mixture was stirred at room temperature for 1 hour. The reaction was monitored by TLC (40% ethylacetate in hexane). The reaction mixture was quenched with chilled water, followed by the addition of aqueous NaOH solution and refluxed at 100° C. for 15 minutes. The reaction mixture was cooled to room temperature and maintained at 0° C. overnight. The precipitate formed was collected, washed with water and dried to afford 11.6 g of the product (94% yield).

$^1$H NMR (300 MHz, DMSO): δ 12.40-12.0 (bs, 1H), 9.93 (s, 1H), 8.30 (s, 1H), 8.1 (d, 1H), 7.5 (d, 1H), 7.30-7.20 (m, 2H)

LCMS: 100%, m/z=146.0 (M+1)

Preparation of Intermediate
1-Ethyl-1H-indole-3-carbaldehyde (I-38b)

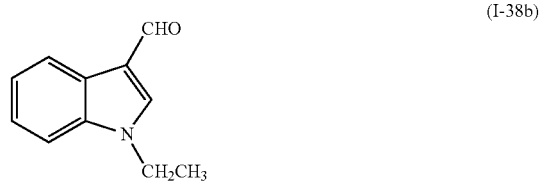 [SMILES: CCn1cc(C=O)c2ccccc21]

(I-38b)

NaH (1.51 g, 37.891 mmol) was added to a solution of 1H-indole-3-carbaldehyde (I-38a: 5 g, 34.447 mmol) in dry DMF (40 mL) at 0° C. and the reaction mixture was stirred for 5 minutes. This was followed by dropwise addition of ethyl iodide (6.45 g, 41.336 mmol) over a period of 5 mins and stirring was continued for a further 1 hr. The reaction was monitored by TLC (40% ethylacetate in hexane). The reaction mixture was quenched with chilled water and filtered. The residue was washed with water and dried to afford 5.2 g of the product (86% yield).

$^1$H NMR (300 MHz, $CDCl_3$): δ 10.0 (s, 1H), 8.3 (d, 1H), 7.79 (s, 1H), 7.4-7.2 (m, 3H), 4.25 (q, 2H), 1.60 (t, 3H)

LCMS: 100%, ink 174.0 (M+1)

Preparation of Intermediate 1-Ethyl-3-(2-nitro-vinyl)-1H-indole (I-38c)

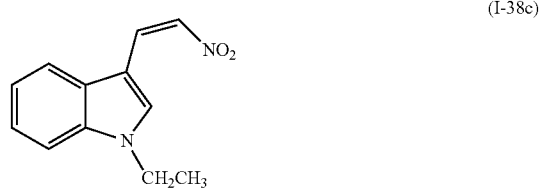 [SMILES: CCn1cc(/C=C\[N+](=O)[O-])c2ccccc21]

(I-38c)

1-Ethyl-1H-indole-3-carbaldehyde (I-38b: 5.2 g, 29.885 mmol), nitromethane (46.81 mL, 866.66 mmol) and ammonium acetate (1.17 g, 15.241 mmol) were taken in a reaction flask. The flask was refluxed for 16 hours under nitrogen atmosphere. The reaction was monitored by TLC (25% ethylacetate in hexane). The reaction mixture was cooled to room temperature and the reaction mixture was partitioned between water and ethylacetate. The organic layer was washed with water, brine solution, dried over $Na_2SO_4$ and concentrated to afford 4.8 g of the product (75% yield).

$^1$H NMR (300 MHz, $CDCl_3$): δ 8.30 (d, 1H), 7.89-7.70 (m, 2H), 7.60 (s, 1H), 7.50-7.29 (m, 3H), 4.24 (q, 2H), 1.62-1.42 (t, 3H)

LCMS: 98.73%, m/z=217.0 (M+1)

Preparation of Intermediate 2-(1-Ethyl-1H-indol-3-yl)-ethylamine (I-38d)

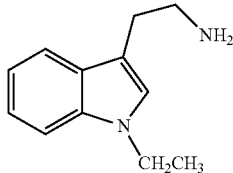

(I-38d)

Using analogous reaction conditions and workup as described in Example 1, 1-ethyl-3-(2-nitro-vinyl)-1H-indole (4.8 g, 22.018 mmol) in dry THF (25 mL) was reacted with LAH (4.17 g, 110.091 mmol) in dry THF (25 mL). The resulting mixture was refluxed for 16 hours under nitrogen atmosphere to afford 4.1 g of the product (98% yield).

$^1$H NMR (300 MHz, CDCl$_3$): δ 7.62 (d, 1H), 7.38-7.30 (d, 1H), 7.28-7.16 (m, 1H), 7.16-7.02 (t, 1H), 6.97 (s, 1H), 4.2-4.1 (q, 2H), 3.05-3.0 (t, 2H), 2.95-2.90 (t, 2H), 1.5-1.4 (t, 3H)

Preparation of Intermediate [2-(1-Ethyl-1H-indol-3-yl)-ethyl]-carbamic acid ethyl ester (I-38e)

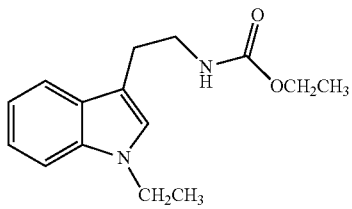

(I-38e)

2-(1-Ethyl-1H-indol-3-yl)-ethylamine (I-38d: 4.1 g, 21.578 mmol) in chloroform (40 mL) was reacted with chloro ethyl formate (2.46 mL, 25.894 mmol) and 2N Na$_2$CO$_3$ solution (40 mL) at 0° C. to afford the crude product. Purification by column chromatography on silica gel (10% ethylacetate in hexane) afforded 4.2 g of the product (72% yield).

$^1$H NMR (300 MHz, CDCl$_3$): δ 7.62 (d, 1H), 7.35 (d, 1H), 7.28-7.20 (m, 1H), 7.16-7.10 (m, 1H), 6.98 (s, 1H), 4.8-4.7 (bs, 1H), 4.20-4.10 (m, 4H), 3.60-3.40 (q, 2H), 2.98 (t, 2H), 1.48 (t, 3H), 1.24 (t, 3H)

LCMS: 71.96%, m/z=261.1 (M+1)

Preparation of Intermediate 9-Ethyl-2,3,4,9-tetrahydro-b-carbolin-1-one (I-38f)

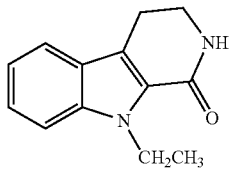

(I-38f)

[2-(1-Ethyl-1H-indol-3-yl)-ethyl]-carbamic acid ethyl ester (I-38e: 4.2 g, 16.09 mmol) in POCl$_3$ (42 mL) was reacted with P$_2$O$_5$ (4.56 g, 32.183 mmol) at 120° C. for 1 hr to afford the crude product. Purification by column chromatography on silica gel (70% ethylacetate in hexane) afforded 0.310 g of the product (9% yield).

$^1$H NMR (300 MHz, CDCl$_3$): δ 7.62 (d, 1H), 7.44-7.30 (m, 2H), 7.20-7.12 (m, 1H), 5.70-5.50 (bs, 1H), 4.69 (q, 2H), 3.70-3.60 (m, 2H), 3.08 (t, 2H), 1.40 (t, 3H)

LCMS: 95.59%, m/z=215.1 (M+1)

Preparation of 9-Ethyl-2-(4-methyl-pyridin-3-yl)-2,3,4,9-tetrahydro-b-carbolin-1-one (38A)

9-Ethyl-2,3,4,9-tetrahydro-b-carbolin-1-one (I-38f: 0.1 g, 0.4672 mmol) was reacted with 3-iodo-4-methyl-pyridine (0.102 g, 0.4672 mmol), 1,4-dioxane (15 mL), copper iodide (0.0089 g, 0.0467 mmol), trans-N,N'-dimethyl-cyclohexyl-1,2-diamine (0.019 g, 0.01401 mmol) and potassium phosphate (0.247 g, 1.168 mmol) to afford the crude product. Purification by column chromatography on silica gel (70% ethylacetate in hexane), followed by preparative HPLC afforded 0.019 g of the product (13.3% yield).

$^1$H NMR (300 MHz, CDCl$_3$): δ 8.55-8.40 (m, 2H), 7.65 (d, 1H), 7.52-7.33 (m, 2H), 7.32-7.12 (m, 2H), 4.78-4.58 (m, 2H), 4.20-4.10 (m, 1H), 4.0-3.8 (m, 1H), 3.32-3.19 (m, 2H), 2.32 (s, 3H), 1.4 (t, 3H)

LCMS: 100%, m/z=306.0 (M+1)
HPLC: 95.19%

Example 39

Preparation of 8-(cyclopropylmethylamino)-7-fluoro-2-(4-methylpyridin-3-yl)-3,4-dihydroisoquinolin-1(2H)-one, acetate salt (39A)

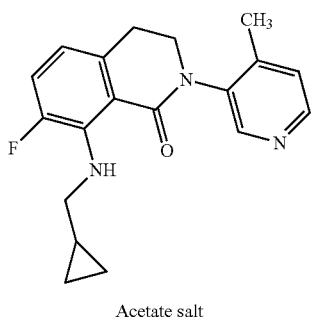

(39A)

Acetate salt

Palladium acetate (0.58 mg, 0.0025 mmol), X-Phos (3.69 g, 0.0077 mmol), t-BuOH (0.66 g, 0.005 mol) and water were taken in a sealed tube under argon atmosphere. The reaction mixture was heated to 80° C. for 1 minute. This was followed by the addition of K$_2$CO$_3$ (49.9 mg, 0.3620 mmol), 8-chloro-7-fluoro-2-(4-methyl-pyridin-3-yl)-3,4-dihydro-2H-isoquinolin-1-one (34A: 75 mg, 0.2586 mmol) and C-cyclopropyl-methylamine (22 mg, 0.3103 mmol) under argon atmosphere. The resulting mixture was refluxed at 110° C. for 1 hour. The reaction was monitored by TLC (100% ethylacetate). The reaction mixture was partitioned between water and ethylacetate. The organic layer was washed with brine solution, dried over Na$_2$SO$_4$ and concentrated. Purification by column chromatography on silica gel (50% ethylacetate in hexane), followed by preparative HPLC afforded 9 mg of the product (10.72% yield).

¹H NMR (300 MHz, CDCl₃): δ 8.50-8.40 (m, 1H), 7.7 (d, 1H), 7.22 (d, 1H), 6.43 (d, 1H), 5.7-5.1 (m, 1H), 4.65-4.40 (bs, 1H), 4.1-3.9 (m, 1H), 3.8-3.6 (m, 1H), 3.26-2.95 (m, 4H), 2.3 (s, 3H), 2.0 (s, 2H), 1.22-1.06 (m, 1H), 0.62 (m, 2H), 0.3 (m, 2H)

LCMS: 95.3%, m/z=326.1 (M+1)

HPLC: 90.43%

Example 40

Preparation of 6,7-dimethoxy-2-(4-methylpyridin-3-yl)-3,4-dihydroisoquinolin-1(2H)-one (40A)

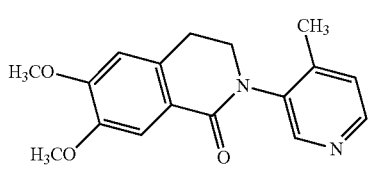
(40A)

Preparation of Intermediate 1,2-Dimethoxy-4-(2-nitro-vinyl)-benzene (I-40a)

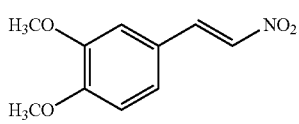
(I-40a)

Using analogous reaction conditions and workup as described in Example 1, 3,4-dimethoxy-benzaldehyde (10 g, 0.06017 mmol) in ethanol (200 mL) was reacted with nitro methane (3.4 mL, 0.06017 mmol) and 10N NaOH (2.52 g) to afford 10 g of the product (79.55% yield).

Preparation of Intermediate 2-(3,4-Dimethoxy-phenyl)-ethylamine (I-40b)

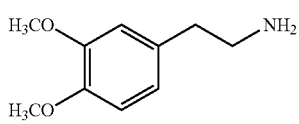
(I-40b)

Using the same procedure and workup as described in Example 15, 1,2-dimethoxy-4-(2-nitro-vinyl)-benzene (I-40a: 4 g, 19.13 mmol) in dry THF (66 mL) was reacted with LiBH₄ (1.6 g, 76.55 mmol) and chloro trimethyl silane (19.3 mL, 152.6 mmol) at 0° C., The resulting mixture was stirred at room temperature for 72 hours to afford 3.46 g of the product (100% yield).

¹H NMR (300 MHz, DMSO): δ 8.50-8.18 (bs, 2H), 7.10-6.51 (m, 3H), 3.84-3.60 (d, 6H), 3.21-2.61 (m, 4H)

Preparation of Intermediate [2-(3,4-Dimethoxy-phenyl)-ethyl]-carbamic acid ethyl ester (I-40c)

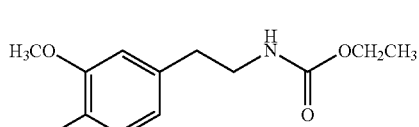
(I-40c)

Using analagous conditions and workup as described in Example 1, 2-(3,4-dimethoxy-phenyl)-ethylamine (I-40b: 3.4 g, 18.784 mmol) in chloroform (38 mL) was reacted with chloro ethyl formate (2.2 mL, 22.54 mmol) and 2N Na₂CO₃ solution (38 mL) to afford the crude product. Purification by column chromatography on silica gel (5% ethylacetate in hexane) afforded 2.8 g of the product (60% yield).

¹H NMR (300 MHz, CDCl₃): δ 6.85-6.65 (m, 3H), 4.75-4.60 (bs, 1H), 4.22-4.02 (m, 2H), 3.87 (s, 6H), 3.40 (q, 2H), 2.75 (t, 2H), 1.22 (t, 3H)

Preparation of Intermediate 6,7-Dimethoxy-3,4-dihydro-2H-isoquinolin-1-one (I-40d)

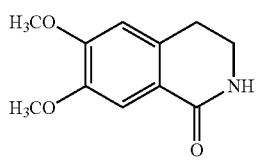
(I-40d)

Using an analogous procedure and workup as described in Example 35, [2-(3,4-dimethoxy-phenyl)-ethyl]-carbamic acid ethyl ester (I-40c: 2.8 g) was reacted with PPA (28 g) at 140° C. for 10 minutes to afford the crude product. Purification by column chromatography on silica gel (40% ethylacetate in hexane) afforded 400 mg of the product (17.4% yield).

¹H NMR (300 MHz, CDCl₃): δ 7.58 (s, 1H), 6.68 (s, 1H), 5.94-5.80 (bs, 1H), 3.94 (s, 6H), 3.60-3.50 (m, 2H), 3.0-2.9 (t, 2H)

LCMS: 100%, m/z=208.1(M+1)

Preparation of 6,7-Dimethoxy-2-(4-methyl-pyridin-3-yl)-3,4-dihydro-2H-isoquinolin-1-one (40A)

Using analogous reaction conditions as described in Example 1, 6,7-dimethoxy-3,4-dihydro-2H-isoquinolin-1-one (I-40d: 100 mg, 0.483 mmol) was reacted with 3-iodo-4-methyl-pyridine (105 mg, 0.483 mmol), 1,4-dioxane (10 mL), copper iodide (9.2 mg, 0.0483 mmol), trans-N,N'-dimethyl-cyclohexyl-1,2-diamine (21.5 mg, 0.144 mmol) and potassium phosphate (255 mg, 1.207 mmol) to afford the crude product. Purification by column chromatography on silica gel (40% ethylacetate in hexane) afforded 35 mg of the product (24% yield).

¹H NMR (300 MHz, CDCl₃): δ 8.50-8.40 (m, 2H), 7.64 (s, 1H), 7.32-7.20 (m, 1H), 6.72 (s, 1H), 4.10-3.92 (m, 7H), 3.84-3.70 (m, 1H), 3.29-3.0 (m, 2H), 2.30 (s, 3H)

LCMS: 100%, m/z=299.1 (M+1)

HPLC: 95.20%

Example 41

Preparation of 6,7-dichloro-2-(4-methylpyridin-3-yl)-3,4-dihydroisoquinolin-1 (2H)-one (41A)

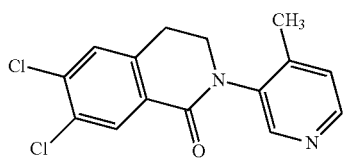

(41A)

Preparation of Intermediate 1,2-Dichloro-4-(2-nitro-vinyl)-benzene (I-41a)

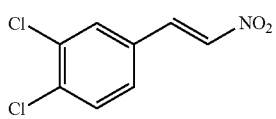

(I-41a)

Using an analogous reaction procedure and workup as described in Example 1, 3,4-dichloro-benzaldehyde (5.6 g, 41.481=01) in ethanol (56 mL) was reacted with nitro methane (2.3 mL, 41.481 mmol), 10N NaOH solution (1.65 g, 41.481 mmol) at 0° C. for 1 hour to afford 5.1 g of the product (75% yield).

¹H NMR (300 MHz, CDCl₃): δ 7.95 (d, 1H), 7.7-7.5 (m, 3H), 7.40 (dd, 1H)

Preparation of Intermediate 2-(3,4-Dichloro-phenyl)-ethylamine (I-41b)

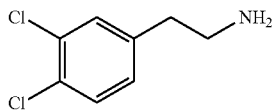

(I-41b)

Using an analogous procedure and workup as described in Example 15, 1,2-dichloro-4-(2-nitro-vinyl)-benzene (I-41a: 5.1 g, 23.831 mmol) in dry THF (51 mL) was reacted with LiBH₄ (2.1 g, 95.327 mmol) and chloro trimethyl silane (20.71 g, 190.64 mmol) at 0° C. The resulting mixture was stirred at room temperature for 72 hours to afford 3.43 g of the crude product which was used in the next step without further purification.

Preparation of Intermediate [2-(3,4-Dichloro-phenyl)-ethyl]-carbamic acid ethyl ester (I-41c)

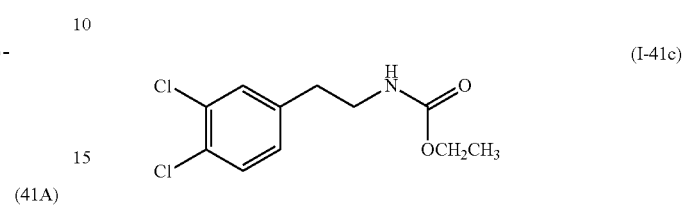

(I-41c)

Using an analogous reaction procedure and workup as described in Example 1, 2-(3,4-dichloro-phenyl)-ethylamine (I-41b: 4.3 g, 22.751 mmol) in chloroform (43 mL) was reacted with chloro ethyl formate (2.6 mL, 27.301 mmol) and 2N Na₂CO₃ solution (43 mL) to afford 3.5 g of the product (59% yield).

¹H NMR (300 MHz, CDCl₃): δ 7.40-7.25 (m, 2H), 7.05-7.0 (d, 1H), 4.82-4.60 (bs, 1H), 4.20-4.05 (m, 2H), 3.40 (q, 2H), 2.75 (t, 2H), 1.25 (t, 3H)

LCMS: 96.39%, m/z=261.9 (M+1)

Preparation of Intermediate 6,7-Dichloro-3,4-dihydro-2H-isoquinolin-1-one (I-41d)

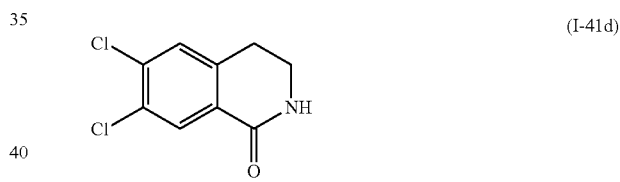

(I-41d)

Using an analogous reaction procedure and workup as described in Example 1, [2-(3,4-dichloro-phenyl)-ethyl]-carbamic acid ethyl ester (I-41c: 3.5 g, 13.409 mmol) in POCl₃ (35 mL) was reacted with P₂O₅ (3.80 g, 26.819 mmol) at 120° C. for 1 hour to afford the crude product. Purification by column chromatography on silica gel (30% ethylacetate in hexane) afforded 0.350 g of the crude product which was used in the next step without further purification.

LCMS: 64.62%, m/z=216.0 (M+1)

Preparation of 6,7-Dichloro-2-(4-methyl-pyridin-3-yl)-3,4-dihydro-2H-isoquinolin-1-one (41A)

Using an analogous reaction conditions as described in example 1, 6,7-dichloro-3,4-dihydro-2H-isoquinolin-1-one (I-41d: 0.15 g, 0.6944 mmol) was reacted with 3-iodo-4-methyl-pyridine (0.152 g, 0.6944 mmol), 1,4-dioxane (20 mL), copper iodide (0.013 g, 0.0494 mmol), trans-N,N'-dimethyl-cyclohexyl-1,2-diamine (0.032 mL, 0.2083 mmol) and potassium phosphate (0.368 g, 1.736 mmol) to afford the crude product. Purification by preparative HPLC afforded 18 mg of the product (8.4% yield).

¹H NMR (300 MHz, CDCl₃): δ 8.50-8.45 (m, 2H), 8.22 (s, 1H), 7.41 (s, 1H), 7.34-7.25 (m, 1H), 4.10-3.95 (m, 1H), 3.87-3.72 (m, 1H), 3.30-3.09 (m, 2H), 2.30 (s, 3H)

LCMS: 99.25%, m/z=309.0 (M+2)
HPLC: 99.3%

Example 42

Preparation of 9-ethyl-3-methyl-2-(pyridin-3-yl)-2,3,4,9-tetrahydro-1H-pyrido[3,4-b]indol-1-one (42A)

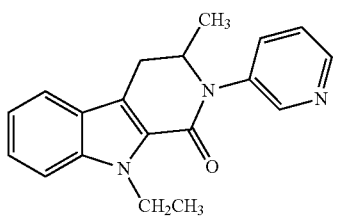
(42A)

Preparation of Intermediate 1-Ethyl-3-(2-nitro-propenyl)-1H-indole (nitroethane)(I-42a)

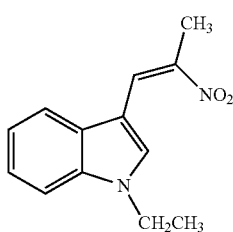
(I-42a)

Using an analogous reaction procedure and workup as described in Example 38, 1-ethyl-1H-indole-3-carbaldehyde (I-38b: 6 g, 34.482 mmol) was reacted with nitro ethane (71.7 mL, 1000.0 mmol), ammonium acetate (1.65 g, 41.481 mmol) to afford the crude product. Purification by column chromatography on silica gel (25% ethylacetate in hexane) afforded 6 g of the product (75% yield).

$^1$H NMR (300 MHz, CDCl$_3$): δ 8.55 (s, 1H), 7.85 (d, 1H), 7.50 (s, 1H), 7.45-7.28 (m, 3H), 4.30 (q, 2H), 2.59 (s, 3H), 1.60 (t, 3H)
LCMS: 94.74%, m/z=231.1 (M+1)

Preparation of Intermediate 2-(1-Ethyl-1H-indol-3-yl)-1-methyl-ethylamine (I-42b)

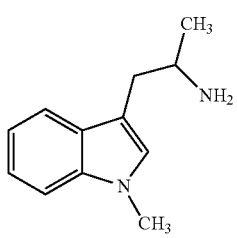
(I-42b)

Using analogous reaction conditions and workup as described in Example 1, 1-ethyl-3-(2-nitro-propenyl)-1H-indole (I-42a: 6 g, 25.9740 mmol) in dry THF (30 mL) was reacted with LAH (4.92 g, 129.870 mmol) in dry THF (30 mL). The resulting mixture was refluxed for 12 hrs under nitrogen atmosphere to afford 5.2 g of the product (98% yield).

$^1$H NMR (300 MHz, CDCl$_3$): δ 7.66-7.60 (d, 1H), 7.38-7.18 (m, 2H), 7.14-7.08 (m, 1H), 6.98 (s, 1H), 4.2-4.1 (q, 2H), 3.35-3.20 (m, 1H), 2.95-2.85 (m, 1H), 2.7-2.6 (m, 1H), 1.46 (t, 3H), 1.2-1.1 (d, 3H)

Preparation of Intermediate [2-(1-Ethyl-1H-indol-3-yl)-1-methyl-ethyl]-carbamic acid ethyl ester (I-42c)

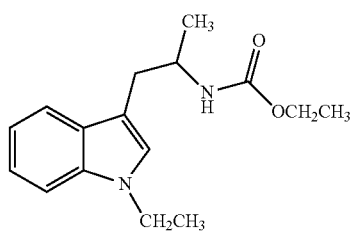
(I-42c)

Using an analogous reaction procedure and workup as described in Example 1, 2-(1-ethyl-1H-indol-3-yl)-1-methyl-ethylamine (I-42b: 5.2 g, 25.6157 mmol) in chloroform (52 mL) was reacted with chloro ethyl formate (2.92 mL, 30.7389 mmol) and 2N Na$_2$CO$_3$ solution (52 mL) to afford 6 g of the product (85% yield).

$^1$H NMR (300 MHz, CDCl$_3$): δ 7.64 (d, 1H), 7.36-7.18 (m, 2H), 7.14-7.06 (m, 1H), 6.96 (s, 1H), 4.7-4.5 (bs, 1H), 4.2-4.0 (m, 4H), 3.10-2.80 (m, 2H), 1.45 (t, 3H), 1.30-1.10 (m, 6H)

Preparation of Intermediate 9-Ethyl-3-methyl-2,3,4,9-tetrahydro-b-carbolin-1-one (I-42d)

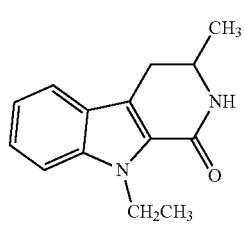
(I-42d)

Using an analogous reaction procedure and workup as described in Example 1, [2-(1-ethyl-1H-indol-3-yl)-1-methyl-ethyl]carbamic acid ethyl ester (I-42c: 3 g, 10.8695 mmol) in POCl$_3$ (30 mL) was reacted with P$_2$O$_5$ (3.080 g, 21.739 mmol) at 120° C. for 1 hour to afford the crude product. Purification by column chromatography on silica gel (25% ethylacetate in hexane) afforded 0.400 g of the product (16.1% yield).

$^1$H NMR (300 MHz, CDCl$_3$): δ 7.60 (d, 1H), 7.45-7.30 (m, 2H), 7.20-7.10 (m, 1H), 5.42-5.38 (bs, 1H), 4.78-4.55 (m, 2H), 4.10-3.95 (m, 1H), 3.14-3.04 (dd, 1H), 2.84-2.72 (m, 1H), 1.44-1.36 (m, 6H)
LCMS: 92.16%, m/z=229.1 (M+1)

Preparation of 9-Ethyl-3-methyl-2-pyridin-3-yl-2,3,4,9-tetrahydro-b-carbolin-1-one (42A)

Using analogous reaction conditions as described in Example 1, 9-ethyl-3-methyl-2,3,4,9-tetrahydro-b-carbolin- 1-one (I-42d: 0.1 g, 0.4386 mmol) was reacted with 3-bromopyridine (0.069 g, 0.4386 mmol), 1,4-dioxane (15 mL), copper iodide (0.008 g, 0.0438 mmol), trans-N,N'-dimethylcyclohexyl-1,2-diamine (0.018 mg, 0.1315 mmol) and potassium phosphate (0.232 g, 1.096 mmol) to afford the crude product. Purification by column chromatography on silica gel (70% ethylacetate in hexane) afforded 46 mg of the product (34% yield).

$^1$H NMR (300 MHz, CDCl$_3$): δ 8.68 (d, 1H), 8.55 (d, 1H), 7.78-7.72 (m, 1H), 7.65 (d, 1H), 7.53-7.32 (m, 3H), 7.26-7.12 (m, 1H), 4.8-4.6 (m, 2H), 4.45-4.30 (m, 1H), 3.65-3.46 (dd, 1H), 3.10-3.0 (dd, 1H), 1.50-1.32 (m, 6H)

LCMS: 100%, m/z=306.4 (M+1)
HPLC: 90.23%

Example 43

Preparation of 3-Methyl-2-pyridin-3-yl-7-trifluoromethyl-3,4-dihydro-2H-isoquinolin-1-one (43A)

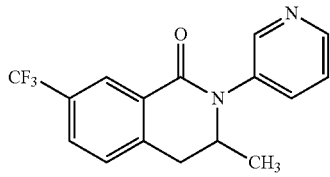

(43A)

Preparation of Intermediate 1-(2-Nitro-propenyl)-4-trifluoromethyl-benzene (I-43a)

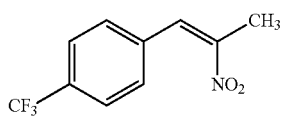

(I-43a)

Nitro ethane (30.94 mL, 430.73 mmol) was added to 4-trifluoromethyl-benzaldehyde (5 g, 28.71 mmol) and ammonium acetate (6.64 g, 86.15 mmol) and the resulting mixture was refluxed at 115° C. overnight. The reaction was monitored by TLC (10% ethylacetate in hexane). The reaction mass was cooled and partitioned between ethylacetate and water. The organic layer was washed with water, brine solution, dried over anhydrous sodium sulphate and concentrated. Purification by column chromatography on silica gel (2% ethylacetate in hexane) afforded 2.85 g of the product (42.93% yield).

$^1$H NMR (300 MHz, CDCl$_3$): δ 8.09 (s, 1H), 7.76-7.68 (m, 2H), 7.58-7.50 (m, 2H), 2.42 (s, 3H)

Preparation of Intermediate 1-Methyl-2-(4-trifluoromethyl-phenyl)-ethylamine (I-43b)

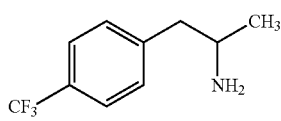

(I-43b)

1-(2-Nitro-propenyl)-4-trifluoromethyl-benzene (I-43a: 2.85 g, 12.33 mmol) was reacted with LiAlH$_4$ (1.87 g, 49.31 mmol) in dry THF (40 mL). The resulting mixture was refluxed for 5 hours at 70° C. The reaction was monitored by TLC (20% ethylacetate in hexane). The reaction mass was cooled to 0° C., quenched with 10% NaOH solution (2 mL) and stirred for 20 minutes. The precipitated solid was filtered, washed with DCM and concentrated under reduced pressure to afford 2.5 g of the crude product which was used for the next step without further purification. LCMS: m/z=204.1 (M+1)

Preparation of Intermediate [1-Methyl-2-(4-trifluoromethyl-phenyl)-ethyl]-carbamic acid ethyl ester (I-43c)

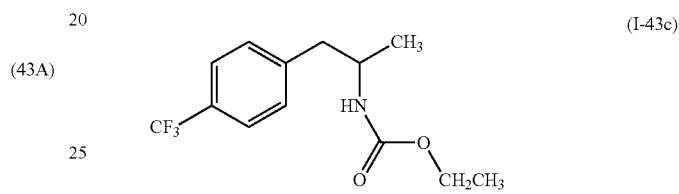

(I-43c)

1-Methyl-2-(4-trifluoromethyl-phenyl)-ethylamine (I-43b: 2.5 g, 0.01476 mmol) in CHCl$_3$ (25 mL) was reacted with chloro ethyl formate (1.69 mL, 0.0177 mmol) and 2N Na$_2$CO$_3$ solution (25 mL) at 0° C. The resulting mixture was stirred at 0° C. for 3 hours to afford the crude product. Purification by column chromatography on silica gel (2% ethylacetate in hexane) afforded 420 mg of the product (12.4% yield).

$^1$H NMR (300 MHz, CDCl$_3$): δ 7.62-7.52 (m, 2H), 7.34-7.24 (m, 2H), 4.6-4.3 (m, 1H), 4.15-4.05 (m, 2H), 3.0-2.7 (m, 2H), 1.4-1.1 (m, 6H). LCMS: 72.15%, m/z=277.0 (M+2)

Preparation of Intermediate 3-Methyl-7-trifluoromethyl-3,4-dihydro-2H-isoquinolin-1-one (I-43d)

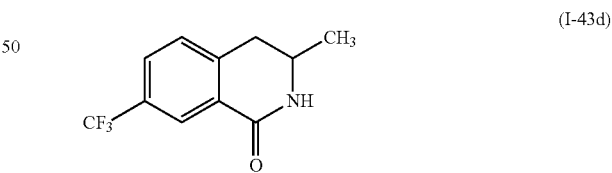

(I-43d)

[1-Methyl-2-(4-trifluoromethyl-phenyl)-ethyl]-carbamic acid ethyl ester (I-43c: 420 mg, 1.525 mmol) in POCl$_3$ (4.2 mL) was refluxed with P$_2$O$_5$ (433 mg, 3.05 mmol) at 110° C. for 2 hours to afford the crude product. The reaction was monitored by TLC (20% ethylacetate in hexane). Purification by column chromatography on silica gel (40% ethylacetate in hexane) afforded 40 mg of the product (11.46% yield).

$^1$H NMR (300 MHz, CDCl$_3$): δ 8.37 (s, 1H), 7.72 (d, 1H), 7.36 (d, 1H), 6.1-6.0 (m, 1H), 4.0-3.85 (m, 1H), 3.10-2.80 (m, 2H), 1.36 (d, 3H)

Preparation of 3-Methyl-2-pyridin-3-yl-7-trifluoromethyl-3,4-dihydro-2H-isoquinolin-1-one (43A)

3-Methyl-7-trifluoromethyl-3,4-dihydro-2H-isoquinolin-1-one (I-43d: 40 mg, 0.1745 mmol) was reacted with 3-bromo-pyridine (19 mg, 0.1163 mmol), 1,4-dioxane (5 mL), copper iodide (4 mg), trans-N,N'-dimethyl-cyclohexyl-1,2-diamine (8 mg) and potassium phosphate (93 mg, 0.4363 mmol). The reaction was monitored by TLC (50% ethylacetate in hexane). The reaction mass was concentrated under reduced pressure and partitioned between ethylacetate and water. The organic layer was washed with water, brine solution, dried over anhydrous sodium sulphate and concentrated. Purification by column chromatography on silica gel (100% ethylacetate in hexane) followed by washing with hexane and ether afforded 22 mg of the product (41.15% yield).

$^1$H NMR (300 MHz, CDCl$_3$): δ 8.75-8.40 (m, 3H), 7.75 (t, 2H), 7.4 (d, 2H), 4.4-4.2 (m, 1H), 3.62 (dd, 1H), 2.98 (dd, 1H), 1.25 (d, 3H). LCMS: 99.55%, m/z=307.0 (M+1). HPLC: 94.33%.

Example 44

Preparation of 5-fluoro-8-methoxy-2-(4-methylpyridin-3-yl) 3,4-dihydroisoquinolin-1(2H)-one (44A)

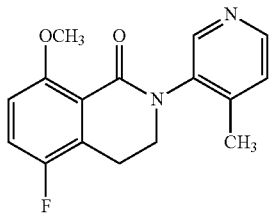

(44A)

Preparation of Intermediate 1-Fluoro-4-methoxy-2-(2-nitro-vinyl)-benzene (I-44a)

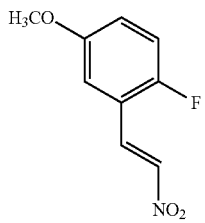

(I-44a)

2-Fluoro-5-methoxy-benzaldehyde (4 g, 25.95 mmol) was reacted with nitro methane (1.58 g, 25.95 mmol), 10N NaOH (2.2 mL, 27.24 mmol) to afford 3 g of the product (58.7% yield).

$^1$H NMR (300 MHz, CDCl$_3$): δ 8.0 (d, 1H), 7.7 (d, 1H), 7.20-6.95 (m, 3H), 3.81 (s, 3H)

Preparation of Intermediate 2-(2-Fluoro-5-methoxyphenyl)-ethylamine (I-44b)

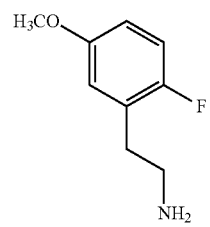

(I-44b)

1-Fluoro-4-methoxy-2-(2-nitro-vinyl)-benzene (3 g, 15.22 mmol) was reacted with chlorotrimethylsilane (13.2 g, 121.51 mmol) and LiBH$_4$ (1.32 g, 60.91 mmol) in dry THF (50 mL) at 0° C. The resulting mixture was stirred for 72 hours at room temperature to afford 2.6 g of the crude product which was used in the next step without further purification.

$^1$H NMR (300 MHz, DMSO): δ 8.70-8.52 (bs, 2H), 7.1 (t, 1H), 6.96-6.78 (m, 2H), 3.73 (s, 3H), 2.96 (s, 4H).

Preparation of [2-(2-Fluoro-5-methoxy-phenyl)-ethyl]-carbamic acid ethyl ester (I-44c)

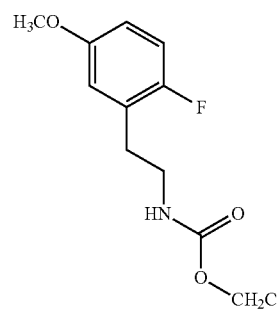

(I-44c)

2-(2-Fluoro-5-methoxy-phenyl)-ethylamine (I-44b: 2.6 g, 15.2 mmol) was reacted with chloro ethyl formate (1.979 g, 18.24 mmol), 2N Na$_2$CO$_3$ solution (30 mL) and chloroform (30 mL) at 0° C. The resulting mixture was stirred for 30 minutes at 0° C. to afford the crude product. Purification by column chromatography on silica gel (5% ethylacetate in hexane) afforded 3 g of the product (81% yield).

$^1$H NMR (300 MHz, CDCl$_3$): 7.0-6.9 (m, 1H), 6.76-6.66 (m, 2H), 4.80-4.68 (bs, 1H), 4.15-4.0 (m, 2H), 3.76 (s, 3H), 3.4 (q, 2H), 2.8 (t, 2H), 1.30-1.20 (t, 3H).

Preparation of 5-Fluoro-8-methoxy-3,4-dihydro-2H-isoquinolin-1-one (I-44d)

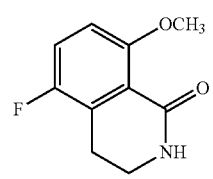

(I-44d)

[2-(2-Fluoro-5-methoxy-phenyl)-ethyl]carbamic acid ethyl ester (I-44c: 1.6 g, 0.006 mol) was reacted with P$_2$O$_5$ (1.87 g, 0.013 mol) and POCl$_3$ (16 mL) and the resulting mixture was refluxed for 4 hrs at 100° C. The reaction was monitored by TLC (100% ethylacetate). The reaction mass was cooled to room temperature and concentrated under reduced pressure. The concentrate was quenched with ice-water and basified with 2N Na$_2$CO$_3$ solution to pH 8. The resulting solution was partitioned between ethyl acetate and water. The organic layer was washed with water, brine solution, dried over anhydrous sodium sulphate and concentrated. Purification by column chromatography on silica gel (2% methanol in DCM) afforded 0.3 g of the product (23.25% yield).

$^1$H NMR (300 MHz, CDCl$_3$): δ 7.20-7.10 (t, 1H), 6.90-6.75 (m, 2H), 3.92 (s, 3H), 3.52-3.42 (m, 2H), 2.94 (t, 2H). LCMS: 93.04%, m/z=196.0 (M+1)

Preparation of 5-Fluoro-8-methoxy-2-(4-methyl-pyridin-3-yl)-3,4-dihydro-2H-isoquinolin-1-one (44A)

5-Fluoro-8-methoxy-3,4-dihydro-2H-isoquinolin-1-one (I-44d: 0.12 g, 0.6 mmol) was refluxed with K$_3$PO$_4$ (0.32 g, 1.5 mmol), 3-Iodo-4-methyl-pyridine (0.175 g, 0.79 mmol), trans-N,N'-dimethyl-cyclohexane-1,2-diamine (0.026 g, 0.18 mmol) and CuI (0.01 g, 0.06 mmol) in 1,4-dioxane (20 mL) at 120° C. overnight. The reaction was monitored by TLC (80% ethylacetate in hexane). The reaction mass was cooled to room temperature, filtered and partitioned between DCM and water. The organic layer was washed with water, brine solution, dried over anhydrous sodium sulphate and concentrated. Purification by column chromatography on silica gel (2% methanol in chloroform) followed by preparative HPLC afforded 25 mg of the product (14.75% yield).

$^1$H NMR (300 MHz, CDCl$_3$): δ 8.55-8.30 (bs, 2H), 7.30-7.15 (m, 2H), 6.95-6.85 (m, 1H), 4.05-3.85 (m, 4H), 3.75-3.60 (m, 1H), 3.25-3.10 (m, 2H), 2.3 (s, 3H).

LCMS: 93.12%, m/z=287.1 (M+1). HPLC: 99.39%

Example 45

Preparation of 6-Fluoro-2-(4-methyl-pyridin-3-yl)-3,4-dihydro-2H-benzo[4,5]thieno[2,3-c]pyridin-1-one (45A)

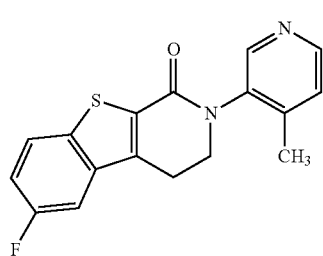
(45A)

Preparation of Intermediate 3-Bromomethyl-5-fluoro-benzo[b]thiophene (I-45a)

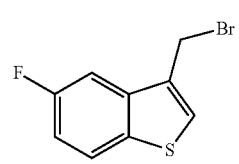
(I-45a)

5-Fluoro-3-methyl-benzo[b]thiophene (1.7 g, 10.24 mmol) was reacted with N-bromo succinimide (2 g, 1126 mmol) and benzoyl peroxide (2 mg) in CCl$_4$ (15 mL). The resulting reaction mass was refluxed using photoelectric radiation. The reaction was monitored by TLC (100% hexane). The reaction mass was quenched with water and separated the CCl$_4$ layer. The aqueous layer was extracted with chloroform and the organic layer was washed with water, brine solution, dried over anhydrous sodium sulphate and concentrated. Purification by column chromatography on silica gel (100% hexane) afforded 1.3 g of the product (52% yield).

$^1$H NMR (300 MHz, CDCl$_3$): δ 7.84-7.75 (m, 1H), 7.60-7.52 (m, 2H), 7.22-7.10 (m, 1H), 4.7 (s, 2H)

Preparation of Intermediate (5-Fluoro-benzo[b]thiophen-3-yl)-acetonitrile (I-45b)

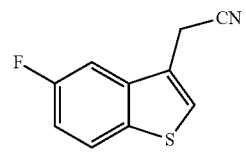
(I-45b)

50% NaCN solution (443 mg, 9.05 mmol) in water (2 mL) was added drop wise to a solution of 3-bromomethyl-5-fluoro-benzo[b]thiophene (I-45a: 1.3 g, 3.32 mmol) in DMF (10 mL) over a period of 5 minutes at 0° C. The resulting reaction mass was stirred at room temperature for 2 hours. The reaction was monitored by TLC (5% ethylacetate in hexane). The reaction mass was quenched with sodium hypochlorite solution and extracted with ethyl acetate. The organic layer was washed with water, brine solution, dried over anhydrous sodium sulphate and concentrated. Purification by column chromatography on silica gel (6% ethylacetate in hexane) afforded 700 mg of the product (68.89% yield).

$^1$H NMR (300 MHz, CDCl$_3$): δ 7.9-7.8 (m, 1H), 7.60 (s, 1H), 7.40-7.35 (m, 1H), 7.25-7.14 (m, 1H), 3.88 (s, 2H)

Preparation of Intermediate 2-(5-Fluoro-benzo[b]thiophen-3-yl)-ethylamine (I-45c)

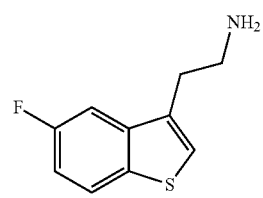
(I-45c)

Methanolic ammonia solution (15 mL) and thiophene solution (1 mL) were added to Raney Ni (5 g) taken in a reaction flask. This was followed by the addition of (5-Fluoro-benzo[b]thiophen-3-yl)-acetonitrile (I-45b: 700 mg, 3.66 mmol) in methanolic ammonia solution (15 mL) at 0° C. The resulting reaction mass was stirred at 10° C. overnight under hydrogen atmosphere. The reaction was monitored by TLC (5% methanol in chloroform). The reaction mass was filtered, washed with methanol and the filtrate was concentrated under reduced pressure to afford 500 mg of the crude product which was used for the next step without further purification. LCMS: 92.76%, m/z=196.1 (M+1)

Preparation of Intermediate [2-(5-Fluoro-benzo[b]thiophen-3-yl)-ethyl]-carbamic acid ethyl ester (I-45d)

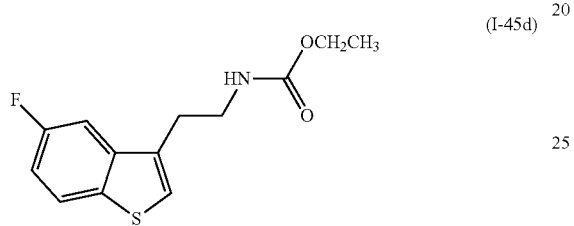

(I-45d)

Using the same reaction conditions and work up as described in example 1, step 3, 2-(5-fluoro-benzo[b]thiophen-3-yl)-ethylamine (I-45c: 500 mg, 2.56 mmol) was reacted with chloro ethyl formate (0.3 mL, 2.82 mmol), 2N Na$_2$CO$_3$ solution (10 mL) and chloroform (15 mL). The resulting mixture was stirred at room temperature for 1 hour to afford the crude product. Purification by column chromatography on silica gel (12% ethyl acetate in hexane) afforded 550 mg of the product (80.52% yield).

$^1$H NMR (300 MHz, CDCl$_3$): δ 7.84-7.74 (m, 1H), 7.50-7.40 (m, 1H), 7.32-7.22 (m, 1H), 7.20-7.08 (m, 1H), 4.90-4.70 (bs, 1H), 4.15 (q, 2H), 3.60-3.40 (q, 2H), 3.05 (t, 2H), 1.25 (t, 3H)

Preparation of Intermediate 6-Fluoro-3,4-dihydro-2H-benzo[4,5]thieno[2,3-c]pyridin-1-one (I-45e)

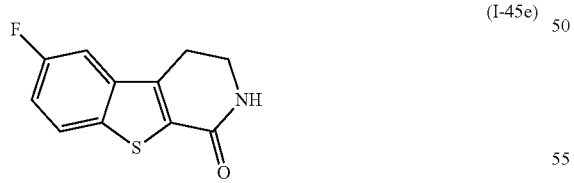

(I-45e)

[2-(5-Fluoro-benzo[b]thiophen-3-yl)-ethyl]-carbamic acid ethyl ester (I-45d: 550 mg, 2.059 mmol) was reacted with P$_2$O$_5$ (461 mg, 4.11 mmol) and POCl$_3$ (7 mL). The resulting mixture was refluxed at 110° C. for 2 hours to afford the crude product. Purification by column chromatography on silica gel (2% methanol in chloroform) afforded 90 mg of the product (19.78% yield).

$^1$H NMR (300 MHz, CDCl$_3$): δ 7.9-7.8 (m, 1H), 7.45-7.39 (dd, 1H), 7.30-7.20 (m, 1H), 6.2-6.0 (bs, 1H), 3.85-3.70 (m, 2H), 3.1 (t, 2H)

Preparation of 6-Fluoro-2-(4-methyl-pyridin-3-yl)-3,4-dihydro-2H-benzo[4,5]thieno[2,3-c]pyridin-1-one (45A)

6-Fluoro-3,4-dihydro-2H-benzo[4,5]thieno[2,3-c]pyridin-1-one (I-45e: 85 mg, 0.384 mmol) was reacted with 3-iodo-4-methyl-pyridine (101 mg, 0.461 mmol), K$_3$PO$_4$ (244 mg, 1.152 mmol), trans-N,N'-dimethyl-cyclohexane-1,2-diamine (16.3 mg, 0.115 mmol), CuI (7.2 mg, 0.038 mmol) and 1,4-dioxane (10 mL). The resulting mixture was refluxed at 120° C. overnight to afford the crude product. Purification by column chromatography on silica gel (2% methanol in chloroform) afforded 45 mg of the product (37.81% yield).

$^1$H NMR (300 MHz, CDCl$_3$): δ 8.80-8.25 (bs, 2H), 7.95-7.80 (m, 1H), 7.45 (d, 1H), 7.35-7.7.20 (m, 2H), 4.3-4.15 (m, 1H), 4.05-3.9 (m, 1H), 3.25 (t, 2H), 2.32 (s, 3H). LCMS: 95.75%, m/z=313.0 (M+1). HPLC: 97.60%

Example 46

Preparation of 9-Ethyl-3-methyl-2-(4-methyl-pyridin-3-yl)-2,3,4,9-tetrahydro-b-carbolin-1-one (46A)

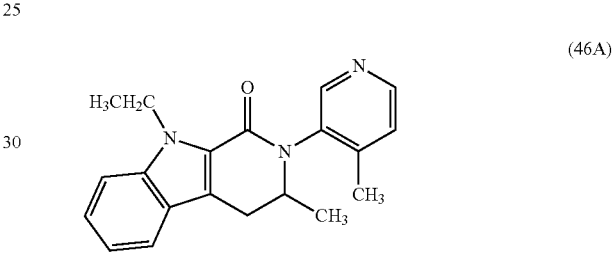

(46A)

9-Ethyl-3-methyl-2,3,4,9-tetrahydro-b-carbolin-1-one (I-42d: 0.150 g, 0.657 mmol) was reacted with 3-iodo-4-methyl-pyridine (0.144 g, 0.657 mmol), K$_3$PO$_4$ (0.348 g, 1.644 mmol), CuI (0.012 g, 0.065 mmol), trans-N,N'-dimethyl-cyclohexane-1,2-diamine (0.028 g, 0.197 mmol) and 1,4-dioxane (15 mL). The resulting mixture was heated at 120° C. for 23 hours to afford the crude product. Purification by column chromatography on silica gel (30% ethyl acetate in hexane) followed by preparative HPLC afforded 9 mg of the product (4.3% yield).

$^1$H NMR (300 MHz, CDCl$_3$): δ 8.55-8.4 (m, 2H), 7.65 (d, 1H), 7.50-7.1 (m, 4H), 4.7-4.6 (m, 2H), 4.45-4.0 (m, 1H), 3.6-3.4 (m, 1H), 3.15-3.0 (m, 1H), 2.32 (s, 3H), 1.5-1.15 (m, 6H). LCMS: 100%, m/z=320.2 (M+1). HPLC: 96.45%

Example 47

Preparation of 8-Fluoro-2-(4-methyl-pyridin-3-yl)-7-trifluoromethyl-3,4-dihydro-2H-isoquinolin-1-one (47A)

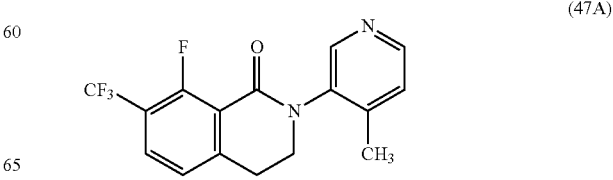

(47A)

Preparation of Intermediate 2-Fluoro-4-(2-nitro-vinyl)-1-trifluoromethyl-benzene (I-47a)

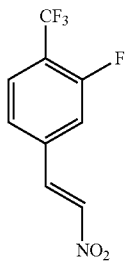

(I-47a)

3-Fluoro-4-trifluoromethyl-benzaldehyde (5 g, 25.9 mmol) was reacted with nitro methane (1.58 g, 25.9 mmol), 10N NaOH (1.08 g, 27.20 mmol) to afford 2.8 g of the product (46.6% yield).

$^1$H NMR (300 MHz, CDCl$_3$): δ 8.04-7.92 (m, 1H), 7.8-7.56 (m, 2H), 7.50-7.36 (m, 2H)

Preparation of 2-(3-Fluoro-4-trifluoromethyl-phenyl)-ethylamine (I-47b)

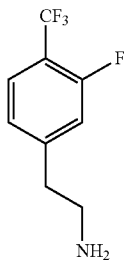

(I-47b)

2-Fluoro-4-(2-nitro-vinyl)-1-trifluoromethyl-benzene (I-47a: 2.8 g, 11.914 mmol) was reacted with chlorotrimethylsilane (10.328 g, 95.07 mmol), LiBH$_4$ (1.03 g 47.65 mmol) and THF (40 mL). The resulting mixture was stirred at room temperature for 72 hours to afford 2.46 g of the product (100% yield), LCMS: 99.49%, m/z=208.0 (M+1)

Preparation of Intermediate [2-(3-Fluoro-4-trifluoromethyl-phenyl)-ethyl]-carbamic acid ethyl ester (I-47c)

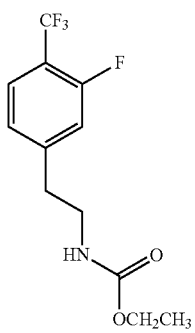

(I-47c)

2-(3-Fluoro-4-trifluoromethyl-phenyl)-ethylamine (I-47b: 2.46 g, 11.88 mmol) was reacted with ethylchloroformate (1.54 g, 14.26 mmol), 2N Na$_2$CO$_3$ solution (24.0 mL) and chloroform (24 mL). The resulting mixture was stirred for 30 minutes at 0° C. to afford 3.0 g of the crude product.

$^1$H NMR (300 MHz, CDCl$_3$): δ 7.55 (t, 1H), 7.09 (t, 2H), 4.75-4.60 (bs, 1H), 4.1 (q, 2H), 3.50-3.35 (q, 2H), 2.89 (t, 2H), 1.22 (t, 3H)

Preparation of Intermediate 8-Fluoro-7-trifluoromethyl-3,4-dihydro-2H-isoquinolin-1-one (I-47d)

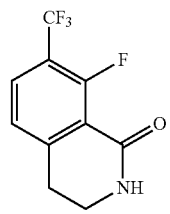

(I-47d)

[2-(3-Fluoro-4-trifluoromethyl-phenyl)-ethyl]-carbamic acid ethyl ester (I-47c: 1.5 g, 5.376 mmol) was reacted with P$_2$O$_5$ (1.52 g, 10.75 mmol) and POCl$_3$ (15 mL). The resulting mixture was refluxed for 1 hour at 110° C. to afford the crude product. Purification by column chromatography on silica gel (50% ethylacetate in hexane) afforded 350 mg of the product (27.97% yield).

$^1$H NMR (300 MHz, CDCl$_3$): δ 7.52 (t, 1H), 7.1-7.0 (t, 2H), 4.33-4.20 (bs, 1H), 3.45 (q, 2H), 2.86 (t, 2H). LCMS: m/z=234.2 (M+1)

Preparation of 8-Fluoro-2-(4-methyl-pyridin-3-yl)-7-trifluoromethyl-3,4-dihydro-2H-isoquinolin-1-one (47A)

8-Fluoro-7-trifluoromethyl-3,4-dihydro-2H-isoquinolin-1-one (I-47d: 150 mg, 0.643 mmol) was reacted with 3-iodo-4-methyl-pyridine (140.98 mg, 0.643 mmol), K$_3$PO$_4$ (346.76 mg, 1.607 mmol), trans-N,N'-dimethyl-cyclohexane-1, 2-diamine (0.03 mL, 0.192 mmol), CuI (12.24 mg, 0.0643 mmol) and 1,4-dioxane (10 mL). The resulting mixture was refluxed for 16 hours at 110° C. to afford the crude product. Purification by column chromatography on silica gel (40% ethylacetate in hexane) followed by preparative HPLC afforded 10 mg of the product (4.8% yield).

$^1$H NMR (300 MHz, CDCl$_3$): δ 8.52-8.42 (m, 2H), 7.3-7.25 (m, 2H), 7.15 (d, 1H), 4.12-4.0 (m, 1H), 3.9-3.75 (m, 1H), 3.32-3.20 (m, 2H), 2.30 (s, 3H). LCMS: 100%, m/z=325.2 (M+1). HPLC: 94.20%

Example 48

Preparation of 3-Methyl-2-(4-methyl-pyridin-3-yl)-7-trifluoromethyl-3,4-dihydro-2H-isoquinolin-1-one (48A)

(48A)

3-Methyl-7-trifluoromethyl-3,4-dihydro-2H-isoquinolin-1-one (I-43d: 200 mg, 0.872 mmol) was reacted with 3-iodo-4-methyl-pyridine (287 mg, 1.308 mmol), K₃PO₄ (463 mg, 2.18 mmol), trans-N,N'-dimethyl-cyclohexane-1, 2-diamine (40 mg), CuI (20 mg) and 1,4-dioxane (5 mL). The resulting mixture was refluxed for 64 hours at 110° C. to afford the crude product. Purification by column chromatography on silica gel (90% ethylacetate in hexane) followed by preparative HPLC afforded 10 mg of the product (3.58% yield).

¹H NMR (300 MHz, CDCl₃): δ 8.60-8.35 (m, 3H), 7.75 (d, 1H), 7.48-7.22 (m, 2H), 4.4-3.9 (m, 1H), 3.65-3.50 (m, 1H), 3.1-2.9 (m, 1H), 2.3 (d, 3H), 1.35-1.10 (m, 3H). LCMS: 90.81%, m/z=320.9 (M+1). HPLC: 99.29%

Example 49

Preparation of 6,7-difluoro-2-(4-methylpyridin-3-yl)-3,4-dihydroisoquinolin-1(2H)-one (49A)

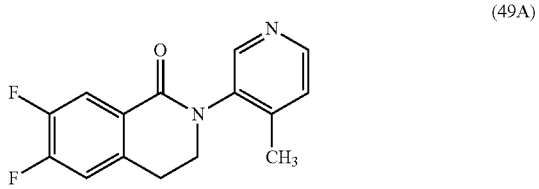 [SMILES: Cc1ccncc1N1CCc2cc(F)c(F)cc2C1=O]

(49A)

Preparation of Intermediate (E)-1,2-Difluoro-4-(2-nitrovinyl)benzene (I-49a)

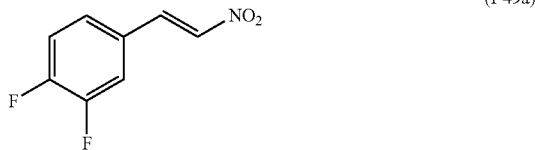

(I-49a)

Using analogous reaction conditions and workup as described in example 1, 3,4-difluorobenzaldehyde (5 g, 35.1864 mmol) in ethanol (175 mL) was reacted math nitro methane (1.9 mL, 35.1864 mmol) and 10N NaOH (1.47 g, 36.9457 mmol) to afford 5 g of the product (76.80% yield). ¹H NMR (CDCl₃, 300 MHz): δ 7.92 (d, 1H), 7.58-7.0 (m, 4H).

Preparation of Intermediate 2-(3, 4-Difluorophenyl)ethanamine (I-49b)

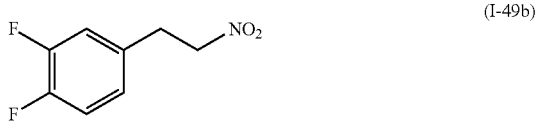 [SMILES: O=[N+]([O-])CCc1ccc(F)c(F)c1]

(I-49b)

Using an analogous procedure and workup as described in for the preparation of intermediate I-15b above. (E-1,2-difluoro-4-(2-nitrovinyl)benzene (I-49a: 5 g, 27.027 mmol) in dry THF (81 mL) as reacted with LiBH₄ (2.35 g, 108.1081 mmol) and chloro trimethyl silane (27.63 ml, 216.216 mmol) at 0° C. The resulting mixture was stirred at room temperature for 3 days to afford 4.2 g of the product (100% yield).

¹H NMR (DMSO, 300 MHz): δ 8.7 (bs, 2H), 7.5-7.3 (m, 2H), 7.2-7.0 (m, 1H), 3.0-2.8 (m, 4H). LCMS: 98.87%, m/z=158.1 (M+1)

Preparation of Intermediate Ethyl 3, 4-difluorophenethylcarbamate (I-19c)

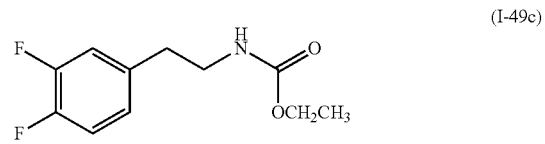 [SMILES: CCOC(=O)NCCc1ccc(F)c(F)c1]

(I-49c)

Using an analogous procedure and workup as described for the preparation of intermediate I-1c above, 2-(3,4-difluorophenyl)ethanamine (I-49b: 4.2 g, 26.7515 mmol) in chloroform (32 mL) was reacted with chloro ethyl formate (3 mL, 32.1019 mmol) and 2N Na₂CO₃ solution (16 mL) to afford 5 g of the crude product which was used in the next step without further purification.

¹H NMR (300 MHz, CDCl₃): δ 7.2-6.9 (m, 3H), 4.7 (bs, 1H), 4.1 (q, 2H), 3.5-3.3 (m, 2H), 2.76 (t, 2H), 2.22 (t, 3H).

Preparation of Intermediate 6, 7-Difluoro-3, 4-dihydroisoquinolin-1(2H)-one (I-49d)

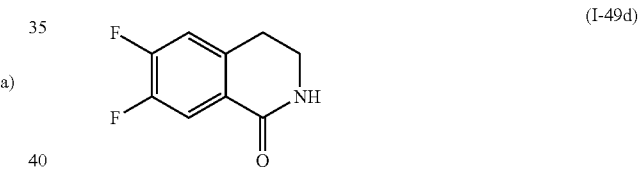

(I-49d)

Using an analogous reaction procedure and workup as described in example 1 for the preparation of intermediate I-1d above, ethyl 3,4-difluorophenethylcarbamate (I-49c: 5 g, 21.8340 mmol) in POCl₃ (43.6 mL) was reacted with P₂O₅ (6.19 g, 43.6681 mmol) at 110° C. for 2 hours to afford the crude product. Purification by column chromatography on silica gel (50% ethyl acetate in hexane) afforded 800 mg of the product (18.91% yield).

¹H NMR (300 MHz, CDCl₃): δ 7.9-7.8 (m, 1H), 7.10-6.84 (m, 1H), 6.70-6.56 (bs, 1H), 3.63-3.53 (m, 2H), 2.95 (t, 2H). LCMS: 78.07%, m/z=184.0(M+1)

Preparation of 6,7-Difluoro-2-(4-methylpyridin-3-yl)-3, 4-dihydroisoquinolin-1(2H)-one (49A)

Using analogous conditions as described in example 1 for the preparation of Compound 1A, 6,7-difluoro-3, 4-dihydroisoquinolin-1(2H)-one (I-49d: 300 mg, 1.6393 mmol) was reacted with 3-iodo-4-methyl-pyridine (359 mg, 1.6393 mmol), 1, 4-dioxane (15 mL), copper iodide (31.2 mg, 0.1639 mmol), trans-N,N'-dimethyl-cyclohexyl-1, 2-diamine (77.3 mL, 0.4917 mmol) and potassium phosphate (868.8 mg, 4.0982 mmol) to afford the crude product. Purification by column chromatography on silica gel (80% ethylacetate in hexane) afforded 110 mg of the product (24% yield).

¹H NMR (300 MHz, CDCl₃): δ 8.5-8.44 (m, 2H), 8.0-7.92 (m, 1H), 7.26 (d, 1H), 7.16-7.06 (m, 1H), 4.1-3.98 (m, 1H), 3.84-3.74 (m, 1H), 3.26-3.06 (m, 2H), 2.3 (s, 3H).
LCMS: 98.58%, m/z=275.0 (M+1). HPLC: 97.58%.

Example 50

Preparation of 8-Fluoro-2-(4-methylpyridin-3-yl)-3,4-dihydrobenzo[4,5]thieno[3,2-c]pyridin-1(2H)-one (50A)

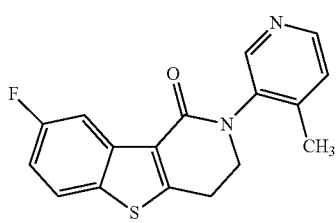
(50A)

Preparation of Intermediate methyl 5-fluorobenzo[b]thiophene-2-carboxylate (I-50a)

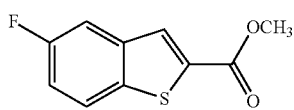
(I-50a)

TEA (3.705 g, 36.619 mmol) was added to a solution of methyl 2-mercaptoacetate (3.293 g, 30.985 mmol) in CH₃CN (12.5 mL). This was followed by the addition of 2,5-difluorobenzaldehyde (4 g, 28.169 mmol) in CH₃CN (12.5 mL) and the resulting reaction mass was refluxed overnight under nitrogen atmosphere. The reaction was monitored by TLC (5% ethyl acetate in hexane). The reaction mass was concentrated under reduced pressure to obtain the crude product. Purification by column chromatography on silica gel (15% ethyl acetate in hexane) afforded 2 g of the product (33.89% yield).

Preparation of Intermediate (5-fluorobenzo[b]thiophen-2-yl)methanol (I-50b)

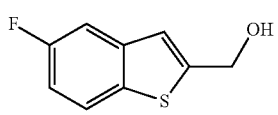
(I-50b)

DIBAL-H (59.4 mL, 59.41 mmol) was added to a solution of methyl 5-fluorobenzo[b]thiophene-2-carboxylate (I-50a: 2.5 g, 11.882 mmol) in THF (75 mL) at −70° C. and the resulting reaction mass was stirred at −10° C. for 2 hours. The reaction was monitored by TLC (30% ethyl acetate in hexane). The reaction mass was quenched with methanol at −70° C. and concentrated under reduced pressure. The crude residue obtained was partitioned between water and ethyl acetate. The organic layer was dried over Na₂SO₄ and concentrated under reduced pressure to afford the crude product. Purification by column chromatography on silica gel (15% ethyl acetate in hexane) afforded 1.8 g of the product (83.33% yield).

Preparation of Intermediate 5-fluorobenzo[b]thiophene-2-carbaldehyde (I-50c)

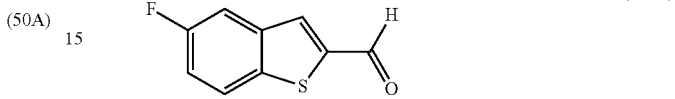
(I-50c)

MnO₂ (4.298 g, 49.45 mmol) was added to a solution of (5-fluorobenzo[b]-thiophen-2-yl)methanol (I-50b: 1.8 g, 9.89 mmol) in DCM (50 mL) and the resulting reaction mass was stirred at 52° C. for 2 hours. The reaction was monitored by TLC (30% ethyl acetate in hexane). The reaction mass was cooled to room temperature, filtered off the catalyst through a celite bed and washed the celite bed with DCM. The filtrate was concentrated under reduced pressure and dried under vacuum to afford 1.5 g of the product (88.23% yield).

Preparation of Intermediate (E)-5-fluoro-2-(2-nitrovinyl)benzo[b]thiophene (I-50d)

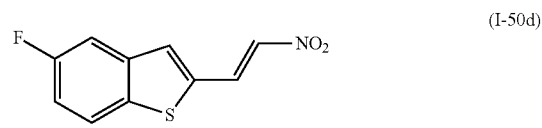 [SMILES: O=[N+]([O-])/C=C/c1cc2cc(F)ccc2s1]
(I-50d)

Using an analogous procedure and workup as described in example 1, for the preparation of Intermediate I-1a above, 5-fluorobenzo[b]thiophene-2-carbaldehyde (1.7 g, 9.444 mmol) was reacted with nitro methane (576.11 mg, 9.444 mmol), 10N NaOH (396.64 mg, 9.916 mmol) and ethanol (25 mL) at 0° C. for 2 hours to afford 1.2 g of the product (57.14% yield).

Preparation of Intermediate 2-(5-fluorobenzo[b]thiophen-2-yl)ethanamine (I-50e)

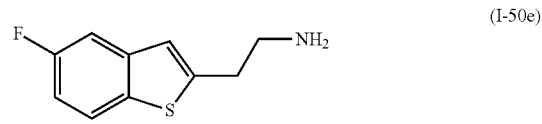 [SMILES: NCCc1cc2cc(F)ccc2s1]
(I-50e)

Using analogous conditions and workup as described for the preparation of I-14b above, (E)-5-fluoro-2-(2-nitrovinyl)benzo[b]thiophene (I-50d: 1.2 g, 5.375 mmol) was reacted with LiBH₄ (468.34 mg, 21.503 mmol), trimethylsilyl chlo- Preparation of Intermediate ethyl 2-(5-fluorobenzo[b]thiophen-2-yl)ethylcarbamate (I-50f)

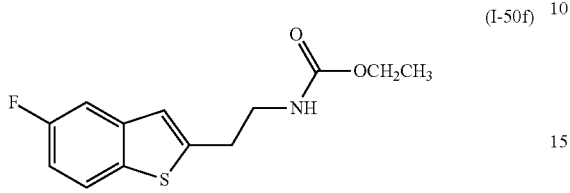

(I-50f)

Using an analogous procedure and workup as described for the preparation of Intermediate I-1c above, 2-(5-fluorobenzo[b]thiophen-2-yl)ethanamine (I-50e: 1 g, 5.128 mmol) was reacted with chloro ethyl formate (667.8 mg, 6.153 mmol), 2N Na$_2$CO$_3$ solution (10 mL) and CHCl$_3$ (25 mL) at 0° C. for 2 hours to afford the crude product. Purification by column chromatography on silica gel (5% ethyl acetate in hexane) afforded 700 mg of the product (53.84% yield).

$^1$H NMR (300 MHz, CDCl$_3$): δ 7.72 (m, 1H), 7.40-7.32 (m, 1H), 7.1-7.0 (m, 2H), 4.8 (bs, 1H), 4.1 (q, 2H), 3.5 (q, 2H), 3.1 (t, 2H), 1.2 (t, 3H). LCMS: 63.84%, m/z=178.9 (M+1)

Preparation of Intermediate 8-Fluoro-3,4-dihydro-2H-benzo[4,5]thieno[3,2-c]pyridin-1-one (I-50g)

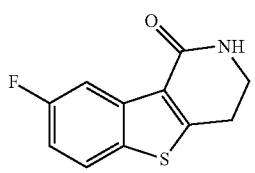

(I-50g)

Using analogous conditions and workup as described for the preparation of Intermediate I-1d above, ethyl 2-(5-fluorobenzo[b]thiophen-2-yl)ethylcarbamate (I-50 f: 700 mg, 2.622 mmol) was reacted with P$_2$O$_5$ (749.78 mg, 5.28 mmol) and POCl$_3$ (10 mL) to afford the crude product. Purification by column chromatography on silica gel (50% ethyl acetate in hexane) afforded 280 mg of the product (48.27% yield).

$^1$H NMR (300 MHz, CDCl$_3$): δ 8.32 (dd, 1H), 7.7 (m, 1H), 7.15-7.08 (m, 1H), 6.1 (bs, 1H), 3.75-3.68 (m, 2H), 3.2 (t, 2H). LCMS: 78.08%, m/z=221.9 (M+1)

Preparation of 8-Fluoro-2-(4-methylpyridine-3-yl)3,4-dihydro-2H-benzo[4,5]thieno[3,2-c]pyridin-1-one (50A)

Using analogous conditions and workup as described for the preparation of Compound 1A, 8-Fluoro-3,4-dihydro-2H-benzo[4,5]thieno[3,2-c]pyridin-1-one (I-50 g: 100 mg, 0.452 mmol) was reacted with 3-iodo-4-methylpyridine (99.09 mg, 0.452 mmol), 1,4-dioxane (5 mL), copper iodide (8.64 mg, 0.0452 mmol), trans-N,N'-dimethyl-cyclohexyl-1,2-diamine (19.25 mg, 0.1356 mmol) and potassium phosphate (287.44 mg, 1.356 mmol) at 115° C. overnight under nitrogen atmosphere to afford the crude product. Purification by column chromatography on silica gel (1.5% methanol in CHCl$_3$) afforded 95 mg of the product (67.37% yield).

$^1$H NMR (300 MHz, DMSO): δ 8.5 (d, 2H), 8.1 (d, 2H), 7.42-7.26 (m, 2H), 4.2 (m, 1H), 3.9 (m, 1H), 3.4 (m, 2H), 2.2 (s, 3H). LCMS: 99.26%, m/z=313.0 (M+1).

HPLC: 95.0%.

Example 51

Preparation of 2-(4-Methylpyridin-3-yl)-7-(trifluoromethoxy)-3,4-dihydroisoquinolin-1(2H)-one (51A)

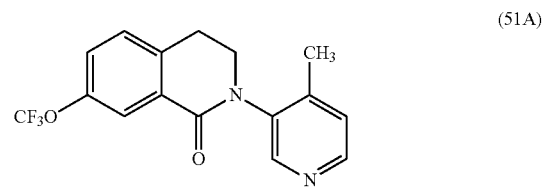

(51A)

Preparation of Intermediate 2-(4-(Trifluoromethoxy)phenyl)acetonitrile (I-51a)

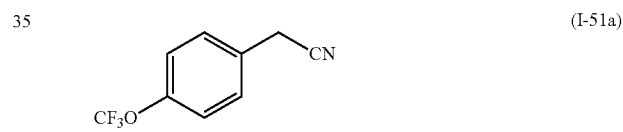

(I-51a)

Using analogous conditions and workup as described for the preparation of I-24a above, 1-(bromomethyl)-4-(trifluoromethoxy)benzene (5 g, 19.607 mmol) in DMSO (30 mL) was reacted with NaCN (1.44 g, 35.1864 mmol). The resulting mixture was stirred at 90° C. for 1 hour to afford 3.8 g of the product (95% yield). $^1$H NMR (300 MHz, CDCl$_3$): 7.45-7.20 (m, 4H), 3.8 (s, 2H)

Preparation of Intermediate 2-(4-(Trifluoromethoxy)phenyl)ethanamine (I-51b)

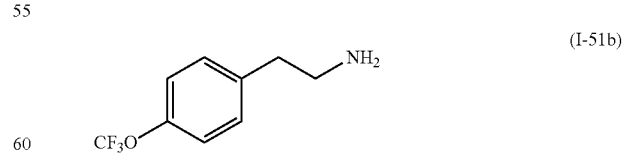

(I-51b)

Using analogous conditions as described for the preparation of Intermediate I-17b, 2-(4-(trifluoromethoxy)phenyl) acetonitrile (I-51a: 3.8 g) in methanolic ammonia (50 mL) was reacted with raney nickel (7 g) and methanol (40 mL) to afford 3.1 g of the product (80% yield).

¹H NMR (300 MHz, CDCl₃): δ 7.30-7.10 (m, 4H), 3.0 (t, 2H), 2.76 (t, 2H), 2.0 (s, 1H), 1.72 (s, 1H). LCMS: 74.12%, m/z=206.0 (M+1)

Preparation of Intermediate Ethyl 4-(trifluoromethoxy)phenethylcarbamate (I-51c)

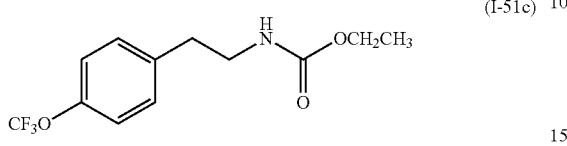

(I-51c)

Using an analogous procedure and workup as described for the preparation of intermediate I-1c above, 2-(4-(trifluoromethoxy)phenyl)ethanamine (I-51b: 3.1 g, 15.1219 mmol) in chloroform (31 mL) was reacted with chloro ethyl formate (1.72 mL, 18.146 mmol) and 2N Na₂CO₃ solution (31 mL) at 0° C. The resulting mixture was stirred at room temperature for 3 hours to afford the crude product. Purification by column chromatography on silica gel (10% ethylacetate in hexane) afforded 3.2 g of the product (76% yield).
¹H NMR (300 MHz, CDCl₃): δ 7.30-7.10 (m, 4H), 4.75-4.65 (m, 1H), 4.15-4.05 (m, 2H), 3.4 (q, 2H), 2.8 (t, 2H), 1.3-1.2 (m, 3H). LCMS: 70.91%, m/z=278.1 (M+1)

Preparation of Intermediate 7-(Trifluoromethoxy)-3,4-dihydroisoquinolin-1(2H)-one (I-51d)

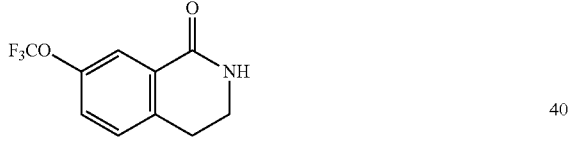

(I-51d)

Using an analogous procedure and workup as described for the preparation of intermediate I-1d above, ethyl 4-(trifluoromethoxy)phenethylcarbamate (I-51c: 3.2 g, 11.5523 mmol) in POCl₃ (32 mL) was reacted with P₂O₅ (3.27 g, 23.104 mmol). The resulting mixture was stirred at 110° C. for 1 hour to afford the crude product. Purification by column chromatography on silica gel (1.5% methanol in DCM) afforded 110 mg of the product (4.1% yield).
¹H NMR (300 MHz, CDCl₃): δ 7.30-7.10 (m, 3H), 4.22 (t, 1H), 3.42 (q, 2H), 2.8 (t, 2H)

Preparation of 2-(4-Methylpyridin-3-yl)-7-(trifluoromethoxy)-3,4-dihydroisoquinolin-1(2H)-one (51A)

Using analogous conditions as described for the preparation of Example 1A above, 7-(trifluoromethoxy)-3,4-dihydroisoquinolin-1(2H)-one (I-51d: 160 mg, 0.6896 mmol) was reacted with 3-iodo-4-methyl-pyridine (151 mg, 0.6896 mmol), 1,4-dioxane (20 mL), copper iodide (13.1 mg, 0.0689 mmol), trans-N,N'-dimethyl-cyclohexyl-1, 2-diamine (29.3 mg, 0.2068 mmol) and potassium phosphate (365 mg, 1.724 mmol) to afford the crude product. Purification by column chromatography on silica gel (40% ethylacetate in hexane), followed by preparative HPLC afforded 12 mg of the product (5.4% yield).

¹H NMR (300 MHz, CDCl₃): δ 8.54-8.42 (bs, 2H), 8.0 (s, 1H), 7.40-7.24 (m, 3H), 4.1-4.0 (m, 1H), 3.85-3.75 (m, 1H), 3.3-3.1 (m, 2H), 2.3 (s, 3H). LCMS: 87.22%, m/z=323.1 (M+1). HPLC: 99.14%

Example 52

Preparation of 2-(4-(Pyrrolidin-1-ylmethyl)pyridin-3-yl)-7-(trifluoromethyl)-3,4-dihydroisoquinolin-1(2H)-one (52A)

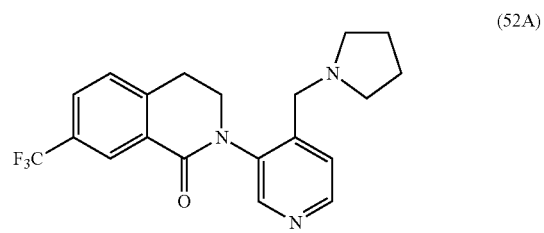 [SMILES: O=C1c2cc(C(F)(F)F)ccc2CCN1c1cnccc1CN1CCCC1]

(52A)

Preparation of Intermediate 3-Bromo-4-(pyrrolidin-1-ylmethyl)pyridine (I-52a)

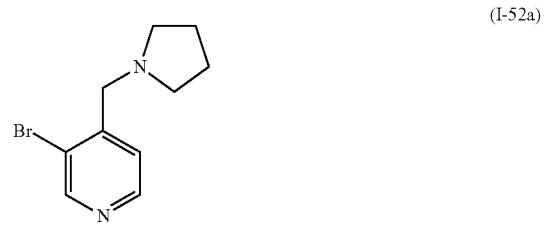 [SMILES: Brc1cnccc1CN1CCCC1]

(I-52a)

Catalytic amount of acetic acid (0.3 mL) was added to a mixture of 3-bromoisonicotinaldehyde (200 mg, 1.075 mmol) and pyrrolidine (0.12 mL, 1.34 mmol) in DCE (20 mL) under nitrogen atmosphere and the resulting mixture was stirred at room temperature for 2.3 hours. This was followed by the addition of sodium triacetoxy-borohydride (342 mg, 1.612 mmol) at 0° C. The reaction mixture was stirred at room temperature overnight. The reaction was monitored by TLC (50% ethylacetate in hexane). The reaction mixture was washed with NaHCO₃ solution and separated the layers. The organic layer was dried over Na₂SO₄ and concentrated to afford 250 mg of the product (96.52% yield).
¹H NMR (300 MHz, CDCl₃): δ 8.65 (s, 1H), 8.5 (d, 1H), 7.5 (d, 1H), 3.7 (s, 2H), 2.65-2.55 (m, 4H), 1.90-1.78 (m, 4H).

Preparation of 2-(4-(Pyrrolidin-1-ylmethyl)pyridin-3-yl)-7-(trifluoromethyl)-3,4-dihydroisoquinolin-1(2H)-one (52A)

Using analogous conditions as described for the preparation of Example 1A above, 7-(trifluoromethyl)-3,4-dihydroisoquinolin-1(2H)-one (I-4-d: 100 mg, 0.465 mmol) was reacted with 3-bromo-4-(pyrrolidin-1-ylmethyl)pyridine (I-52a: 140 mg, 0.558 mmol), 1,4-dioxane (10 mL), copper iodide (8.8 mg, 0.0465 mmol), trans-N,N'-dimethyl-cyclohexyl-1, 2-diamine (19.8 mg, 0.139 mmol) and potassium phosphate (295 mg, 1.395 mmol) to afford the crude product.

Purification by column chromatography on silica gel (12% methanol in CHCl₃), followed by preparative HPLC afforded 7 mg of the product (4.02% yield).

¹H NMR (300 MHz, CDCl₃): δ 8.56 (d, 1H), 8.5 (s, 1H), 8.42 (s, 1H), 7.76 (d, 1H), 7.54 (d, 1H), 7.42 (d, 1H), 4.1-4.0 (m, 1H), 3.9-3.8 (m, 1H), 3.75-3.65 (m, 1H), 3.5 (d, 1H), 3.40-3.26 (m, 1H), 3.25-3.10 (m, 1H), 2.5 (d, 4H), 1.7 (m, 4H). LCMS: 92.94%, m/z=376.1 (M+1). HPLC: 94.42%

Example 53

Preparation of 2-(4-((cyclopropylamino)methyl)pyridin-3-yl)-7-(trifluoromethyl)-3,4-dihydroisoquinolin-1(2H)-one (53A)

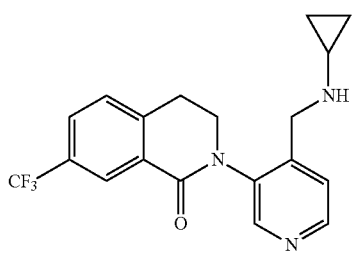
(53A)

Preparation of Intermediate 3-bromo-4-(dimethoxymethyl)pyridine (I-53a)

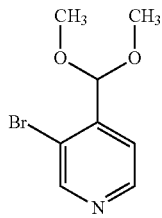
(I-53a)

p-Toluene sulphonic acid (PTSA) (613.5 mg, 3.225 mmol) was added to a stirred solution of 3-bromoisonicotinaldehyde (500 mg, 2.688 mmol) in methanol (20 mL) and the resulting reaction mixture was stirred for 3 hours at 75° C. The reaction was monitored by TLC (10% ethyl acetate in hexane). The reaction mixture was cooled to room temperature and concentrated under reduced pressure. The crude residue was diluted with ice, basified using saturated NaHCO₃ solution and extracted using ethyl acetate. The organic layer was washed with water, brine solution, dried over Na₂SO₄ and concentrated under reduced pressure. Purification by column chromatography on silica gel (10% ethyl acetate in hexane) afforded 600 mg of the product (96.3% yield).

Preparation of Intermediate 2-(4-(dimethoxymethyl)pyridin-3-yl)-7-(trifluoromethyl)-3,4-dihydroisoquinolin-1(2H)-one (I-53b)

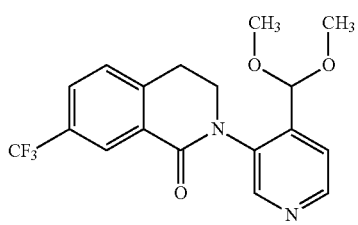
(I-53b)

Using analogous conditions as described for the preparation of Example 1A above, 7-trifluoromethyl-3,4-dihydro-2H-isoquinolin-1-one (I-4-d: 505.4 mg, 2.3503 mmol) was reacted with 3-Bromo-4-dimethoxymethyl-pyridine (I-52a: 600 mg, 2.5854 mmol), 1,4-dioxane (20 mL), copper iodide (44.6 mg, 0.2348 mmol), trans-N,N'-dimethyl-cyclohexyl-1,2-diamine (80.9 mg, 0.7052 mmol) and potassium phosphate (1.49 g, 7.0507 mmol) to afford the crude product. Purification by column chromatography on silica gel (1% methanol in CHCl₃) afforded 850 mg of the product (98.8% yield).

Preparation of Intermediate 3-(1-oxo-7-(trifluoromethyl)-3,4-dihydroisoquinolin-2(1H)-yl) isonicotinaldehyde (I-53c)

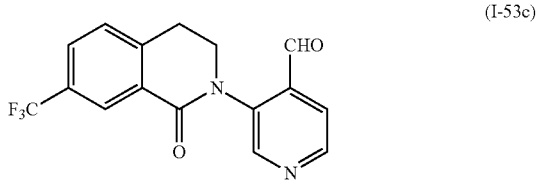 [SMILES: O=Cc1ccncc1N1CCc2ccc(C(F)(F)F)cc2C1=O]
(I-53c)

p-Toluene sulphonic acid (PTSA) (4.3 g, 23.093 mmol) was added to a stirred solution of 2-(4-dimethoxymethyl-pyridin-3-yl)-7-trifluoromethyl-3,4-dihydro-2H-isoquinolin-1-one (I-53b: 900 mg, 2.4568 mmol) in acetone (30 mL) and water (30 mL) and resulting reaction mixture was stirred for 48 hours at room temperature. The reaction mass was distilled under vacuum and the crude residue was dissolved in methanol (20 mL). This was followed by the addition of 2 N HCl (10 mL) and refluxed the resulting reaction mass for 3 hours. The reaction was monitored by TLC (10% methanol in CHCl₃). The reaction mixture was cooled to room temperature and concentrated under reduced pressure. The crude residue was diluted with ice, basified using saturated NaHCO₃ solution and extracted using CHCl₃. The organic layer was washed with water, brine solution, dried over Na₂SO₄ and concentrated under reduced pressure. Purification by column chromatography on silica gel (2% methanol in CHCl₃) afforded 110 mg of the product (14% yield).

LCMS: 58.53%, m/z=321.1 (M+1).

Preparation of 2-(4-((cyclopropylamino)methyl)pyridin-3-yl)-7-(trifluoromethyl)-3,4-dihydroisoquinolin-1(2H)-one (53A)

Cyclopropanamine (25.8 μL, 0.3737 mmol) was added to a stirred solution of 3-(1-oxo-7-(trifluoromethyl)-3,4-dihydroisoquinolin-2(1H)-yl)isonicotinaldehyde (I-53c: 100 mg, 0.3114 mmol) in acetic acid (5 mL) and resulting reaction mixture was stirred for 4 hours at room temperature. The reaction mass was cooled to 0° C. and added NaBH(OCH₃)₃ (99 mg, 0.4674 mmol). The resulting reaction mass was stirred for 12 hours at room temperature. The reaction was monitored by TLC (10% methanol in CHCl₃). The reaction mass was concentrated under reduced pressure, the crude residue obtained was diluted with ice, basified using saturated NaHCO₃ solution to pH 7 and extracted using CHCl₃. The organic layer was washed with water, brine solution, dried over Na₂SO₄ and concentrated under reduced pressure. Purification by column chromatography on silica gel (2% methanol in CHCl₃) afforded 25 mg of the product (22% yield).

¹H NMR (400 MHz, CDCl₃): δ 8.56 (d, 1H), 8.5 (s, 1H), 8.42 (s, 1H), 7.76 (dd, 1H), 7.46 (dd, 2H), 4.1-4.0 (m, 1H), 3.90-3.76 (m, 4H), 3.40-3.15 (m, 2H), 2.2-2.1 (m, 1H), 0.46-0.40 (m, 2H), 0.38-0.28 (m, 2H). LCMS: 50.16%, m/z=362.1 (M+1). HPLC: 96.65%

Example 54

Preparation of 2-(1-methyl-1H-imidazol-5-yl)-7-(trifluoromethyl)-3,4-dihydroisoquinolin-1(2H)-one (54A)

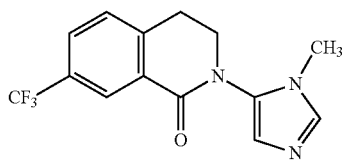
(54A)

Using analogous conditions as described for the preparation of Example 1A above, 7-(trifluoromethyl)-3,4-dihydroisoquinolin-1(2H)-one (I-4-d: 150 mg, 0.6849 mmol) was reacted with 5-bromo-1-methyl-1H-imidazole (165 mg, 1.0273 mmol), 1,4-dioxane (3 mL), copper iodide (13.01 mg, 0.0685 mmol), trans-N,N'-dimethyl-cyclohexyl-1,2-diamine (29.17 mg, 0.205 mmol) and potassium phosphate (434.6 mg, 2.05 mmol) to afford the crude product. Purification by column chromatography on silica gel (2% methanol in CHCl$_3$) afforded 50 mg of the product (24.75% yield).

$^1$H NMR (300 MHz, CDCl$_3$): δ 8.4 (s, 1H), 7.76 (d, 1H), 7.42 (d, 1H), 3.94 (bs, 2H), 3.54 (s, 3H), 3.24 (s, 2H). LCMS: 65.43% (34.56%), m/z=296.0 (M+1).

HPLC: 97.28%

Example 55

Preparation of 6,7-dichloro-2-(4-(trifluoromethyl)pyridin-3-yl)-3,4-dihydroisoquinolin-1(2H)-one (55)

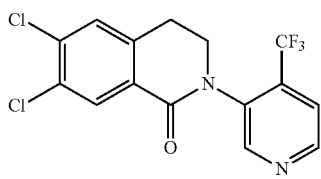
(55A)

Preparation of Intermediate (E)-1,2-dichloro-4-(2-nitrovinyl)benzene (I-55a)

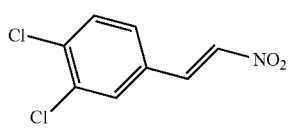
(I-55a)

Using analogous conditions and workup as described for the preparation of intermediate I-1a above, 3,4-dichlorobenzaldehyde (10 g, 74.074 mmol) in ethanol (100 mL) was reacted with nitro methane (4.12 mL, 74.074 mmol) and 10N NaOH (2.96 g in 7.4 mL of H$_2$O, 74.074 mmol) to afford 6.2 g of the product (39% yield).

Preparation of Intermediate 2-(3,4-dichlorophenyl)ethanamine (I-55b)

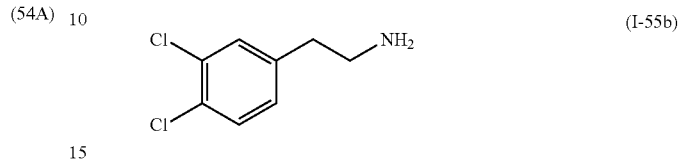
(I-55b)

Using an analogous procedure and workup as described for the preparation of intermediate I-15b, (E)-1,2-dichloro-4-(2-nitrovinyl)benzene (I-55a: 6.2 g, 28.97 mmol) in dry THF (62 mL) was reacted with LiBH$_4$ (2.52 g, 115.887 mmol) and chlorotrimethylsilane (25.17 g, 231.768 mmol) at 0° C. The resulting mixture was stirred at room temperature for 40 hours to afford 5.3 g of the product (98% yield).

Preparation of Intermediate Ethyl 3,4-dichloroyhenethylcarbamate (I-55c)

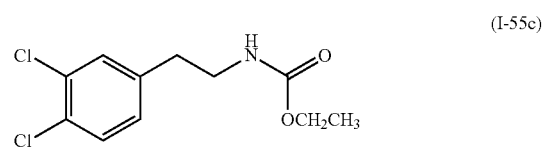 [SMILES: CCOC(=O)NCCc1ccc(Cl)c(Cl)c1]
(I-55c)

Using an analogous procedure and workup as described for the preparation of intermediate I-1c above, 2-(3,4-dichlorophenyl)ethanamine (I-55b: 5.3 g, 28.042 mmol) in chloroform (53 mL) was reacted with chloroethylformate (3.2 mL, 33.65 mmol) and 2N Na$_2$CO$_3$ solution (53 mL) to afford the crude product. Purification by column chromatography on silica gel (15% ethyl acetate in hexane) afforded 7 g of the product (95.7% yield).

Preparation of Intermediate 6,7-Dichloro-3,4-dihydroisoquinolin-1(2H)-one (I-55d)

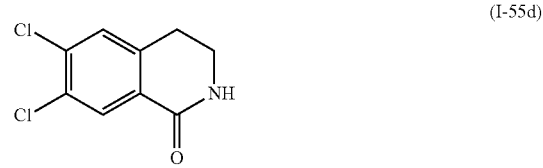 [SMILES: O=C1NCCc2cc(Cl)c(Cl)cc21]
(I-55d)

Using an analogous procedure and workup as described for the preparation of intermediate I-1d above, ethyl 3,4-dichlorophenethylcarbamate (I-55c: 6 g, 22.989 mmol) in POCl$_3$ (60 mL) was reacted with P$_2$O$_5$ (6.52 g, 45.977 mmol) at 120° C. for 1 hour to afford the crude product. Purification by column chromatography on silica gel (30% ethylacetate in hexane) afforded 1.01 g of the product. LCMS: 53.61%, m/z=216.0 (M+1)

Preparation of 6,7-dichloro-2-(4-(trifluoromethyl)pyridin-3-yl)-3,4-dihydroisoquinolin-1(2H)-one (55A)

Using an analogous procedure and workup as described for the preparation of Example 1A above, 6,7-dichloro-3,4-dihydroisoquinolin-1(2H)-one (I-55d: 100 mg, 0.463 mmol) was reacted with 3-bromo-4-(trifluoromethyl)pyridine (115 mg, 0.509 mmol), 1,4-dioxane (3 mL), copper iodide (7 mg, 0.046 mmol), trans-N,N'-dimethyl-cyclohexyl-1,2-diamine (20 mg, 0.1388 mmol) and potassium phosphate (245 mg, 1.157 mmol) in a sealed tube at 120° C. for 16 hours to afford the crude product. Purification by column chromatography on silica gel (20% ethylacetate in hexane) afforded 14 mg of the product (8.3% yield).

$^1$H NMR (400 MHz, CDCl$_3$): δ 8.84 (d, 1H), 8.7 (s, 1H), 8.2 (s, 1H), 7.7 (d, 1H), 7.4 (s, 1H), 4.04-3.95 (m, 1H), 3.82-3.74 (m, 1H), 3.35-3.25 (m, 1H), 3.1-3.0 (m, 1H). LCMS: 89.53%, m/z=362.0 (M+1). HPLC: 92.73%

Example 56

Preparation of 2-(5-fluoropyridin-3-yl)-6-(trifluoromethyl)-3,4-dihydroisoquinolin-(2H)-one (56A)

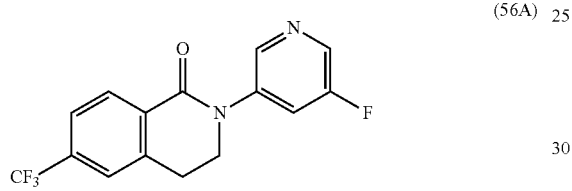

(56A)

Using an analogous procedure as described for the preparation of example 1A above, 6-(trifluoromethyl)-3,4-dihydroisoquinolin-1(2H)-one (I-17c: 120 mg, 0.558 mmol) was reacted with 3-bromo-5-fluoropyridine (147 mg, 0.8372 mmol), 1,4-dioxane (10 mL), copper iodide (32 mg, 0.1674 mmol), trans-N,N'-dimethyl-cyclohexyl-1,2-diamine (24 mg, 0.1674 mmol) and potassium phosphate (400 mg, 1.395 mmol) in a microwave vial at 115° C. overnight. The reaction was monitored by TLC (50% ethyl acetate in hexane). The reaction mass was concentrated under reduced pressure and the crude residue was partitioned between water and DCM. The organic layer was washed with water, brine solution, dried over Na$_2$SO$_4$ and concentrated under reduced pressure to afford the crude product. Purification by column chromatography on silica gel (35% ethyl acetate in hexane) afforded 60 mg of the product (34.68% yield).

$^1$H NMR (400 MHz, CDCl$_3$): δ 8.52 (s, 1H), 8.4 (d, 1H), 8.28 (d, 1H), 7.70-7.62 (m, 2H), 7.56 (s, 1H), 4.1 (t, 2H), 3.28 (t, 2H). LCMS: 98.80%, m/z=311.0 (M+1). HPLC: 99.09%

Example 57

Preparation of 8-Fluoro-2-(4-trifluoromethylpyridine-3-yl)-3,4-dihydro-2H-benzo[4,5]thieno[3,2-c]pyridin-1-one (57A)

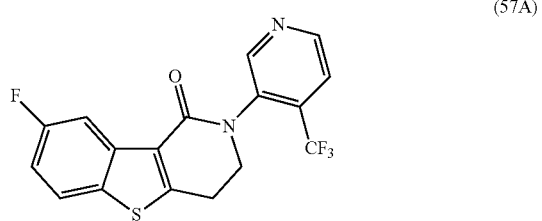 [SMILES: O=C1c2c(sc3ccc(F)cc23)CCN1c1cnccc1C(F)(F)F]

(57A)

Using analogous conditions and workup as described for the preparation of Example 1A above, 8-fluoro-3,4-dihydro-2H-benzo[4,5]thieno[3,2-c]pyridin-1-one (I-50g: 100 mg, 0.452 mmol) was reacted with 3-bromo-4-trifluoromethylpyridine (102.26 mg, 0.452 mmol), 1,4-dioxane (3 mL), copper iodide (8.58 mg, 0.0452 mmol), trans-N,N'-dimethyl-cyclohexyl-1,2-diamine (19.25 mg, 0.135 mmol) and potassium phosphate (286.56 mg, 1.35 mmol) in a vial at 115° C. overnight under nitrogen atmosphere to afford the crude product. Purification by preparative HPLC afforded 15 mg of the product (9.09% yield).

$^1$H NMR (300 MHz, CDCl$_3$): δ 8.85 (d, 1H), 8.75 (s, 1H), 8.3 (dd, 1H), 7.85-7.68 (m, 2H), 7.2-7.1 (m, 1H), 4.25-4.10 (m, 1H), 3.9-3.8 (m, 1H), 3.6-3.4 (m, 1H), 3.3-3.2 (m, 1H). LCMS: 100%, m/z=366.8 (M+1). HPLC: 98.88%

Example 58

Preparation of 2-(4-trifluoromethylpyridine-3-yl)-3,4-dihydro-2H-benzo[4,5]thieno[3,2-c]pyridin-1-one (58A)

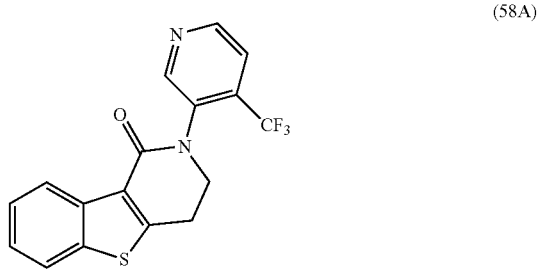 [SMILES: O=C1c2c(sc3ccccc23)CCN1c1cnccc1C(F)(F)F]

(58A)

X-Phos (35 mg, 0.0739 mmol) and Pd$_2$(dba)$_3$ (45 mg, 0.0492 mmol) were added to a previously degassed solution of 3,4-dihydro-2H-benzo[4,5]thieno[3,2-c]pyridin-1-one (I-9d: 100 mg, 0.4919 mmol), K$_3$PO$_4$ (313 mg, 1.4759 mmol) and 1,4-dioxane (5 mL) in a sealed tube. This was followed by the addition of 3-bromo-4-(trifluoromethyl)pyridine (134 mg, 0.5903 mmol) and the resulting reaction mass was heated at 120° C. for 48 hours. The reaction was monitored by TLC (50% ethyl acetate in hexane). The reaction mass was partitioned between water and ethylacetate. The organic layer was washed with water, brine solution, dried over Na$_2$SO$_4$ and concentrated to afford the crude product. Purification by column chromatography on silica gel (30% ethyl acetate in hexane), followed by preparative HPLC afforded 14 mg of the product (8.18% yield).

$^1$H NMR (400 MHz, CDCl$_3$): δ 8.85 (d, 1H), 8.78 (s, 1H), 8.6 (d, 1H), 7.85 (d, 1H), 7.7 (d, 1H), 7.50-7.38 (m, 2H), 4.2-4.1 (m, 1H), 3.92-3.86 (m, 1H), 3.58-3.45 (m, 1H), 3.3-3.2 (m, 1H). LCMS: 98.93%, m/z=348.7 (M+1). HPLC: 95.59%

Example 59

Preparation of 5-ethyl-8-fluoro-2-(4-methylpyridin-3-yl)-2,3,4,5-tetrahydro-1H-pyrido[4,3-b]indol-1-one (59A)

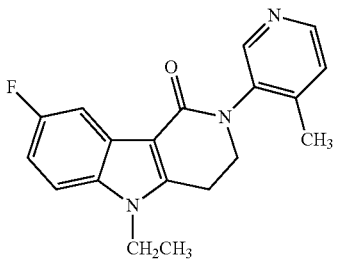
(59A)

Preparation of Intermediate 3-(tert-butoxycarbonylamino)propanoic acid (I-59a)

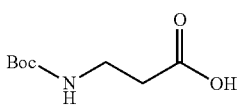
(I-59a)

Boc anhydride (79.61 g, 0.3647 mmol) was added slowly to a cooled solution of 3-aminopropanoic acid (25 g, 0.2806 mmol) in 10% NaOH (250 mL) and the resulting reaction mass was allowed to stir at room temperature for 3 hours. The reaction was monitored by TLC (10% methanol in CHCl$_3$). The reaction mass was diluted with ethyl acetate, neutralized using citric acid and separated the layers. The organic layer was washed with water, brine solution, dried over anhydrous Na$_2$SO$_4$, washed with hexane at 0° C. and concentrated to afford 50 g of the product (94.17% yield).

$^1$H NMR (300 MHz, CDCl$_3$): δ 5.1 (s, 1H), 3.4 (t, 2H), 2.6 (q, 2H), 1.4 (s, 9H).

LCMS: 90.97%, m/z=134.0 (M+1)

Preparation of Intermediate tert-butyl 3-(2,2-dimethyl-4,6-dioxo-1,3-dioxan-5-yl)-3-oxopropylcarbamate (I-59b)

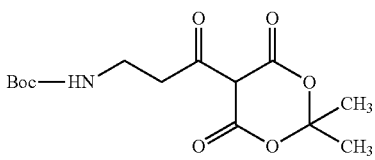
(I-59b)

EDCI (59.39 g, 310.8 mmol) was added at 0° C. to a stirred solution of 3-(tert-butoxycarbonylamino)propanoic acid (I-59a: 49 g, 258.9 mmol), meldrum's acid (41.05 g, 284.8 mmol) and DMAP (47.4 g, 388.5 mmol) in DCM (490 mL) and the resulting reaction mass was allowed to stir at room temperature overnight. The reaction was monitored by TLC (10% methanol in CHCl$_3$). The reaction mass was washed with 5% KHSO$_4$ solution and separated the layers. The organic layer was dried over Na$_2$SO$_4$ and concentrated to afford 70 g of the product (85.8% yield).

$^1$H NMR (300 MHz, CDCl$_3$): δ 4.9 (bs, 1H), 3.55 (q, 2H), 3.45-3.25 (t, 3H), 1.75 (s, 6H), 1.4 (s, 9H)

Preparation of Intermediate tert-butyl 2,4-dioxopiperidine-1-carboxylate (I-59c)

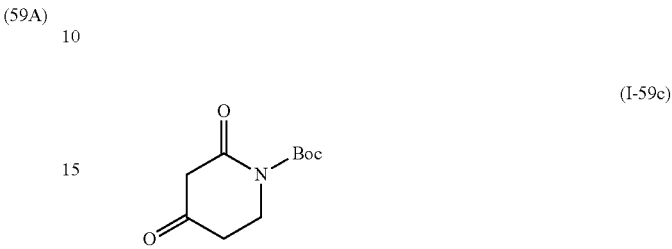
(I-59c)

Tert-butyl 3-(2,2-dimethyl-4,6-dioxo-1,3-dioxan-5-yl)-3-oxopropylcarbamate (I-59b: 50 g, 158.57 mmol) was dissolved in ethyl acetate (500 mL) at room temperature under nitrogen atmosphere and the resulting reaction mass was heated at 105° C. for 20 hours. The reaction was monitored by TLC (10% methanol in DCM). The reaction mass was cooled to room temperature and concentrated under reduced pressure to afford the crude product. Purification by ether-wash afforded 28 g of the product (83% yield).

$^1$H NMR (300 MHz, CDCl$_3$): δ 4.1 (t, 2H), 3.5 (s, 2H), 2.6 (t, 2H), 1.55 (s, 9H)

Preparation of Intermediate piperidine-2,4-dione (I-59d)

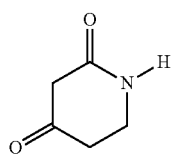
(I-59d)

TFA (140 mL) was added drop wise to a solution of tert-butyl 2,4-dioxopiperidine-1-carboxylate (I-59c: 28 g, 131.45 mmol) in DCM (280 mL) at 0° C. and the resulting reaction mass was stirred at room temperature for 1 hour. The reaction was monitored by TLC (10% methanol in DCM). The reaction mass was concentrated under reduced pressure to afford the crude product which was dried under high vacuum and washed with ether to afford 14 g of the product (94% yield).

Preparation of Intermediate 4-(4-fluorophenylamino)-5,6-dihydropyridin-2(1H)-one (I-59e)

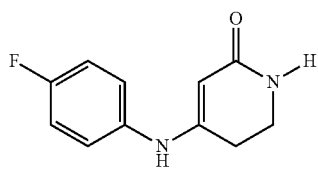
(I-59e)

Piperidine-2,4-dione (I-59d: 10 g, 88.40 mmol) and 4-fluoroaniline (9.82 g, 88.40 mmol) were heated at 120° C. for 5 hours under argon atmosphere. The reaction was monitored by TLC (10% methanol in DCM). The reaction mass was cooled to room temperature, diluted with ether and stirred for 20 minutes. The solid precipitated was collected by filtration to afford 7 g of the product (38.46% yield).

Preparation of Intermediate 8-fluoro-2,3,4,5-tetrahydro-1H-pyrido[4,3-b]indol-1-one (I-59f)

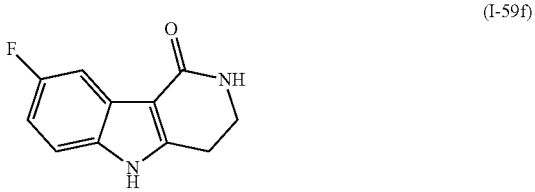 [SMILES: O=C1NCCc2[nH]c3ccc(F)cc3c21]

(I-59f)

Cu(OAc)$_2$ (9.69 g, 53.39 mmol) was added to a stirred solution of 4-(4-fluorophenylamino)-5,6-dihydropyridin-2 (1H)-one (I-59e: 5 g, 24.27 mmol) and Pd(OAc)$_2$ (490 mg, 2.18 mmol) in DMF (96 mL) under argon atmosphere and the resulting reaction mass was heated at 130° C. for 2 hours. The reaction was monitored by TLC (5% methanol in DCM). The reaction mass was cooled to room temperature and filtered through a celite bed. The filtrate was partitioned between water and ethyl acetate. The organic layer was washed with water, brine solution, dried over Na$_2$SO$_4$ and concentrated to afford the crude product. Purification by column chromatography on silica gel (1% methanol in DCM) afforded 2.2 g of the product (44.7% yield).

$^1$H NMR (300 MHz, DMSO): δ 11.8 (s, 1H), 7.54-7.30 (m, 1H), 7.12-6.90 (m, 2H), 3.5-3.4 (m, 2H), 2.96 (t, 2H).

Preparation of Intermediate 5-ethyl-8-fluoro-2,3,4,5-tetrahydro-1H-pyrido[4,3-b]indol-1-one (I-59g)

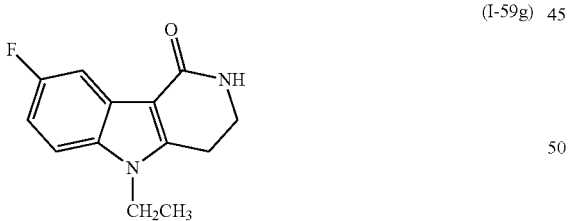

(I-59g)

8-Fluoro-2,3,4,5-tetrahydro-1H-pyrido[4,3-b]indol-1-one (I-59f: 500 mg, 2.44 mmol) in DMF (200 mL) was reacted with 60% NaH (196 mg, 8.16 mmol) and ethyl iodide (456 mg, 2.92 mmol) to afford the crude product. The reaction mass was quenched with chilled water and extracted with ethyl acetate. The organic layer was washed with water, brine solution, dried over Na$_2$SO$_4$ and concentrated to afford the crude product. Purification by column chromatography on silica gel (1% methanol in DCM) afforded 120 mg of the product (21.2% yield).

$^1$H NMR (300 MHz, DMSO): δ 7.60-7.52 (m, 2H), 7.16-6.96 (m, 2H), 4.2 (q, 2H), 3.52-3.40 (m, 2H), 3.0 (t, 2H), 1.25 (t, 3H). LCMS: 94.55%, m/z=233.1 (M+1)

Preparation of 5-Ethyl-8-fluoro-2-(4-methylpyridin-3-yl)-2,3,4,5-tetrahydro-1H-pyrido[4,3-]indol-1-one (59A)

5-Ethyl-8-fluoro-2,3,4,5-tetrahydro-1H-pyrido[4,3-b]indol-1-one (I-59g: 120 mg, 0.517 mmol) was reacted with 3-iodo-4-methylpyridine (147.2 mg, 0.672 mmol), 1,4-dioxane (15 mL), copper iodide (9.8 mg, 0.0517 mmol), trans-N,N'-dimethyl-cyclohexyl-1,2-diamine (23.1 mg, 0.155 mmol) and potassium phosphate (273.4 mg, 1.29 mmol) at 120° C. overnight to afford the crude product. Purification by column chromatography on silica gel (1% methanol in DCM) afforded 80 mg of the product (48.1% yield).

$^1$H NMR (300 MHz, CDCl$_3$): δ 8.55-8.4 (m, 2H), 7.85 (dd, 1H), 7.32-7.2 (m, 2H), 7.05-6.98 (m, 1H), 4.30-4.15 (m, 3H), 3.98-3.88 (m, 1H), 3.3-3.1 (m, 2H), 2.3 (s, 3H), 1.45 (t, 3H). LCMS: 98.65%, m/z=324.2 (M+1). HPLC: 90.19%

Example 60

Preparation of 8-fluoro-2-(4-methylpyridin-3-yl)-2,3,4,5-tetrahydro-1H-pyrido[4,3-b]indol-1-one (60A)

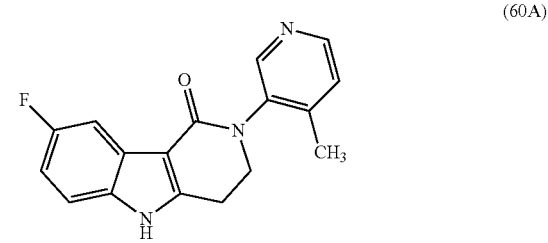 [SMILES: Cc1ccncc1N1CCc2[nH]c3ccc(F)cc3c2C1=O]

(60A)

Preparation of Intermediate 8-fluoro-5-(phenylsulfonyl)-2,3,4,5-tetrahydro-1H-pyrido[4,3-b]indol-1-one (I-60a)

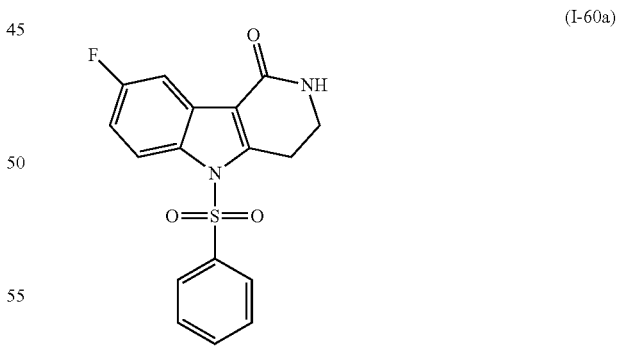

(I-60a)

60% NaH (196 mg, 8.16 mmol) was added to a stirred solution of 8-fluoro-2,3,4,5-tetrahydro-1H-pyrido[4,3-b]indol-1-one (500 mg, 2.44 mmol) in DMF (20 mL) at −10° C. and stirred for 10 minutes at room temperature. This was followed by the addition of benzene sulfonyl chloride (517 mg, 2.92 mmol) at 0° C. and the resulting reaction mass was stirred at room temperature for 5 minutes. The reaction was monitored by TLC (5% methanol in DCM). The reaction mass was quenched with ice and extracted using ethyl acetate.

The organic layer was washed with water, brine solution, dried over Na₂SO₄ and concentrated to afford the crude product. Purification by column chromatography on silica gel (0.5% methanol in DCM) afforded 450 mg of the product (53.6% yield).

¹H NMR (300 MHz, CDCl₃): δ 8.1 (m, 1H), 7.90-7.76 (m, 3H), 7.68-7.56 (m, 1H), 7.5 (m, 2H), 7.14-7.04 (m, 1H), 5.6 (s, 1H), 3.7-3.6 (m, 2H), 3.4 (t, 2H). LCMS: 96.11%, m/z=345.0 (M+1)

Preparation of 8-fluoro-2-(4-methylpyridin-3-yl)-5-(phenylsulfonyl)-2,3,4,5-tetrahydro-1H-pyrido[4,3-b]indol-1-one (I-60b)

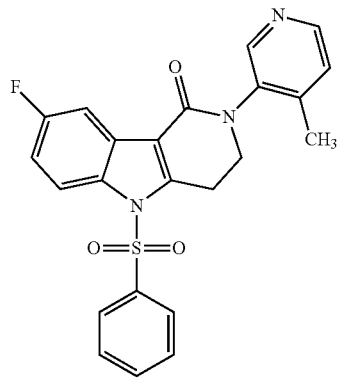

(I-60b)

Using analogous reaction conditions and work up as described for the preparation of Example 1A, 8-fluoro-5-(phenylsulfonyl)-2,3,4,5-tetrahydro-1H-pyrido[4,3-b]indol-1-one (I-60a: 450 mg, 1.308 mmol) was reacted with 3-iodo-4-methylpyridine (286 mg, 1.308 mmol), 1,4-dioxane (25 mL), copper iodide (25 mg, 0.13 mmol), trans-N,N'-dimethyl-cyclohexyl-1,2-diamine (58.46 mg, 0.392 mmol) and potassium phosphate (693 mg, 3.27 mmol) at 120° C. overnight to afford the crude product. Purification by column chromatography on silica gel (5% methanol in DCM) afforded 60 mg of the product (15% yield).

Preparation of 8-Fluoro-2-(4-methylpyridin-3-yl)-2,3,4,5-tetrahydro-1H-pyrido[4,3-b]indol-1-one (60A)

1M TBAF (0.3 mL, 0.274 mmol) was added to a solution of 8-fluoro-2-(4-methylpyridin-3-yl)-5-(phenylsulfonyl)-2,3,4,5-tetrahydro-1H-pyrido[4,3-b]indol-1-one (I-60b: 60 mg, 0.137 mmol) in THF (5 mL) at 0° C. and the resulting reaction mass was refluxed for 1 hour. The reaction was monitored by TLC (5% methanol in DCM). The reaction mass was concentrated under reduced pressure and the crude residue was partitioned between water and ethyl acetate. The organic layer was washed with water, brine solution, dried over Na₂SO₄ and concentrated to afford the crude product. Purification by preparative HPLC afforded 20 mg of the product (52% yield).

¹H NMR (400 MHz, DMSO): δ 8.5-8.3 (m, 2H), 7.6-7.3 (m, 3H), 7.02-6.98 (m, 1H), 4.2-4.1 (m, 1H), 3.82-3.68 (m, 1H), 3.1-3.25 (m, 2H), 2.2 (s, 3H). LCMS: 100%, m/z=296.0 (M+1). HPLC: 96.36%

Example 61

Preparation of 2-(4-methylpyridin-3-yl)-2,3,4,9-tetrahydro-1H-pyrido[3,4-b]indol-1-one (61A)

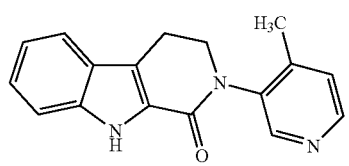

(61A)

Preparation of Intermediate 1-(4-methoxybenzyl)-1H-indole-3-carbaldehyde (I-61a)

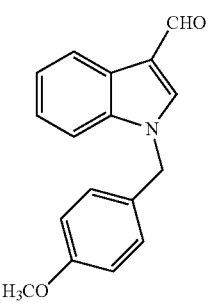

(I-61a)

Using analogous procedure as those described to prepare intermediate I-38b, 1H-Indole-3-carbaldehyde (10 g, 68.96 mmol) was reacted with 1-(chloromethyl)-4-methoxybenzene (11.26 mL, 82.75 mmol) and 60% NaH (5.5 g, 137.92 mmol) in DMF (140 mL) at room temperature for 1 hour to afford 20 g of the product.

¹H NMR (400 MHz, CDCl₃): δ 10 (s, 1H), 8.3 (d, 1H), 7.7 (s, 1H), 7.40-7.25 (m, 3H), 7.15 (d, 2H), 6.9 (d, 2H), 5.3 (s, 2H), 3.8 (s, 3H). LCMS: 92.67%, m/z 266.0 (M+1)

Preparation of Intermediate (Z)-1-(4-methoxybenzyl)-3-(2-nitrovinyl)-1H-indole (I-61b)

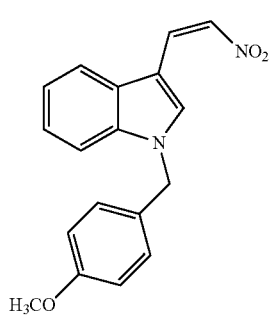

(I-61b)

1-(4-Methoxybenzyl)-1H-indole-3-carbaldehyde (I-61a: 22 g, 83.01 mmol) was refluxed overnight with nitromethane (146 g, 2407 mmol) and ammonium acetate (3.26 g, 42.33 mmol) to afford the crude product. The reaction mass was cooled to room temperature and filtered. The solid collected was washed with water and dried under reduced pressure to afford 20 g of the product (76% yield).

¹H NMR (400 MHz, CDCl₃): δ 8.24 (d, 1H), 7.82-7.74 (m, 2H), 7.52 (s, 1H), 7.44-7.30 (m, 3H), 7.14 (d, 2H), 6.9 (d, 2H), 5.3 (s, 2H), 3.8 (s, 2H)

Preparation of Intermediate 2-(1-(4-methoxybenzyl)-1H-indol-3-yl)ethanamine (I-61c)

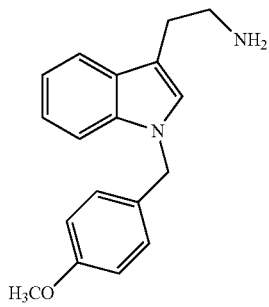

(Z)-1-(4-Methoxybenzyl)-3-(2-nitrovinyl)-1H-indole (5 g, 15.72 mmol) in dry THF (32 mL) was reacted with LAH (2.98 g, 78.61 mmol) in dry THF (32 mL). The resulting mixture was refluxed for 16 hours under nitrogen atmosphere to afford 4.6 g of the product (100% yield).
LCMS: 87.49%, m/z=264.1 (M+1).

Preparation of Intermediate ethyl 2-(1-(4-methoxybenzyl)-1H-indol-3-yl)ethylcarbamate (I-61d)

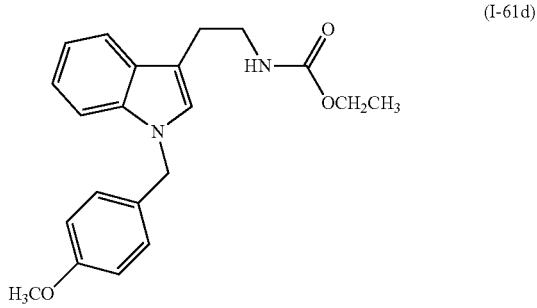 [SMILES: CCOC(=O)NCCc1cn(Cc2ccc(OC)cc2)c2ccccc12]

2-(1-(4-Methoxybenzyl)-1H-indol-3-yl)ethanamine (I-61c: 5 g, 17.85 mmol) was reacted with chloro ethyl formate (2.32 g, 21.42 mmol) and 2N $Na_2CO_3$ solution (36 mL) in chloroform (36 mL) to afford 5.6 g of the product (90% yield).

Preparation of Intermediate 2,3,4,9-tetrahydro-1H-pyrido[3,4-b]indol-1-one (I-61e)

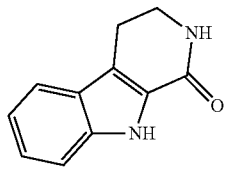

Ethyl 2-(1-(4-methoxybenzyl)-1H-indol-3-yl)ethylcarbamate (I-61d: 4.5 g, 12.78 mmol) and poly phosphoric acid (45 g) were heated at 120° C. for 1 hour. The reaction mass was quenched with ice and extracted using ethyl acetate. The organic layer was washed with brine solution, dried over $Na_2SO_4$ and concentrated under reduced pressure to afford the crude product. Purification by column chromatography on silica gel (40% ethyl acetate in hexane) afforded 250 mg of the product (10% yield).

Preparation of 2-(4-methylpyridin-3-yl)-2,3,4,9-tetrahydro-1H-pyrido[3,4-b]indol-1-one (61A)

2,3,4,9-tetrahydro-1H-pyrido[3,4-b]indol-1-one (I-61e: 250 mg, 1.34 mmol) was reacted with 3-iodo-4-methylpyridine (294.3 mg, 1.34 mmol), 1,4-dioxane (10 mL), copper iodide (25.6 mg, 0.134 mmol), trans-N,N'-dimethyl-cyclohexyl-1,2-diamine (59.8 mg, 0.402 mmol) and potassium phosphate (710 mg, 3.35 mmol) at 120° C. overnight to afford the crude product. Purification by column chromatography on silica gel (40% ethyl acetate in hexane), followed by preparative HPLC afforded 5 mg of the product (2% yield).
$^1$H NMR (400 MHz, $CDCl_3$): δ 9.2 (s, 1H), 8.54-8.42 (m, 2H), 7.62 (d, 1H), 7.44-7.30 (m, 2H), 7.26-7.16 (m, 2H), 4.25-4.15 (m, 1H), 4.0-3.88 (m, 1H), 3.3-3.2 (m, 2H), 2.3 (s, 3H). LCMS: 96.64%, m/z=278.2 (M+1). HPLC: 96.90%

Example 62

Preparation of 2-(4-methylpyridin-3-yl)-2,5-dihydro-1H-pyrido[4,3-b]indol-1-one (62A)

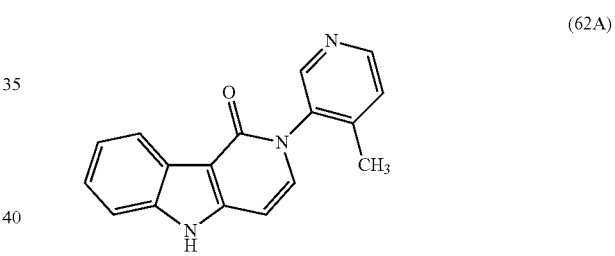

Preparation of Intermediate 2,5-dihydro-1H-pyrido[4,3-b]indol-1-one (I-62a)

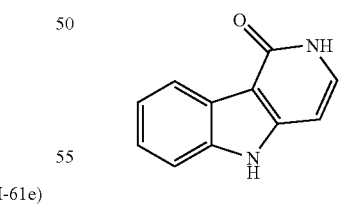

4-Hydroxypyridin-2(1H)-one (3 g, 27 mmol) and phenylhydrazine (8.74 g, 81 mmol) in diphenyl ether (54 mL) were heated at 240° C. for 5 hours in a Dean Stark apparatus. The reaction mass was cooled to room temperature, diluted with benzene, stirred for 2 hours and filtered. The solid collected was dried under high vacuum and washed with ether to afford 3 g of the product (60% yield).
$^1$H NMR (300 MHz, DMSO): δ 11.8 (s, 1H), 11.1 (s, 1H), 8.1 (d, 1H), 7.5 (d, 1H), 7.35-7.15 (m, 3H), 6.5 (d, 1H). LCMS: 84.53%, m/z=185.0 (M+1)

Preparation of 2-(4-methylpyridin-3-yl)-2,5-dihydro-1H-pyrido[4,3-b]indol-1-one (62A)

2,5-dihydro-1H-pyrido[4,3-b]indol-1-one (I-62a: 500 mg, 2.71 mmol), 3-iodo-4-methylpyridine (892 mg, 4 mmol), 8-hydroxy quinoline (79 mg, 0.542 mmol) and $K_2CO_3$ (560 mg, 4.06 mmol) were added to a previously degassed solution of DMSO (10 mL). This was followed by the addition of CuI (103.2 mg, 0.542 mmol) and the resulting reaction mass was heated at 150° C. for 16 hours in a sealed tube. The reaction was monitored by TLC (5% methanol in DCM). The reaction mass was quenched with water, diluted using ethyl acetate and filtered. The filtrate was extracted using ethyl acetate, washed the organic layer with water, brine solution, dried over $Na_2SO_4$ and concentrated under reduced pressure to afford the crude product. Purification by column chromatography on silica gel (1% methanol in DCM), followed by preparative HPLC afforded 40 mg of the product (5.4% yield).
$^1$H NMR (400 MHz, DMSO): δ 8.55 (d, 1H), 8.45 (s, 1H), 8.1 (d, 1H), 7.55-7.45 (m, 3H), 7.3 (t, 1H), 7.2 (t, 1H), 6.7 (d, 1H), 2.2 (s, 3H). LCMS: 100%, m/z=276.1 (M+1). HPLC: 97.43%

Example 63

Preparation of 2-(4-(trifluoromethyl)pyridin-3-yl)-2,5-dihydro-1H-pyrido[4,3-b]indol-1-one (63A)

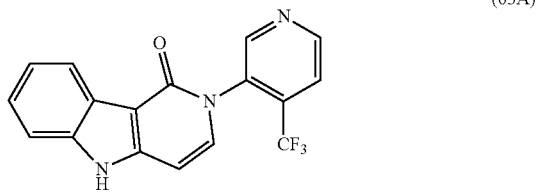

(63A)

Using analogous reaction conditions and work up as described for the preparation of 62A above, 2,5-dihydro-1H-pyrido[4,3-b]indol-1-one (I-62a: 200 mg, 1.08 mmol) was reacted with 3-bromo-4-trifluoromethylpyridine (368.4 mg, 1.63 mmol), 8-hydroxy quinoline (31.3 mg, 0.216 mmol), $K_2CO_3$ (223.5 mg, 1.62 mmol), copper iodide (41.14 mg, 0.216 mmol) and DMSO (5 mL) to afford the crude product. Purification by column chromatography on silica gel (2% methanol in DCM), followed by preparative HPLC afforded 5 mg of the product (1.5% yield).
$^1$H NMR (400 MHz, DMSO): δ 9 (d, 1H), 8.9 (s, 1H), 8.1-8.0 (m, 2H), 7.6 (dd, 2H), 7.35 (t, 1H), 7.2 (t, 1H), 6.75 (d, 1H). LCMS: 97.04%, m/z=329.8 (M+1).
HPLC: 98.92%

Example 64

Preparation of 8-fluoro-2-(4-(trifluoromethyl)pyridin-3-yl)-2,5-dihydro-1H-pyrido[4,3-b]indol-1-one (64A)

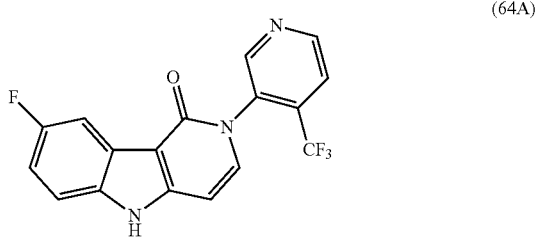 [SMILES: O=c1c2c(ccn1-c1cnccc1C(F)(F)F)[nH]c1ccc(F)cc12]

(64A)

Preparation of Intermediate 8-fluoro-2,5-dihydro-1H-pyrido[4,3-b]indol-1-one (I-64a)

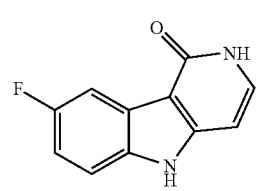

(I-64a)

4-Hydroxypyridin-2(1H)-one (1 g, 0.009 mol) and (4-fluorophenyl)hydrazine (3.6 g, 0.027 mol) in diphenyl ether (20 mL) were heated at 250° C. for 5 hours to afford the crude product. Purification by washing with hexane, followed by column chromatography on silica gel (1.5% methanol in DCM) afforded 330 mg of the product (17.36% yield).
$^1$H NMR (400 MHz, DMSO): δ 11.8 (s, 1H), 11.2 (s, 1H), 7.74 (dd, 1H), 7.5 (m, 1H), 7.32 (t, 1H), 7.2-7.1 (m, 1H), 6.5 (d, 1H). LCMS: 85.96%, m/z=202.9 (M+1)

Preparation of Intermediate 8-fluoro-5-(4-methoxybenzyl)-2,5-dihydro-1H-pyrido[4,3-b]indol-1-one (I-64b)

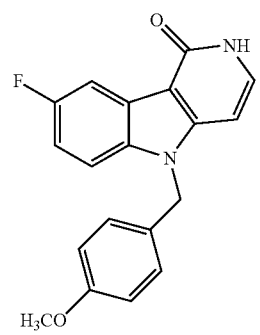

(I-64b)

8-Fluoro-2,5-dihydro-1H-pyrido[4,3-b]indol-1-one (I-64a: 0.15 g, 0.00074 mol) was reacted with 1-(chloromethyl)-4-methoxybenzene (0.14 g, 0.00092 mol), NaH (0.058 g, 0.058 mol) and DMF (10 mL) to afford the crude product. Purification by column chromatography on silica gel (1.5% methanol in DCM) afforded 0.15 g of the product (65.21% yield).
$^1$H NMR (400 MHz, DMSO): δ 11.4 (s, 1H), 7.8 (dd, 1H), 7.65 (m, 1H), 7.4 (t, 1H), 7.2-7.1 (m, 3H), 6.8 (dd, 3H), 5.55 (s, 2H), 3.8 (s, 3H). LCMS: 84.57%, m/z=322.9 (M+1)

Preparation of Intermediate 8-fluoro-5-(4-methoxybenzyl)-2-(4-(trifluoromethyl)pyridin-3-yl)-2,5-dihydro-1H-pyrido[4,3-b]indol-1-one (I-64c)

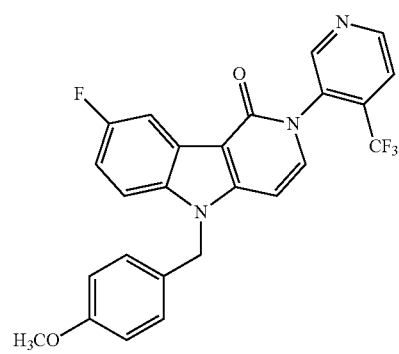

(I-64c)

8-Fluoro-5-(4-methoxybenzyl)-2,5-dihydro-1H-pyrido[4,3-b]indol-1-one (I-64b: 0.15 g, 0.00046 mol) was reacted with 3-bromo-4-(trifluoromethyl)pyridine (0.13 g, 0.00058 mol), 8-hydroxy quinoline (0.016 g, 0.00011 mol), $K_2CO_3$ (0.19 g, 0.0013 mol), CuI (0.026 g, 0.00013 mol) and DMSO (3 mL) to afford the crude product. The reaction mass was cooled to room temperature, added to ammonia solution in water and extracted with ethyl acetate. The organic layer was washed with brine solution and concentrated under reduced pressure to afford the crude product. Purification by column chromatography on silica gel (1% methanol in $CHCl_3$) afforded 95 mg of the product (45.23% yield).

Preparation of 8-fluoro-2-(4-(trifluoromethyl)pyridin-3-yl)-2,5-dihydro-1H-pyrido[4,3-b]indol-1-one (64A)

Anisole (0.25 mL) was added to a stirred solution of 8-fluoro-5-(4-methoxybenzyl)-2-(4-(trifluoromethyl)pyridin-3-yl)-2,5-dihydro-1H-pyrido[4,3-b]indol-1-one (I-64c: 95 mg, 0.203 mmol) in TFA (10 mL) under nitrogen atmosphere and the resulting reaction mass was refluxed at 80° C. overnight. The reaction was monitored by TLC (80% ethyl acetate in hexane). The reaction mass was cooled to room temperature, concentrated under reduced pressure, basified using $NaHCO_3$ solution to pH 8 and extracted using ethyl acetate. The aqueous layer was extracted with ethyl acetate and the combined organic layers were concentrated under reduced pressure to afford the crude product. Purification by column chromatography on silica gel (2% methanol in DCM), followed by preparative HPLC afforded 9 mg of the product (75% yield).
$^1$H NMR (400 MHz, $CDCl_3$): δ 8.9 (d, 1H), 8.8 (d, 2H), 8.0 (dd, 1H), 7.75 (d, 1H), 7.4 (m, 1H), 7.2-7.1 (m, 2H), 6.6 (d, 1H). LCMS: 100%, m/z=348.0 (M+1).
HPLC: 98.27%

Example 65

Preparation of 2-(4-methylpyridin-3-yl)-3,4-dihydro-2,7-naphthyridin-1(2H)-one (65A)

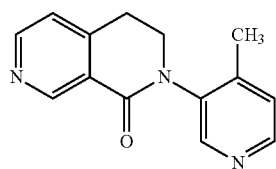
(65A)

Preparation of Intermediate methyl 2-(3-cyanopyridin-4-yl)acetate (I-65a)

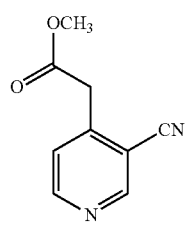
(I-65a)

1M LiHMDS (45 mL, 44.794 mmol) was added to a solution of 4-methylnicotinonitrile (2.52 g, 21.33 mmol) in THF (15 mL) at −78° C. and the resulting reaction mass was stirred at −78° C. for 1 hour. This was followed by the addition of dimethyl carbonate (1.98 mL, 23.464 mmol) and stirred the resulting reaction mass at −78° C. for 1 hour and further at 0° C. for 2 hours. The reaction was monitored by TLC (30% ethyl acetate in hexane). The reaction mass was quenched with saturated $NH_4Cl$ solution and extracted using ethyl acetate. The organic layer was washed with water, brine solution, dried over anhydrous sodium sulphate and concentrated under reduced pressure to afford the crude product. Purification by column chromatography on silica gel (25% ethyl acetate in hexane) afforded 530 mg of the product (14.10% yield).
$^1$H NMR (300 MHz, $CDCl_3$): δ 8.9 (s, 1H), 8.79 (d, 1H), 7.4 (d, 1H), 3.9 (s, 2H), 3.79 (s, 3H)

Preparation of Intermediate 4-(2-hydroxyethyl)nicotinonitrile (I-65b)

(I-65b)

NaBH$_4$ (228 mg, 6.023 mmol) was added portion wise over a period of 20 minutes to a solution of methyl 2-(3-cyanopyridin-4-yl)acetate (I-65a: 530 mg, 3.011 mmol) in ethanol (6 mL) at 0° C. and the resulting reaction mass was stirred at 0° C. for 4 hours. The reaction was monitored by TLC (50% ethyl acetate in hexane). The reaction mass was quenched with saturated NH4Cl solution and extracted using ethyl acetate. The organic layer was washed with water, brine solution, dried over $Na_2SO_4$ and concentrated under reduced pressure to afford the crude product. Purification by column chromatography on silica gel (2% methanol in DCM) afforded 100 mg of the product (22.42% yield).
$^1$H NMR (300 MHz, $CDCl_3$): δ 8.85 (s, 1H), 8.7 (d, 1H), 7.4 (d, 1H), 4.0 (t, 2H), 3.1 (t, 2H). LCMS: 99.03%, m/z=149.1 (M+1)

Preparation of Intermediate 3,4-dihydro-1H-pyrano[3,4-c]pyridin-1-one (I-65c)

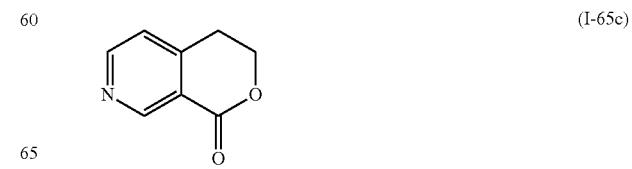
(I-65c)

4-(2-Hydroxyethyl)nicotinonitrile (I-65b: 1.1 g) in concentrated HCl (30 mL) was refluxed overnight. The reaction was monitored by TLC (10% methanol in CHCl₃). The reaction mass was concentrated under reduced pressure and the crude residue was dissolved in water. The resulting reaction mass was basified with saturated NaHCO₃ solution and extracted using ethyl acetate. The organic layer was washed with brine solution, dried over Na₂SO₄ and concentrated under reduced pressure to afford 750 mg of the product (67.75% yield).

$^1$H NMR (300 MHz, CDCl₃): δ 9.21 (s, 1H), 8.78 (d, 1H), 7.21 (d, 1H), 4.6 (t, 2H), 3.1 (t, 2H)

Preparation of Intermediate 4-(2-hydroxyethyl)-N-(4-methoxybenzyl)nicotinamide (I-65d)

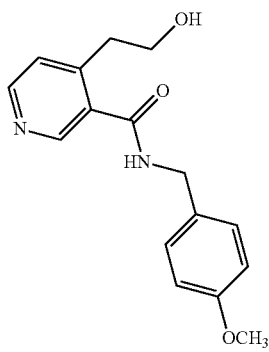
(I-65d)

(4-Methoxyphenyl) methanamine (6.57 mL, 50.676 mmol) was added to a solution of 3,4-dihydro-1H-pyrano[3,4-c]pyridin-1-one (I-65c: 750 mg, 5.068 mmol) in THF (15 mL) and the resulting reaction mass was refluxed for 48 hours. The reaction was monitored by TLC (10% methanol in CHCl₃). The reaction mass was cooled to 0° C., neutralized with 1N HCl and extracted using DCM. The organic layer was dried over anhydrous Na₂SO₄ and concentrated under reduced pressure to afford 1.5 g of the product.

$^1$H NMR (300 MHz, DMSO): δ 9.1 (t, 1H), 8.55 (m, 2H), 7.45-7.20 (m, 3H), 6.9 (m, 2H), 4.4 (d, 2H), 3.8-3.6 (m, 5H), 2.9 (t, 2H). LCMS: 99.31%, m/z=287.1 (M+1)

Preparation of 2-(4-methoxybenzyl)-3,4-dihydro-2,7-naphthyridin-1(2H)-one (I-65e)

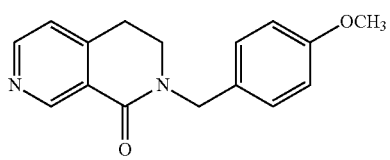
(I-65e)

DEAD (1.094 g, 6.286 mmol) was added drop wise to a solution of 4-(2-hydroxyethyl)-N-(4-methoxybenzyl)nicotinamide (I-65d: 1.5 g, 5.238 mmol) and PPh₃ (2.784 g, 10.477 mmol) in THF (40 mL) at 0° C. and the resulting reaction mass was stirred at room temperature for 1 hour. The reaction was monitored by TLC (10% methanol in CHCl₃). The reaction mass was concentrated under reduced pressure and the crude residue was purified by column chromatography on silica gel (3% methanol in DCM) to afford 700 mg of the product (49.82% yield).

$^1$H NMR (300 MHz, CDCl₃): δ 9.3 (s, 1H), 8.6 (d, 1H), 7.28 (m, 2H), 7.1 (d, 1H), 6.88 (d, 2H), 4.71 (s, 2H), 3.8 (s, 3H), 3.5 (t, 2H), 2.91 (t, 2H). LCMS: 91.79%, m/z=269.0 (M+1)

Preparation of Intermediate 3,4-dihydro-2,7-naphthyridin-1(2H)-one (I-65f)

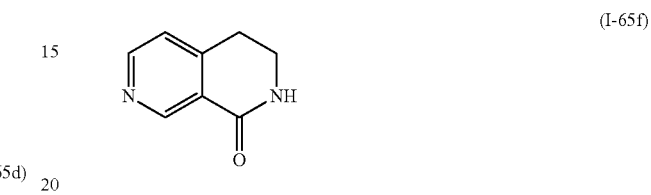
(I-65f)

2-(4-Methoxybenzyl)-3,4-dihydro-2,7-naphthyridin-1 (2H)-one (I-65e: 700 mg, 2.6089 mmol) and p-toluene sulphonic acid (1.985 g, 10.436 mmol) in toluene (15 mL) were refluxed for 6 hours. The reaction was monitored by TLC (10% methanol in CHCl₃). The reaction mass was neutralized with sodium carbonate solution, distilled off the solvent and added 10% methanol in CHCl₃. The solid precipitated was filtered and distilled off the solvent to afford the crude product. Purification by column chromatography on silica gel (7% methanol in DCM) afforded 280 mg of the product (72.53% yield).

$^1$H NMR (300 MHz, CDCl₃): δ 9.2 (s, 1H), 8.65 (d, 1H), 7.18 (d, 1H), 6.3 (bs, 1H), 3.65-3.58 (m, 2H), 3.0 (t, 2H)

Preparation of 2-(4-methylpyridin-3-yl)-3,4-dihydro-2,7-naphthyridin-1(2H)-one (65A)

3,4-Dihydro-2,7-naphthyridin-1(2H)-one (I-65f: 80 mg, 0.5399 mmol) was reacted with 3-iodo-4-methylpyridine (177 mg, 0.8099 mmol), copper iodide (8 mg, 10% w/w), trans-N,N'-dimethyl-cyclohexyl-1,2-diamine (16 mg, 20% w/w) and potassium phosphate (287 mg, 1.3498 mmol) in 1,4-dioxane (5 mL) to afford the crude product. Purification by column chromatography on silica gel (3% methanol in CHCl₃), followed by preparative HPLC afforded 16 mg of the product (12.4% yield).

$^1$H NMR (300 MHz, CDCl₃): δ 9.3 (s, 1H), 8.7 (d, 1H), 8.5 (s, 2H), 7.27 (d, 2H), 4.15-4.0 (m, 1H), 3.90-3.78 (m, 1H), 3.3-3.1 (m, 2H), 2.3 (s, 3H). LCMS: 99.26%, m/z=240.1 (M+1). HPLC: 96.11%

Example 66

Preparation of 8-(4-methylpyridin-3-yl)-7,8-dihydrothiazolo[4,5-h]isoquinolin-9(6H)-one (66A)

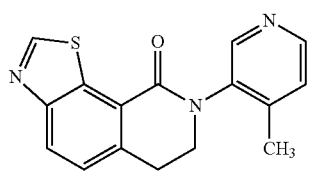
(66A)

Preparation of Intermediate 7-amino-3,4-dihydroisoquinolin-1(2H)-one (I-66a)

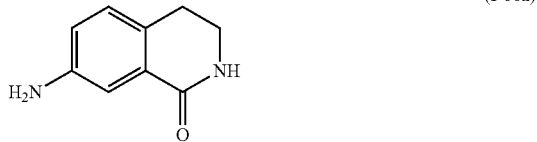

Using analogous reaction conditions, work up and purification as described for the preparation of intermediate I-24c above, 7-Nitro-3,4-dihydro-2H-isoquinolin-1-one (I-24a: 2.5 g, 0.013 mol) in methanol (50 mL) was reacted with 10% Pd—C (0.5 g) to afford the crude product, which was washed with n-hexane to afford 1.8 g of the product (85.71% yield).

$^1$H NMR (300 MHz, DMSO): δ 7.9 (s, 1H), 7.4 (s, 1H), 7.1 (d, 1H), 6.9 (d, 1H), 3.3 (s, 2H), 2.8 (t, 2H). LCMS: 95.63%, m/z=163.1 (M+1)

Preparation of Intermediate 2-amino-7,8-dihydrothiazolo[4,5-h]isoquinolin-9(6H)-one (I-66b)

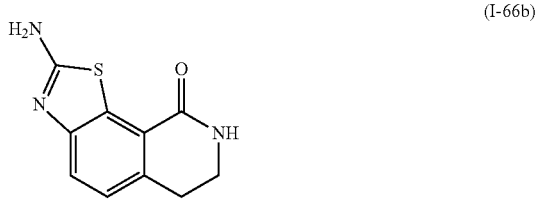 [SMILES: Nc1nc2ccc3c(c2s1)C(=O)NCC3]

Potassium thiocyanate (8.62 g, 0.088 mol) was added to a stirred solution of 7-amino-3,4-dihydroisoquinolin-1(2H)-one (I-66a: 1.8 g, 0.01 mol) in acetic acid (60 mL) at −10° C. and this was followed by the addition of bromine (5.33 g, 0.033 mol). The resulting reaction mass was stirred at −10° C. for 3 hours and further at room temperature overnight. The reaction was monitored by TLC (100% ethyl acetate). The reaction mass was diluted with ice water and filtered. The resulting mixture was basified at 0° C. using KOH solution to pH 10 and extracted using ethyl acetate. The organic layer was concentrated under reduced pressure to afford the crude product. Purification by column chromatography on silica gel (20% ethyl acetate in hexane) afforded 1.4 g of the product (58.33% yield).

$^1$H NMR (300 MHz, DMSO): δ 8.04 (s, 1H), 7.4 (t, 3H), 7.14 (d, 1H), 3.46-3.3 (m, 2H), 2.9 (t, 2H). LCMS: 94.14%, m/z=294.3 (M+1)

Preparation of 7,8-dihydrothiazolo[4,5-h]isoquinolin-9(6H)-one (I-66c)

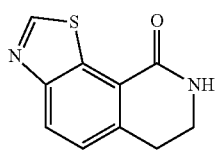

2-Amino-7,8-dihydrothiazolo[4,5-h]isoquinolin-9(6H)-one (I-66b: 1.4 g, 0.006 mol) in orthophosphorous acid (30 mL) was heated at 40° C. when a clear solution was formed. This was followed by the addition of NaNO$_2$ (2.64 g, 0.038 mol) and H$_2$O (10 mL) at 0° C. The resulting reaction mass was stirred at 0° C. for 30 minutes and added hypo phosphorous acid (35 mL). The reaction mass was stirred at 0° C. for 2 hours. The reaction was monitored by TLC (100% ethyl acetate). The reaction mass was diluted with ice-water, basified with KOH solution to pH 10 and extracted using ethyl acetate. The organic layer was concentrated under reduced pressure to afford the crude product. Purification by column chromatography on silica gel (60% ethyl acetate in hexane) afforded 130 mg of the product (10% yield). LCMS: 99.03%, m/z=205.1 (M+1)

Preparation of 8-(4-methylpyridin-3-yl)-7,8-dihydrothiazolo[4,5-h]isoquinolin-9(6H)-one (66A)

7,8-Dihydrothiazolo[4,5-h]isoquinolin-9(6H)-one (I-66c: 0.13 g, 0.0006 mol) was reacted with 3-iodo-4-methylpyridine (0.15 g, 0.0007 mol), copper iodide (0.036 g, 0.00019 mol), trans-N,N'-dimethyl-cyclohexyl-1,2-diamine (0.027 g, 0.00019 mol) and potassium phosphate (0.45 g, 0.0015 mol) in 1,4-dioxane (10 mL) to afford the crude product. Purification by column chromatography on silica gel (2% methanol in DCM) afforded 36 mg of the product (20.2% yield).

$^1$H NMR (300 MHz, CDCl$_3$): δ 9.1 (s, 1H), 8.55-8.45 (m, 2H), 8.3 (d, 1H), 7.5 (d, 1H), 7.3 (s, 1H), 4.25-4.10 (m, 1H), 3.95-3.80 (m, 1H), 3.5-3.3 (m, 2H), 2.35 (s, 3H). LCMS: 100%, m/z=296.1 (M+1). HPLC: 95.35%

Example 67

Synthesis of 2-(4-methylpyridin-3-yl)-3,4-dihydro-2,6-naphthyridin-1(2H)-one (67A)

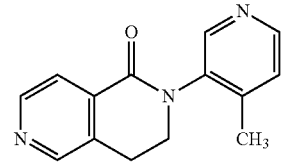

Preparation of Intermediate 3-(2-ethoxy-2-oxoethyl)pyridine-1-oxide (I-67a)

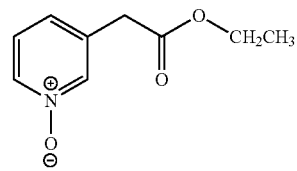

m-Chloro perbenzoic acid (6.2 g, 36.06 mmol) in CHCl$_3$ (30 mL) was added drop wise to a solution of ethyl 2-(pyridin-3-yl)acetate (3.5 g, 21.21 mmol) in CHCl$_3$ (30 mL) at room temperature under nitrogen atmosphere and the resulting reaction mass was stirred at room temperature for 5 hours. The reaction was monitored by TLC (10% methanol in chloroform). The reaction mass was basified using aqueous NaHCO$_3$ solution to pH 7 and extracted using CHCl$_3$. The organic layer was dried over sodium sulphate and concentrated under reduced pressure to afford 4.8 g of the crude product. LCMS: 60.09%, m/z=182.0 (M+1)

Preparation of Intermediate 3-(2-ethoxy-2-oxoethyl)pyridine-1-oxide ethyl iodide (I-67b)

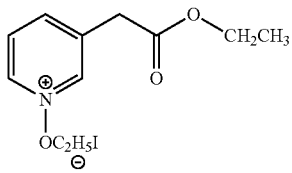

(I-67b)

3-(2-Ethoxy-2-oxoethyl)pyridine-1-oxide (I-67a: 4.8 g, 26.66 mmol) in iodoethane (7.67 mL, 95.99 mmol) was stirred at room temperature for 144 hours under nitrogen atmosphere. The reaction was monitored by TLC (10% methanol in chloroform). The reaction mass was concentrated under reduced pressure to afford 5.3 g of the crude product.

Preparation of Intermediate ethyl 2-(4-cyanopyridin-3-yl)acetate (I-67c)

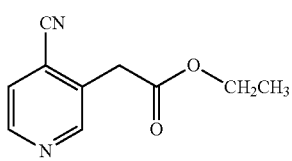

(I-67c)

KCN (2.64 g, 31.44 mmol) in water (8 mL) was added drop wise over a period of 20 minutes to a solution of 3-(2-ethoxy-2-oxoethyl)pyridine-1-oxide ethyl iodide (I-67b: 5.3 g, 15.72 mmol) in ethanol-water (7:3 ratio, 30 mL) at 50° C. and heating was further continued for another 30 minutes. The reaction was monitored by TLC (50% ethyl acetate in hexane). The reaction mass was quenched using ice and extracted using DCM. The organic layer was dried over sodium sulphate and concentrated under reduced pressure to afford the crude product. Purification by column chromatography on silica gel (1% methanol in CHCl$_3$) afforded 2.4 g of the product.
$^1$H NMR (300 MHz, CDCl$_3$): δ 8.78-8.68 (m, 2H), 7.56 (d, 1H), 4.25 (q, 2H), 3.9 (s, 2H), 1.3 (t, 3H). LCMS: 90.94%, m/z=191.0 (M+1)

Preparation of Intermediate 3-(2-hydroxyethyl)isonicotinonitrile (I-67d)

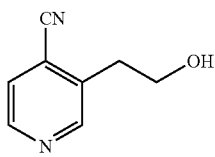

(I-67d)

Ethyl 2-(4-cyanopyridin-3-yl)acetate (2.3 g, 12.10 mmol) was reacted with NaBH$_4$ (919 mg, 24.21 mmol) and ethanol (20 mL) at room temperature for 72 hours to afford the crude product. Purification by column chromatography on silica gel (2% methanol in CHCl$_3$) afforded 650 mg of the product.

Preparation of Intermediate 3,4-dihydro-1H-pyrano[4,3-c]pyridin-1-one (I-67e)

(I-67e)

3-(2-Hydroxyethyl) isonicotinonitrile (I-67d: 650 mg, 4.362 mmol) was heated with concentrated HCl (10 mL) at 100° C. overnight. The reaction mass was neutralized with NaHCO$_3$ solution, extracted using DCM and the organic layer was concentrated under reduced pressure to afford the crude product. Purification by column chromatography on silica gel (1% methanol in CHCl$_3$) afforded 100 mg of the product (15.29% yield).
$^1$H NMR (300 MHz, CDCl$_3$): δ 8.76 (d, 2H), 7.9 (d, 1H), 4.62 (t, 2H), 3.1 (t, 2H)

Preparation of Intermediate 3-(2-hydroxyethyl)-N-(4-methoxybenzyl)isonicotinamide (I-67f)

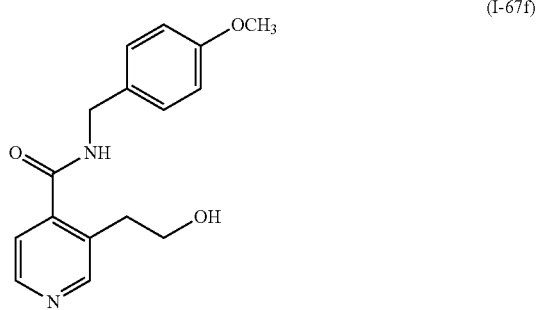 [SMILES: COc1ccc(CNC(=O)c2ccncc2CCO)cc1]

(I-67f)

3,4-Dihydro-1H-pyrano[4,3-c]pyridin-1-one (I-67e: 100 mg, (0.666 mmol) in THF (1 mL) was refluxed with p-methoxybenzylamine (0.9 mL, 6.66 mmol) to afford 220 mg of the crude product. LCMS: 95.54%, m/z=287.1 (M+1)

Preparation of Intermediate 2-(4-methoxybenzyl)-3,4-dihydro-2,6-naphthyridin-1(2H)-one (I-67g)

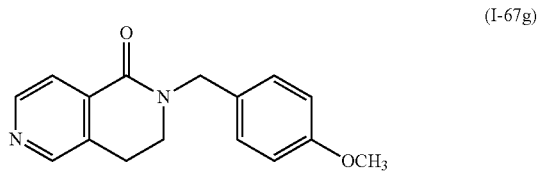 [SMILES: COc1ccc(CN2CCc3cnccc3C2=O)cc1]

(I-67g)

3-(2-Hydroxyethyl)-N-(4-methoxybenzyl)isonicotinamide (220 mg, 0.769 mmol) was reacted with PPh$_3$ (403 mg, 1.538 mmol), DEAD (0.15 mL, 0.922 mmol) and THF (10 mL) to afford the crude product. Purification by column chromatography on silica gel (1% methanol in CHCl₃) afforded 300 mg of the product. LCMS: 66.95%, m/z=269.0 (M+1)

Preparation of Intermediate
3,4-dihydro-2,6-naphthyridin-1(2H)-one (I-67h)

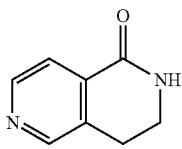

(I-67h)

2-(4-Methoxybenzyl)-3,4-dihydro-2,6-naphthyridin-1(2H)-one (I-67g: 300 mg, 1.119 mmol) was reacted with p-toluene sulfonic acid (851 mg, 4.476 mmol) and toluene (10 mL) at 110° C. for 4 hours. The reaction mass was concentrated under reduced pressure, neutralized with 1N HCl solution to pH 7 and extracted using DCM. The organic layer was dried over anhydrous Na₂SO₄ and concentrated under reduced pressure to afford the crude product. Purification by column chromatography on silica gel (2% methanol in CHCl₃) afforded 45 mg of the product (27.10% yield).

¹H NMR (400 MHz, CDCl₃): δ 8.7-8.6 (m, 2H), 7.9 (s, 1H), 6.2 (s, 1H), 3.6 (t, 2H), 3.0 (t, 2H). LCMS: 98.8%, m/z=149.0 (M+1)

Synthesis of 2-(4-methylpyridin-3-yl)-3,4-dihydro-2,6-naphthyridin-1(2H)-one (67A)

3,4-Dihydro-2,6-naphthyridin-1(2H)-one (I-67h: 45 mg, 0.304 mmol) was reacted with 3-iodo-4-methylpyridine (100 mg, 0.456 mmol), copper iodide (5.7 mg, 0.0304 mmol), trans-N,N'-dimethyl-cyclohexyl-1,2-diamine (12.95 mg, 0.0912 mmol) and potassium phosphate (193.3 mg, 0.912 mmol) in 1,4-dioxane (5 mL) to afford the crude product. Purification by column chromatography on silica gel (4% methanol in CHCl₃), followed by preparative HPLC afforded 11 mg of the product (15.27% yield).

¹H NMR (400 MHz, CDCl₃): δ 8.75-8.63 (m, 2H), 8.47 (s, 2H), 7.95 (d, 1H), 7.30-7.23 (m, 1H), 4.12-4.02 (m, 1H), 3.88-3.80 (m, 1H), 3.26-3.18 (m, 2H), 2.3 (s, 3H). LCMS: 99.27%, m/z=240.1 (M+1). HPLC: 98.39%

Example 68

Preparation of 2-(5-fluoropyridin-3-yl)-7-(trifluoromethyl)isoquinolin-1(2H)-one (68A)

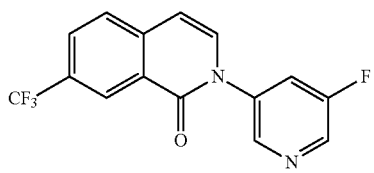

(68A)

7-Trifluoromethyl-2H-isoquinolin-1-one (I-29d: 0.1 g, 0.00046 mol) was reacted with 3-bromo-5-fluoropyridine (0.099 g, 0.00056 mol), 8-hydroxy quinoline (0.013 g, 0.00009 mol), K₂CO₃ (0.161 g, 0.0011 mol), CuI (0.017 g, 0.00009 mol) and 1,4-dioxane (5 mL) to afford the crude product. The reaction mass was cooled to room temperature, diluted with DCM, washed with ammonia solution and separated the layers. The organic layer was washed with brine solution, dried over Na₂SO₄ and concentrated under reduced pressure to afford the crude product. Purification by column chromatography on silica gel (0.5% methanol in DCM), followed by hexane-wash afforded 66.5 mg of the product (47.14% yield).

¹H NMR (400 MHz, CDCl₃): δ 8.74 (s, 1H), 8.56 (d, 2H), 7.92 (m, 1H), 7.72-7.66 (m, 2H), 7.28 (m, 1H), 6.7 (d, 1H). LCMS: 89.34%, m/z=309.0 (M+1).
HPLC: 95.28%

Example 69

Preparation of 7-(4-methylpyridin-3-yl)-6,7-dihydro-1H-pyrazolo[4,3-g]isoquinolin-8(5H)-one (69A)

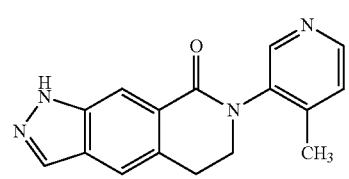

(69A)

Preparation of Intermediate (E)-1-methyl-3-(2-nitrovinyl)benzene (I-69a)

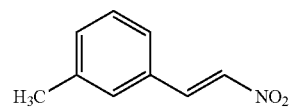

(I-69a)

3-Methylbenzaldehyde (21 g, 174.273 mmol) was reacted with nitro methane (967 mL, 174.273 mmol), NaOH solution (6.7 g, 174.273 mmol in 17.32 mL H₂O) and ethanol (210 mL) at 0° C. for 2 hours. The reaction mass was quenched using cold 50% HCl solution (60 mL) and extracted using ethyl acetate. The organic layer was dried over anhydrous Na₂SO₄ and concentrated under reduced pressure to afford 27 g of the product (95% yield).

¹H NMR (300 MHz, CDCl₃): δ 8.1 (d, 1H), 7.7 (d, 1H), 7.5-7.4 (m, 4H), 2.5 (s, 3H)

Preparation of Intermediate 2-m-tolylethanamine (I-69b)

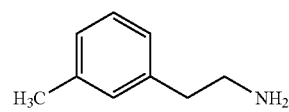

(I-69b)

(E)-1-Methyl-3-(2-nitrovinyl)benzene (9 g, 55.214 mmol) was reacted with LiBH₄ (4.81 g, 2220.85 mmol), trimethylsilyl chloride (55.86 mL, 441.7 mmol) and dry THF (120 mL) to afford 15 g of the crude product.

Preparation of Intermediate ethyl 3-methylphenethylcarbamate (I-69c)

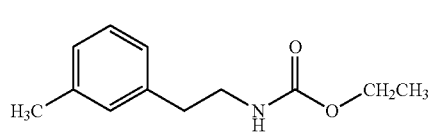
(I-69c)

2-m-Tolylethanamine (11 g, 81.48 mmol) in chloroform (110 mL) was reacted with chloro ethyl formate (9.30 mL, 97.777 mmol) and 2N $Na_2CO_3$ solution (110 mL) at 0° C. to afford the crude product. Purification by column chromatography on silica gel (7% ethyl acetate in hexane) afforded 7.5 g of the product (44% yield).

Preparation of Intermediate 6-methyl-3,4-dihydroisoquinolin-1(2H)-one (I-69d)

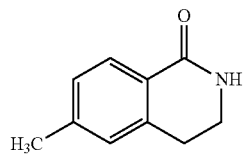
(I-69d)

Ethyl 3-methylphenethylcarbamate (I-69c: 13.5 g, 65.217 mmol) was reacted with $P_2O_5$ (18.51 g, 130.434 mmol) and $POCl_3$ (135 mL) at 110° C. for 1 hour. The reaction mass was concentrated under reduced pressure, quenched with ice, basified using saturated $NaHCO_3$ solution and extracted using ethyl acetate. The organic layer was washed with brine solution, dried over $Na_2SO_4$ and concentrated under reduced pressure to afford the crude product. Purification by column chromatography on silica gel (1% methanol in DCM) afforded 2 g of the product (19% yield). LCMS: 75.24%, m/z=162.3 (M+1)

Preparation of Intermediate 6-methyl-2-(4-methylpyridin-3-yl)-3,4-dihydroisoquinolin-1(2H)-one (I-69e)

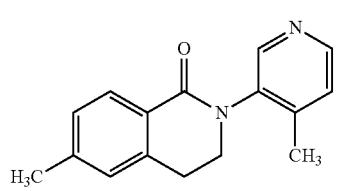
(I-69e)

6-Methyl-3,4-dihydroisoquinolin-1(2H)-one (I-69f: 2 g, 12.422 mmol) was reacted with 3-iodo-4-methyl-pyridine (2.72 g, 12.422 mmol), 1,4-dioxane (70 mL), copper iodide (236 mg, 1.2422 mmol), trans-N,N'-dimethyl-cyclohexyl-1,2-diamine (530 mg, 3.727 mmol) and potassium phosphate (6.58 g, 31.055 mmol) to afford the crude product. Purification by column chromatography on silica gel (1% methanol in DCM) afforded 1 g of the product (31.8% yield).
LCMS: 98.66%, m/z=253.0 (M+1)

Preparation of Intermediate 6-methyl-2-(4-methylpyridin-3-yl)-7-nitro-3,4-dihydroisoquinolin-1(2H)-one (I-69f)

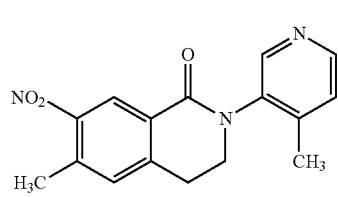
(I-69f)

6-Methyl-2-(4-methylpyridin-3-yl)-3,4-dihydroisoquinolin-1(2H)-one (I-69e: 1 g, 3.953 mmol) in conc. $H_2SO_4$ (11.9 mL) was reacted with $KNO_3$ (439 mg, 4.348 mmol) to afford 940 mg of the product (80.3% yield).
$^1$H NMR (400 MHz, DMSO): δ 9.1 (s, 1H), 8.8 (d, 1H), 8.5 (s, 1H), 8.0 (d, 1H), 7.65 (s, 1H), 4.2-4.1 (m, 1H), 3.96-3.6 (m, 1H), 3.4-3.3 (m, 2H), 2.66 (s, 3H), 2.48 (s, 3H). LCMS: 99.15%, m/z=298.1 (M+1)

Preparation of Intermediate 7-amino-6-methyl-2-(4-methylpyridin-3-yl)-3,4-dihydroisoquinolin-1(2H)-one (I-69g)

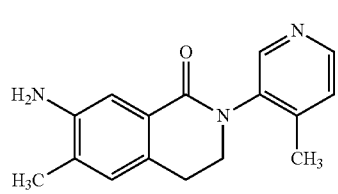
(I-69g)

6-Methyl-2-(4-methylpyridin-3-yl)-7-nitro-3,4-dihydroisoquinolin-1(2H)-one (I-69f: 940 mg, 3.154 mmol) was reacted with 10% Pd—C (200 mg) and methanol (15 mL) to afford 400 mg of the product (36% yield). LCMS: 79.19%, m/z=268.1 (M+1)

Preparation of Intermediate 1-acetyl-7-(4-methylpyridin-3-yl)-6,7-dihydro-1H-pyrozolo[4,3-g]isoquinolin-8(5H)-one (I-69h)

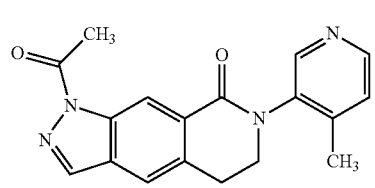
(I-69h)

Potassium acetate (153 mg, 1.567 mmol) and acetic anhydride (0.282 mL, 2.985 mmol) were added to a solution of 7-amino-6-methyl-2-(4-methylpyridin-3-yl)-3,4-dihydroisoquinolin-1(2H)-one (I-69g: 400 mg, 1.4925 mmol) in CHCl₃ (15 mL) at 0° C. and the resulting reaction mass was stirred at room temperature for 10 minutes. This was followed by the addition of 18-crown-6-ether (78 mg, 0.2985 mmol) and isoamyl nitrite (0.44 mL, 3.284 mmol) and the reaction mass was refluxed for 24 hours, The reaction was monitored by TLC (100% ethyl acetate). The reaction mass was extracted using chloroform. The organic layer was washed with saturated NaHCO₃ solution, dried over anhydrous Na₂SO₄ and concentrated under reduced pressure to afford the crude product. Purification by column chromatography on silica gel (100% ethyl acetate) afforded 80 mg of the product (16.7% yield).

LCMS: 67.73%, m/z=321.1 (M+1)

Preparation of 7-(4-methylpyridin-3-yl)-6,7-dihydro-1H-pyrazolo[4,3-g]isoquinolin-8(5H)-one (69A)

6N HCl (5 mL) was added drop wise to a solution of 1-acetyl-7-(4-methylpyridin-3-yl)-6,7-dihydro-1H-pyrazolo[4,3-g]isoquinolin-8(5H)-one (I-69h: 80 mg, 0.249 mmol) in methanol (5 ml) at 0° C. and the resulting reaction mass was stirred at room temperature for 36 hours. The reaction was monitored by TLC (100% ethyl acetate). The reaction mass was concentrated under reduced pressure, basified using saturated NaHCO₃ solution and extracted using ethyl acetate. The organic layer was dried over Na₂SO₄ and concentrated under reduced pressure to afford the crude product. Purification by column chromatography on silica gel (100% ethyl acetate), followed by preparative HPLC afforded 8 mg of the product (11.5% yield).

¹H NMR (400 MHz, CDCl₃): δ 8.54-8.42 (m, 2H), 8.12 (s, 1H), 7.66 (s, 1H), 7.3 (d, 1H), 4.12-4.02 (m, 1H), 3.88-3.80 (m, 1H), 3.44-3.26 (m, 2H), 2.36 (s, 3H).

LCMS: 100%, m/z=279.1 (M+1). HPLC: 97.50%

Example 70

Preparation of 3-methyl-7-(trifluoromethyl)-2-(4-(trifluoromethyl)pyridin-3-yl)-3,4-dihydroisoquinolin-1(2H)-one (70A)

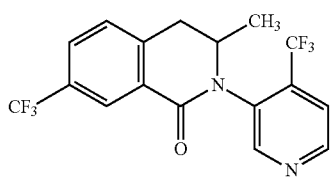
(70A)

3-Methyl-7-(trifluoromethyl)-3,4-dihydroisoquinolin-1(2H)-one (I-43d: 60 mg, 0.26 mmol) was reacted with 3-bromo-4-(trifluoromethyl)-pyridine (88 mg, 0.39 mmol), 1,4-dioxane (5 mL), copper iodide (14 mg, 0.078 mmol), trans-N,N'-dimethyl-cyclohexyl-1,2-diamine (3.7 mg, 0.026 mmol) and potassium phosphate (166 mg, 1.78 mmol) to afford the crude product. Purification by column chromatography on silica gel (1.5% methanol in CHCl₃), followed by preparative HPLC afforded 3.8 mg of the product (3.8% yield).

¹H NMR (CDCl₃, 300 MHz): δ 8.82-8.80 (d, 1H), 8.67 (s, 1H), 8.38 (s, 1H), 7.8-7.66 (m, 2H), 7.46-7.38 (d, 4.1-3.97 (m, 1H), 3.7-3.6 (dd, 1H), 3.00-2.88 (dd, 1H), 1.35-1.28 (dd, 3H),

LCMS: 97.76%, m/z=375.0 (M+1), HPLC: 95.00%.

Example 71

Preparation of 6-methyl-2-(4-(trifluoromethyl)pyridin-3-yl)-3,4-dihydroisoquinolin-1(2H)-one (71A)

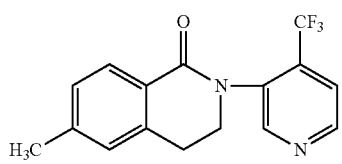
(71A)

6-Methyl-3,4-dihydroisoquinolin-1(2H)-one (I-69d: 500 mg, 3.1 mmol) was reacted with 3-bromo-4-trifluoromethyl)-pyridine (842 mg, 3.72 mmol), 1,4-dioxane (20 mL), copper iodide (59 mg, 0.31 mmol), trans-N,N'-dimethyl-cyclohexyl-1,2-diamine (44 mg, 0.31 mmol and potassium phosphate (1.64 g, 7.76 mmol) 2 days at 120° C. to afford the crude product. Purification by column chromatography on silica gel (2% methanol in CHCl₃) afforded 150 mg of the product (15.7% yield).

Example 72

Preparation of 7-(4-(trifluoromethyl)pyridin-3-yl)-6,7-dihydro-1H-pyrazolo[4,3-g]isoquinolin-8(5H)-one (72A)

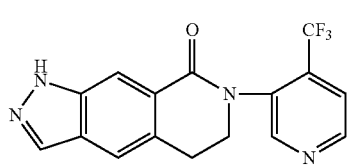
(72A)

Preparation of Intermediate 6-methyl-7-nitro-2-(4-(trifluoromethyl)pyridin-3-yl)-3,4-dihydroisoquinolin-1(2H)-one (I-72a)

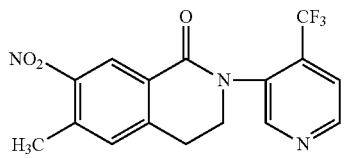
(I-72a)

6-Methyl-2-(4-(trifluoromethyl)pyridin-3-yl)-3,4-dihydroisoquinolin-1(2H)-one (71A: 450 mg, 1.465 mmol) was reacted with concentrated H₂SO₄ (4.4 mL) and KNO₃ (163 mg, 1.6126 mmol) for 2 hours to afford 350 mg of the product (68% yield).

¹H NMR (300 MHz, CDCl₃): δ 8.86-8.84 (d, 1H), 8.7 (s, 1H), 7.72-7.69 (d, 1H), 7.29 (s, 1H), 4.07-3.98 (m, 1H), 3.85-3.77 (m, 1H), 3.41-3.32 (m, 1H), 3.17-3.10 (m, 1H), 2.68 (s, 3H). LCMS: 97.281%, m/z=351.9 (M+1).

Preparation of Intermediate 7-amino-6-methyl-2-(4-(trifluoromethyl)pyridin-3-yl)-3,4-dihydroisoquinolin-1(2H)-one (I-72b)

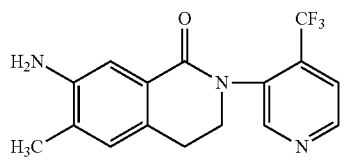

(I-72b)

6-Methyl-7-nitro-2-(4-(trifluoromethyl)pyridin-3-yl)-3,4-dihydroisoquinolin-1(2H)-one (72A: 350 mg, 1 mol) in methanol (10 mL) was reduced with 10% Pd/C (100 mg) to afford 300 mg of the product (93.7% yield).

$^1$H NMR (300 MHz, CDCl$_3$): δ 8.79-8.78 (d, 1H), 8.70-8.68 (d, 1H), 7.66-7.64 (d, 1H), 7.42 (s, 1H), 7.00-6.97 (d, 1H), 3.96-3.88 (m, 1H), 3.75-3.70 (m, 1H), 2.99-2.89 (m, 2H), 2.23 (s, 3H). LCMS: 54.09%, m/z=322.0 (M+1)

Preparation of 1-acetyl-7-(4-(trifluoromethyl)pyridin-3-yl)-6,7-dihydro-1H-pyrazolo[4,3-g]isoquinolin-8(5H)-one (I-72c)

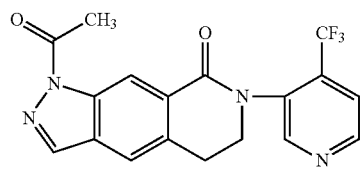

(I-72c)

7-Amino-6-methyl-2-(4-(trifluoromethyl)pyridin-3-yl)-3,4-dihydroisoquinolin-1(2H)-one (I-72b: 300 mg, 1.11 mmol) in chloroform (10 mL) was reacted with potassium acetate (153 mg, 1.56 mmol), acetic anhydride (0.213 mL, 2.23 mmol), 18-crown-6-ether (59 mg, 0.223 mmol) and isoamylnitrite (0.33 mL, 2.46 mmol) for 24 hours to afford the crude product. Purification by column chromatography on silica gel (100% ethyl acetate) afforded 80 mg of the product (16.7% yield).

$^1$H NMR (300 MHz, CDCl$_3$): δ 9.25 (s, 1H), 8.89-8.82 (d, 1H), 8.73 (s, 1H), 8.16 (s, 1H), 8.69-8.67 (d, 1H), 8.63 (s, 1H), 4.04-3.98 (m, 1H), 3.88-3.80 (m, 1H), 3.50-3.4 (m, 1H), 3.32-3.2 (m, 1H), 2.8 (s, 3H), LCMS: 98.44%, 375.1 (M+1)

Preparation of 7-(4-(trifluoromethyl)pyridin-3-yl)-6,7-dihydro-1H-pyrazolo[4,3-g]isoquinolin-8(5H)-one (72A)

1-Acetyl-7-(4-(trifluoromethyl)pyridin-3-yl)-6,7-dihydro-1H-pyrazolo[4,3-g]isoquinolin-8(5H)-one (I-72c: 45 mg, 12 mmmol) in chloroform was deacylated with 6N HCl for 16 hours. Purification by column chromatography on silica gel (4% methanol in DCM) afforded 15 mg of the product (37.5% yield).

$^1$H NMR (CDCl$_3$, 400 MHz): δ 10.33 (s, 1H), 8.83-8.82 (d, 1H), 8.73 (s, 1H), 8.37 (s, 1H), 8.12 (s, 1H), 7.69-7.68 (d, 1H), 7.65 (s, 1H), 4.53-3.98 (td, 1H), 3.86-3.80 (m, 1H), 3.49-3.41 (m, 1H), 3.26-3.20 (dt, 1H), LCMS: 96.02%, m/z—333.1 (M+1). HPLC: 91.76%

Example 73

Preparation of 2-(4-cyclopropylpyridin-3-yl)-7-(trifluoromethyl)-3,4-dihydroisoquinolin-1(2H)-one (73A)

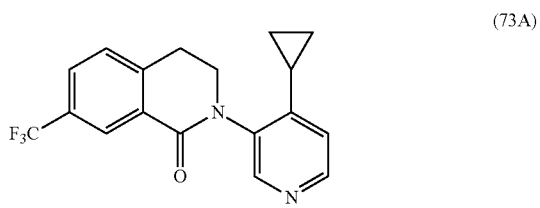 [SMILES: O=C1c2cc(C(F)(F)F)ccc2CCN1c1cnccc1C1CC1]

(73A)

Preparation of Intermediate 4-cyclopropyl-3-nitropyridine (I-73a)

(I-73a)

4-Chloro-3-nitropyridine (100 mg, 0.630 mmol) and cyclopropyl boronic acid (10.0 mg, 0.091 mmol) were added to a solution of xylene (3 mL) previously purged with argon (10 min). The reaction mixture was purged with argon for a further 15 mins, followed by the addition of potassium carbonate (174.35 mg, 1.26 mmol) and Pd(PPh$_3$)$_4$ (34.5 mg, 0.063 mmol). The resulting mixture was heated to reflux at 130° C. overnight. The reaction was monitored by TLC (30% ethyl acetate in hexane). The reaction mixture was cooled and concentrated to afford the crude product. Purification by column chromatography on silica gel (15% ethyl acetate in hexane) afforded 110 mg of the product (100% yield). LCMS: 99.09%, m/z=165 (M+1)

Preparation of Intermediate 4-cyclopropylpyridin-3-amine (I-73b)

(I-73b)

Zinc powder (223.2 mg, 3.41 mmol) and ammonium chloride solution (365 mg, 6.8 mmol) were added to a stirred solution of 4-cyclopropyl-3-nitropyridine (70 mg, 0.426 mmol) in dry THF (2 mL) at 0° C. and the resulting mixture was stirred at room temperature for 1 hour. The reaction was monitored by TLC (10% methanol in CHCl$_3$). The organic layer was concentrated and washed with pentane to afford 450 mg of the product (100% yield).

¹H NMR (CDCl₃, 300 MHz): δ 8.10 (s, 1H), 7.95 (d, 1H), 6.90 (d, 1H), 4.1 (bs, 2H), 1.75-1.60 (m, 1H), 1.10-0.95 (q, 2H), 0.70-0.60 (q, 2H). LCMS: 84.5%, m/z=135.1 (M+1)

Preparation of Intermediate 4-cyclopropyl-3-iodopyridine (I-73c)

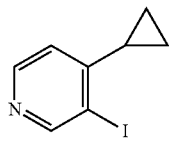

(I-73c)

Isoamyl nitrite (2.62 gm, 22.38 mmol) was added to a stirred solution of 4-cyclopropylpyridin-3-amine (I-73b: 1.0 gm, 7.46 mmol) in dry THF (15 mL) under argon atmosphere. This was followed by the addition of diiodomethane (3.0 mL, 22.38 mmol) and copper iodide (1.42 gm, 7.46 mmol). The resulting mixture was refluxed at 80° C. for 1 hour. The reaction mixture was cooled, filtered and the filtrate was partitioned between ethyl acetate and water. The organic layer was concentrated to yield the crude product. Purification by column chromatography on silica gel (15% ethyl acetate in hexane) afforded 600 mg of the product (34% yield).

¹H NMR (CDCl₃, 400 MHz): δ 8.84 (s, 1H), 8.35-8.34 (d, 1H), 6.73-6.71 (d, 1H) 2.10-2.04 (m, 1H), 1.17-1.12 (m, 2H), 0.78-0.74 (m, 2H).

Preparation of 2-(4-cyclopropylpyridin-3-yl)-7-(trifluoromethyl)-3,4-dihydroisoquinolin-1(2H)-one (73A)

7-(trifluoromethyl)-3,4-dihydroisoquinolin-1(2H)-one (I-4-d: 100 mg, 0.465 mmol) was reacted with 4-cyclopropyl-3-iodopyridine (I-73c: 125.3 mg, 0.51 mmol), 1,4-dioxane (5 mL), copper iodide (8.8 mg, 0.0465 mmol), trans-N,N'-dimethyl-cyclohexyl-1,2-diamine (6.6 mg, 0.0465 mmol) and potassium phosphate (246 mg, 1.16 mmol). The resulting mixture was stirred for 24 hours at 120° C. The reaction was monitored by TLC (10% methanol in CHCl₃). The reaction mixture was concentrated to afford the crude product. Purification by column chromatography on silica gel (2% methanol in CHCl₃), followed by preparative HPLC afforded 20 mg of the product (12.9% yield).

¹H NMR (CDCl₃, 400 MHz): δ 8.4 (s, 3H), 7.7-7.75 (d, 1H), 7.44-7.42 (d, 1H), 6.87-6.85 (d, 1H), 4.03-4.0 (m, 1H), 3.95-3.90 (m, 1H), 3.3-3.25 (m, 2H), 1.95-1.93 (m, 1H), 1.12-1.06 (m, 2H), 0.99-0.95 (m, 1H), 0.73-0.69 (m, 1H). LCMS: 100%, m/z=333 (M+1). HPLC: 99.48%

Example 74

Preparation of 7-chloro-2-(4-cyclopropylpyridin-3-yl)-3,4-dihydroisoquinolin-1 (2H)-one (74A)

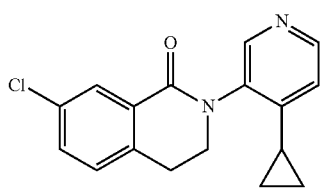

(74A)

7-Chloro-3,4-dihydroisoquinolin-1(2H)-one (I-1d: 100 mg, 0.552 mmol) was reacted with 4-cyclopropyl-3-iodopyridine (I-73c: 162 mg, 0.662 mmol), 1,4-dioxane (5 mL), copper iodide (31 mg, 0.165 mmol), trans-N,N'-dimethyl-cyclohexyl-1,2-diamine (8 mg, 0.055 mmol) and potassium phosphate (351 mg, 1.657 mmol for 48 hours at 120° C. to afford the crude product. Purification by column chromatography on silica gel (2% methanol in CHCl₃) afforded 42 mg of the product (25.45% yield).

¹H NMR (CDCl₃, 300 MHz): δ8.44-8.42 (m, 2H), 8.134-8.132 (d, 1H), 7.48-7.44 (dd, 1H), 7.26-7.21 (m, 1H), 6.83-6.82 (d, 1H), 3.99-3.86 (m, 2H), 3.22-3.14 (m, 2H), 2.02-1.45 (m, 1H), 1.09-0.92 (m, 3H), 0.71-0.6 (m, 1H). LCMS: 98.89%, m/z=299.0 (M+1). HPLC: 94.47%.

Example 75

Preparation of 7-chloro-2-(4-ethylpyridin-3-yl)-3,4-dihydroisoquinolin-1(2H)-one (75A)

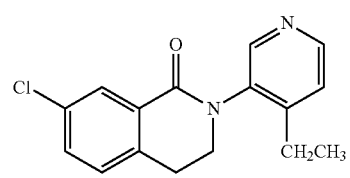

(75A)

7-Chloro-3,4-dihydroisoquinolin-1(2H)-one (I-1d: 100 mg, 0.552 mmol) was reacted with 3-bromo-4-ethyl pyridine (133.5 mg, 0.718 mmol), 1,4-dioxane (5 mL), copper iodide (10.48 mg, 0.0555 mmol), trans-N,N'-dimethyl-cyclohexyl-1,2-diamine (7.8 mg, 0.055 mmol) and potassium phosphate (351 mg, 1.657 mmol for 48 hours at 120° C. to afford the crude product. Purification by column chromatography on silica gel (50% ethyl acetate in hexane), followed by preparative HPLC afforded 25 mg of the product (15.72% yield).

¹H NMR (CDCl₃, 400 MHz): δ 8.52-8.51 (d, 1H), 8.44 (s, 1H), 8.12-8.11 (d, 1H), 7.48-7.44 (dd, 1H), 7.36-7.29 (d, 1H), 7.24-7.22 (d, 1H), 4.04-3.08 (m, 1H), 3.77.3.71 (m, 1H), 3.34-3.09 (m, 2H), 2.70-2.58 (m, 2H), 1.27-1.20 (m, 3H). LCMS: 100% m/z=287.1 (M+1). HPLC: 99.54%.

Example 76

Preparation of 2-(4-cyclopropylpyridin-3-yl)-3,4-dihydrobenzo[4,5]thieno[3,2-c]pyridin-1(2H)-one (76A)

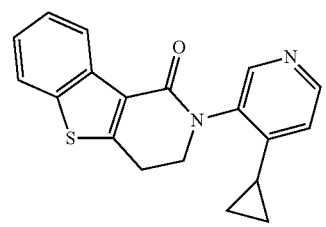 [SMILES: O=C1c2c(sc3ccccc23)CCN1c1cnccc1C1CC1]

3,4-Dihydro-2H-benzo[4,5]thieno[3,2-c]pyridin-1-one (I-9d: 100 mg, 0.491 mmol) was reacted with 4-cyclopropyl-3-iodo-pyridine (I-73c: 133 mg, 0.65 mmol), 1,4-dioxane (3 mL), copper iodide (9.31 mg, 0.049 mmol), trans-N,N'-dimethyl-cyclohexyl-1,2-diamine (6.9 mg, 0.049 mmol) and potassium phosphate (313.3 mg, 1.47 mmol) to afford the crude product. Purification by column chromatography on silica gel (1% methanol in CHCl₃) afforded 46.8 mg of the product (29.8% yield).

¹H NMR (CDCl₃, 300 MHz): δ 8.626-8.62 (d, 1H), 8.49-8.44 (m, 2H), 7.83-7.81 (d, 1H), 7.46-7.38 (m, 2H), 6.84-6.83 (d, 1H), 4.17-4.12 (m, 1H), 4.0-3.98 (m, 1H), 3.42-3.34 (m, 2H), 2.03-1.9 (m, 1H), 1.1-0.9 (m, 2H), 0.7-0.69 (m, 2H). LCMS: 94.04%, m/z=321.1 (M+1)

HPLC: 95.09%.

Example 77

Preparation of 8-fluoro-7-(trifluoromethyl)-2-(4-(trifluoromethyl)pyridin-3-yl)-3,4-dihydroisoquinolin-1(2H)-one (77A)

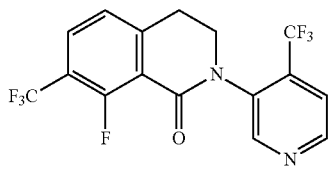

Preparation of Intermediate 3-(3-fluoro-4-trifluoromethyl)phenyl)acrylic acid (I-77a)

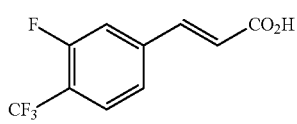

Malonic acid (3.09 g, 0.02976 mol) and piperidine (0.168 mL, 0.00198 mol) were added to a solution of 3-fluoro-4-(trifluoromethyl)benzaldehyde (5 g, 0.0198 mol) in pyridine (50 mL) at room temperature under nitrogen atmosphere. The resulting mixture was refluxed at 70° C. for 12 hours under nitrogen atmosphere. The reaction was monitored by TLC (5% methanol in CHCl₃). The reaction mixture was cooled to room temperature, acidified to pH~2 using 6N HCl and filtered. The residue was washed with n-hexane (20 mL) and dried under reduced pressure to afford 5.5 g of the crude product which was used in the next step without further purification.

¹H NMR (DMSO-D₆, 400 MHz): δ 13.00-12.21 (bs, 1H), 8.10-7.86 (m, 2H), 7.85-7.53 (m, 3H).

Preparation of Intermediate 3-(3-fluoro-4-(trifluoromethyl)phenyl)propanoic acid (I-77b)

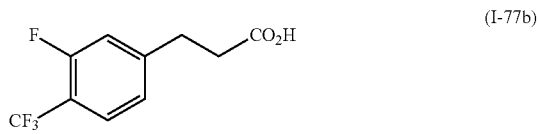 [SMILES: O=C(O)CCc1ccc(C(F)(F)F)c(F)c1]

10% NiX was added to a stirred solution of 3-(3-fluoro-4-(trifluoromethyl)phenyl)-acrylic acid (I-77a: 5.5 g, 0.0234 mol) in methanol. The resulting mixture was stirred under hydrogen atmosphere for 4 hours. The reaction was monitored by TLC (5% methanol in CHCl₃). The catalyst was filtered through celite bed and the solvent distilled under reduced pressure to afford the crude product. Purification by column chromatography on silica gel (2% methanol in CHCl₃) afforded 4.5 g of the product (81.8% yield).

¹H NMR (DMSO-D₆, 400 MHz): δ 12.7-12.21 (bs, 1H), 7.86-7.6 (m, 1H), 7.5-7.35 (d, H), 7.31-7.22 (d, 1H), 3.2-2.83 (m, 2H), 2.67-2.52 (m, 2H).

Preparation of Intermediate 7-fluoro-6-(trifluoromethyl)-2,3-dihydro-1H-inden-1-one (I-77c)

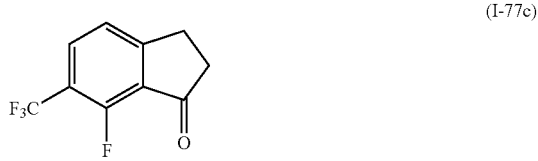 [SMILES: O=C1CCc2ccc(C(F)(F)F)c(F)c21]

Chlorosulfonic acid (12.6 mL) was added to a stirred solution of 3-(3-fluoro-4-(trifluoromethyl)phenyl)propanoic acid (I-77b: 1.0 g, 4.2707 mmol). The resulting mixture was stirred for 5 hours at 0° C. The reaction was monitored by TLC (20% ethyl acetate in hexane). The reaction mixture was quenched with ice water and extracted with chloroform (2×150 mL). The organic layer was dried over Na₂SO₄ and concentrated under reduced pressure to afford the crude product. Purification by column chromatography on silica gel (5% ethyl acetate in hexane), afforded 550 mg of the product (58.9% yield).

¹H NMR (CDCl₃, 400 MHz): δ 8.09-8.02 (d, 1H), 7.35-7.3 (d, 1H), 3.23-3.2 (m, 2H), 2.81-2.73 (m, 2H).

Preparation of Intermediate 8-fluoro-7-(trifluoromethyl)-3,4-dihydroisoquinolin-1(2H)-one (I-77d)

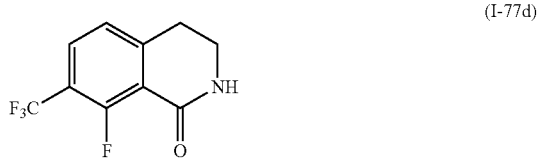 [SMILES: O=C1NCCc2ccc(C(F)(F)F)c(F)c21]

Sodium azide (492 mg, 7.5688 mmol) was added portion wise to a stirred solution of 7-fluoro-6-(trifluoromethyl)-2,3-dihydro-1H-inden-1-one (I-77c: 500 mg, 2.2935 mmol) in TFA (15 mL) over a period of 5 hours at 80° C. The reaction was monitored by TLC (5% methanol in CHCl$_3$). The reaction mixture was concentrated under reduced pressure, followed by the addition of ice. The precipitated solid was filtered, washed with water (20 mL) and dried under reduced pressure to yield the crude product. Purification by column chromatography on silica gel (2% methanol in CHCl$_3$) afforded 300 mg of the product (56.1% yield).

$^1$H NMR (CDCl$_3$, 400 MHz): δ 8.4-8.3 (d, 1H), 7.1-7.0 (d, 1H), 6.4-6.2 (bs, 1H), 3.72-3.6 (m, 2H), 3.1-3.0 (m, 2H).

Preparation of 8-fluoro-7-(trifluoromethyl)-2-(4-(trifluoromethyl)pyridin-3-yl)-3,4-dihydroisoquinolin-1(2H)-one (77A)

8-Fluoro-7-(trifluoromethyl)-3,4-dihydroisoquinolin-1(2H)-one (I-77d: 100 mg, 0.4288 mmol) was reacted with 3-bromo-4-(trifluoromethyl)-pyridine (120 mg, 0.5575 mmol), 1,4-dioxane (5 mL), copper iodide (8.1 mg, 0.0428 mmol), trans-N,N'-dimethyl-cyclohexyl-1,2-diamine (6.1 mg, 0.0428 mmol) and potassium phosphate (273 mg, 1.2866 mmol) to afford the crude product. Purification by column chromatography on silica gel (2% methanol in CHCl$_3$), followed by preparative HPLC afforded 25 mg of the product (15.4% yield).

$^1$H NMR (CDCl$_3$, 300 MHz): δ 8.86-8.82 (d, 1H), 8.7 (s, 1H), 8.45-8.41 (d, 1H), 7.72-7.68 (d, 1H), 7.18-7.12 (d, 1H), 4.34-4.2 (bs, 1H), 4.1-3.8 (m, 1H), 3.86-3.74 (m, 1H), 3.48-3.1 (m, 1H), 3.2-3.06 (m, 1H). LCMS: 91.17%, m/z=379.1 (M+1). HPLC: 99.50%.

Example 78

Preparation of 6-fluoro-2-(4-(trifluoromethyl)pyridin-3-yl)-3,4-dihydroisoquinolin-1(2H)-one (78A)

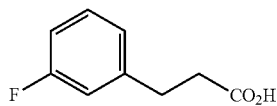

Preparation of Intermediate 3-(3-fluorophenyl)acrylic acid (I-78a)

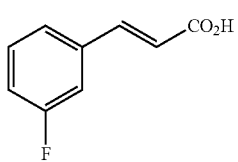

3-Fluorobenzaldehyde (5 g, 40.28 mmol) in pyridine (50 mL) was reacted with malonic acid (5.4 g, 52.3 mmol) and piperidine (343 mg, 4.0 mmol) at 75° C. for 12 hours to afford 6.6 g (96.9%) of the crude product which was used in the next step without further purification.

$^1$H NMR (DMSO-D$_6$, 300 MHz): δ 13.00-12.21 (bs, 1H), 7.64-7.4 (m, 4H), 7.3-7.2 (t, 1H), 6.68-6.58 (d, 1H).

Preparation of Intermediate 3-(3-fluorophenyl)propanoic acid (I-78b)

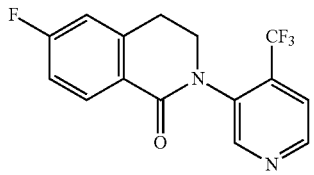

3-(3-Fluorophenyl)acrylic acid (I-78a: 6.4 gm, 38.5 mmol) in methanol (100 mL) was reduced with 10% Pd/C (640 mg) to afford the crude product, 5 g (80.69% yield).

$^1$H NMR (CDCl$_3$, 300 MHz): δ 11.00-10.00 (bs, 1H), 7.4-7.3 (m, 1H), 7.1-6.8 (m, 3H), 3.0-2.9 (t, 2H), 2.75-2.64 (t, 2H).

Preparation of Intermediate 5-fluoro-2,3-dihydro-1H-inden-1-one (I-78c)

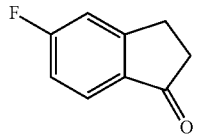

3-(3-Fluorophenyl)propanoic acid (I-78b: 2.0 gm, 11.8 mmol) was cyclized with chlorosulfonic acid (20 mL) to afford the crude product. Purification by column chromatography on silica gel (10% ethyl acetate in hexane), afforded 1.2 g of the product (70.5% yield).

$^1$H NMR (CDCl$_3$, 300 MHz): δ 7.8-7.74 (m, 1H), 7.18-7.02 (m, 2H), 3.24-3.18 (t, 2H), 2.8-2.7 (t, 2H).

Preparation of Intermediate 6-fluoro-3,4-dihydroisoquinolin-1(2H)-one (I-78d)

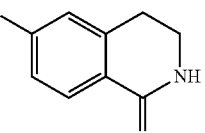

5-Fluoro-2,3-dihydro-1H-inden-1-one (I-78c: 1.2 g, 8.0 mmol) in TFA (20 mL) was reacted with sodium azide (1.7 g, 26.4 mmol) to afforded 550 mg of the product (46.2% yield).

$^1$H NMR (CDCl$_3$, 300 MHz): δ 8.8 (bs, 1H), 6.9-6.84 (t, 2H), 6.8-6.7 (m, 1H), 3.0-2.9 (t, 2H), 2.7-2.6 (t, 2H).

Preparation of 6-fluoro-2-(4-(trifluoromethyl)pyridin-3-yl)-3,4-dihydroisoquinolin-1(2H)-one (78A)

6-Fluoro-3,4-dihydroisoquinolin-1(2H)-one (I-78d: 500 mg, 3.029 mmol) was reacted with 3-bromo-4-(trifluoromethyl)-pyridine (890 mg, 3.93 mmol), 1,4-dioxane (15 mL), copper iodide (57.5 mg, 0.30 mmol), trans-N,N'-dimethyl-cyclohexyl-1,2-diamine (43 mg, 0.302 mmol) and potassium phosphate (1.92 g, 9.08 mmol) for 36 hours at 120° C. to afford the crude product. Purification by column chromatography on silica gel (2% methanol in $CHCl_3$), afforded 600 mg of the product (64.5% yield).

$^1$H NMR ($CDCl_3$, 300 MHz): δ 8.86-8.80 (d, 1H), 8.7 (s, 1H), 8.2-8.1 (m, 1H), 7.7-7.64 (d, 1H), 7.19-7.0 (m, 1H), 6.99-6.96 (d, 1H), 4.03-3.9 (m, 1H), 3.83-3.73 (m, 1H), 3.3-3.3 (m, 1H), 3.09-3.02 (m, 1H). LCMS: 87.32%, m/z=311.1 (M+1).
HPLC: 96.54%

Example 79

Preparation of 6-fluoro-7-iodo-2-(4-(trifluoromethyl) pyridin-3-yl)-3,4-dihydroisoquinolin-1(2H)-one (79A)

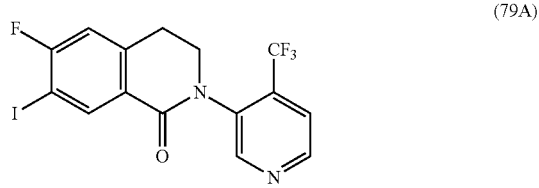 [SMILES: O=C1c2cc(I)c(F)cc2CCN1c1cnccc1C(F)(F)F]

Preparation of Intermediate 6-fluoro-7-nitro-2-(4-(trifluoromethyl)pyridin-3-yl)-3,4-dihydroisoquinolin-1(2H)-one (I-79a)

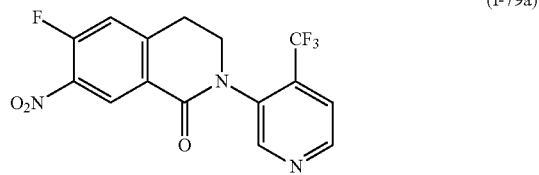

6-Fluoro-2-(4-(trifluoromethyl)pyridin-3-yl)-3,4-dihydroisoquinolin-1(2H)-one (78A: 600 mg, 1.93 mmol) was reacted with concentrated $H_2SO_4$ (5 mL) and $KNO_3$ (215.2 mg, 2.12 mmol) for 4 hours to afford 550 mg of the product (79.9% yield).

$^1$H NMR ($CDCl_3$, 300 MHz): δ8.86-8.83 (m, 2H), 8.7 (s, 1H), 7.71-7.67 (d, 1H), 7.22 (s, 1H), 4.13-4.0 (m, 1H), 3.9-3.8 (m, 1H), 3.5-3.3 (m, 1H), 3.25-3.02 (m, 1H). LCMS: 84.59%, m/z=357.1 (M+1).

Preparation of Intermediate 7-amino-6-fluoro-2-(4-(trifluoromethyl)pyridin-3-yl)-3,4-dihydroisoquinolin-1(2H)-one (I-79b)

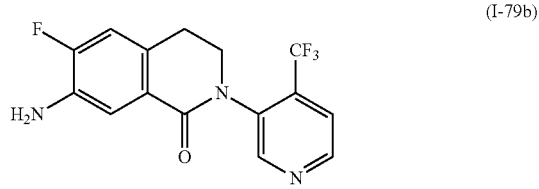 [SMILES: O=C1c2cc([N+](=O)[O-])c(F)cc2CCN1c1cnccc1C(F)(F)F]

Iron powder (431.4 mg, 7.72) and acetic acid (10 mL) were added to a stirred solution of 6-fluoro-7-nitro-2-(4-(trifluoromethyl)pyridin-3-yl)-3,4-dihydroisoquinolin-1(2H)-one (I-79a: 550 mg, 1.54 mmol) in THF (5 mL). The resulting mixture was stirred for 4 hours at 70° C. The reaction was monitored by TLC (30% ethyl acetate in hexane). The catalyst was filtered through celite bed and the solvent concentrated under reduced pressure to afford 400 mg of the product (80% yield).

Preparation of 6-fluoro-7-iodo-2-(4-(trifluoromethyl) pyridin-3-yl)-3,4-dihydroisoquinolin-1(2H)-one (79A)

Isoamylnitrite (0.4 mL, 3.2198 mmol), diiodomethane (0.4 mL, 5.36 mmol) and CuI (203.9 mg, 1.07 mmol) were added to a stirred solution of 7-amino-6-fluoro-2-(4-(trifluoromethyl)pyridin-3-yl)-3,4-dihydroisoquinolin-1(2H)-one (I-79b: 350 mg, 1.07 mmol) in dry THF (10 mL). The resulting mixture was stirred for 1 hour at 70° C. The reaction was monitored by TLC (40% ethyl acetate in hexane). The reaction mixture was concentrated to yield the crude product. Purification by column chromatography on silica gel (30% ethyl acetate in hexane), followed by preparative HPLC afforded 15 mg of the product (10% yield).

$^1$H NMR ($CDCl_3$, 300 MHz): δ8.9-8.6 (m, 2H), 8.54-8.5 (d, 1H), 7.7 (s, 1H), 7.0-6.86 (d, 1H), 4.1-3.9 (td, 1H), 3.83-3.73 (m, 1H), 3.35-3.32 (m, 1H), 3.1-2.96 (dt, 1H). LCMS: 100% m/z=436.9 (M+1). HPLC: 91.85%

Example 80

Preparation of 7-chloro-6-fluoro-2-(4-(trifluoromethyl)pyridin-3-yl)-3,4-dihydroisoquinolin-1(2H)-one (80A)

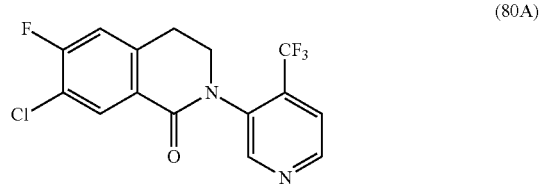 [SMILES: O=C1c2cc(Cl)c(F)cc2CCN1c1cnccc1C(F)(F)F]

Isoamylnitrite (107.7 mg, 0.91 mmol) was added to the stirred solution of 7-amino-6-fluoro-2-(4-(trifluoromethyl) pyridin-3-yl)-3,4-dihydroisoquinolin-1(2H)-one (I-79b: 100 mg, 0.306 mmol) in $CCl_4$ (10 mL). The resulting mixture was stirred for 1 hour at 70° C. The reaction was monitored by TLC (5% methanol in $CHCl_3$). The reaction mixture was concentrated to yield the crude product. Purification by column chromatography on silica gel (2% methanol in $CHCl_3$), followed by preparative HPLC afforded 10 mg of the product (10% yield).

$^1$H NMR ($CDCl_3$, 300 MHz): δ 8.82-8.80 (d, 1H), 8.7 (s, 1H), 8.2 (d, 1H), 7.72-7.6 (d, 1H), 7.1-7.08 (d, 1H), 4.03-3.9 (m, 1H), 3.83-3.73 (m, 1H), 3.34-3.3 (m, 1H), 3.1-3.02 (m, 1H). LCMS: 100%, m/z=345 (M+1). HPLC: 90.144%

Example 81

Preparation of 2-(4-cyclopropylpyridin-3-yl)-6-fluoro-3,4-dihydroisoquinolin-1(2H)-one (81A)

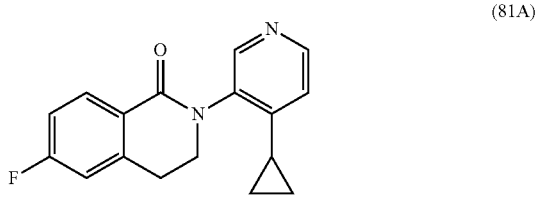 [SMILES: O=C1c2ccc(F)cc2CCN1c1cnccc1C1CC1]

(81A)

6-Fluoro-3,4-dihydroisoquinolin-1(2H)-one (I-78d: 500 mg, 3.02938 mmol) was reacted with 3-iodo-4-cyclopropyl-pyridine 816 mg, 3.3323 mmol), 1,4-dioxane (10 mL), copper iodide (57.3 mg, 0.3 mmol), trans-N,N'-dimethyl-cyclohexyl-1,2-diamine (43 mg, 0.30 mmol) and potassium phosphate (1.92 g, 9.0 mmol) to afford the crude product. Purification by column chromatography on silica gel (2% methanol in CHCl$_3$) afforded 700 mg of the product (81.9% yield).

$^1$H NMR (CDCl$_3$, 300 MHz): δ 8.5-8.4 (bs, 2H), 8.19-8.14 (m, 1H), 7.1-7.04 (m, 1H), 6.99-6.95 (dd, 1H), 6.83-6.8 (d, 1H), 4.0-3.96 (m, 1H), 3.9-3.86 (m, 1H), 3.25-3.1 (m, 2H), 2.0-1.9 (m, 1H), 1.1-1.0 (m, 2H), 0.95-0.9 (m, 1H)), 0.7-0.6 (m, 1H). LCMS: 100%, m/z=283.2 (M+1).

Example 82

Preparation of 7-chloro-2-(4-cyclopropylpyridin-3-yl)-6-fluoro-3,4-dihydroisoquinolin-1(2H)-one (82A)

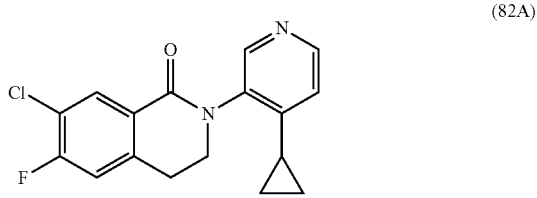 [SMILES: O=C1c2cc(Cl)c(F)cc2CCN1c1cnccc1C1CC1]

(82A)

Preparation of 2-(4-cyclopropylpyridin-3-yl)-6-fluoro-7-nitro-3,4-dihydroisoquinolin-1(2H)-one (I-82a)

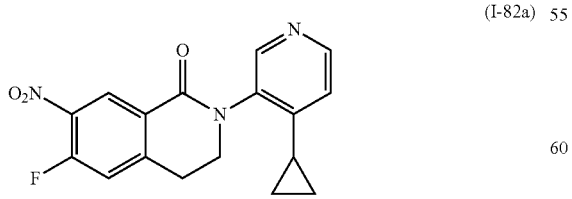

(I-82a)

2-(4-Cyclopropylpyridin-3-yl)-6-fluoro-3,4-dihydroisoquinolin-1(2H)-one (81A: 700 mg, 2.482 mmol) was reacted with conc. H$_2$SO$_4$ (5 mL) and KNO$_3$ (276 mg, 2.73 mmol) for 4 hours to afford 400 mg of the product (49.14% yield).

$^1$H NMR (DMSO-D$_6$, 300 MHz): δ 8.85 (s, 1H), 8.7-8.65 (d, 1H), 8.6-8.55 (d, 1H), 7.8-7.7 (d, 1H), 7.45-7.4 (d, 1H), 3.5-3.3 (m, 3H), 2.3-2.1 (m, 1H), 1.4-0.9 (m, 5H). LCMS: 98.82%, m/z=328.1(M+1)

Preparation of Intermediate 7-amino-2-(4-cyclopropylpyridin-3-yl)-6-fluoro-3,4-dihydroisoquinolin-1(2H)-one (I-82b)

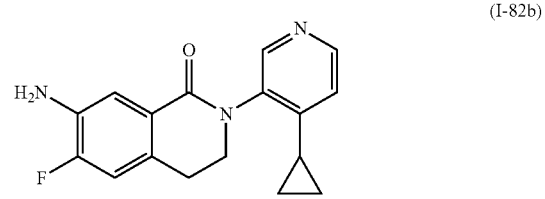 [SMILES: O=C1c2cc([N+](=O)[O-])c(F)cc2CCN1c1cnccc1C1CC1]

(I-82b)

2-(4-Cyclopropylpyridin-3-yl)-6-fluoro-7-nitro-3,4-dihydroisoquinolin-1(2H)-one (I-82a: 400 mg, 1.219 mmol) was reduced with iron powder (340 mg, 6.09 mmol) and acetic acid (10 mL) in THF (10 mL) at 75° C. for 4 hours to afford 350 mg of the product (96.6% yield).

$^1$H NMR (DMSO-D$_6$, 300 MHz): δ 8.4-8.3 (m, 2H), 7.4-7.3 (d, 1H), 7.06-6.9 (m, 2H), 5.26 (s, 2H), 3.95-3.85 (m, 1H), 3.75-3.65 (m, 1H), 3.01-2.98 (m, 2H), 1.95-1.85 (m, 1H) 1.2-0.6 (m, 5H). LCMS: 96.01%, m/z=298.1(M+1)

Preparation of 7-chloro-2-(4-cyclopropylpyridin-3-yl)-6-fluoro-3,4-dihydroisoquinolin-1(2H)-one (82A)

Isoamylnitrite (39 mg, 0.335 mmol), CuCl$_2$ (33.69 mg, 0.25 mmol) were added to a stirred solution of 7-amino-2-(4-cyclopropylpyridin-3-yl)-6-fluoro-3,4-dihydroisoquinolin-1(2H)-one (I-82b: 50 mg, 0.167 mmol) in acetonitrile (5 mL). The resulting mixture was stirred for 4 hours at room temperature. The reaction was monitored by TLC (100% ethyl acetate). The reaction mixture was concentrated to yield the crude product. Purification by column chromatography on silica gel (100% ethyl acetate), followed by preparative HPLC afforded 15 mg of the product (10% yield).

$^1$H NMR (CD$_3$OD, 400 MHz): δ 8.41-8.37 (m, 2H), 8.09-8.07 (d, 1H), 7.32-7.30 (d, 1H), 7.05-7.04 (d, 1H), 4.06-4.01 (m, 1H), 4.00-3.88 (m, 1H), 3.28-3.19 (m, 2H), 2.02-1.96 (m, 1H), 1.12-1.08 (m, 2H), 1.02-0.93 (m, 1H), 0.8-0.77 (m, 1H). LCMS: 99.11%, m/z=317(M+1). HPLC: 99.15%.

Example 83

Preparation of 6-fluoro-2-(4-methylpyridin-3-yl)-3,4-dihydroisoquinolin-1(2H)-one (83A)

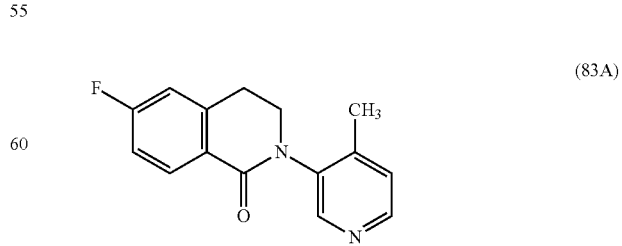

(83A)

6-Fluoro-3,4-dihydroisoquinolin-1(2H)-one (I-78d: 250 mg, 1.5146 mmol) was reacted with 3-iodo-4-methyl-pyridine (365 mg, 1.66 mmol), 1,4-dioxane (10 mL), copper iodide (29 mg, 0.151 mmol), trans-N,N'-dimethyl-cyclohexyl-1,2-diamine (21.5 mg, 0.151 mmol) and potassium phosphate (965 mg, 4.54 mmol) for 14 hours at 120° C. to afford the crude product. Purification by column chromatography on silica gel (2% methanol in CHCl$_3$) afforded 350 mg of the product (90.4% yield).

$^1$H NMR (CDCl$_3$, 300 MHz): δ8.55-8.45 (m, 2H), 8.19-8.14 (m, 1H), 7.25 (s, 1H), 7.15-7.05 (td, 1H), 7.00-6.96 (dd, 1H), 4.04-4.00 (m, 1H), 3.80-3.76 (m, 1H), 3.24-3.15 (m, 2H), 2.30 (s, 3H).

Example 84

Preparation of 7-chloro-6-fluoro-2-(4-methylpyridin-3-yl)-3,4-dihydroisoquinolin-1(2H)-one (84A)

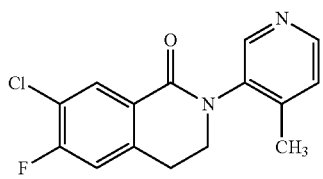

(84A)

Preparation of Intermediate 6-fluoro-7-nitro-2-(4-methyl-pyridin-3-yl)-3,4-dihydroisoquinolin-1(2H)-one (I-84a)

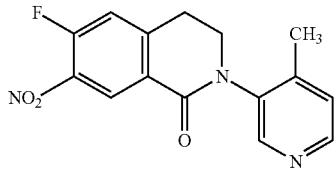

(I-84a)

6-Fluoro-2-(4-methylpyridin-3-yl)-3,4-dihydroisoquinolin-1(2H)-one (83A: 350 mg, 1.38 mmol) was reacted with conc. H$_2$SO$_4$ (4 mL) and KNO$_3$ (154 mg, 1.52 mmol) for 4 hours to afford 250 mg of the product (60.0% yield).

$^1$H NMR (DMSO-D$_6$, 400 MHz): δ8.84 (s, 1H), 8.68-8.67 (d, 1H), 8.56-8.54 (d, 1H), 7.83-7.82 (d, 1H), 7.76-7.73 (d, 1H), 4.15-4.05 (m, 1H), 3.92-3.80 (m, 1H), 3.38-3.31 (m, 2H), 2.39 (s, 3H).

Preparation of Intermediate 7-amino-6-fluoro-2-(4-methylpyridin-3-yl)-3,4-dihydroisoquinolin-1(2H)-one (I-84b)

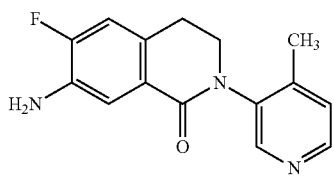

(I-84b)

6-Fluoro-7-nitro-2-(4-methyl-pyridin-3-yl)-3,4-dihydroisoquinolin-1(2H)-one (I-84a: 150 mg, 0.498 mmol) was reduced with iron powder (139 mg, 2.4 mmol) and acetic acid (5 mL) in THF (5 mL) at 70° C. for 4 hours to afford 130 mg of the product (96.2% yield).

$^1$H NMR (DMSO-D$_6$, 300 MHz): δ8.45 (s, 1H), 8.39-8.37 (d, 1H), 7.41-7.34 (m, 2H), 7.06-7.02 (d, 1H), 5.27 (s, 2H), 3.92-3.87 (m, 1H), 3.68-3.64 (m, 1H), 3.06-2.91 (m, 2H) 2.19 (s, 3H).

Preparation of 7-chloro-6-fluoro-2-(4-methylpyridin-3-yl)-3,4-dihydroisoquinolin-1(2H)-one (84A)

7-Amino-6-fluoro-2-(4-methylpyridin-3-yl)-3,4-dihydroisoquinolin-1(2H)-one (I-84b: 130 mg, 0.47 mmol) in acetonitrile (10 mL) was reacted with isoamylnitrite (112.2 mg, 0.959 mmol), and CuCl$_2$ (96.7 mg, 0.719 mmol) to yield the crude product. Purification by column chromatography on silica gel (2% methanol in CHCl$_3$), followed by preparative HPLC afforded 35 mg of the product (25.1% yield).

$^1$H NMR (CDCl$_3$, 400 MHz): δ8.5-8.42 (m, 2H), 8.22-8.18 (d, 1H), 7.23 (s, 1H), 7.08-7.06 (m, 1H), 4.05-3.9 (m, 1H), 3.80-3.76 (m, 1H), 3.24-3.09 (m, 2H), 2.28 (s, 1H). LCMS: 99.37%, m/z=291(M+1). HPLC: 99.5%.

Example 85

Preparation of 6-chloro-7-(trifluoromethyl)-2-(4-(trifluoromethyl)pyridin-3-yl)-3,4-dihydroisoquinolin-1(2H)-one (85A)

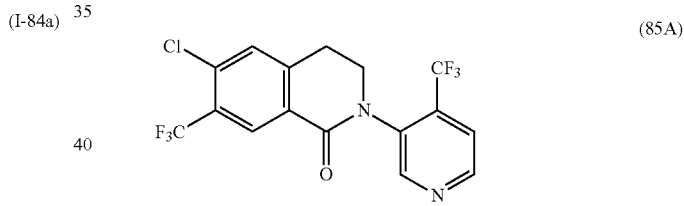

(85A)

Preparation of Intermediate ethyl 3-(3-chloro-4-(trifluoromethyl)phenyl)acrylate (I-85a)

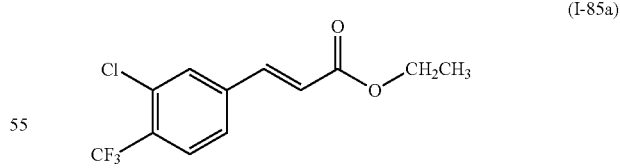

(I-85a)

DABCO (86.4 mg, 0.7 mmol), Pd(OAc)$_2$ (86.5 mg, 0.38 mmol), 4-bromo-2-chloro-1-(trifluoromethyl)benzene (5.0 g, 19.2 mmol) and ethyl acrylate (2.86 g, 28.9 mmol) were added to a stirred solution of K$_2$CO$_3$ (2.6 g, 19.27 mmol) in DMF degassed previously for 20 minutes. The resulting mixture was stirred for 1 hour at 110° C. The reaction was monitored by TLC (5% ethyl acetate in hexane). Purification by column chromatography on silica gel (5% ethyl acetate in hexane) afforded 5.0 g of the product (94.3% yield).

¹H NMR (CDCl₃, 400 MHz): δ 7.75-7.7 (d, 1H), 7.68-7.62 (d, 1H), 7.6 (s, 1H), 7.54-7.46 (d, 1H), 6.54-6.48 (d, 1H), 4.3-4.2 (q, 2H), 1.4-1.32 (t, 3H).

Preparation of Intermediate ethyl 3-(3-chloro-4-(trifluoromethyl)phenyl)propanoate (I-85b)

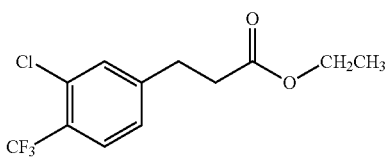
(I-85b)

10% Pd/C (300 mg) and ZnBr (807 mg, 3.58 mmol) were added to a stirred solution of ethyl 3-(3-chloro-4-(trifluoromethyl)phenyl acrylate (I-85a: 5.0 g, 17.92 mmol) in ethyl acetate (100 mL) and the resulting mixture was stirred for 3 days at room temperature. The reaction was monitored by TLC (1% ethyl acetate in hexane). The catalyst was filtered through celite bed and the solvent concentrated under reduced pressure to afford the product 4.8 g (96.0%)

¹H NMR (CDCl₃, 400 MHz): δ 7.64-7.58 (d, 1H), 7.38 (s, 1H), 7.24-7.18 (d, 1H), 4.22-4.1 (m, 2H), 3.02-2.9 (m, 2H), 2.7-2.6 (m, 2H), 1.3-1.2 (m, 3H).

Preparation of Intermediate 3-(3-chloro-4-(trifluoromethyl)phenyl)propanoic acid (I-85c)

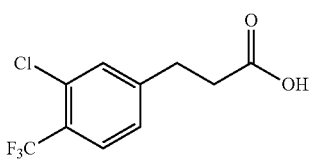
(I-85c)

1N NaOH solution was added to a stirred solution of ethyl 3-(3-chloro-4-(trifluoromethyl)phenyl)propanoate (I-85b: 4.8 g, 17.8 mmol) in ethanol and the resulting mixture was stirred at room temperature for 1 hour. The reaction was monitored by TLC (2% ethyl acetate in hexane). The reaction mixture was concentrated under reduced pressure, quenched with ice, acidified with 1N HCl and extracted with DCM (2×150 mL). The organic layer was dried over Na₂SO₄ and concentrated under reduced pressure to afford the product 4.2 g (97.6%).

¹H NMR (CDCl₃, 400 MHz): δ 7.62-7.6 (d, 1H), 7.38 (s, 1H), 7.24-7.14 (d, 1H), 3.04-2.96 (t, 2H), 2.76-2.68 (t, 2H).

Preparation of Intermediate 5-chloro-6-(trifluoromethyl)-2,3-dihydro-1H-inden-1-one (I-85d)

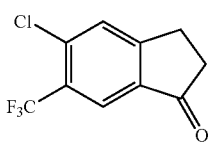
(I-85d)

3-(3-Chloro-4-(trifluoromethyl)phenyl)propanoic acid (I-85c: 1.0 g, 3.96 mmol) was reacted with chlorosulfonic acid (12.6 mL) for 5 hours at 0° C. Purification by column chromatography on silica gel (10% ethyl acetate in hexane) afforded 650 mg of the product 69.8% yield).

¹H NMR (CDCl₃, 400 MHz): δ 8.1 (s, 1H), 7.68 (s, 1H), 3.24-3.18 (t, 2H), 2.8-2.76 (t, 2H).

Preparation of Intermediate 6-chloro-7-(trifluoromethyl)-3,4-dihydroisoquinolin-1(2H)-one (I-85e)

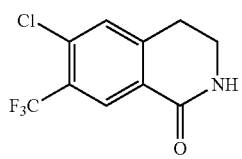
(I-85e)

5-Chloro-6-(trifluoromethyl)-2,3-dihydro-1H-inden-1-one (I-85d: 600 mg, 2.5575 mmol) in TFA (25 mL) was reacted with sodium azide (549 mg, 8.439 mmol) for 5 hours at 80° C. Purification by column chromatography on silica gel (1% methanol in CHCl₃), afforded 350 mg of the product (54.8% yield).

¹H NMR (CDCl₃, 400 MHz): δ8.4 (s, 1H), 7.4 (s, 1H), 6.5-6.45 (bs, 1H), 3.68-3.58 (m, 2H), 3.08-3.02 (m, 2H).

Preparation of 6-chloro-7-(trifluoromethyl)-2-(4-(trifluoromethyl)pyridin-3-yl)-3,4-dihydroisoquinolin-1(2H)-one (85A)

6-Chloro-7-(trifluoromethyl)-3,4-dihydroisoquinolin-1 (2H)-one (I-85e: 100 mg, 0.4 mmol) was reacted with 3-bromo-4-(trifluoromethyl)-pyridine (117.6 mg, 0.520 mmol), 1,4-dioxane (5 mL), copper iodide (7.6 mg, 0.04 mmol), trans-N,N'-dimethyl-cyclohexyl-1,2-diamine (5.6 mg, 0.04 mmol) and potassium phosphate (255.6 mg, 1.2 mmol) to afford the crude product. Purification by preparative HPLC afforded 15 mg of the product (10% yield).

¹H NMR (CDCl₃, 400 MHz): δ 8.85-8.84 (d, 1H), 8.71 (s, 1H), 8.4 (s, 1H), 7.70-7.68 (d, 1H), 7.4 (s, 1H), 4.1-4.0 (m, 1H), 3.83-3.73 (m, 1H), 3.48-3.32 (m, 1H), 3.1-3.08 (m, 1H). LCMS: 97.0%, m/z=395.0 (M+1). HPLC: 95.0%.

Example 86

Preparation of 7-chloro-6-methoxy-2-(4-methylpyridin-3-yl)-3,4-dihydroisoquinolin-1(2H)-one (86A)

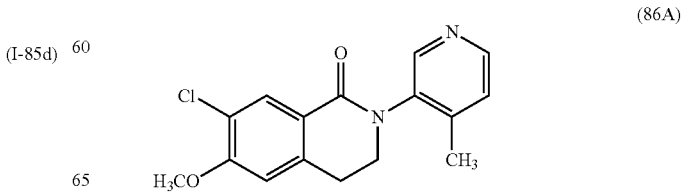
(86A)

Preparation of Intermediate 1-chloro-2-methoxy-4-(2-nitrovinyl)benzene (I-86a)

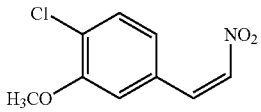
(I-86a)

4-Chloro-3-methoxybenzaldehyde (1 g, 5.88 mmol) in ethanol (10 mL) was reacted with nitro methane (358 mg, 5.88 mmol) and 10N NaOH (0.6 mL, 28.11 mmol). The resulting mixture was stirred at 0° C. for 3 hours to afford 800 mg of the product (66.6% yield).

$^1$H NMR (CDCl$_3$, 300 MHz): δ 7.97-7.93 (m, 1H), 7.59-7.55 (m, 1H), 7.45-7.426 (m, 1H), 7.1-7.09 (dd, 1H), 7.03-7.0 (d, 1H), 3.95 (s, 3H).

Preparation of Intermediate 2-(4-chloro-3-methoxyphenyl)ethanamine (I-86b)

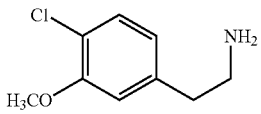
(I-86b)

1-Chloro-2-methoxy-4-(2-nitrovinyl)benzene (I-86a: 800 mg, 3.74 mmol) in dry THF (10 mL) was reacted with LAH (278 mg, 7.48 mmol) in dry THF (10 mL) to afford 700 mg of the product (100%).

$^1$H NMR (CDCl$_3$, 300 MHz): δ 7.28-7.26 (m, 1H), 6.76-6.73 (m, 2H), 3.89 (s, 3H), 2.99-2.94 (m, 2H), 2.75-2.70 (m, 2H).

Preparation of Intermediate ethyl 4-chloro-3-methoxyphenethylcarbamate (I-86c)

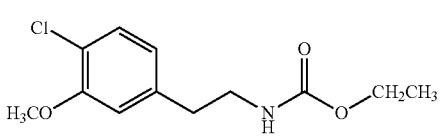
(I-86c)

2-(4-Chloro-3-methoxyphenyl)ethanamine (I-86b: 700 mg, 3.743 mmol) in chloroform (10 mL) was reacted with chloro ethyl formate (487 mg, 4.49 mmol) and 2N Na$_2$CO$_3$ solution (10 mL) at 0° C. The resulting mixture was stirred at room temperature for 1 hour to afford the crude product. Purification by column chromatography on silica gel (10% ethyl acetate in hexane) afforded 500 mg of the product (51.8% yield).

$^1$H NMR (CDCl$_3$, 300 MHz): δ 7.29-7.26 (m, 1H), 6.75-6.71 (m, 2H), 4.7-4.6 (bs, 1H), 4.10-4.07 (m, 2H), 3.9 (s, 3H), 3.43-3.39 (m, 2H), 2.81-2.76 (m, 2H), 1.28-1.20 (m, 2H).

Preparation of Intermediate 7-chloro-6-methoxy-3,4-dihydroisoquinolin-1(2H)-one (I-86d)

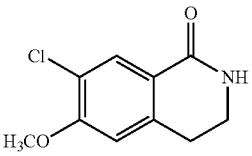
(I-86d)

Ethyl 4-chloro-3-methoxyphenethylcarbamate (I-86c: 500 mg, 1.7063 mmol) in POCl$_3$ (10 mL) was reacted with P$_2$O$_5$ (484 mg, 3.41 mmol). The resulting mixture was stirred at 110° C. for 1 hour to afford the crude product. Purification by column chromatography on silica gel (2% methanol in CHCl$_3$) afforded 200 mg of the product (55.5% yield).

$^1$H NMR (DMSO-D$_6$, 300 MHz): δ 7.9-7.8 (bs, 1H), 7.751 (s, 1H), 7.10 (s, 1H), 3.9 (s, 3H), 3.43-3.39 (m, 2H), 2.91-2.89 (m, 2H).

Preparation of 7-chloro-6-methoxy-2-(4-methylpyridin-3-yl)-3,4-dihydroisoquinolin-1(2H)-one (86A)

7-Chloro-6-methoxy-3,4-dihydroisoquinolin-1(2H)-one (I-86d: 200 mg, 0.946 mmol) was reacted with 3-iodo-4-methylpyridine (228.2 mg, 1.042 mmol), 1,4-dioxane (5 mL), copper iodide (18 mg, 0.094 mmol), trans-N,N'-dimethyl-cyclohexyl-1,2-diamine (13.4 mg, 0.095 mmol) and potassium phosphate (603.3 mg, 2.84 mmol) for 48 hours at 120° C. to afford the crude product. Purification by column chromatography on silica gel (2% methanol in CHCl$_3$) afforded 150 mg of the product (52.4% yield).

$^1$H NMR (DMSO-D$_6$, 300 MHz): δ 8.5-8.3 (d, 2H), 7.8 (s, 1H), 7.4 (d, 1H), 7.3 (s, 1H), 4.03-3.80 (m, 4H), 3.6-3.50 (m, 1H), 3.3-3.0 (m, 2H), 2.2 (s, 1H). LCMS: 98.37%, m/z=303.2 (M+1). HPLC: 94.28%

Example 87

Preparation of 7-chloro-6-hydroxy-2-(4-methylpyridin-3-yl)-3,4-dihydroisoquinolin-1(2H)-one (87A)

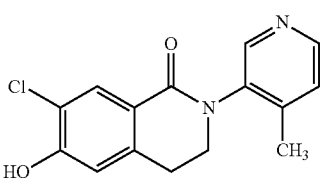
(87A)

BBr$_3$ (4.4 mL) was added to a stirred solution of 7-chloro-6-methoxy-2-(4-methylpyridin-3-yl)-3,4-dihydroisoquinolin-1(2H)-one (86A: 450 mg, 1.480 mmol) in DCM (10 mL) at 0° C. The resulting mixture was stirred for 14 hours at room temperature. The reaction was monitored by TLC (5% methanol in CHCl$_3$). The mixture was slowly quenched with ice water extracted with chloroform (2×50 mL). The organic layer was dried over Na₂SO₄ and concentrated under reduced pressure to afford the crude product. Purification by column chromatography on silica gel (2% methanol in CHCl₃), afforded 300 mg of the product (70.4% yield).

¹H NMR (DMSO-D₆, 300 MHz): δ 11.3-11.1 (bs, 1H), 8.93 (s, 1H), 8.74-8.72 (d, 1H), 7.96-7.94 (d, 1H), 7.8 (s, 1H), 6.94 (s, 1H), 4.02-3.79 (m, 4H), 2.41 (s, 3H). LCMS: 98.68%, m/z=289.0 (M+1).

Example 88

Preparation of 7-chloro-2-(4-methylpyridin-3-yl)-1-oxo-1,2,3,4-tetrahydroisoquinoline-6-carbonitrile (88A)

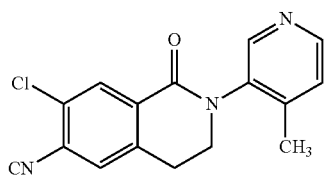

(88A)

Preparation of Intermediate 7-chloro-2-(4-methylpyridin-3-yl)-1-oxo-1,2,3,4-tetrahydroisoquinolin-6-yl trifluoromethanesulfonate (I-88a)

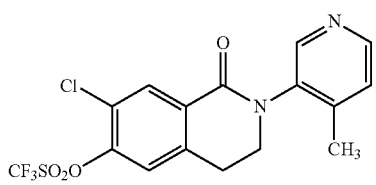

(I-88a)

KHMDS (0.23 mL (0.91M), 0.21 mmol) was added to a solution of 7-chloro-6-hydroxy-2-(4-methylpyridin-3-yl)-3,4-dihydroisoquinolin-1(2H)-one (87A: 50 mg, 0.1736 mmol) in THF (5 mL) at −10° C. and stirred at −10° C. for 20 minutes, then cooled to −78° C., followed by the addition of N-phenyl trifluoromethanesulfonamide (68.2 mg, 0.190 mmol). The resulting mixture was stirred at room temperature for 60 minutes. The reaction was monitored by TLC (5% methanol in CHCl₃). The reaction mixture was quenched with saturated NH₄Cl solution and partitioned between water and ethyl acetate. The organic layer was dried over Na₂SO₄ and concentrated under reduced pressure to afford the crude product. Purification by column chromatography on silica gel (2% methanol in CHCl₃) afforded 50 mg of the product (70% yield).

¹H NMR (CDCl₃, 400 MHz): δ 8.6-8.4 (m, 2H), 8.31 (s, 1H), 7.32-7.27 (m, 2H), 4.22-4.0 (m, 1H), 3.84-3.83 (m, 1H), 3.24-3.22 (m, 2H), 2.91 (s, 3H).

Preparation of 7-chloro-2-(4-methylpyridin-3-yl)-1-oxo-1,2,3,4-tetrahydroisoquinoline-6-carbonitrile (88A)

Pd₂(dba)₃ (17.4 mg, 0.018 mmol), dppf (42.2 mg, 0.076 mmol) and Zn(CN)₂ (65 mg, 0.6 mmol) were added to previously degassed 7-chloro-2-(4-methylpyridin-3-yl)-1-oxo-1,2,3,4-tetrahydroisoquinolin-6-yl trifluoromethane sulfonate (I-87a: 200 mg, 0.476 mmol) in DMF (3 mL). The resulting mixture was stirred for 18 hours at 80° C. The reaction was monitored by TLC (5% methanol in CHCl₃). The reaction mixture was cooled to room temperature, poured into saturated Na₂CO₃ solution and extracted with ethyl acetate. The organic layer was dried over Na₂SO₄ and concentrated under reduced pressure to afford the crude product. Purification by column chromatography on silica gel (2% methanol in CHCl₃), followed by preparative HPLC afforded 5 mg of the product (10.6% yield).

¹H NMR (CDCl₃, 400 MHz): δ 8.6-8.4 (m, 2H), 8.31 (s, 1H), 7.8 (s, 1H), 7.3 (s, 1H), 4.1-4.0 (m, 1H), 3.84-3.73 (m, 1H), 3.24-3.21 (m, 2H), 2.29 (s, 3H). LCMS: 95.70%, m/z=298 (M+1). HPLC: 97.73%

Example 89

Preparation of 7-chloro-2-(4-cyclopropylpyridin-3-yl)-6-methoxy-3,4-dihydroisoquinolin-1(2H)-one (89A)

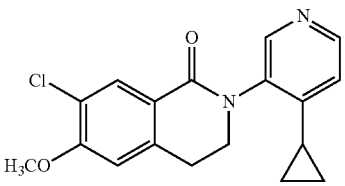

(89A)

7-Chloro-6-methoxy-3,4-dihydroisoquinolin-1(2H)-one 100 mg, 0.473 mmol) was reacted with 4-cyclopropyl-3-iodopyridine (I-73c: 127.6 mg, 0.521 mmol), 1,4-dioxane (5 mL), copper iodide (9.3 mg, 0.047 mmol), trans-N,N'-dimethyl-cyclohexyl-1,2-diamine (6.7 mg, 0.047 mmol) and potassium phosphate (301.6 mg, 1.421 mmol) for 12 hours at 120° C. to afford the crude product. Purification by column chromatography on silica gel (2% methanol in CHCl₃), followed by preparative HPLC afford 35 mg of the product ¹H NMR (CDCl₃, 400 MHz): δ 8.5-8.4 (bs, 2H), 8.19 (s, 1H), 6.85-6.8 (d, 1H), 6.7 (s, 1H), 4.0 (s, 3H), 3.95-3.7 (m, 2H), 3.2-3.1 (m, 2H), 2.0-1.9 (m, 1H), 1.1-1.0 (m, 2H), 1.0-0.9 (m, 1H), 0.8-0.7 (m, 1H). LCMS: 100%, m/z=329.1(M+1). HPLC: 99.0%

Example 90

Preparation of Intermediate 7-chloro-6-hydroxy-2-(4-cyclopropylpyridin-3-yl)-3,4-dihydroisoquinolin-1(2H)-one (90A)

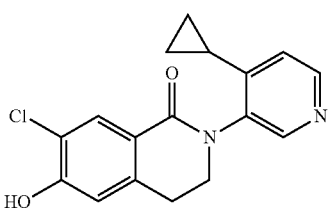

(90A)

7-Chloro-6-methoxy-2-(4-cyclopropylpyridin-3-yl)-3,4-dihydroisoquinolin-1(2H)-one (89A: 200 mg, 0.6 mmol) in DCM (5 mL) was demethylated with BBr$_3$ (1.8 mL) at 0° C. for 2 hours to afford 180 mg of the product (94.7% yield).

$^1$H NMR (DMSO-D$_6$, 300 MHz): δ 11.1 (bs, 1H), 8.87 (s, 1H), 8.67-8.65 (d, 1H), 7.85-7.83 (m, 1H), 7.48-7.46 (d, 1H), 6.95 (s, 1H), 3.18-3.12 (m, 4H), 2.20-2.10 (m, 1H) 1.33-0.87 (m, 4H).

Example 91

Preparation of 7-chloro-2-(4-cyclopropylpyridin-3-yl)-1-oxo-1,2,3,4-tetrahydroisoquinoline-6-carbonitrile (91A)

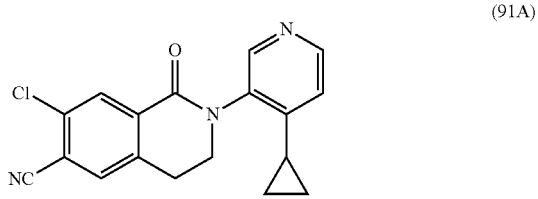 [SMILES: N#Cc1cc2c(cc1Cl)C(=O)N(c1cnccc1C1CC1)CC2]

(91A)

Preparation of Intermediate 7-chloro-2-(4-cyclopropylpyridin-3-yl)-1-oxo-1,2,3,4-tetrahydroisoquinolin-6-yl trifluoromethanesulfonate (I-91a)

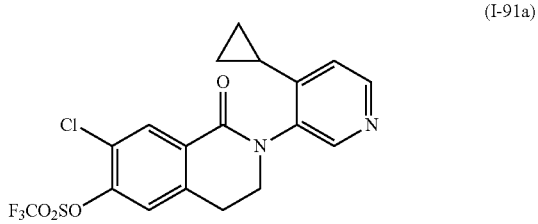

(I-91a)

7-Chloro-6-hydroxy-2-(4-cyclopropylpyridin-3-yl)-3,4-dihydroisoquinolin-1(2H)-one (90A: 180 mg, 0.57 mmol) was reacted with KHMDS (0.71 mL, 0.71 mmol) in THF (10 mL) and N-phenyl trifluoromethanesulfonamide (226 mg, 0.630 mmol) to afford the crude product. Purification by column chromatography on silica gel (1% methanol in CHCl$_3$) afforded 170 mg of the product (66.6% yield).

$^1$H NMR (CDCl$_3$, 300 MHz): δ8.50-8.40 (m, 2H), 8.35 (s, 1H), 7.35-7.30 (bs, 1H), 6.90-6.80 (d, 1H), 4.10-3.90 (m, 2H), 3.30-3.10 (m, 2H), 1.95-1.85 (m, 1H) 1.15-0.95 (m, 2H), 0.85-0.75 (m, 2H). LCMS: 97.11%, m/z=447 (M+1)

Preparation of 7-chloro-2-(4-cyclopropylpyridin-3-yl)-1-oxo-1,2,3,4-tetrahydroisoquinoline-6-carbonitrile (91A)

7-Chloro-2-(4-cyclopropylpyridin-3-yl)-1-oxo-1,2,3,4-tetrahydroisoquinolin-6-yl trifluoromethanesulfonate (I-91a: 170 mg, 0.381 mmol) in DMF (3 mL) was reacted with Pd$_2$(dba)$_3$ (6.97 mg, 0.007 mmol), dppf (16.9 mg, 0.003 mmol) and Zn(CN)$_2$ (26.8 mg, 0.228 mmol) for 24 hours at 80° C. to afford the crude product. Purification by column chromatography on silica gel (2% methanol in CHCl$_3$) followed by preparative HPLC afforded 30 mg of the product (24.3% yield).

$^1$H NMR (CDCl$_3$, 400 MHz): δ 8.46-8.45 (d, 1H), 8.42 (s, 1H), 8.28 (s, 1H), 7.63 (s, 1H), 6.86-6.84 (d, 1H), 4.05-3.97 (m, 1H), 3.94-3.87 (m, 1H), 3.29-3.17 (m, 2H), 1.90-1.84 (m, 1H), 1.1-1.0 (m, 2H), 0.97-0.95 (m, 1H), 0.7-0.67 (m, 1H).

LCMS: 98.75%, m/z=324.1(M+1). HPLC: 99.37%.

Pharmacological Testing

The abbreviations listed below and used in the preparations below have the corresponding meanings.
CYP Cytochrome P450
CPM Counts per minute
Cyt b5 Cytochrome b5
DMSO Dimethyl sulfoxide
DHEA Dehydroepiandrosterone
NADPH Nicotinamide adenine dinucleotide phosphate Human and Rat-Cytochrome P450, 17-20 Lyase 1) Cytochrome P450, 17-20 Lyase (CYP17-Lyase) Assay Development Using Recombinant Human CYP17 Enzyme and 17-α-Hydroxy Pregnenolone [21-3H] as the Substrate.

Cytochrome P450, 17-α-Hydroxylase, 17-20 lyase (CYP17) is a multi functional enzyme that plays a key role in the biosynthesis of steroid hormones. It catalyses both conventional hydroxylation and also the carbon-carbon bond cleavage reactions (Peter Lee-Robichaud et al, Biochem. J, (1997) 321, 857-63). In the hydroxylation reaction, it converts progesterone and pregnenolone to the corresponding hydroxylated products 17-α-hydroxy progesterone and 17-α-hydroxy pregnenolone. In the lyase reaction, it catalyzes the conversion of these hydroxylated substrates to Androstenedione and Dehydroepiandrosterone (DHEA) respectively. In the Cyp17 lyase assay described here, the conversion of 17-α-hydroxy pregnenolone to Dehydroepiandrosterone and acetic acid is being monitored.

The hydroxylation and cleavage activities are catalyzed sequentially at the common active site of Cyp17 and proceed through transfer of two electrons from NADPH via its redox partner, cytochrome P450 reductase (CPR). The reaction mechanism for each activity is thought to involve formation of distinct iron-oxygen complexes. Cytochromeb5 selectively stimulates the lyase activity and has no significant effect on its hydroxylase activity. Lyase activity is stimulated by cytochrome b5 up to 10-fold in reconstituted assays with insignificant stimulation of the hydroxylase activity (M K Akthar et al, Journal of Endocrinology (2005) 187, 267-274 and Katagiri M et al, Biophysical Research Communications (1982) 108, 379-384).

Assay method was adopted from a published protocol with some modifications to suit our requirements (Dmitry N Grigoryev et al, Analytical Biochemistry, (1999) 267, 319-330). The conversion of 17-α-hydroxy pregnenolone to Dehydroepiandrosterone is accompanied by the release of acetic acid. In the Cyp17 lyase assay, 17-α-hydroxy pregnenolone labeled with tritium (3H) at position 21 is used as the substrate. Chloroform extraction removes the radioactive steroids and acetic acid is taken into aqueous layer. The tritiated acetic acid released in the assay thus extracted is quantified to determine the enzyme activity.

Initial buffer conditions were, 50 mM Phosphate buffer, pH 7.5 was used as the starting buffer for Cyp17 lyase activity based on the data published in US patent publication No. US2004/0198773 A1. This buffer was found to be suitable for regular Cyp17 lyase assay. Human Cyp 17 gene was cloned and expressed in Adenoviral expression system in A549 cell lines. The purified cell membrane preparations were used as the source for Human CYP17 enzyme. Total protein concentration: 8 mg/mL.

To identify the appropriate concentration of the enzyme required for the assay, concentration dependent enzyme activity was determined at a substrate (17-α-hydroxypregnenolone [21-3H]) concentration of 0.5 µM (Vincent C. O. Nijar, et al., *J Med Chem*, (1998) 41, 902-912). The protein activity was found to be in the linear range up to 20 µg, the highest concentration tested. Based on the enzyme concentration curve and stock concentration, 15 µg was selected for the assay. At this protein concentration, the S/N ratio was 30, with a good signal window ($CPM_{Pos.Ctrl}$-$CPM_{Blank}$=1650)

$K_m$ (Michaelis Menton constant) is a measure of the binding affinity of substrate to the enzyme. 17-α-hydroxy pregnenolone [21-3H] is a substrate for 17, 20 lyase enzyme. $K_m$ for this substrate was determined by monitoring the tritiated acetic acid release as a function of substrate concentration. Concentration of 17-α-hydroxy-pregnenolone [21-3H] was varied from 0.03125 µM to 1 µM. For the $K_m$ determination, the data was fit to a hyperbolic equation (Graphpad Prism® software IV). The $K_m$ was estimated as 0.25 µM, close to the reported value. (Dmitry N. Grigoryev et al, *Analytical Biochemistry* (1999) 267, 319-330)

For routine screening, the assay was set up with 16 µg of enzyme in 50 µL reaction volume. 17α-hydroxy pregnenolone [21-3H] was added to a final concentration of 0.25 µM. NADPH is used at a final concentration of 4.2 mM. Total reaction volume was made up to 50 µL with 50 mM Phosphate buffer pH 7.5. The reaction mixture was incubated at room temperature for 90 minutes with gentle shaking. The reaction was stopped by the addition of 100 µL of buffer. 500 µL of 5% freshly prepared activated charcoal was added to the solution and mixed well by vortexing. The samples were centrifuged at 17568×g for 5 minutes. (14000 rpm). The supernatant was carefully transferred to fresh tube and 1.3 mL of scintillation fluid was added, mixed by vortexing.

The radioactivity was measured in a 1450 MicroBeta Tri-Lux™ scintillation counter from Wallac-Perkin Elmer®, USA. The measurements were carried out in 2.0 mL Eppendorf™ tubes. Each tube was counted for 1 minute. The amount of tritiated acetic acid released is proportional to the lyase activity. Percent lyase activity in presence of inhibitor was calculated using the formula given below.

$$\% \text{ Lyase activity} = \frac{CPM_{sample} - CPM_{blank}}{CPM_{Pos.\ Ctrl} - CPM_{Blank}} \times 100$$

Sample: Enzyme reaction in presence of inhibitor.
Positive control: Enzyme reaction without inhibitor but containing DMSO at 1% final concentration.
Blank—Contains all reagents except enzyme.
% Inhibition=100%−% Lyase activity For $IC_{50}$ determination, the % inhibition was plotted as a function of inhibitor concentration. The data was fitted to sigmoidal equation using Graphpad Prism® software IV to generate $IC_{50}$ values.

Dose-response studies by standard compounds Abiraterone and Ketoconazole were carried out as part of assay optimization.

For the Rat CYP 17 Lyase Model:

The same procedure described above was used but using rat testes microsomes as the source and with a substrate concentration of 0.5 µM.

The results for the compounds tested from the Examples above using the assay above are listed in Table 1 below.

TABLE 1

| Example No. | Compound | Lyase IC 50 nM Human | hCYP17 Lyase % Inh |
|---|---|---|---|
| 1A | 7-Chloro-2-pyridin-3-yl-3,4-dihydro-2H-isoquinolin-1-one | 60 | — |
| 2A | 7-Chloro-2-(4-methyl-pyridin-3-yl)-3,4-dihydro-2H-isoquinolin-1-one | 37 | — |
| 3A | 7-(4-Fluoro-phenyl)-2-(4-methyl-pyridin-3-yl)-3,4-dihydro-2H-isoquinolin-1-one | 1207 | — |
| 4A | 2-(4-Methyl-pyridin-3-yl)-7-trifluoromethyl-3,4-dihydro-2H-isoquinolin-1-one | 5.5 | — |
| 5A | 6-(4-Methyl-pyridin-3-yl)-5,6-dihydro-4H-thieno[2,3-c]pyridin-7-one | — | 91% at 10 µM |
| 6A | 6-Pyridin-3-yl-5,6-dihydro-4H-thieno[2,3-c]pyridin-7-one | — | 48% at 10 µM |
| 7A | 5-(4-Methyl-pyridin-3-yl)-6,7-dihydro-5H-thieno[3,2-c]pyridin-4-one | — | 75% at 10 µM |
| 8A | 5-Pyridin-3-yl-6,7-dihydro-5H-thieno[3,2-c]pyridin-4-one | — | 27% at 10 µM |
| 9A | 2-(4-Methyl-pyridin-3-yl)-3,4-dihydro-2H-benzo[4,5]thieno[3,2-c]pyridin-1-one | 1.5 | — |
| 10A | 2-(4-Methyl-pyridin-3-yl)-3,4-dihydro-2H-benzo[h]isoquinolin-1-one | 3.5 | — |
| 11A | 6-Methoxy-2-(4-methyl-pyridin-3-yl)-3,4-dihydro-2H-isoquinolin-1-one | 214 | — |
| 11B | 6-Hydroxy-2-(4-methyl-pyridin-3-yl)-3,4-dihydro-2H-isoquinolin-1-one | 139 | — |

TABLE 1-continued

| Example No. | Compound | Lyase IC 50 nM Human | hCYP17 Lyase % Inh |
|---|---|---|---|
| 12A | 5-Chloro-2-(4-methyl-pyridin-3-yl)-3,4-dihydro-2H-isoquinolin-1-one | — | 64% at 10 μM |
| 13A | 5-Methoxy-2-(4-methyl-pyridin-3-yl)-3,4-dihydro-2H-isoquinolin-1-one | 917 | — |
| 14A | 2-(4-Fluoro-phenyl)-5-(4-methyl-pyridin-3-yl)-6,7-dihydro-5H-thieno[3,2-c]pyridin-4-one | 755 | — |
| 15A | 3-(4-Fluoro-phenyl)-5-(4-methyl-pyridin-3-yl)-6,7-dihydro-5H-thieno[3,2-c]pyridin-4-one | — | 35% at 10 μM |
| 16A | 2-Pyridin-3-yl-7-trifluoromethyl-3,4-dihydro-2H-isoquinolin-1-one | 175 | — |
| 17A | 2-(4-Methyl-pyridin-3-yl)-6-trifluoromethyl-3,4-dihydro-2H-isoquinolin-1-one | 95 | — |
| 18A | 2-(5-Fluoro-pyridin-3-yl)-7-trifluoromethyl-3,4-dihydro-2H-isoquinolin-1-one | 334 | — |
| 19A | 7-Trifluoromethyl-3,4-dihydro-[2,4']biisoquinolinyl-1-one | 44 | — |
| 20A | 4,4-Dimethyl-2-(4-methyl-pyridin-3-yl)-7-trifluoromethyl-3,4-dihydro-2H-isoquinolin-1-one | 369 | — |
| 21A | 7-Trifluoromethyl-2-(4-trifluoromethyl-pyridin-3-yl)-3,4-dihydro-2H-isoquinolin-1-one | 56 | — |
| 22A | 2-(4-Methyl-pyridin-3-yl)-5-trifluoromethyl-3,4-dihydro-2H-isoquinolin-1-one | — | 42% at 10 μM |
| 23A | 2-(4-Methyl-pyridin-3-yl)-3,4-dihydro-2H-isoquinolin-1-one | 227 | — |
| 24A | Cyclopropanecarboxylic acid [2-(4-methyl-pyridin-3-yl)-1-oxo-1,2-dihydro-isoquinolin-7-yl]-amide | — | 53% at 10 μM |
| 25A | Cyclopropanecarboxylic acid [2-(4-methyl-pyridin-3-yl)-1-oxo-1,2,3,4-tetrahydro-isoquinolin-7-yl]-amide | — | 35% at 10 μM |
| 26A | 7-Methoxy-2-(4-methyl-pyridin-3-yl)-3,4-dihydro-2H-isoquinolin-1-one | 17 | — |
| 27A | 7-Hydroxy-2-(4-methyl-pyridin-3-yl)-3,4-dihydro-2H-isoquinolin-1-one | 83 | — |
| 28A | 1-Ethyl-6-(4-methyl-pyridin-3-yl)-1,4,5,6-tetrahydro-pyrrolo[2,3-c]pyridin-7-one | 70 | — |
| 29A | 2-(4-Methyl-pyridin-3-yl)-7-trifluoromethyl-2H-isoquinolin-1-one | — | 66% at 10 μM |
| 30A | 2-(4-methylpyridin-3-yl)-7-(phenylamino)-3,4-dihydroisoquinolin-1(2H)-one | — | 41% at 10 μM |
| 31A | 7-(cyclopropylmethoxy)-2-(4-methylpyridin-3-yl)-3,4-dihydroisoquinolin-1(2H)-one | 727 | — |
| 32A | 2-(4-methylpyridin-3-yl)-1-oxo-1,2,3,4-tetrahydroisoquinoline-7-carbonitrile | 301 | — |
| 33A | 7-chloro-8-fluoro-2-(4-methylpyridin-3-yl)-3,4-dihydroisoquinolin-1(2H)-one | 13 | — |
| 34A | 8-chloro-7-fluoro-2-(4-methylpyridin-3-yl)-3,4-dihydroisoquinolin-1(2H)-one | 149 | — |

TABLE 1-continued

| Example No. | Compound | Lyase IC 50 nM Human | hCYP17 Lyase % Inh |
|---|---|---|---|
| 35A | 2-(4-methylpyridin-3-yl)-7-(4-(trifluoromethyl)pyridin-2-yloxy)-3,4-dihydroisoquinolin-1(2H)-one | — | 60% at 10 μM |
| 36A | 2-(pyridin-3-yl)-7-(trifluoromethyl)isoquinolin-1(2H)-one | 54 | — |
| 37A | 7-(5-fluoropyrimidin-2-yloxy)-2-(4-methylpyridin-3-yl)-3,4-dihydroisoquinolin-1(2H)-one | — | 63% at 10 μM |
| 38A | 9-ethyl-2-(4-methylpyridin-3-yl)-2,3,4,9-tetrahydro-1H-pyrido[3,4-b]indol-1-one | 23 | — |
| 39A | 8-(cyclopropylmethylamino)-7-fluoro-2-(4-methylpyridin-3-yl)-3,4-dihydroisoquinolin-1(2H)-one, acetate salt | — | 76% at 10 μM |
| 40A | 6,7-dimethoxy-2-(4-methylpyridin-3-yl)-3,4-dihydroisoquinolin-1(2H)-one | — | 12% at 10 μM |
| 41A | 6,7-dichloro-2-(4-methylpyridin-3-yl)-3,4-dihydroisoquinolin-1(2H)-one | — | 10% at 10 μM |
| 42A | 9-ethyl-3-methyl-2-(pyridin-3-yl)-2,3,4,9-tetrahydro-1H-pyrido[3,4-b]indol-1-one | 55 | — |
| 43A | 3-methyl-2-(pyridin-3-yl)-7-(trifluoromethyl)-3,4-dihydroisoquinolin-1(2H)-one | 15 | — |
| 44A | 5-fluoro-8-methoxy-2-(4-methylpyridin-3-yl)-3,4-dihydroisoquinolin-1(2H)-one | — | 8% at 10 μM |
| 45A | 6-Fluoro-2-(4-methyl-pyridin-3-yl)-3,4-dihydro-2H-benzo[4,5]thieno[2,3-c]pyridin-1-one | 211 | — |
| 46A | 9-Ethyl-3-methyl-2-(4-methyl-pyridin-3-yl)-2,3,4,9-tetrahydro-b-carbolin-1-one | 44 | — |
| 47A | 8-Fluoro-2-(4-methyl-pyridin-3-yl)-7-trifluoromethyl-3,4-dihydro-2H-isoquinolin-1-one | 12 | — |
| 48A | 3-Methyl-2-(4-methyl-pyridin-3-yl)-7-trifluoromethyl-3,4-dihydro-2H-isoquinolin-1-one | 16 | — |
| 49A | 6,7-Difluoro-2-(4-methylpyridin-3-yl)-3,4-dihydroisoquinolin-1(2H)-one | 159 | — |
| 50A | 8-Fluoro-2-(4-methylpyridine-3-yl)3,4-dihydro-2H-benzo[4,5]thieno[3,2-c]pyridin-1-one | 6 | — |
| 51A | 2-(4-Methylpyridin-3-yl)-7-(trifluoromethoxy)-3,4-dihydroisoquinolin-1(2H)-one | 22 | — |
| 52A | 2-(4-(Pyrrolidin-1-ylmethyl)pyridin-3-yl)-7-(trifluoromethyl)-3,4-dihydroisoquinolin-1(2H)-one | 556 | — |
| 53A | 2-(4-((Cyclopropylamino)methyl)pyridin-3-yl)-7-(trifluoromethyl)-3,4-dihydroisoquinolin-1(2H)-one | 50 | — |
| 54A | 2-(1-Methyl-1H-imidazol-5-yl)-7-(trifluoromethyl)-3,4-dihydroisoquinolin-1(2H)-one | 19 | — |
| 55A | 6,7-Dichloro-2-(4-(trifluoromethyl)pyridin-3-yl)-3,4-dihydroisoquinolin-1(2H)-one | 125 | — |
| 56A | 2-(5-Fluoropyridin-3-yl)-6-(trifluoromethyl)-3,4-dihydroisoquinolin-1(2H)-one | 1111 | — |
| 57A | 8-Fluoro-2-(4-trifluoromethylpyridine-3-yl)3,4-dihydro-2H- | 548 | — |

TABLE 1-continued

| Example No. | Compound | Lyase IC 50 nM Human | hCYP17 Lyase % Inh |
|---|---|---|---|
| | benzo[4,5]thieno[3,2-c]pyridin-1-one | | |
| 58A | 2-(4-Trifluoromethylpyridine-3-yl)3,4-dihydro-2H-benzo[4,5]thieno[3,2-c]pyridin-1-one | 218 | — |
| 59A | 5-Ethyl-8-fluoro-2-(4-methylpyridin-3-yl)-2,3,4,5-tetrahydro-1H-pyrido[4,3-b]indol-1-one | 29 | — |
| 60A | 8-Fluoro-2-(4-methylpyridin-3-yl)-2,3,4,5-tetrahydro-1H-pyrido[4,3-b]indol-1-one | 9 | — |
| 61A | 2-(4-Methylpyridin-3-yl)-2,3,4,9-tetrahydro-1H-pyrido[3,4-b]indol-1-one | 1507 | — |
| 62A | 2-(4-Methyl pyridin-3-yl)-2,5-dihydro-1H-pyrido[4,3-b]indol-1-one | 17 | — |
| 63A | 2-(4-(Trifluoromethyl)pyridin-3-yl)-2,5-dihydro-1H-pyrido[4,3-b]indol-1-one | NOT ACTIVE | — |
| 64A | 8-Fluoro-2-(4-(trifluoromethyl)pyridin-3-yl)-2,5-dihydro-1H-pyrido[4,3-b]indol-1-one | 829 | — |
| 65A | 2-(4-Methylpyridin-3-yl)-3,4-dihydro-2,7-naphthyridin-1(2H)-one | 1143 | — |
| 66A | 8-(4-Methylpyridin-3-yl)-7,8-dihydrothiazolo[4,5-h]isoquinolin-9(6H)-one | 11 | — |
| 67A | 2-(4-Methylpyridin-3-yl)-3,4-dihydro-2,6-naphthyridin-1(2H)-one | 716 | — |
| 68A | 2-(5-Fluoropyridin-3-yl)-7-(trifluoromethyl) isoquinolin-1(2H)-one | 282 | — |
| 69A | 7-(4-Methyl pyridin-3-yl)-6,7-dihydro-1H-pyrazolo[4,3-g]isoquinolin-8(5H)-one | 93 | — |
| 70A | 3-Methyl-7-(trifluoromethyl)-2-(4-(trifluoromethyl)pyridin-3-yl)-3,4-dihydroisoquinolin-1(2H)-one | 744 | — |
| 71A | 6-Methyl-2-(4-(trifluoromethyl)pyridin-3-yl)-3,4-dihydroisoquinolin-1(2H)-one | — | — |
| 72A | 7-(4-(trifluoromethyl)pyridin-3-yl)-6,7-dihydro-1H-pyrazolo[4,3-g]isoquinolin-8(5H)-one | 730 | — |
| 73A | 2-(4-Cyclopropylpyridin-3-yl)-7-(trifluoromethyl)-3,4-dihydroisoquinolin-1(2H)-one | 14 | — |
| 74A | 7-Chloro-2-(4-cyclopropylpyridin-3-yl)-3,4-dihydroisoquinolin-1(2H)-one | 23 | — |
| 75A | 7-Chloro-2-(4-ethylpyridin-3-yl)-3,4-dihydroisoquinolin-1(2H)-one | 8 | — |
| 76A | 2-(4-Cyclopropylpyridin-3-yl)-3,4-dihydrobenzo[4,5]thieno[3,2-c]pyridin-1(2H)-one | 4.2 | — |
| 77A | 8-Fluoro-7-(trifluoromethyl)-2-(4-(trifluoromethyl)pyridin-3-yl)-3,4-dihydroisoquinolin-1(2H)-one | 167 | — |
| 78A | 6-Fluoro-2-(4-(trifluoromethyl)pyridin-3-yl)-3,4-dihydroisoquinolin-1(2H)-one | Not active | — |

TABLE 1-continued

| Example No. | Compound | Lyase IC 50 nM Human | hCYP17 Lyase % Inh |
|---|---|---|---|
| 79A | 6-Fluoro-7-iodo-2-(4-(trifluoromethyl)pyridin-3-yl)-3,4-dihydroisoquinolin-1(2H)-one | 19 | — |
| 80A | 7-Chloro-6-fluoro-2-(4-(trifluoromethyl)pyridin-3-yl)-3,4-dihydroisoquinolin-1(2H)-one | 173 | — |
| 81A | 2-(4-Cyclopropylpyridin-3-yl)-6-fluoro-3,4-dihydroisoquinolin-1(2H)-one | — | — |
| 82A | 7-Chloro-2-(4-cyclopropylpyridin-3-yl)-6-fluoro-3,4-dihydroisoquinolin-1(2H)-one | 3 | — |
| 83A | 6-Fluoro-2-(4-methylpyridin-3-yl)-3,4-dihydroisoquinolin-1(2H)-one | — | — |
| 84A | 7-Chloro-6-fluoro-2-(4-methylpyridin-3-yl)-3,4-dihydroisoquinolin-1(2H)-one | 5.3 | — |
| 85A | 6-Chloro-7-(trifluoromethyl)-2-(4-(trifluoromethyl)pridin-3-yl)-3,4-dihydroisoquinolin-1(2H)-one | 108 | — |
| 86A | 7-Chloro-6-methoxy-2-(4-methylpyridin-3-yl)-3,4-dihydroisoquinolin-1(2H)-one | 11 | — |
| 87A | 7-Chloro-6-hydroxy-2-(4-methylpyridin-3-yl)-3,4-dihydroisoquinolin-1(2H)-one | — | — |
| 88A | 7-Chloro-2-(4-methylpyridin-3-yl)-1-oxo-1,2,3,4-tetrahydroisoquinoline-6-carbonitrile | 11 | — |
| 89A | 7-Chloro-2-(4-cyclopropylpyridin-3-yl)-6-methoxy-3,4-dihydroisoquinolin-1(2H)-one | 10 | — |
| 90A | 7-Chloro-6-hydroxy-2-(4-cyclopropylpyridin-3-yl)-3,4-dihydroisoquinolin-1(2H)-one | — | — |
| 91A | 7-Chloro-2-(4-cyclopropylpyridin-3-yl)-1-oxo-1,2,3,4-tetrahydroisoquinoline-6-carbonitrile | 11 | — |

What is claimed is:

1. A compound of Formula (I)

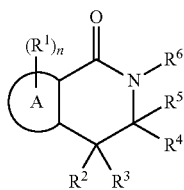

(I)

wherein:
ring A is a 5- to 6-membered heteroaryl containing 1 to 3 heteroatoms each independently selected from N, O or S;
n is 0, 1, 2, or 3;
$R^1$ is halo, $(C_1$-$C_4)$alkyl, halo-substituted $(C_1$-$C_4)$alkyl, —OH, CN, —$NR^{1a}R^{1b}$, —O—$R^{1c}$, or phenyl optionally substituted with 1 to 3 substituents selected from halo, $(C_1$-$C_4)$alkyl, or halo-substituted $(C_1$-$C_4)$alkyl, where $R^{1a}$ is H or $(C_1$-$C_4)$alkyl, $R^{1b}$ is $(C_1$-$C_4)$alkyl, —C(O)—$(C_1$-$C_4)$alkyl, —C(O)—$(C_3$-$C_6)$cycloalkyl, phenyl, or —$CH_2$—$(C_3$-$C_6)$cycloalkyl, and $R^{1c}$ is $(C_1$-$C_4)$alkyl, halo-substituted $(C_1$-$C_4)$alkyl, —$CH_2$—$(C_3$-$C_6)$cycloalkyl, or 5- to 6-membered heteroaryl containing 1 to 3 heteroatoms selected from O, N or S and optionally substituted with 1 to 3 substituents selected from halo, $(C_1$-$C_4)$alkyl, or halo-substituted $(C_1$-$C_4)$ alkyl;

$R^2$, $R^3$, $R^4$, and $R^5$ are each independently H or $(C_1$-$C_4)$ alkyl, or $R^2$ or $R^3$ taken together with $R^4$ or $R^5$ forms a double bond or a cyclopropyl;

$R^6$ is pyridin-3-yl optionally substituted with 1 to 3 substituents each independently selected from halo, —OH, —CN, $(C_1$-$C_4)$alkyl, halo-substituted$(C_1$-$C_4)$alkyl, hydroxy-substituted $(C_1$-$C_4)$alkyl, $(C_3$-$C_5)$cycloalkyl, where said cycloalkyl is optionally substituted with hydroxy, —$NH_2$, —$NH(C_1$-$C_4)$alkyl, —$N((C_1$-$C_4)$alkyl$)_2$, —NHC(O)—$(C_1$-$C_4)$alkyl, —$C(O)NH_2$, —C(O)—$NH(C_1$-$C_4)$alkyl, —C(O)—$N((C_1$-$C_4)$alkyl$)_2$, —C(O)—O$(C_1$-$C_4)$alkyl, —$(CH_2)_r$—O$(C_1$-$C_4)$ alkyl, —(CH$_2$)$_r$—CH(O(C$_1$-C$_4$)alkyl)$_2$, —(CH$_2$)$_r$—NH—(C$_3$-C$_6$)cycloalkyl, or pyrrolidinl-yl-(CH$_2$)$_r$—, where r is 0, 1 or 2;

or a pharmaceutically acceptable salt thereof.

2. A compound of claim 1 selected from the group consisting of

1-Ethyl-6-(4-methyl-pyridin-3-yl)-1,4,5,6-tetrahydro-pyrrolo[2,3-c]pyridin-7-one;

9-Ethyl-2-(4-methylpyridin-3-yl)-2,3,4,9-tetrahydro-1H-pyrido[3,4-b]indo-1one;

9-Ethyl-3-methyl-2-(pyridin-3-yl)-2,3,4,9-tetrahydro-1H-pyrido[3,4-b]indol-1-one;

9-Ethyl-3-methyl-2-(4-methyl-pyridin-3-yl)-2,3,4,9-tetrahydro-b-carbolin-1-one;

2-(4-Methylpyridin-3-yl)-3,4-dihydro-2H-benzo[4,5]thieno[3,2-c]pyridine-1-one;

8-Fluoro-2-(4-methylpyridine-3-yl)3,4-dihydro-2H-benzo[4,5]thieno[3,2-c]pyridin-1-one;

5-Ethyl-8-fluoro-2-(4-methylpyridin-3-yl)-2,3,4,5-tetrahydro-1H-pyrido[4,3-b]indo-1-one;

8-Fluoro-2-(4-methylpyridin-3-yl)-2,3,4,5-tetrahydro-1H-pyrido[4,3-b]indol-1-one;

2-(4-Methyl pyridin-3-yl)-2,5-dihydro-1H-pyrido[4,3-b]indol-1-one;

8-(4-Methylpyridin-3-yl)-7,8-dihydrothiazolo[4,5-h]isoquinolin-9(6H)-one;

7-(4-Methyl pyridin-3-yl)-6,7-dihydro-1H-pyrazolo[4,3-g]isoquinolin-8(5H)-one; and 2-(4-Cyclopropylpyridin-3-yl)-3,4-dihydrobenzo[4,5]thieno[3,2-c]pyridin-1(2H)-one;

or a pharmaceutically acceptable salt thereof.

3. A pharmaceutical composition comprising a compound of claim 2 or a pharmaceutically acceptable salt thereof, and a pharmaceutically acceptable carrier or excipient.

4. The pharmaceutical composition of claim 3 further comprising at least one additional pharmaceutical agent wherein said at least one additional pharmaceutical agent is an anticancer agent, chemotherapy agent, or antiproliferative compound.

5. A method for treating a disease, disorder, or syndrome mediated by Cyp17 inhibition comprising administering a compound of claim 1 to a subject in need of such treatment.

6. A method for treating a disease, disorder, or syndrome mediated by Cyp17 inhibition comprising administering a pharmaceutical composition of claim 3 to a subject in need of such treatment.

7. A method for treating a disease, disorder or syndrome mediated by Cyp17 inhibition comprising administering
   a first composition comprising a compound of claim 1, or a pharmaceutically acceptable salt thereof, and a pharmaceutically acceptable carrier or excipient; and
   (ii) a second composition comprising at least one additional pharmaceutical agent and a pharmaceutically acceptable carrier or excipient;
   wherein said at least one additional pharmaceutical agent is an anticancer agent, chemotherapy agent, or antiproliferative compound.

8. The method of claim 7 wherein said first composition and said second composition are administered simultaneously.

9. The method of claim 7 wherein said first composition and said second composition are administered sequentially in any order.

* * * * *